US012779149B2

(12) United States Patent
Alarcon

(10) Patent No.: US 12,779,149 B2
(45) Date of Patent: Nov. 3, 2026

(54) SYSTEM FOR ANALYZING AND CONTROLLING CONSUMABLE MEDIA DOSING INFORMATION

(71) Applicant: Wellness Insight Technologies, Inc., San Jose, CA (US)

(72) Inventor: Ramon Alarcon, Los Gatos, CA (US)

(73) Assignee: WELLNESS INSIGHT TECHNOLOGIES, INC., San Jose, CA (US)

( * ) Notice: Subject to any disclaimer, the term of this patent is extended or adjusted under 35 U.S.C. 154(b) by 682 days.

(21) Appl. No.: 18/211,072

(22) Filed: Jun. 16, 2023

(65) Prior Publication Data

US 2023/0330364 A1 Oct. 19, 2023

Related U.S. Application Data

(63) Continuation of application No. 16/520,148, filed on Jul. 23, 2019, now Pat. No. 11,744,965.

(Continued)

(51) Int. Cl.

*A61M 15/06* (2006.01)
*A24F 40/10* (2020.01)

(Continued)

(52) U.S. Cl.

CPC ............. *A61M 15/06* (2013.01); *A24F 40/42* (2020.01); *A24F 40/48* (2020.01); *A24F 40/50* (2020.01);

(Continued)

(58) Field of Classification Search

CPC .......... A24F 40/10; A24F 40/20; A24F 40/42; A24F 40/48; A24F 40/50; A24F 40/60;

(Continued)

(56) References Cited

U.S. PATENT DOCUMENTS 5,950,619 A * 9/1999 van der Linden ........................... A61M 15/0085 128/200.14
8,235,037 B2 8/2012 Hale et al.

(Continued)

FOREIGN PATENT DOCUMENTS

CN 106102487 A 11/2016
CN 106163305 A 11/2016

(Continued)

OTHER PUBLICATIONS

First Office Action for CN App No. 2019800623200 dated Jan. 12, 2024, 19 pgs.

(Continued)

*Primary Examiner* — Joseph D. Boecker
(74) *Attorney, Agent, or Firm* — Procopio, Cory, Hargreaves & Savitch LLP

(57) ABSTRACT

A vaporizing article, comprises a vaporizer drive circuit; one or more memories configured to store a percentage of at least one constituent in an inhalation media, one or more compensation values for at least one compensation category for the at least one constituent, and instructions; and a control circuit comprising a processor coupled with the one or more memories configured to run the instructions, the instructions configured to cause the processor to: receive a dose target for a constituent; determine whether to perform compensation for an inhalation media dose in order to ensure the dose target is met; when compensation is to be performed, determine the properly compensated inhalation media dose based on an associated compensation value for the constituent; and control the vaporizer drive circuit so as to dispense a compensated dose of the inhalation media.

39 Claims, 63 Drawing Sheets

Related U.S. Application Data

(60) Provisional application No. 62/827,071, filed on Mar. 31, 2019, provisional application No. 62/758,443, filed on Nov. 9, 2018, provisional application No. 62/736,881, filed on Sep. 26, 2018, provisional application No. 62/702,298, filed on Jul. 23, 2018.

(51) Int. Cl.

| | |
|---|---|
| ***A24F 40/42*** | (2020.01) |
| ***A24F 40/48*** | (2020.01) |
| ***A24F 40/50*** | (2020.01) |
| ***A24F 40/57*** | (2020.01) |
| ***A24F 40/60*** | (2020.01) |
| ***A24F 40/65*** | (2020.01) |
| ***A61M 11/00*** | (2006.01) |
| ***A61M 11/04*** | (2006.01) |
| ***A61M 15/00*** | (2006.01) |
| ***G16H 20/13*** | (2018.01) |
| ***G16H 40/63*** | (2018.01) |

(52) U.S. Cl.

CPC .............. *A24F 40/57* (2020.01); *A24F 40/60* (2020.01); *A24F 40/65* (2020.01); *A61M 11/042* (2014.02); *A61M 15/0065* (2013.01); *A61M 15/0066* (2014.02); *G16H 20/13* (2018.01); *G16H 40/63* (2018.01); *A24F 40/10* (2020.01); *A61M 11/006* (2014.02); *A61M 15/008* (2014.02); *A61M 2205/3306* (2013.01); *A61M 2205/3553* (2013.01)

(58) Field of Classification Search

CPC ............... A24F 40/65; A61M 15/0065; A61M 15/0066; A61M 15/0068; A61M 15/008; A61M 15/06; A61M 11/007; A61M 11/042

See application file for complete search history.

(56) References Cited

U.S. PATENT DOCUMENTS

| | | | | |
|---|---|---|---|---|
| 9,775,379 | B2 | 10/2017 | Davidson et al. | |
| 9,814,271 | B2 | 11/2017 | Goggin et al. | |
| 9,833,021 | B2 | 12/2017 | Perez et al. | |
| 10,251,423 | B2 | 4/2019 | Mamoun et al. | |
| 11,035,704 | B2 | 6/2021 | Kane | |
| 2004/0231667 | A1* | 11/2004 | Horton ................ | A61M 15/008 128/202.13 |
| 2005/0161467 | A1 | 7/2005 | Jones | |
| 2005/0171476 | A1* | 8/2005 | Judson .............. | A61M 5/14566 604/131 |
| 2005/0172957 | A1 | 8/2005 | Childers et al. | |
| 2007/0062520 | A1* | 3/2007 | Nobutani .......... | A61M 15/0085 128/200.14 |
| 2008/0308580 | A1* | 12/2008 | Gaydos ................. | G01F 11/029 222/333 |
| 2009/0133691 | A1* | 5/2009 | Yamada ............... | A61M 11/005 128/200.16 |
| 2011/0253135 | A1 | 10/2011 | Hale et al. | |
| 2013/0276799 | A1 | 10/2013 | Davidson et al. | |
| 2015/0208731 | A1 | 7/2015 | Malamud et al. | |
| 2015/0367366 | A1* | 12/2015 | Edwards .................. | A23G 1/50 239/302 |
| 2016/0157524 | A1 | 6/2016 | Bowen et al. | |
| 2016/0166564 | A1 | 6/2016 | Myers et al. | |
| 2016/0337362 | A1 | 11/2016 | Cameron | |
| 2017/0172211 | A1* | 6/2017 | Batista .................. | A24F 40/485 |
| 2017/0262613 | A1 | 9/2017 | Ljungberg | |
| 2018/0177958 | A1* | 6/2018 | Wilder .............. | A61M 15/0021 |
| 2018/0296778 | A1* | 10/2018 | Hacker ................... | A24F 40/50 |
| 2019/0142072 | A1 | 5/2019 | Tsuji et al. | |
| 2019/0167923 | A1 | 6/2019 | Kessler et al. | |
| 2024/0065338 | A1* | 2/2024 | Alarcon .................. | G07F 13/08 |

FOREIGN PATENT DOCUMENTS

| | | | |
|---|---|---|---|
| CN | 107427067 | A | 12/2017 |
| EP | 1882488 | A2 | 1/2008 |
| WO | 2016150922 | A2 | 9/2016 |
| WO | 2017122201 | A1 | 7/2017 |
| WO | 2018020402 | A1 | 2/2018 |

OTHER PUBLICATIONS

International Search Report and Written Opinion issued in International Application No. PCT/US2019/043104, dated Nov. 8, 2019, 10 pages.

* cited by examiner

205

| Memory Address Location | Descriptor |
|---|---|
| 0001 | Device Serial number |
| 0002 | Media serial number |
| 0003 | Manufacturing Date |
| 0004 | Expiration Date |
| 0005 | Batch # |
| 0006 | Manufacturing location |
| 0007 | Manufacturing parameter #1 |
| 0008 | Manufacturing parameter #2 |
| 0009 | Manufacturing parameter #n |
| 0010 | Media type |
| 0011 | Media constituent component #1 quantity |
| 0012 | Media constituent component #2 quantity |
| 0013 | Media constituent component #n quantity |
| 0014 | Number of inhalation events |
| 0015 | Total duration of inhalation events |
| 0016 | Allowable number of inhalations |
| 0017 | Testing information |
| 0018 | Media fill amount |
| 0019 | Media amount consumed |
| 0020 | Media amount remaining |
| 0021 | Plunger Position |
| 0022 | Heater setting |
| 0023 | Media viscosity |
| 0024 | User #1 data |
| 0025 | User #2 data |
| 0026 | User #n data |
| 0027 | Parameter #1 |
| 0028 | Parameter #2 |
| 0029 | Parameter #n |

FIG 16A

SYSTEM FOR ANALYZING AND CONTROLLING CONSUMABLE MEDIA DOSING INFORMATION

CROSS-REFERENCE TO RELATED APPLICATIONS

This application is Continuation Application of U.S. patent application Ser. No. 16/520,148, filed Jul. 23, 2019, which claims the benefit of U.S. Patent Application No. 62/702,298, filed on Jul. 23, 2018, U.S. Patent Application No. 62/736,881, filed on Sep. 26, 2018, U.S. Patent Application No. 62/758,443, filed on Nov. 9, 2018, and U.S. Patent Application No. 62/827,071, filed on Mar. 31, 2019, the disclosures of which are each incorporated herein in their entirety by reference.

FIELD OF THE DISCLOSURE

The present disclosure relates to a system, a method, and a device for delivering doses and electronically sharing dosing information of an inhalation media, and more particularly for electronic vaporizer products.

BACKGROUND OF THE DISCLOSURE

Personal vaporizers are a popular alternative to traditional *cannabis* and tobacco leaf-based cigarettes that must be combusted in order to generate smoke for inhalation. Personal vaporizers provide a vapor for inhalation, but do not produce certain byproducts of combustion that can be harmful to human health. Personal vaporizers are electronic inhalers that vaporize or atomize a liquid solution into an aerosol that can then be delivered to a user. A typical vaporizer has two main parts–1) a housing containing a battery and control electronics and 2) a liquid storage component. The housing holding the battery typically includes a rechargeable lithium-ion (Li-ion) battery and an activation sensor. The liquid storage component typically includes a liquid solution, an atomizer and a mouthpiece, although the atomizer can reside in the housing in certain configurations. The atomizer typically includes a heating element that vaporizes the liquid solution. Certain advanced vaporizers also have the ability to communicate with a computer network, typically via a wireless connection to a mobile phone.

SUMMARY OF THE DISCLOSURE

According to an aspect of the disclosure, a vaporizing article, comprises a vaporizer drive circuit; one or more memories configured to store a percentage of at least one constituent in an inhalation media, one or more compensation values for at least one compensation category for the at least one constituent, and instructions; and a control circuit comprising a processor coupled with the one or more memories configured to run the instructions, the instructions configured to cause the processor to: receive a dose target for a constituent; determine whether to perform compensation for an inhalation media dose in order to ensure the dose target is met; when compensation is to be performed, determine the properly compensated inhalation media dose based on an associated compensation value for the constituent; and control the vaporizer drive circuit so as to dispense a compensated dose of the inhalation media.

Additional features, advantages, and embodiments of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings:

FIG. 16A shows an example of data that can be programmed into a cartridge component according to an aspect of the disclosure.

DETAILED DESCRIPTION OF THE DISCLOSURE

Figure 1A:
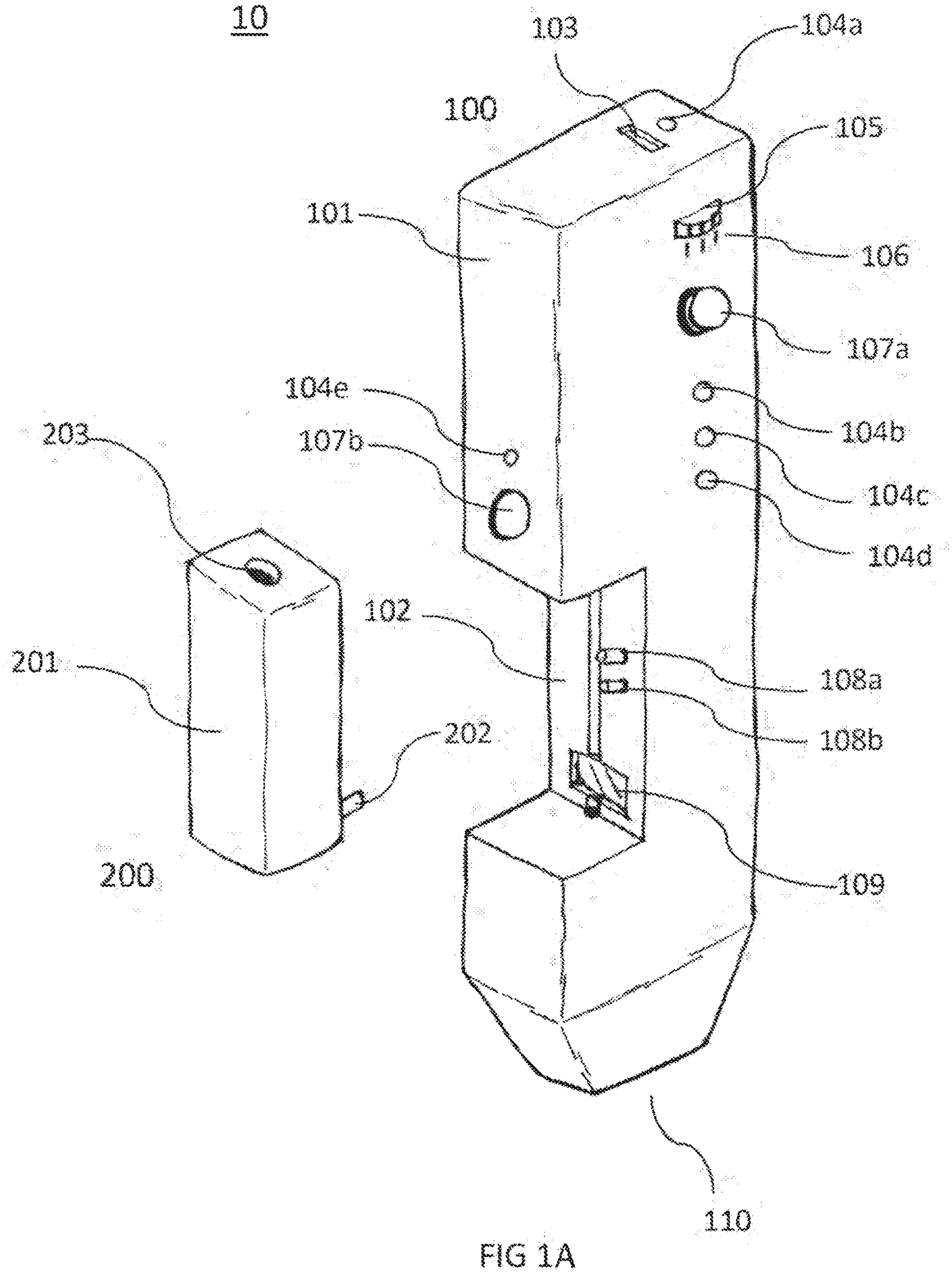
FIG. 1A shows an example of a vaporizer article that is constructed according to an aspect of the disclosure.

The disclosure and the various features and advantageous details thereof are explained more fully with reference to the non-limiting embodiments and examples that are described and/or illustrated in the accompanying drawings and detailed in the following. It should be noted that the features illustrated in the drawings are not necessarily drawn to scale, and features of one embodiment can be employed with other embodiments as the skilled artisan would recognize, even if not explicitly stated herein. Descriptions of well-known components and processing techniques can be omitted so as to not unnecessarily obscure the embodiments of the disclosure. The examples used herein are intended merely to facilitate an understanding of ways in which the disclosure can be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

FIG. 1A shows an example of a vaporizer article 10 according to an aspect of the disclosure. In the instant example, the vaporizer article 10 is comprised of a control device 100 and a media containing cartridge 200. The control device 100 is comprised of a housing 101 that is constructed to house certain components as well as be of a shape and size that enables the user to easily hold and carry the vaporizer article 10. The housing 101 can typically be made of injection molded plastic, metal, or other common engineering materials. The control device 100 has a cartridge receiving area 102 that is designed so as to be mated with the cartridge 200. The cartridge 200 is comprised of a cartridge housing 201 that is constructed to house certain components as well as the inhalation media. The cartridge housing 201 can typically be comprised of injection molded plastic, metal or other common engineering materials. Because the inner portion of the cartridge housing 201 can come into direct contact with the inhalation media, the material(s) of the cartridge housing are selected so as to minimize possible chemical reaction with the inhalation media. In the present example, control device 100 is configured to be mated with one cartridge 200, however, it should be noted that, in other embodiments, control device 100 can be configured to receive and dispense inhalation media from a plurality of simultaneously connected cartridges 200 in an independently addressable manner. Alternatively, the cartridge 200 can be configured to have a plurality of inhalation media storage areas 206 and plungers 204 configured to function with a control device 100 capable of dispensing inhalation media from such a configured cartridge 200.

Figure 2:
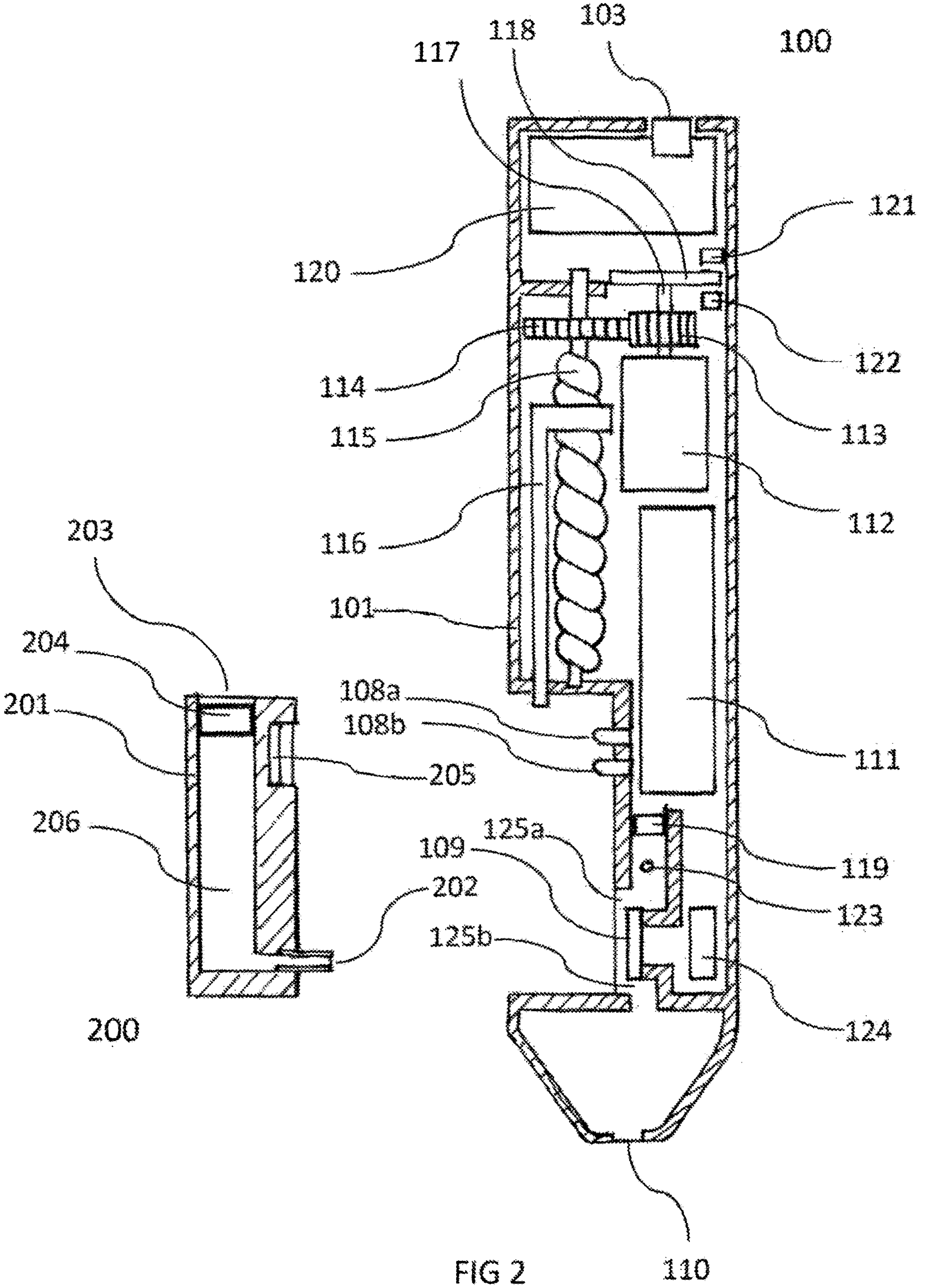
FIG. 2 shows an internal view of the vaporizer article shown in FIG. 1A.

The control device 100 has a charge connector 103 that can be connected to a power source for the purpose of charging a battery 111, shown in FIG. 2. The control device 100 can also contain a number of indicator lights 104*a* through 104*e*. In the instant example, indictor light 104*a* is used to indicate when the control device 100 is being charged through the charge connector 103. For example, indicator light 104*a* can shine red while the battery 111 is charging and can turn off when charging is complete. Indicator light 104*b* can be used to indicate the charge status of the battery 111. In the instant example, indicator light 104*b* can change color from green when fully charged to red when fully discharged. In other embodiments, indicator light 104*b* can be replaced by a light bar that indicates the charge level of the battery 111.

The control device 100 is constructed so as to be able to deliver a precise dose of inhalation media stored in the cartridge 200. In the example shown in FIG. 1A, the user selects the dose by turning a dose selector dial 105. The housing 101 can contain dose level marks 106 in order to assist the user in setting the dose level. In other embodiments, the dose level marks 106 can be accompanied by text or icons indicating the quantity of media to be dispensed. Once the user selects the desired dose, he can press the dosing button 107*a*. When the dosing button 107*a* is depressed, a precise amount of media is expressed onto the vaporizer element 109, examples of which are described below, via the cartridge outlet 202. While the media is being expressed, indicator light 104*c* can illuminate to indicate that the media is being expressed. Furthermore, the indicator light 104*c* can illuminate in a different manner to indicate when the media has been fully expressed. For example, it can illuminate in a different color and/or a blinking pattern. If the dosing button 107*a* is depressed but the previous dose of media has not been vaporized by the vaporizer element 109, the control device 100 can be configured to not express media onto the vaporizer element 109. In this scenario, the indicator light 104*c* can illuminate in a distinct color or pattern so as to indicate that a dose has already been expressed. In other embodiments, the indicator light 104*c* can be configured to not illuminate in order to indicate that no further media was expressed.

Once the media has been fully expressed, the user can activate the vaporizer element 109 by placing a portion of the vaporizing article 10 to his mouth and inhaling through the vapor outlet 110. When the user inhales, electrical current is provided to the vaporizer element 109 which causes it to heat up and vaporize the inhalation media present on the vaporizer element 109. The vapor combines with air to form an aerosol that is inhaled by the user. After repeated doses and inhalations, the inhalation media within the cartridge 200 can be entirely consumed. At this time, the user can replace the empty cartridge 200 with a new full cartridge 200 by first pressing the cartridge release button 107*b* in order to initiate the release process. Indicator light 104*e* can indicate when the operation of the release process by blinking in a pattern then illuminate in a steady manner when the release process has been completed and the cartridge 200 is ready for removal. Alternatively, indicator light 104*e* can change colors to indicate the release process action and completion. It should be noted that the user does not necessarily need to wait until the cartridge 200 is empty before replacing it. For example, if the user wishes to swap between 2 different cartridges 200 containing different inhalation media, the user can employ the release process in order to enable the swap.

The control device 100 has the ability to send information to a computing device. Appropriate communication methods include, but are not limited to: USB, Bluetooth, Zigbee, Wi-Fi, and digital cellular. In the preferred embodiment, Bluetooth is used to exchange data with a mobile computing device. In this case, indicator light 104*d* can be used to indicate the status of communication. For example, when pairing, indicator light 104*d* can blink or alternate between different colors. When the communication link has been established, indicator light 104*d* can illuminate in a steady color. When communication is off, indicator light 104*d* can be off.

Figure 1B:
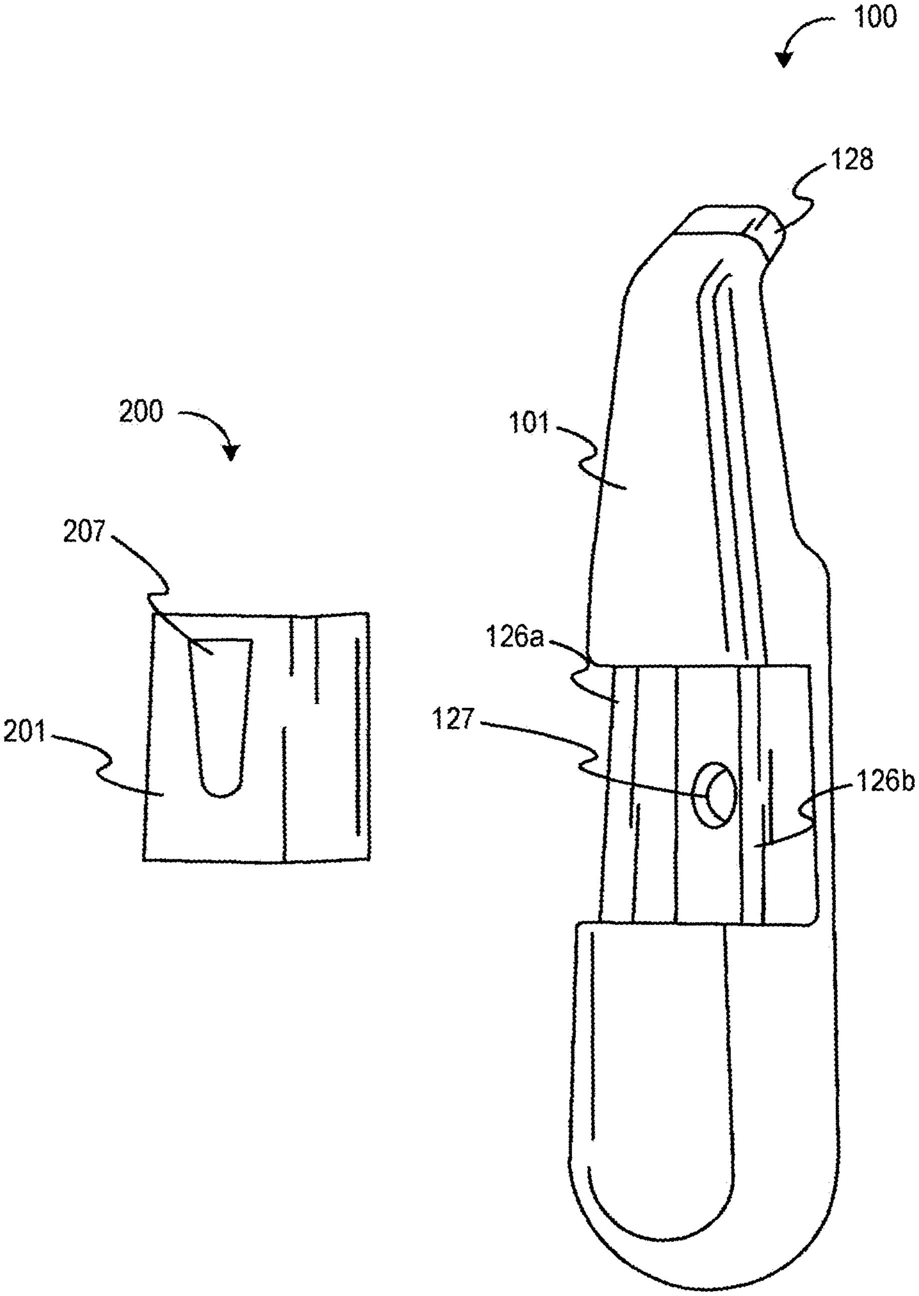
FIG. 1B shows another example form of a vaporizer article that is constructed according to an aspect of the disclosure.
Figure 1C:
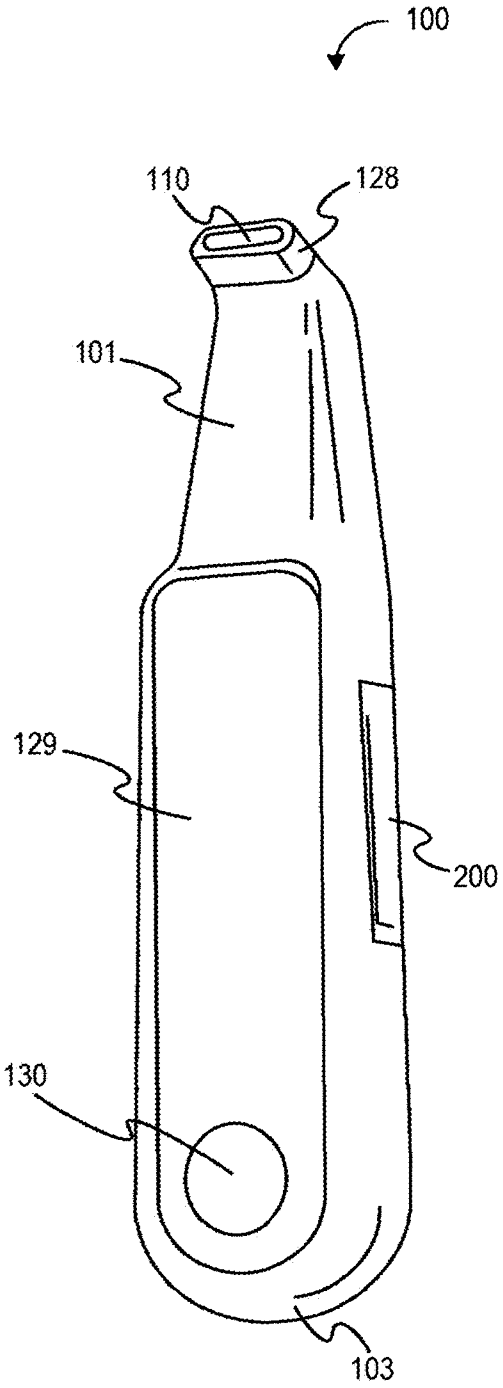
FIG. 1C shows another example user interface of a vaporizer article that is constructed according to an aspect of the disclosure.

FIGS. 1B and 1C show an alternative embodiment of the vaporizing article 10, comprised of a control device 100 and a cartridge 200. In this example, the housing 101 has a shape that is easy to hold and operate. The inhalation outlet 110 is located within a mouthpiece 128. The mouthpiece 128 can be permanently fixed or integral to the housing 101 or, in other embodiments, can be detachable to allow for other users to share the same control device 100 in a more sanitary manner by using their own mouthpiece 128. In the embodiment shown in FIGS. 1B and 1C, alignment features 126*a* and 126*b* are provided to allow for the easy alignment of the cartridge 200. The cartridge 200 has corresponding mating features (not shown) that are shaped so as to accept alignment features 126*a* and 126*b*. The control device 100 can also contain a magnet 127 that serves to help retain the cartridge 200 via magnetic attraction to a magnet (not shown) or piece of ferrous metal (not shown) located within the cartridge 200. Alternatively, the magnet can be located within the cartridge 200 and the ferrous metal can be located within the housing 101. In the embodiment shown in FIGS.

1B and 1C, the cartridge housing 201 contains a viewing window 207 to allow the user to see the inhalation media for the purpose of understanding the nature and/or amount of the inhalation media present in the cartridge 200. The viewing window 207 can be comprised of an opening in the cartridge housing 201 that provides for the viewing of a clear portion of the cartridge housing 201 that contains the inhalation media. The clear portion of the cartridge housing 201 can be integral to the cartridge housing 201 or it can be constructed from multiple individual components assembled to create the viewing window 207.

Control device 100 can incorporate a display screen 129 and control pad 130. The display screen can display information and provide for device controls including, but not limited to: the amount of inhalation media remaining in the cartridge 200, the charge status of the battery 111, the status of wireless communication, the amount of inhalation media to be dosed, characteristic information about the inhalation media, operational status of the control device 100, response to dosing commands, options for dosing, dosing inputs, health statistics, advertisements, brand logos, command input options, screen brightness controls, charging options, vaporizer settings, maintenance functions, message notifications, messages, dose sharing options, social media messages, and power options. In this embodiment, the display screen can replace the function of one or more of the indicator lights 104*a* through 104*e*. The user interacts with the control device 100 via the control pad 130. The control pad 130 can replace the function of the dose selector dial 105 and/or buttons 107*a* and 107*b*. The control pad 130 can be used to navigate through the information displayed on the display screen 129, select what information is displayed, and provide input to the control device 100. The control pad 130 can be comprised of a rigid or semi-rigid portion covering one or more switches (not shown) configured to detect menu navigation and selection inputs. Alternatively, the control pad 130 can be a capacitive or pressure sensing surface capable of detecting the position of the user's finger and/or gestures created by the motion of the user's finger and interpreting such input for the purpose of navigating and/or selecting items on the display screen 129. In certain embodiments, the control pad 130 can be equipped with a fingerprint reading sensor that can be used to unlock/enable the control device 100 according to a list of authorized users and associated fingerprints stored in memory 1503. In an alternative embodiment, the display screen 129 is touch sensitive, allowing the user to navigate and/or select items directly on the display screen 129, thereby eliminating or reducing the need for the control pad 130. In such an embodiment, the user can also unlock/enable the control device 100 by entering/drawing a security pattern associated with an authorized user on the display screen 129.

FIG. 2 shows section views of the control device 100 and cartridge 200 embodiments from FIG. 1. The control device 100 contains a control circuit 120 that governs the operation of the control device 100. The control circuit 120 is connected to the charge connector 103 for the purpose of receiving power and charging the battery 111. The control circuit 120 accepts inputs from buttons 107*a* and 107*b* as well as from the dose selector dial 105 and can alternatively be configured to accept input from a control pad 130. The control circuit governs the operation of indicator lights 104*a* through 104*e* and can also be configured to drive a display screen 129. When the control circuit 120 receives a dosing level command related to a target dose it determines the drive signal needed to express, dispense, deliver, etc., the desired about of inhalation media. The inhalation media is expressed via the action of the plunger driver 116 moving the plunger 204 a determined distance in order to change the volume of the inhalation media storage area 206 by a determined amount and thusly force a precise amount of inhalation media through the cartridge outlet 202. When the cartridge 200 is mated with the control device 100, the plunger driver 116 is aligned with the driver opening 203 and the plunger 204. The plunger driver 116 can have a female threaded portion that is connected to a drive screw 115. In the embodiment shown in FIG. 2, the plunger driver 116 is not co-axial with the drive screw 115, however, alternative embodiments of the plunger driver 116 consist of a co-axial configuration where the plunger driver 116 fully encompasses all but one end of the drive screw 115 when in the fully retracted position. In the embodiment shown in FIG. 2, the drive screw 115 is constrained by the housing 101 in all degrees of freedom except rotation about its major axis. The drive screw 115 is rigidly connected to a driven gear 114 or alternatively can be integrally formed with the driven gear 114. Driven gear 114 is driven by drive gear 113 which in turn is rigidly connector to the motor shaft 117 of the dispensing motor 112. It should be noted that drive gear 113 can be replaced with a series of gears or gearhead with multiple gear stages in order to achieve the necessary torque to drive the system. This torque amplification through gearing scheme is employed in order to be able the use a small motor while still deliver sufficient drive force at the plunger driver 116. If size constraints are not a concern, or sufficiently high-torque motors are available within the size constraints, the gears can be eliminated and the plunger driver 116 can be driven directly from dispensing motor 112.

An optical encoder disk 118 is connected to the motor shaft 117. The optical encoder disk 118 can be connected to the drive gear 113 side of the dispensing motor 112 or can be connected on the opposite end of the dispensing motor 112, provided that a portion of the motor shaft 117 extends past the non-gear side of the housing of the dispensing motor 112. In other embodiments, the optical encoder disk 118 can be mounted to the drive screw 115 or a gear, however, mounting the optical encoder disk 118 to the motor shaft 117 can be preferred because it provides higher resolution determination of the position of the plunger driver 116 due to the gear ratio between the drive gear 113 and the plunger driver 116. The optical encoder disk 118 is comprised of a series of equally spaced and sized openings that allows light from an emitter 121 to be received by photo detector 122 when the opening is aligned with the emitter 121 and light from the emitter 121 to be blocked when the opening is not aligned. As the motor shaft 117 rotates, the photo detector 122 will produce a digital signal where the rate of the digital signal transitions corresponds to the rotational rate of the motor shaft 117. Since the emitter 121 and photo detector 122 are electrically connected to the control circuit 120, the control circuit 120 can use this rate information to calculate how much the motor has turned and thus, how far the plunger driver 116 has traveled. Alternatively, the control circuit 120 can be configured to use position information rather than rate information from the photo detector 122 in order to determine how far the plunger driver 116 has traveled. For example, leveraging the fact that the rotation of the optical encoder disk 118 from one opening (or closure) to the next corresponds to a known amount of travel of the plunger driver 116, the control circuit 120, which is electrically connected to the dispensing motor 112, can activate the dispensing motor 112 and begin to count the number of openings (or closures) that are detected by the photo detector 122 until the desired number of openings (or closures) that corresponds to the desired plunger driver 116 travel has been achieved. Once this has been achieved, the control circuit 120 can terminate the drive signal to the dispensing motor 112. In this way, the control circuit 120 having determined how far to drive the plunger driver 116 in order to deliver a requested amount of inhalation media, and controlling the motor to achieve this travel, the precise dose is dispensed onto the vaporizer element 109.

The preceding description describes a system that uses a particular style of drive train and particular style of sensor in order to achieve the dosing function. Alternative approaches can be used to achieve this function. For example, the dispensing motor 112 can be a stepper motor whereby the drive signal determines an incremental advancement of the motor shaft 117, thus eliminating the need for the optical encoder disk 118, emitter 121 and photo detector 122. Alternatively, the dispensing motor 112 can be a linear motor. In this case, the linear motor can be directly connected to the plunger driver 116 or be connected via a linear drivetrain. Also, rather than a gear style drivetrain, the system can employ linkages, belts and pulleys or cable drives to connect the plunger driver 116 to the dispensing motor 112. The optical encoder disk 118, emitter 121 and photo detector 122 can be replaced by a Hall Effect sensor where the Hall Effect magnet portion takes the place of the optical encoder disk 118 and is mounted to a portion of the motor shaft 117. The Hall Effect magnet can have one or more sets of magnetic poles. In this case, one or more Hall Effect sensors, which replace the photo detector 112 can be mounted to a stationary portion of the dispensing motor 112, a stationary PCB or a stationary portion of the housing 101 and be configured to detect the rotation of the Hall Effect magnet. The Hall Effect sensor can provide substantially the same functionality to the control circuit 120 as that provided by the photo detector 122. Alternatively, optical encoder disk 118, emitter 121 and photo detector 122 can be replaced by a potentiometer attached to a portion of the motor shaft 117. Alternatively, an optical linear encoder, linear Hall Effect sensor or linear potentiometer can be mounted to or integrally formed with the plunger driver 116.

After a dose is expressed onto the vaporizer element 109, the user can trigger vaporization by inhaling through the inhalation outlet 110. When the user inhales, a corresponding change in pressure is detected by the inhalation sensor 119. The signal is read by the control circuit 120 which in turn activates the vaporizer element 109. Fresh air can flow into the control device 100 via an air inlet 123. The size of the air inlet 123 can substantially determine the resistance to air flow, otherwise known as "draw resistance." A larger air inlet 123 can result in lower draw resistance than a smaller air inlet 123. Draw resistance can be an important experiential characteristic for users seeking to mimic the characteristics of traditional cigarettes. An air inlet 123 having an opening area of between 2 $mm^2$ and 6 $mm^2$ can be optimal to replicate the draw resistance of traditional cigarettes. After the air enters via the air inlet 123, air then flows through an upstream passageway 125*a* in the housing 101 and past the vaporizer element 109 where the vapor initially combines with air to form an aerosol and is entrained into the air stream. The aerosol then continues through an outlet passageway 125*b* and exits the housing 101 via the inhalation outlet 110. The inlet passageway 125*a* and outlet passageway 125*b* can be integral to the housing 101 or can be formed by the union of the housing 101 and the cartridge housing 201. Inlet passageway 125*a* and outlet passageway 125*b* can also be sized so as to govern the draw resistance. The cavity formed by the union of the of cartridge housing 201 with the space immediately surrounding the vaporizer element 109 can determine the particle or droplet size of the aerosol. The larger the cavity size, the more small vapor droplets accrete to form larger droplets within the aerosol, resulting in an aerosol with a larger average particle size. The cavity size can be designed so as to produce the optimal particle size for the uptake of inhalation media. A secondary air inlet (not shown) can optionally be included at or downstream from the vaporizer element 109 in order to provide additional air to mix with the aerosol and produce a cooler aerosol for inhalation by the user.

The control device 100 can also contain a vibration transducer 124 that can be connected to the control circuit 120. The control circuit 120 can activate the vibration transducer 124 in order to signal the activation state of the vaporizer element 109 to the user and/or the completion of vaporization of the inhalation media that was expressed onto the vaporizer element 109. Such non-visual communication with the user can be beneficial as it can be difficult for the user to see visible indicators on the control device 100 during inhalation.

The cartridge 200 can also contain a readable/writeable memory IC 205, e.g. EEPROM, in order to store information including, but not limited to: identity information, the characteristics of the inhalation media, dosing information, control information, and usage information. The memory IC 205 can be used to track how much inhalation media has been previously expressed and how much remains in the inhalation media storage area 206. For example, a new cartridge 200 can include a memory IC 205 that has been programed with the number of optical encoder disk 118 counts (limit) that corresponds to how far the plunger driver 116 must advance to fully evacuate the inhalation media storage area 206. Upon the dispensing of each dose, a running total of the number of counts that have been dispensed thus far can be written to the memory IC 205 by the control circuit 120. This is done via one or more electrical connectors 108. This example uses two electrical connectors 108*a* and 108*b* which are in electrical communication with the control circuit 120 and make electrical contact with the memory IC 205 when the cartridge 200 is properly mated with the control device 100. The electrical connectors 108*a* and 108*b* can be flexible metal contacts, spring loaded pins, or other compliant conductive contacts. Before, during or after dispensing each dose, the control circuit 120 can compare the running total of the number of counts that have been dispensed with the limit. When the numbers are equal, the control circuit 120 can indicate that the cartridge 200 is empty. In addition, the running total number of counts recorded in the memory IC 205 can be used by the control circuit 120 to determine how far it must retract the plunger driver 116 in order to provide for the separation of the cartridge 200 from the housing 101. If the cartridge 200 is separated from the control device 100 before the cartridge 200 is empty, then the user later wants to reconnect the cartridge 200 in order to consume additional doses, the control circuit 120 can use the running total number of counts information stored in the memory IC 205 to determine how far to drive the plunger driver 116 to reestablish contact with the plunger 204 before dispensing the next dose and resuming adding to the running total number of counts.

The embodiment shown in FIG. 2 employs a single cartridge 200 and corresponding dispensing system, however, alternative embodiments exist that accommodate 2 or more cartridges 200 simultaneously. In these embodiments, there can be a corresponding number of plunger drivers 116, transmissions, and dispensing motors 112. The control circuit 120 can be configured to calculate the quantity of inhalation media to be dispensed from each cartridge 200 onto one or more vaporizer elements 109 and drive the dispensing motors 112 to achieve the desired dose.

Additional embodiments of the control device 100 exist where the vaporizer element 109 is eliminated. In these embodiments, the media inside the cartridge is to be ingested orally rather than inhaled. Such embodiments are configured so that when media is expressed from the cartridge 200, the media is expressed directly into the user's mouth.

Figure 3:
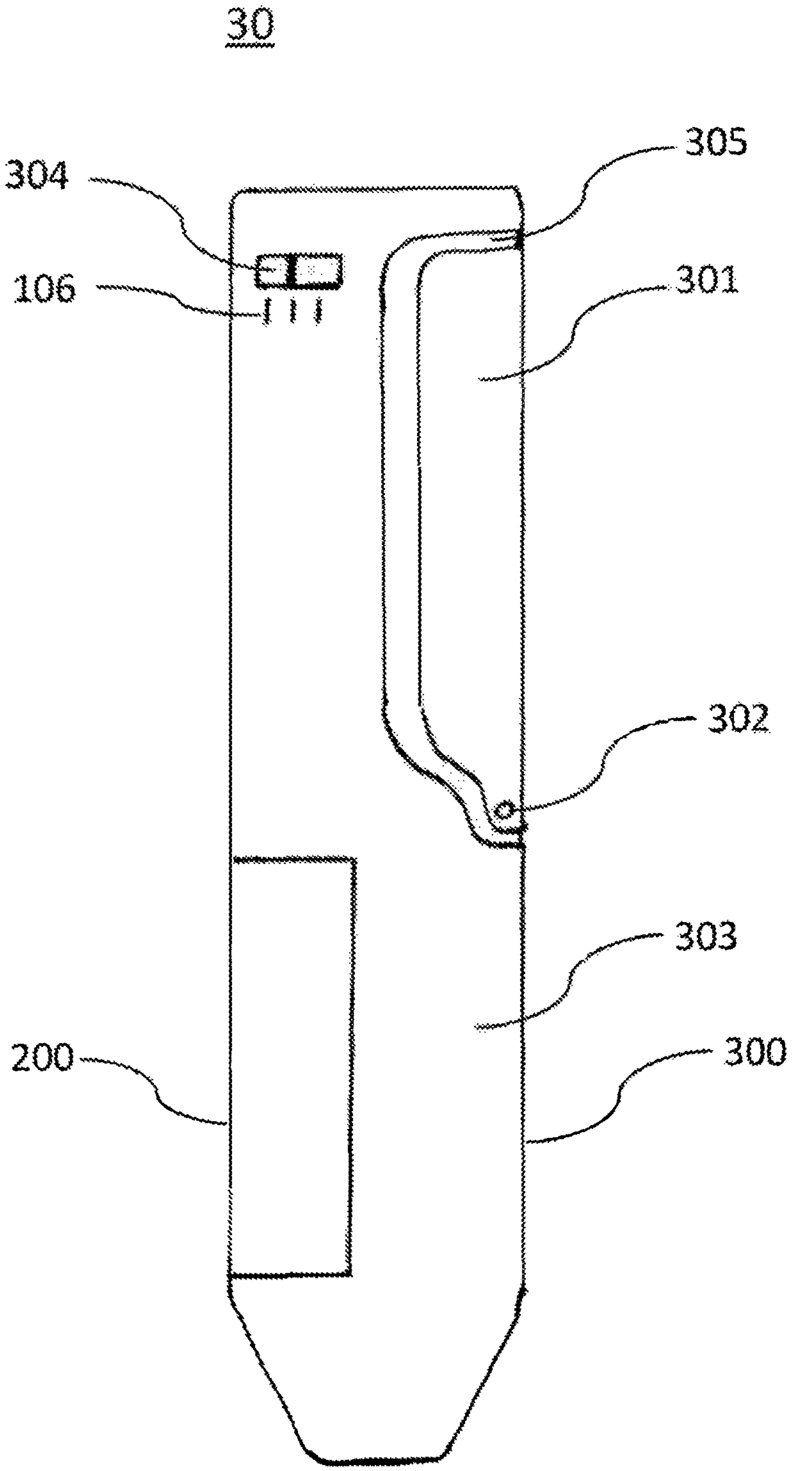
FIG. 3 shows another example of a vaporizer article that is constructed according to an aspect of the disclosure.

FIG. 3 describes a manual vaporizer article 30. The manual vaporizer article 30 is substantially similar to the vaporizer article 10, the primary difference being that the dispensing of inhalation media is accomplished through manual action rather than being driven by a dispensing motor 112. In this embodiment, the components responsible for vaporization, charging, data exchange, and indication can be similar or even identical. The cartridge 200 shown in FIG. 1*a* can be used in conjunction with either a control device 100 or a manual control device 300. The manual control device 300 is comprised of a manual housing 303 which can typically be constructed from injection molded plastic, metal, or other common engineering materials. The manual vaporizer article 30 employs a dispensing lever 301 that acts upon a drive system internal to the manual control device 300. A lever clearance space 305 is formed by a gap between the manual housing 303 and the dispensing lever 301. This allows the dispensing lever 301 to move relative to the manual housing 303. The dispensing lever pivots around the lever pivot 302. The manual housing 303 also contains dose level marks 106 and a manual dose selector dial 304.

Figure 4A:
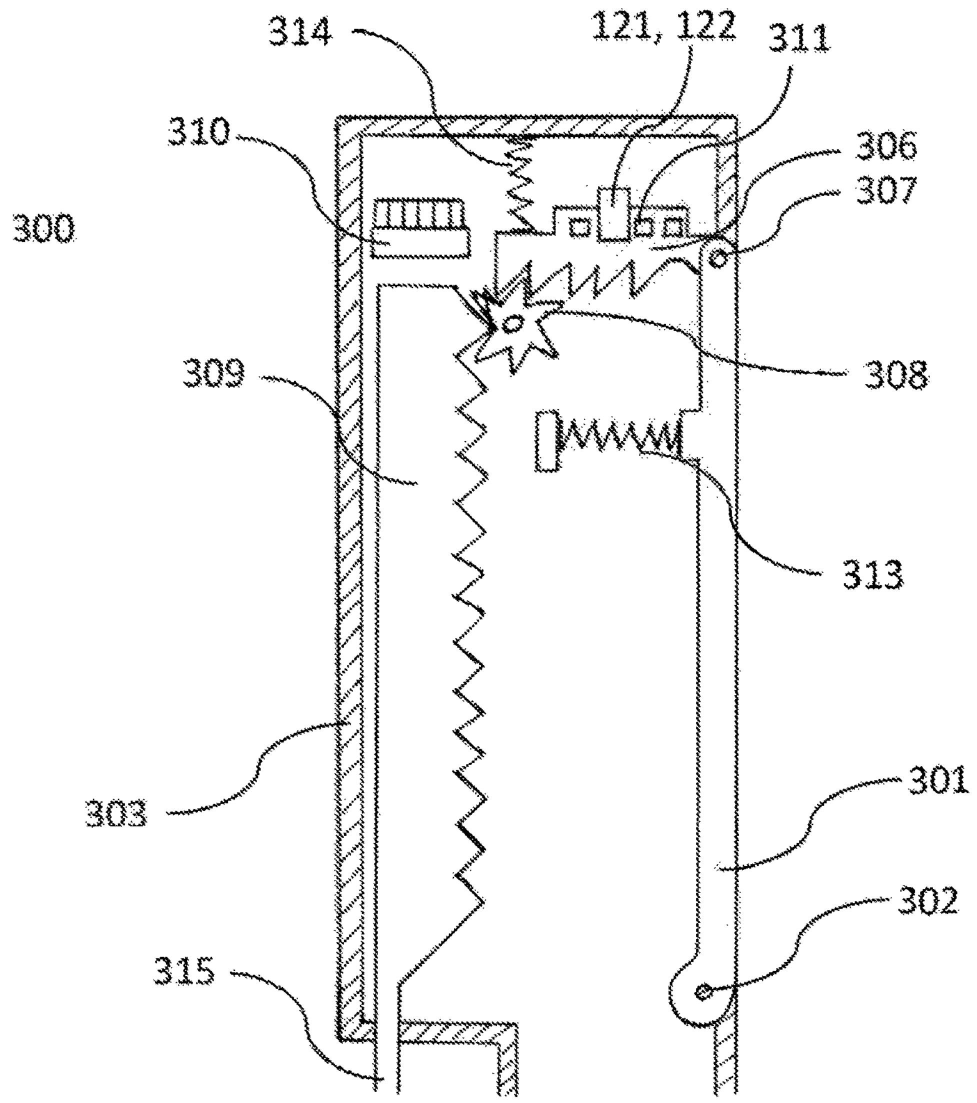
FIG. 4A and FIG. 4B show internal views of the vaporizer article shown in FIG. 3.
Figure 4B:
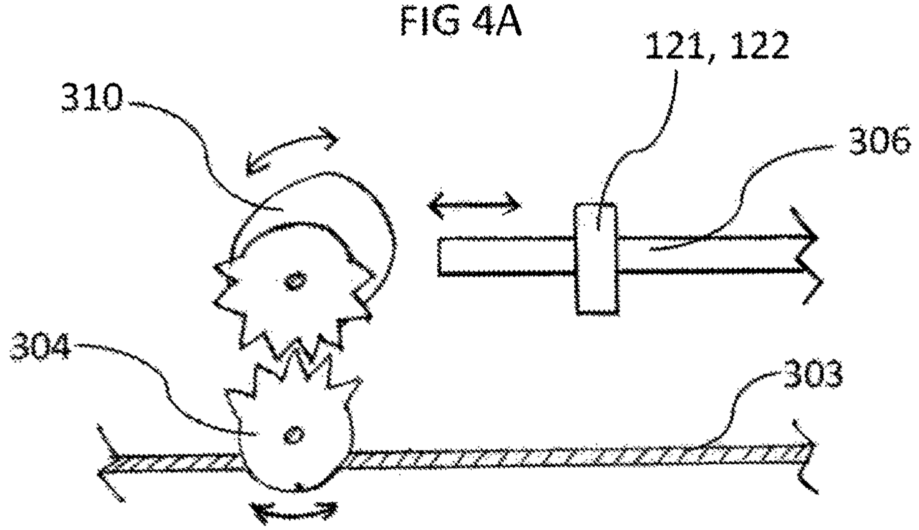

FIGS. 4A and 4B show section and detail views of the manual control device 300. The user interacts with the manual control device 300 by first selecting a dose via the manual dose selector dial 304. The manual dose selector dial 304 can rotate about a single axis that is established by a feature in the manual housing 303. The manual dose selector dial 304 has a gear tooth portion that mates with a corresponding gear tooth portion of the rotary dose limit stop 310. The rotary dose limit stop 310 rotates around an axis that is established by a feature in the manual housing 303 and also consists of an off-axis or elliptical portion. As the rotary dose limit stop 310 rotates about its gear portion center, the outer surface of its off-axis or elliptical portion moves closer to or farther away from the drive rack 306. In this manner, the rotary dose limit stop 310 establishes the extent to which the drive rack 306 can travel. When the user presses the dispensing lever 301, which is connected to the drive rack 306 by a rotary joint 307, the drive rack 306 causes the pinion 308 to rotate, which in turn causes the manual driven rack 309 to advance. The manual plunger driver 315, which can either be rigidly connected to or integrally formed with the manual driven rack 309, pushes on the plunger 204. In this manner, the rotational position of the manual dose selector dial 304 controls the amount of inhalation media that is expressed onto the vaporizer element 109.

The motion of the drive rack 306 is detected via an emitter 121 and photo detector 122 arranged to detect light passing through linear encoder windows 311 which can be integrally formed or rigidly fixed to the drive rack 306. The emitter 121 and photo detector 122 can be formed into a single component with a cut-out or area through which the linear encoder windows 311 can travel. The signal from the photo detector 122 is provided to the control circuit 120. In this way, the control circuit 120 is presented with signal information that can be used to control the functions of the manual control device 300. In some embodiments, a Hall Effect sensor and magnet can be used in place of photo detector 122 and linear encoder windows 311.

After the user releases the dispensing lever 301, return spring 313 pushes the dispensing lever 301 back to its initial position. In order to maintain the manual plunger driver 315 in its most recent position, a ratchet system is provided to allow the drive rack 306 to disengage from the pinion 308. The gear teeth of the drive rack 306 and pinion 308 are shaped so as to remain engaged when driven in one direction but disengage when moved in the opposite direction. As the dispensing lever 301 returns to its initial position, drive rack 306 can pivot about rotary joint 307, allowing its gear teeth to lift off and disengage from the pinion 308. A ratchet spring 314 is provided to push the drive rack 306 back toward the pinion 308 so that it can reengage when the dispensing lever 301 returns to its initial position. The ratchet spring 314 is configured to be a compression type spring however, embodiments exist where it can be a tension spring. The return force of the ratchet spring 314 is generally light in nature, providing sufficient force to promote engagement when moving in the dispensing direction but not so much force so as to prevent disengagement when the drive rack 306 is returning to its initial position after dosing.

Unlike the vaporizer article 10 which electronically controls how much inhalation media is expressed onto the vaporizing element, the manual vaporizer article 30 does not prevent the user from placing more inhalation media on the vaporizer element 109 than can be vaporized at once or than can be reasonably held by the vaporizer element 109. However, this limitation can be mitigated by using the signal from the optical detector 122 to inform the control circuit 120 so that it can track and inform the user how much inhalation media has been expressed and when limits or recommended amounts are approached or exceeded.

Figure 5:
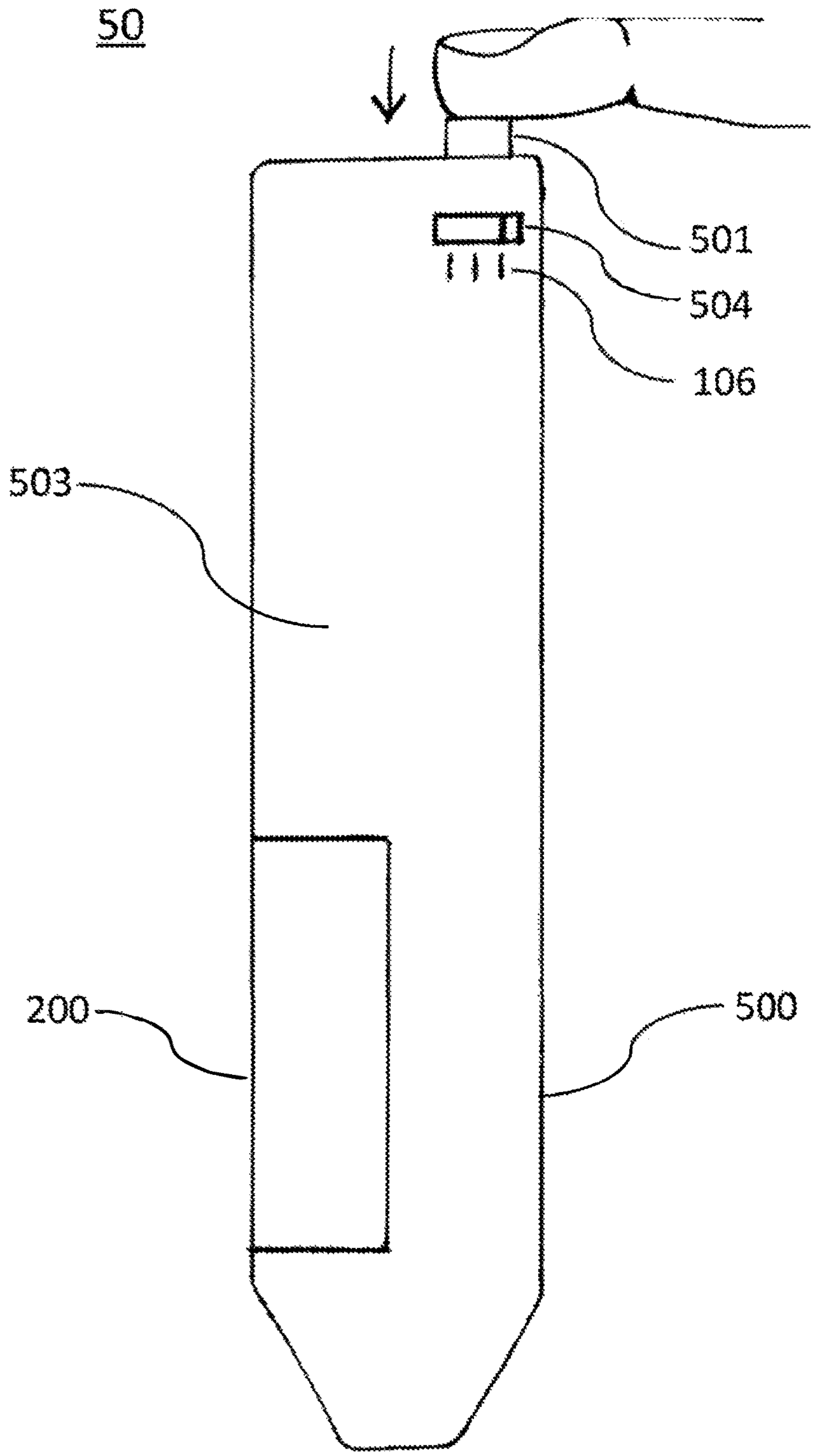
FIG. 5 shows another example of a vaporizer article that is constructed according to an aspect of the disclosure.

FIG. 5 shows an alternative embodiment of a manual vaporizer article 30. Similar to the manual vaporizer article 30, dispensing of inhalation media in push button vaporizer article 50 is accomplished through manual action rather than being driven by a dispensing motor 112. In this embodiment, the components responsible for vaporization, charging, data exchange, and indication can be similar or even identical. The cartridge 200 can be used in conjunction with any of a control device 100, manual control device 300 and push button control device 500. The push button control device 500 is comprised of a push button housing 503 which can typically be constructed from injection molded plastic, metal, or other common engineering materials. The push button vaporizer article 50 employs a dispensing push button 501 that acts upon a drive system internal to the push button control device 500. The push button housing 503 also contains dose level marks 106 and a push button dose selector dial 504.

Figure 6A:
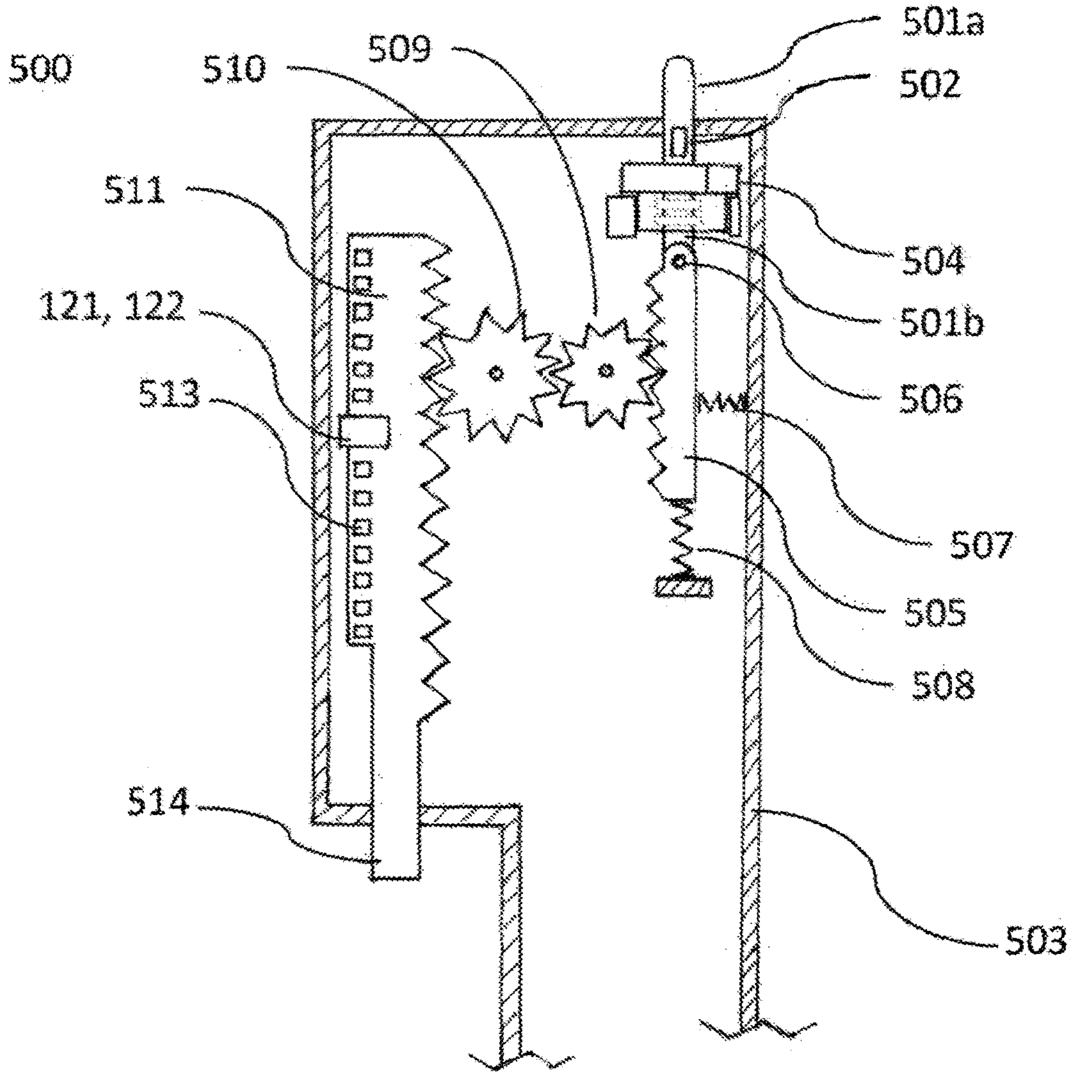
FIG. 6A and FIG. 6B show internal views of the vaporizer article shown in FIG. 5.
Figure 6B:
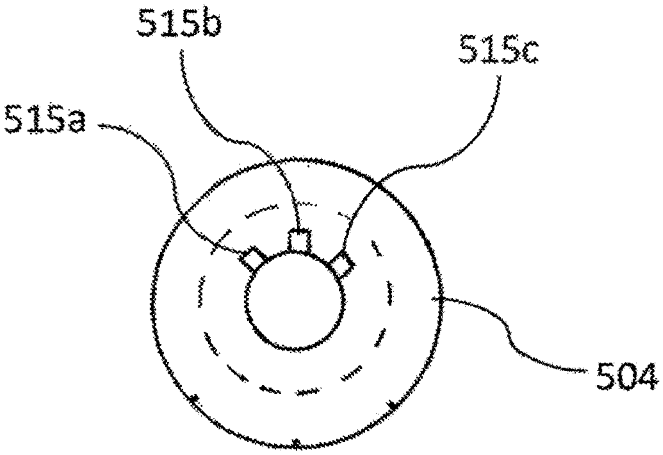

FIGS. 6A and 6B show section and detail views of the push button control device 500. The user interacts with the push button control device 500 by first selecting a dose via the push button dose selector dial 504. The push button dose selector dial 504 can rotate about a single axis that is established by the push button body 501*b*. The push button dose selector dial 504 has one or more internal grooves 515*a*, 515*b* and 515*c*, each having an open end toward the push button key 502 and a closed end on the opposite end of each internal groove 515*a-c*. The closed end of each internal groove 515*a-c* is different distance away from the commonly shared open end. When a particular internal groove, for example internal groove 515*a* is aligned with the push button key 502, and the push button tip 501*a* is pressed by the user, the push button body 501*b* can travel to a depth limited by the contact of the push button key 502 with the closed end of the internal groove 515*a*. When the push button dose selector dial 504 is rotated such that internal groove 515*b* is aligned with the push button key 502, and the push button tip 501*a* is pressed by the user, the push button body 501*b* can now travel to a different depth, the depth limited by the contact of the push button key 502 with the closed end of the internal groove 515*b*.

When the user presses the push button tip 501*a*, the push button body 501*b* causes the push button drive rack 505 to move. The push button body 501*b* is connected to the push button drive rack 505 via the push button rotary joint 506. As the push button drive rack 505 travels, the push button drive gear 509 and push button driven gear 510 rotate, which in turn causes the push button driven rack 511 to advance. The push button plunger driver 514, which can either be rigidly connected to or integrally formed with the push button driven rack 511, pushes on the plunger 204. In this manner, the rotational position of the manual dose selector dial 504 controls the amount of inhalation media that is expressed onto the vaporizer element 109.

The motion of the push button driven rack 511 is detected via an emitter 121 and photo detector 122 arranged to detect light passing through push button linear encoder windows 513 which can be integrally formed or rigidly fixed to the push button driven rack 511. The emitter 121 and photo detector 122 can be formed into a single component with a cut-out or area through which the push button linear encoder windows 513 can travel. The signal from the photo detector 122 is provided to the control circuit 120. In this way, the control circuit 120 is presented with signal information that can be used to control the functions of the push button control device 500. In some embodiments, a Hall Effect sensor and magnet can be used in place of photo detector 122 and push button linear encoder windows 513.

After the user releases the push button tip 501*a*, push button return spring 508 pushes the push button drive rack 505 back to its initial position. In order to maintain the push button plunger driver 514 in its most recent position, a ratchet system is provided to allow the push button drive rack 505 to disengage from the push button drive gear 509. The gear teeth of the push button drive rack 505 and push button drive gear 509 are shaped so as to remain engaged when driven in one direction but disengage when moved in the opposite direction. As the push button body 501*b* returns to its initial position, the push button drive rack 505 can pivot about the push button rotary joint 506, allowing its gear teeth to lift off and disengage from the push button drive gear 509. A push button ratchet spring 507 is provided to push the push button drive rack 505 back toward the push button drive gear 509 so that it can reengage when the push button body 501*b* returns to its initial position. The push button ratchet spring 507 is configured to be a compression type spring, however, embodiments exist where it can be a tension spring. The return force of the push button ratchet spring 507 is generally light in nature, providing sufficient force to promote engagement when moving in the dispensing direction but not so much force so as to prevent disengagement when the push button drive rack 505 is returning to its initial position after dosing.

Figure 7:
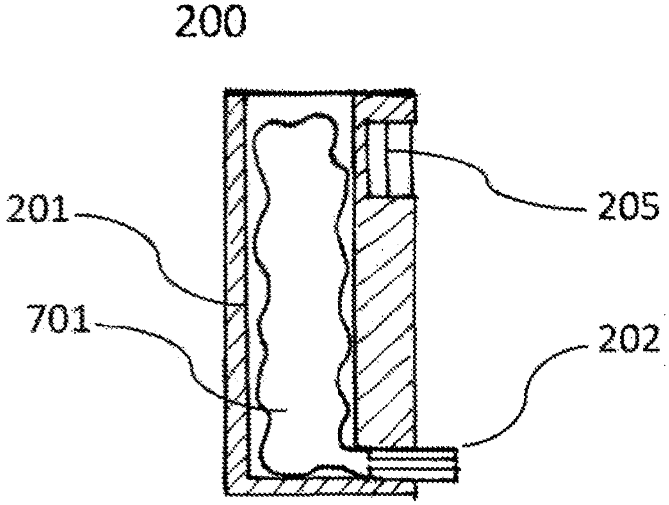
FIG. 7 shows another example of a cartridge (media storage element) that is constructed according to an aspect of the disclosure.

FIG. 7 shows a section view of an alternative embodiment of the cartridge 200. In this embodiment, the cartridge housing 201 has an internal portion that contains a flexible inhalation media bag 701 which is connected to the cartridge outlet 202. Inhalation media is stored in the inhalation media bag 701. In this embodiment, the plunger driver 116 presses directly onto the inhalation media bag 701 in order to express inhalation media via the cartridge outlet 202. The material(s) of the inhalation media bag 701 are selected so as to minimize possible chemical reaction with the inhalation media.

Figure 8A:
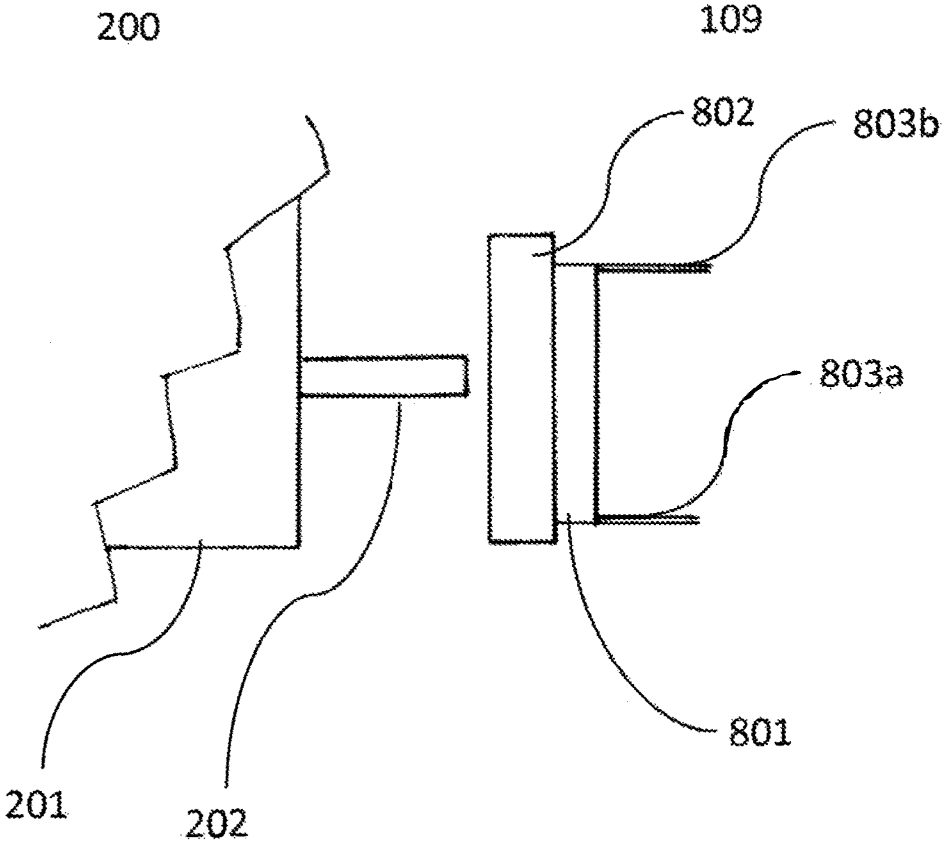
FIG. 8A shows an example of an atomizer that is constructed according to an aspect of the disclosure.

FIG. 8A shows a vaporizer element 109 constructed according to an aspect of the disclosure. In this embodiment, the vaporizer element 109 includes a heating element 801, substrate 802 and heater leads 803*a* and 803*b*. The substrate 802 can be constructed using a thin piece of ceramic, glass, or other material that conducts thermal energy well while conducting electrical current poorly. Example dimensions of a substrate 802 are 6 mm×6 mm×1 mm. By keeping the substrate 802 thin, heat energy can more easily transfer from the heating element 801 to the surface of the substrate 802 that is closest to the cartridge outlet 202. Keeping the substrate 802 thin enables the use of materials, such as glass, that do not conduct thermal energy as rapidly as other suitable materials. Heating element 801 is comprised of a resistive heating element that produces heat when electrical current passes through the material. The heating element 801 can be a resistive compound that is deposited onto one or more surfaces of the substrate 802 using deposition techniques commonly employed in the manufacture of electronic componentry. Alternatively, the heating element 801 can be a resistance wire formed into a flat shape and brought into contact with one or more surfaces of the substrate 802 or embedded within substrate 802. Typical resistance wire materials include alloys of nickel-chromium, titanium, Kanthal and other suitable materials. Typical resistance values for the heating element 801 range from 0.1 Ohms to 5 Ohms.

Heater leads 803*a* and 803*b* provide electrical connection between the heating element 801 and the control circuit 120. The heater leads 803*a* and 803*b* can be soldered, welded or otherwise mechanically held in contact with the heating element 801. The substrate 802 is located in close proximity to the cartridge outlet 202, preferably without touching. By maintaining proximity, small amounts or droplets of inhalation media can bridge the distance between the cartridge outlet 202 and the substrate 802 then spread out over the surface of the substrate 802. In addition to enabling droplets to bridge, the condition of proximity without touching ensures that the cartridge outlet 202 neither damages the substrate 802 nor thermally couples with it, ensuring that the system does not waste energy heating the cartridge outlet 202 and the components to which it is physically connected. A typical distance between the substrate 802 and cartridge outlet 202 ranges from 0.1 mm to 1.0 mm. This distance can also be tailored to the viscosity of the inhalation media; lower viscosity inhalation media may not be able to bridge larger gaps and therefore require smaller gaps to reliably bridge from outlet 202 to substrate 802.

Figure 8B:
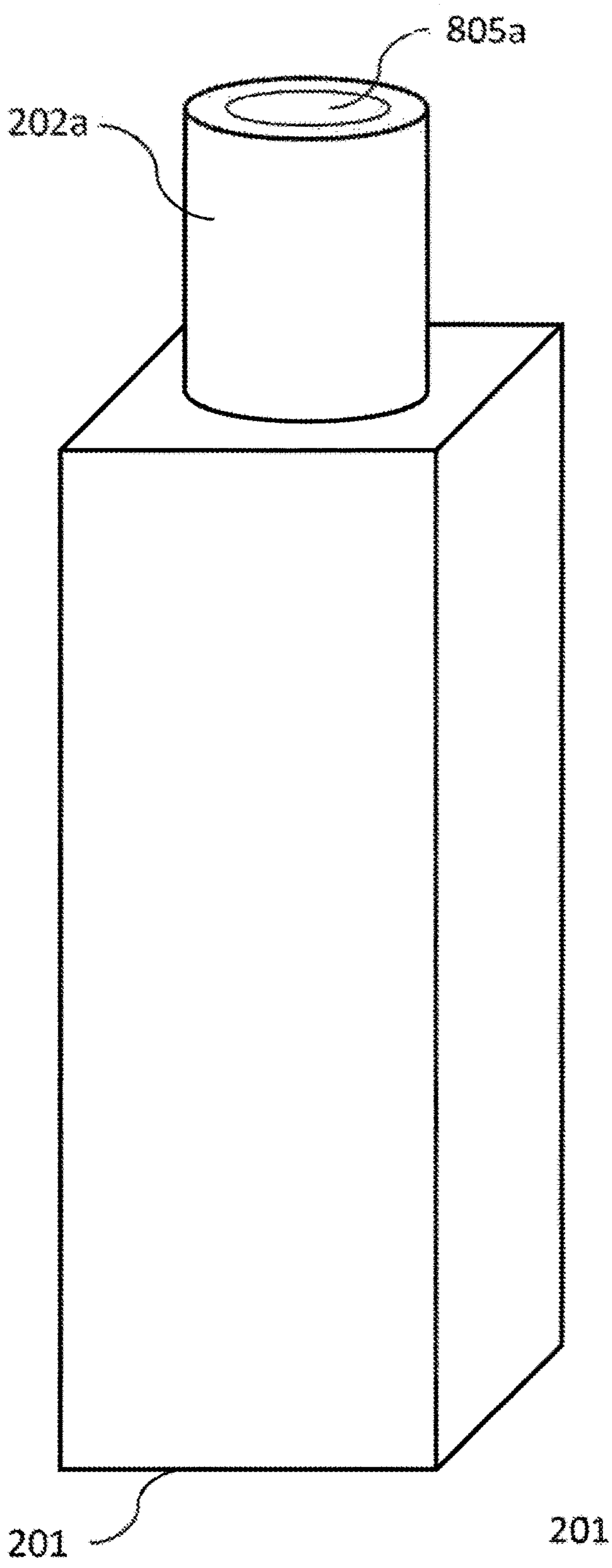
FIGS. 8B and 8C show examples of a cartridge that is constructed according to an aspect of the disclosure.
Figure 8C:
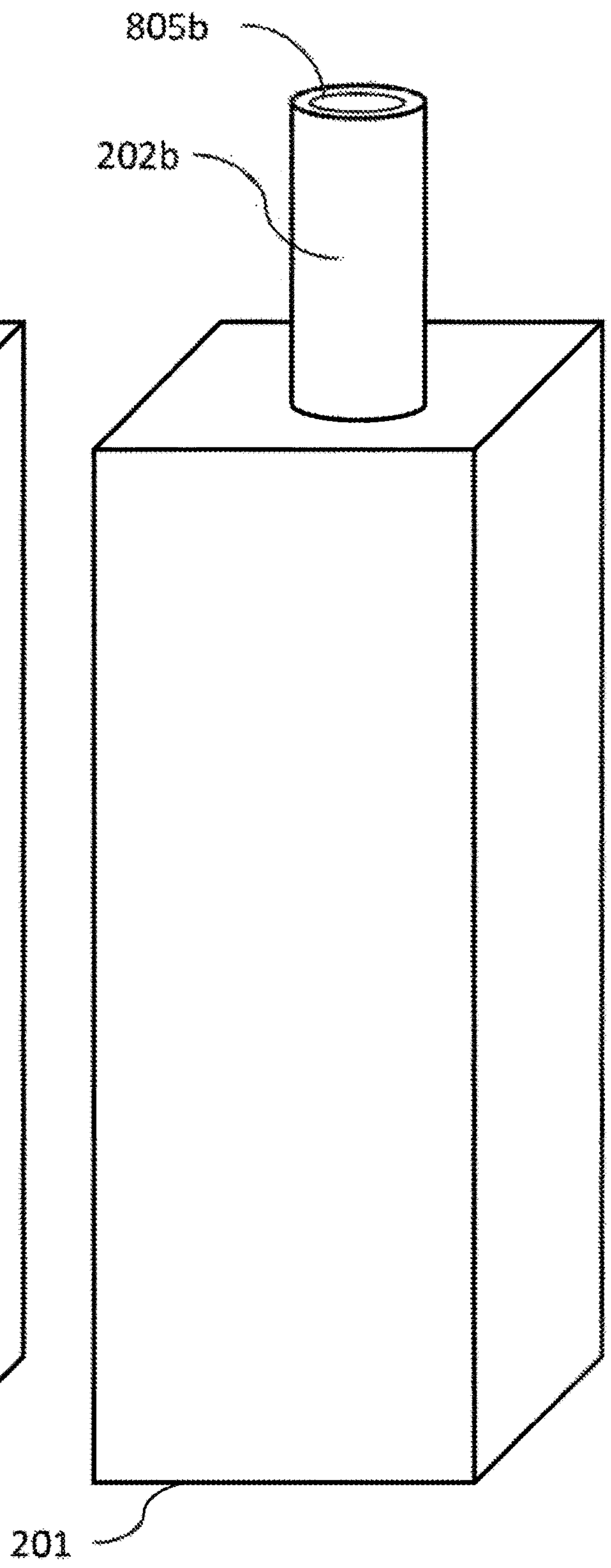

In order to accommodate a range of viscosities of inhalation media, the diameter of the cartridge outlet 202 can be sized according to the viscosity of the inhalation media. FIGS. 8B and 8C show two example embodiments of cartridge outlet 202. By way of example, cartridge outlet 202*a* and cartridge outlet inner diameter 805*a* can be sized to be larger for more viscous inhalation media. The larger size allows the inhalation media to pass through without excessive resistance that can lead to requiring a larger dispensing motor 112, drive gear 113 and/or gearhead capable of producing more force. Care must be taken so that the cartridge outlet inner diameter 805*a* is not so large as to allow inhalation media to leak out when no pressure is applied to the plunger 204. The optimal size for a given viscosity inhalation media can be determined by conducting one or more of static, vibration, ambient pressure cycling, and temperature cycling testing at multiple orientations, for example the orientation where the cartridge outlet 202 is oriented below the inhalation media storage area 206 so that gravity can act to drive the inhalation media out of the cartridge outlet 202, then selecting the largest size possible that does not exhibit leakage. A typical cartridge outlet 202 sized to work with higher viscosity inhalation media can be in the range of 10 gauge to 20 gauge. By contrast, cartridge outlet 202*b* and cartridge outlet inner diameter 805*b* can be sized to be smaller in order to function properly with lower viscosity inhalation media. The smaller size reduces the ability of the inhalation media to leak out. A typical cartridge outlet 202 sized to work with lower viscosity inhalation media can be in the range of 20 gauge to 28 gauge. The tip of the cartridge outlet can also be shaped or cut at an angle to further support the bridging of droplets without leakage.

Figure 9:
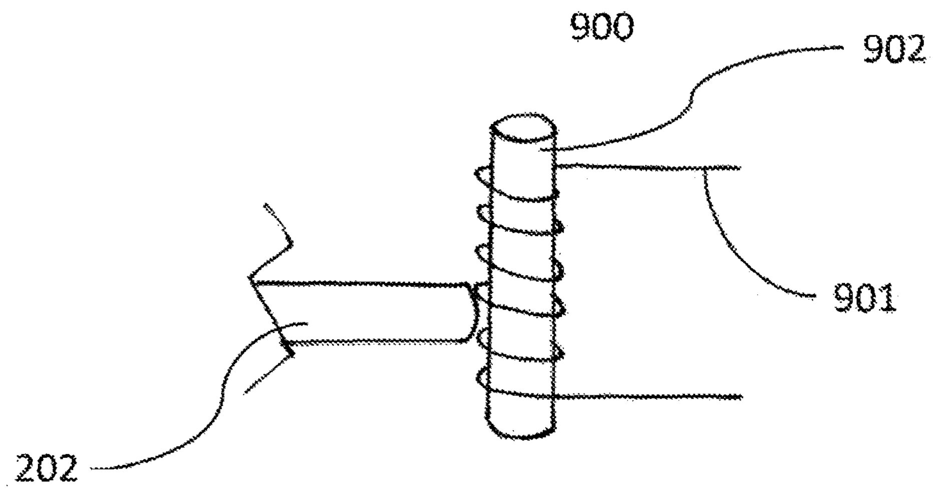
FIG. 9 shows another example of an atomizer that is constructed according to an aspect of the disclosure.

FIG. 9 shows a cylindrical vaporizer element 900 which can be used as vaporizer element 109 and it should be understood that future references to vaporizer element 109 can replaced with cylindrical vaporizer element 900 without impacting functionality. Cylindrical vaporizer element 900 is comprised of a cylindrical heater 901 and a heater core 902. Cylindrical vaporizer element 900 can be oriented such that air flow induced by the user's inhalation can flow over the surface of the cylindrical vaporizer element 900 in a direction that is substantially parallel or orthogonal to the primary axis of the heater core. The cylindrical heater 901 can be constructed using resistance wire. When formed by resistance wire, the ends of the cylindrical heater 901 can serve as electrical connections in the same manner as heater leads 803*a* and 803*b*. Alternatively, dedicated low resistance wire (not shown) can be connected to the cylindrical heater 901 as close as possible to the heater core 902. Doing so maximizes efficiency and ensures that only portions of the cylindrical heater 901 that are in contact with the heater core 902 become hot. Heater core 902 can be made of ceramic, glass, or other materials. When constructed from non-porous materials, the surface of the heater core 902 can be smooth. In such case, inhalation media can spread to form a thin layer covering the outer surface of the heater core 902. Typical resistance values for the cylindrical heater 901 range from 0.1 Ohms to 5 Ohms. Similar to the vaporizer element 109, the cylindrical vaporizer element 900 functions best when there is close proximity between the cartridge outlet 202 and the cylindrical vaporizer element 900. Alternatively, the cylindrical heater 901 can be formed on the surface of the heater core 902 by depositing a resistive compound. In this embodiment, heater leads (not shown) can be provided in order to establish an electrical connection to the control circuit 120. In another alternative embodiment, the heater core 902 is made of a porous material such as a porous ceramic, non-conductive treated metal mesh, cotton, stranded or woven silica or other similar material. The cylindrical heater 901 can be wrapped around the heater core 902 or it can be integrally formed such that the cylindrical heater 901 is embedded in the heater core 902. By using a porous material for the heater core 902, an increased amount of inhalation media can be dispensed onto the cylindrical vaporizer element 900 at any one instant because of the porous material's ability to store liquid. The porous material also allows the inhalation media to spread from the location where it is dispensed via capillary action.

Figure 10:
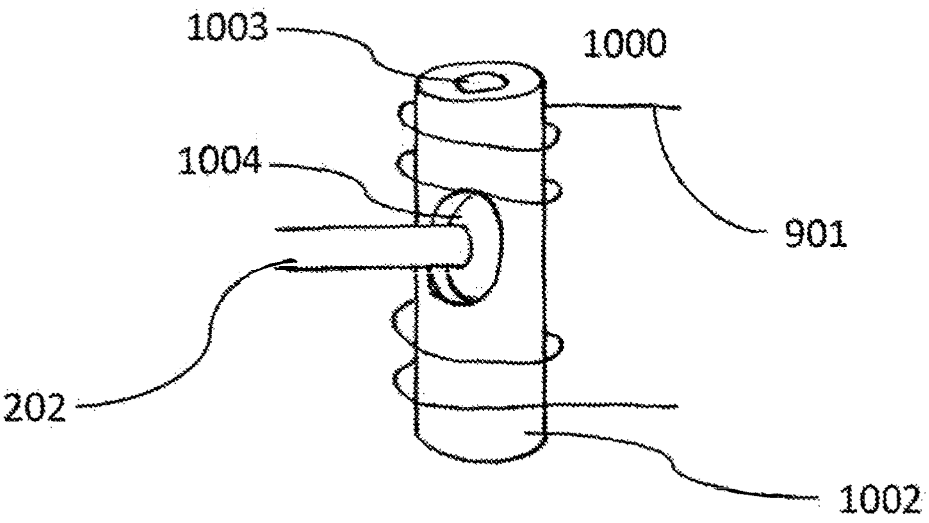
FIG. 10 shows another example of an atomizer that is constructed according to an aspect of the disclosure.

FIG. 10 shows a center hole cylindrical vaporizer element 1000 which can be used as vaporizer element 109 and it should be understood that future references to vaporizer element 109 can replaced with center hole cylindrical vaporizer element 1000 without impacting functionality. The center hole cylindrical vaporizer element 1000 can be constructed from similar materials to cylindrical vaporizer element 900. The center hole heater core 1002 has a through hole 1003 that runs axially through the center hole heater core 1002. It also has a center hole 1004 that provides an opening through which cartridge outlet 202 can dispense inhalation media into the through hole 1003. When the cylindrical heater 901 is energized, the center hole heater core 1002 heats up, vaporizing inhalation media that has been dispensed into the through hole 1003. Air flow induced by the user's inhalation can flow through the through hole 1003, entraining the vaporized inhalation media that has begun to mix with air to form an aerosol.

Figure 11:
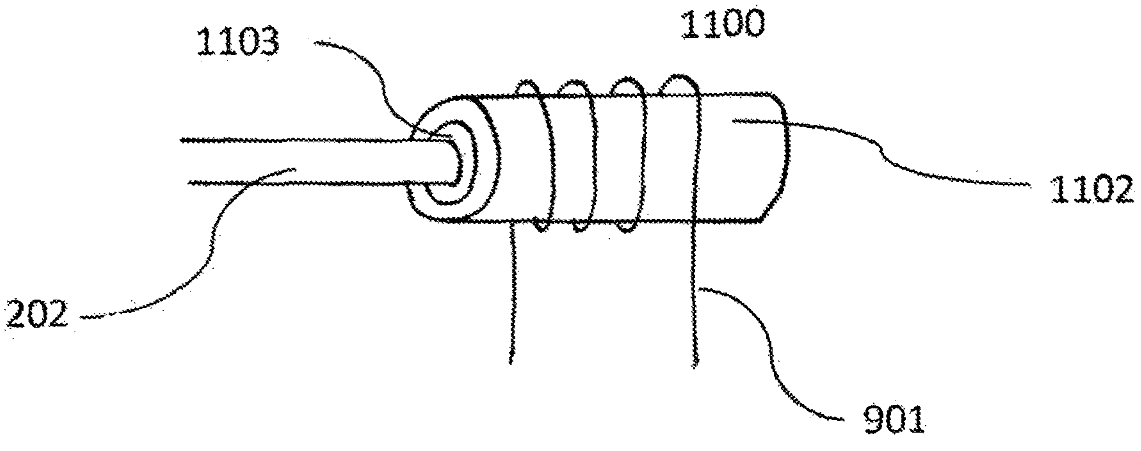
FIG. 11 shows another example of an atomizer that is constructed according to an aspect of the disclosure.

FIG. 11 shows a through hole cylindrical vaporizer element 1100 which can be used as cylindrical vaporizer element 109 and it should be understood that future references to vaporizer element 109 can replaced with through hole cylindrical vaporizer element 1100 without impacting functionality. The through hole cylindrical vaporizer element 1100 can be constructed from similar materials to cylindrical vaporizer element 900. The through hole heater core 1102 has an axial through hole 1103 that runs axially through the through hole heater core 1102. Cartridge outlet 202 can dispense inhalation media into axial through hole 1103. When the cylindrical heater 901 is energized, the through hole heater core 1102 heats up, vaporizing inhalation media that has been dispensed into axial through hole 1103. Air flow induced by the user's inhalation can flow through the axial through hole 1103, entraining the vaporized inhalation media that has begun to mix with air to form an aerosol. Alternatively, if the through hole heater core 1102 is made of a porous material, inhalation media can travel from the axial through hole to the outer surfaces of the through hole heater core 1102, where it can be vaporized and entrained by air flow that is substantially parallel or orthogonal to the major axis of the through hole heater core 1102. In another embodiment, where a porous material is used, one or both ends of the through hole heater core 1102 can be tapered to a point or surface that is designed to accept the droplets of inhalation media dispensed from the cartridge outlet 202. The inhalation media can spread from this point or surface throughout the entire through hole heater core 1102 via capillary action. This point or surface allows the cartridge outlet 202 to be positioned somewhat remotely from the cylindrical heater 901, thus minimizing the cartridge outlet's exposure to high temperatures. This point or surface can also be a convenient geometric reference feature used to locate the through hole cylindrical vaporizer element 1100 relative to the cartridge outlet 202.

Figure 12:
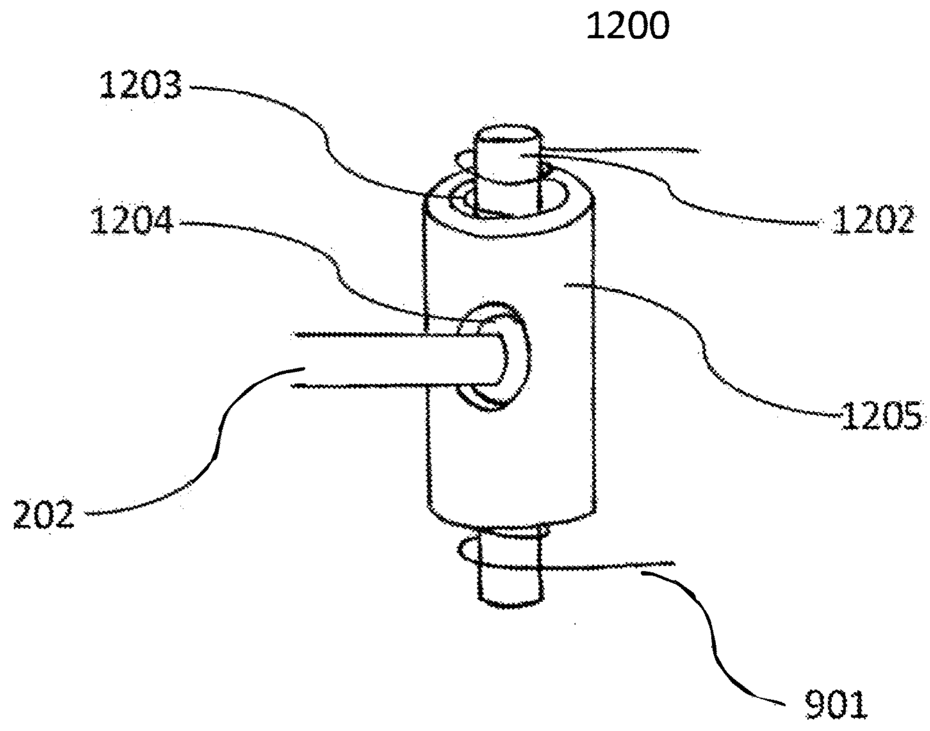
FIG. 12 shows another example of an atomizer that is constructed according to an aspect of the disclosure.

FIG. 12 shows a compound cylindrical vaporizer element 1200 which can be used as cylindrical vaporizer element 109 and it should be understood that future references to vaporizer element 109 can replaced with compound cylindrical vaporizer element 1200 without impacting functionality. The compound cylindrical vaporizer element 1200 can be constructed of similar materials to cylindrical vaporizer element 900. The outer core 1205 has a compound through hole 1203 that runs axially through the outer core 1205. The cylindrical heater 901 and compound heater core 1202 are located in the compound through hole 1203. The outer core 1205 also has a compound through hole 1204 through which the cartridge outlet 202 can dispense inhalation media. Air flow induced by the user's inhalation can flow through the compound through hole 1203, entraining the vaporized inhalation media that has begun to mix with air to form an aerosol. In the primary embodiment of compound cylindrical vaporizer element 1200, inhalation media is dispensed onto the compound core 1202 which serves to provide support for the cylindrical heater 901 and provide a surface to disperse the inhalation media. In an alternative embodiment of the compound cylindrical vaporizer element 1200, the compound heater core 1202 is eliminated and inhalation media is dispensed onto the interior walls of the outer core 1205 which can be in direct contact with the cylindrical heater 901.

Figure 13:
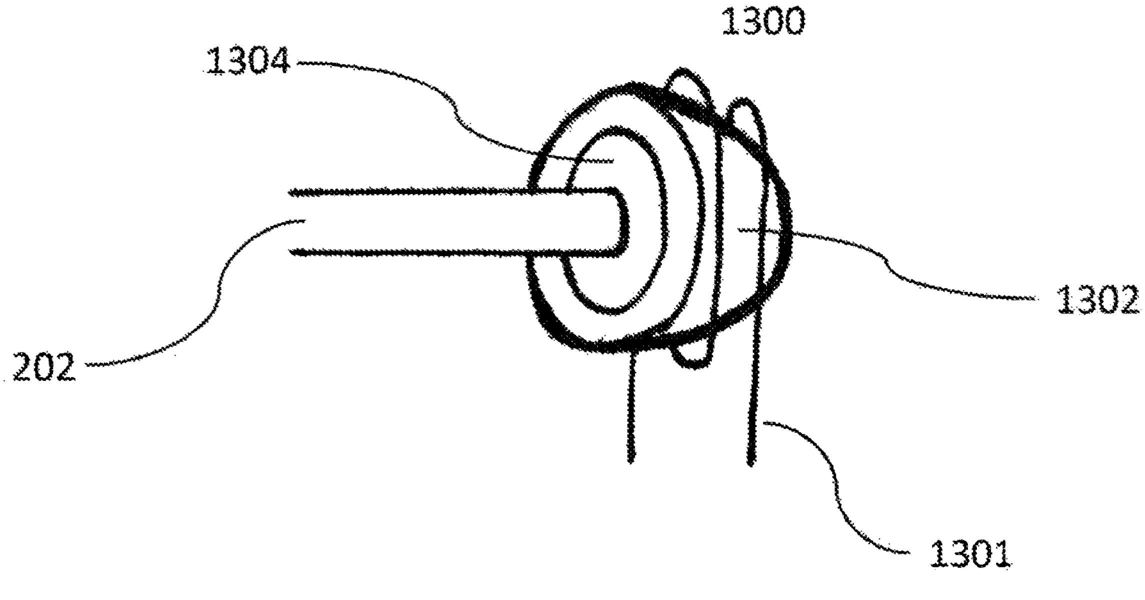
FIG. 13 shows another example of an atomizer that is constructed according to an aspect of the disclosure.

FIG. 13 shows a crucible vaporizer element 1300 which can be used as vaporizer element 109 and it should be understood that future references to vaporizer element 109 can replaced with crucible vaporizer element 1300 without impacting functionality. Crucible vaporizer element 1300 is comprised of a crucible heater 1301 and a crucible core 1302. Crucible heater 1301 is substantially similar to cylindrical heater 901, the primary difference being that it is shaped to interface with crucible core 1302. As with cylindrical heater 901, crucible heater can be made from resistance wire, chemical deposition or other methods described earlier. The crucible vaporizer element 1300 can be constructed from similar materials as cylindrical vaporizer element 900. Crucible core 1302 can have a shape that is substantially similar to a hemisphere with a hollow region 1304 into which inhalation media can be dispensed. When the crucible heater 1301 is energized, the hollow region 1304 heats up, vaporizing inhalation media that has been dispensed. Alternatively, if the crucible core 1302 is constructed using a porous material, inhalation media can travel through the walls of the crucible core 1302 where it can come into contact with the crucible heater 1301 and be vaporized.

Over an extended period of use, it is possible for the heat transfer properties of the vaporizer element 109 to degrade, particularly as residue from inhalation media accumulates on the surfaces of the vaporizer element 109. In addition, if a user switches from one cartridge 200 containing one type of inhalation media to a different cartridge 200 containing a different type of inhalation media, some residual inhalation media from the first cartridge 200 can remain on the vaporizer element 109.

Figure 14A:
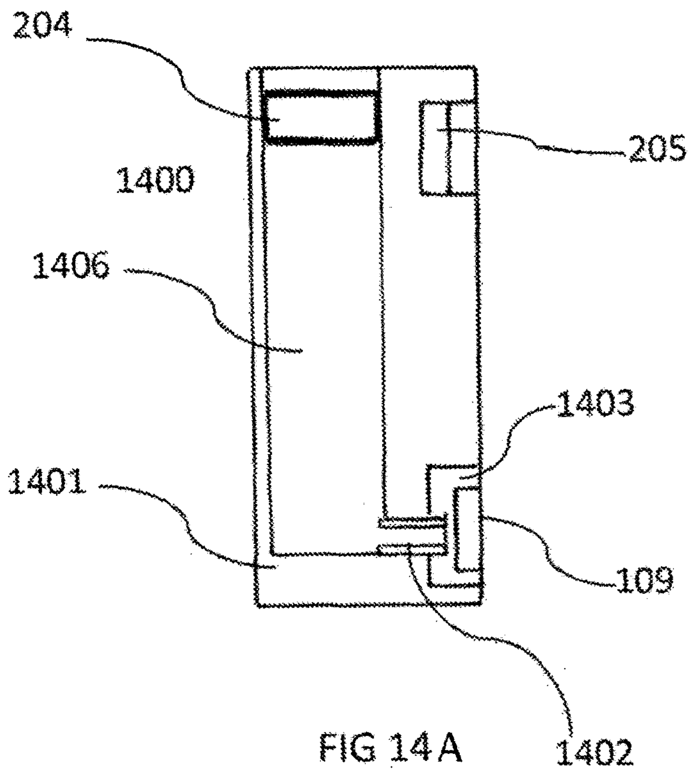
FIGS. 14A, 14B show additional example configurations of a cartridge constructed according to aspects of the disclosure.

FIG. 14A shows an integrated cartridge 1400 incorporates the vaporizer element 109 into its structure. This means that the vaporizer element 109 is eliminated from the control device 100. This mitigates the two aforementioned problems. Additional electrical contacts similar to electrical contacts 108*a* and 108*b* can be provided to establish an electrical connection between the integrated cartridge 1400 and the control device 100. The integrated cartridge 1400 includes an integrated cartridge housing 1401 which provides structure and establishes an integrated media storage area 1406. As plunger 204 is moved, the integrated media storage area 1406 decreases in volume, forcing inhalation media out of the integrated cartridge outlet 1402, which can be similar in construction and material to cartridge outlet 202, and onto the vaporizer element 109. It should be understood that vaporizer element 109 can replaced with any of cylindrical vaporizer element 900, center hole cylindrical vaporizer element 1000, through hole cylindrical vaporizer element 1100, compound cylindrical vaporizer element 1200 or crucible vaporizer element 1300 without impacting functionality.

The integrated cartridge 1400 can also include an integrated air flow path 1403 whereby air flow induced by the user's inhalation is directed from the control device 100, past the vaporizer element 109, then back through the control device 100 toward the vapor outlet 110. A sealing surface (not shown) can be added between the control device 100 and integrated cartridge 1400 to better ensure that air and aerosol flow through this desired path. The integrated cartridge 1400 can also contain a memory IC 205 for the purposes described before. In an alternative embodiment of the integrated cartridge 1400, the plunger 204 and integrated cartridge outlet 1402 can be preassembled along with a stand-alone media storage component 1404 (not shown) to form a stand-alone media pre-assembly 1405. The stand-alone media storage component 1404 can be substantially tubular in nature with one end designed to accept the plunger 204 and the other designed to interface with the integrated cartridge outlet 1402. For ease of assembly, the stand-alone media pre-assembly 1405 can be filled with inhalation media, purged of excess air, then inserted into the integrated cartridge housing 1401. The integrated cartridge housing 1401 can provide one or more one-way retention features that prevent the removal of the stand-alone media pre-assembly 1405 once it has been fully inserted.

Figure 14B:
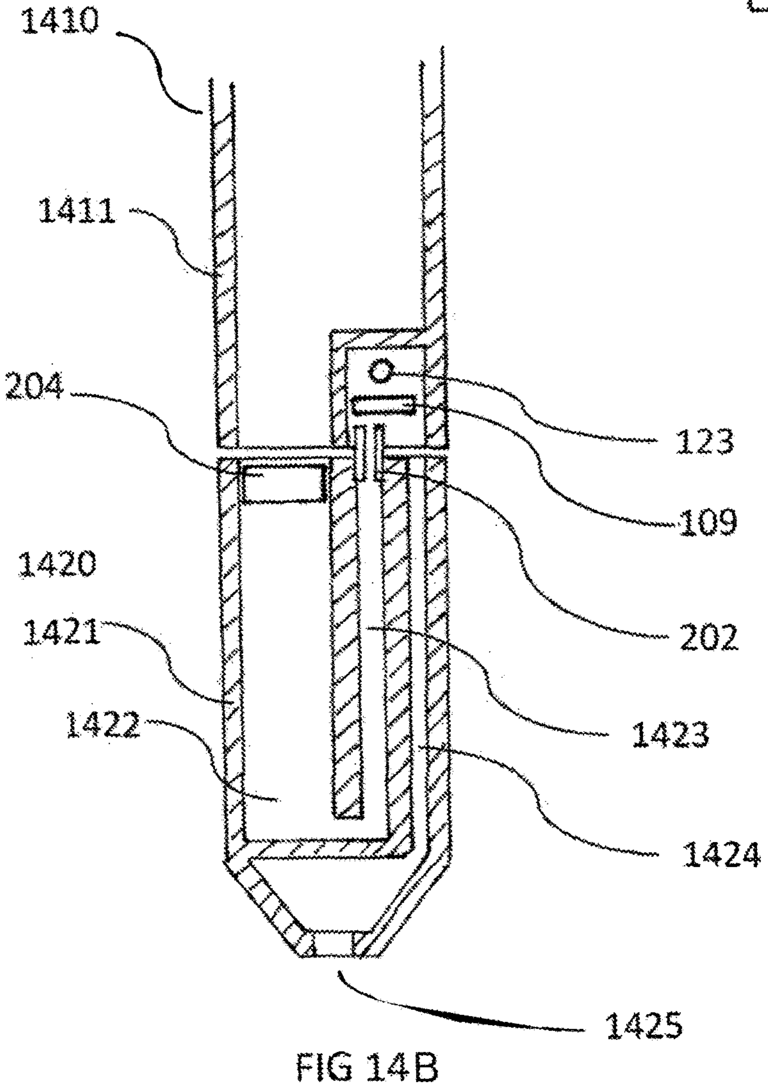

FIG. 14B shows section view of a vaporizer cartridge 10 comprising an in-line cartridge 1420 and an in-line control device 1410. The embodiment is functionally similar to the system described before with the primary difference being that the in-line cartridge 1420 is positioned in-line between the in-line control device 1410 and the user's mouth. The in-line cartridge 1420 can be comprised of an in-line housing 1421 that is configured to accept the plunger 204 and cartridge outlet 202. The in-line housing 1421 provides an in-line media storage area 1422 and forms an outlet channel 1423 that directs inhalation media toward the cartridge outlet 202 as the plunger 204 is depressed by the in-line control device 1410. The inhalation media is expressed onto the vaporizer element 109 located in a region of the in-line control device housing 1411. Air enters the in-line control device housing 1411 via an air inlet 123. Air flows past the vaporizer element 109 where it entrains the vaporized inhalation media that has begun to mix with air to form an aerosol into the air stream, then proceeds toward the in-line vapor outlet 1425 via a vapor return channel 1424 provided in the in-line housing 1421. A seal (not shown) can be provided between the in-line cartridge 1420 and the in-line control device 1410 in order to ensure proper air and aerosol flow. Similar to the cartridge 200, the in-line cartridge 1420 can also contain a memory IC 205.

Figure 14C:
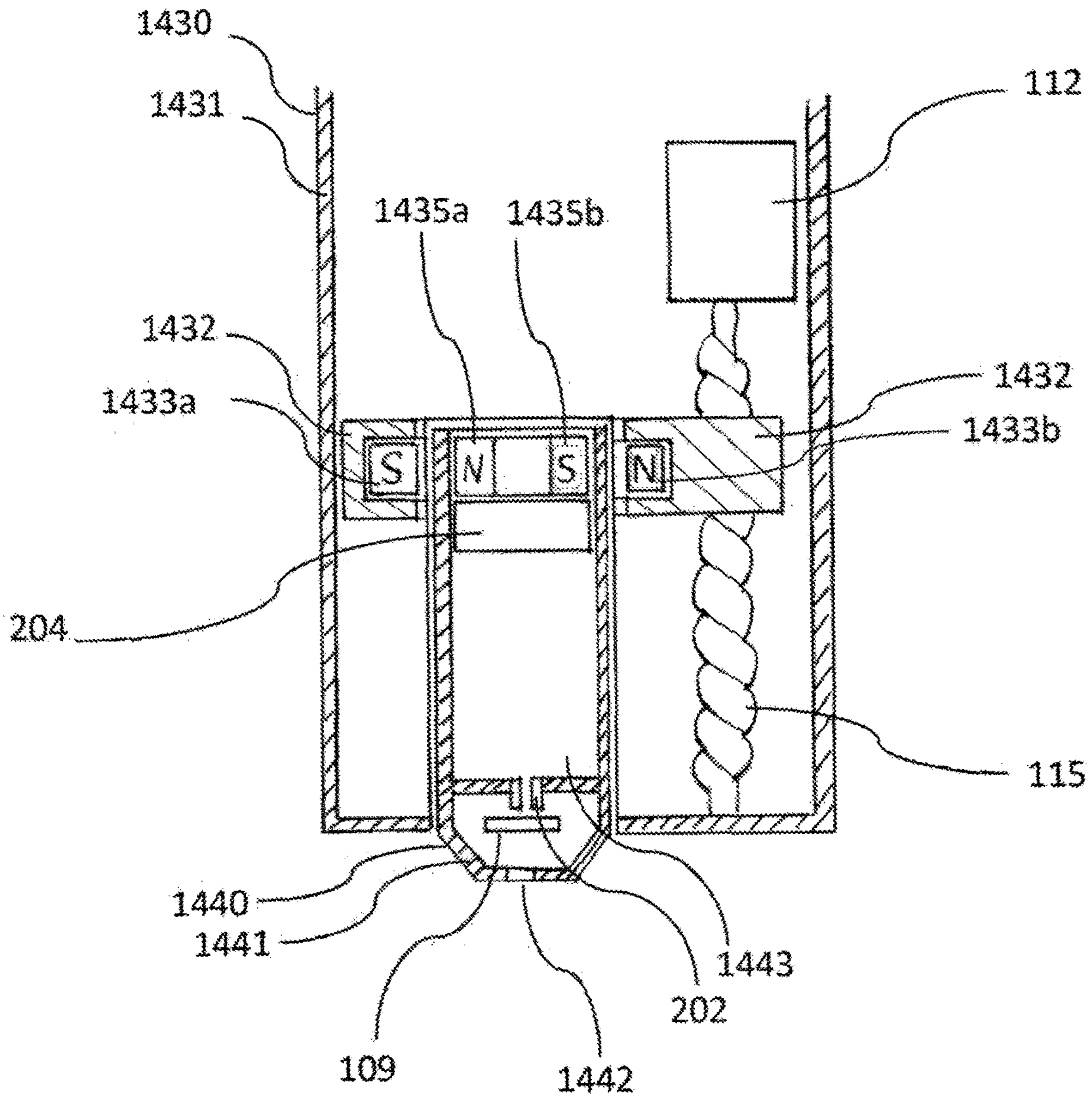
FIG. 14C shows another example of a vaporizer article that is constructed according to an aspect of the disclosure.

FIG. 14C shows a section view of a magnetic cartridge 1440 and magnetic control device 1430. This embodiment is functionally similar to the system described before with the primary difference being that the magnetic control device 1430 uses magnetic coupling to drive the plunger 204 in the magnetic cartridge 1440. The magnetic control device housing 1431 is shaped so as to accept a significant portion of the magnetic cartridge housing 1441. The magnetic control housing 1431 can include retention features (not shown) that serve to hold and align the magnetic cartridge 1441. The dispensing motor 112 turns drive screw 115 which in turn causes magnetic driver 1432 to move up or down within the magnetic housing 1431 depending on the direction in which the dispensing motor 112 rotates. The magnetic driver 1432 can be shaped such that it can hold drive magnet 1433. Drive magnet 1433 can have an annular shape through which the magnetic cartridge housing 1441 fits. Drive magnet 1433 can alternatively be comprised of multiple discrete magnets arranged around the magnetic cartridge housing 1441. The magnetic cartridge contains driven magnet 1435. Driven magnet 1435 can be a single magnet shaped substantially like a disk or can be comprised of multiple discrete magnets.

Driven magnet 1435 is coupled to the plunger 204. Drive magnet 1433 can contain drive magnetic poles 1433*a* and 1433*b*. Driven magnet 1435 can contain driven magnetic poles 1435*a* and 1435*b*. The aforementioned magnets are aligned so as to provide a magnetic coupling such that when the magnetic driver 1432 moves, the plunger 204 follows its motion. In this way, the magnetic control device 1430 can cause inhalation media stored within magnetic cartridge media storage area 1443 to be dispensed via cartridge outlet 202 onto vaporizer element 109 where it can be vaporized to mix with air to form an aerosol for inhalation via magnetic vapor outlet 1442. The magnetic control device 1430 can contain one or more electrical connectors 108 (not shown) to provide power to the vaporizer element 109 and electrical communication with memory IC 205 (not shown).

Figure 14D:
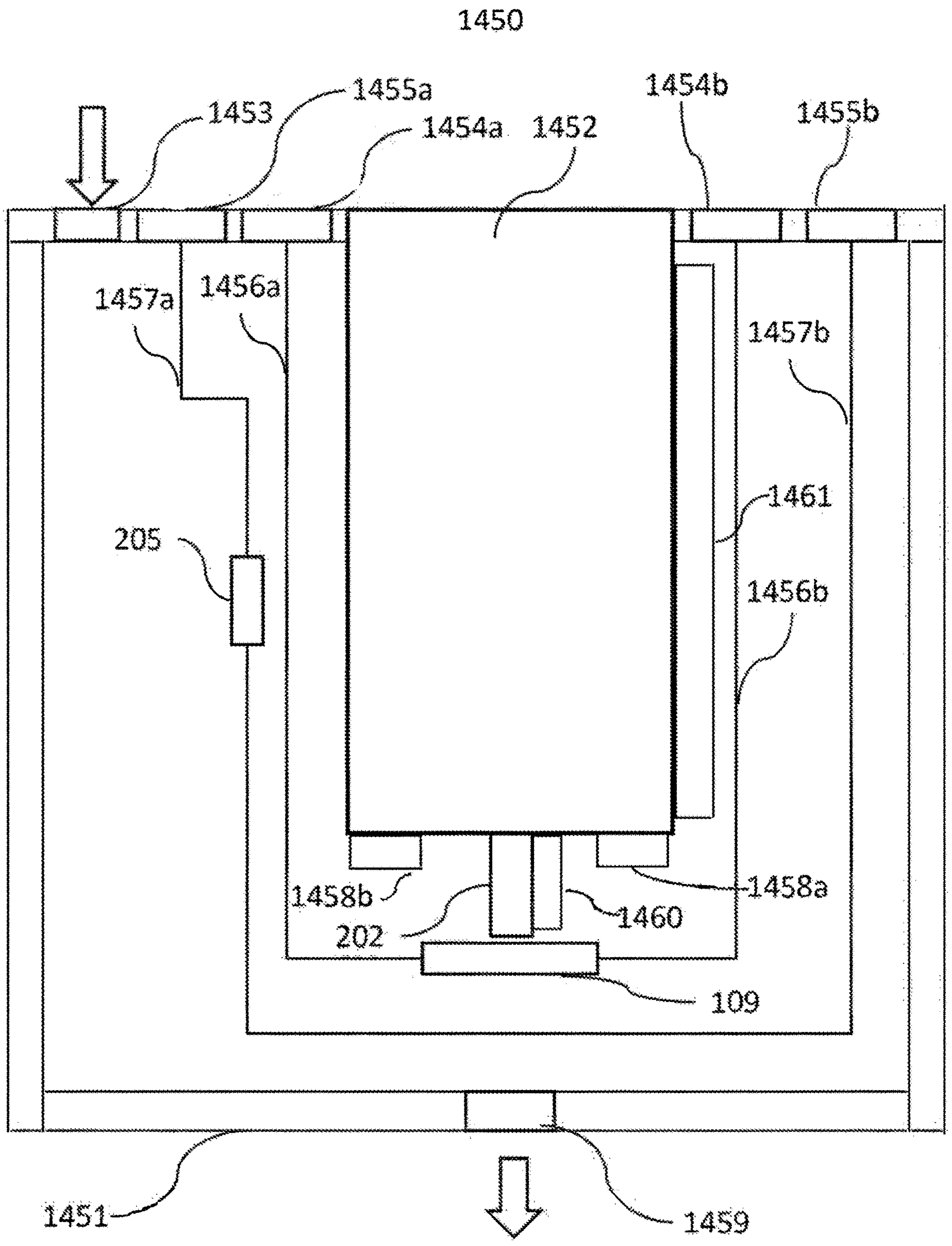
FIGS. 14D and 14E show examples of a cartridge that is constructed according to an aspect of the disclosure.

FIG. 14D shows a partially sectioned view of an alternative embodiment of an insert cartridge 1450. This embodiment is functionally similar to and incorporates aspects of the integrated cartridge 1400 and the in-line cartridge 1420. Like the in-line cartridge 1420, the insert cartridge 1450 is connectable removable from the control device and contains an insert cartridge vapor outlet 1459 similar to the in-line vapor outlet 1425. Aerosol is intended to flow directly from insert cartridge vapor outlet 1459 into the user's mouth. And like the integrated cartridge 1400, the vaporizer element 109 is contained within the insert cartridge 1450. Insert cartridge 1450 is configured so that insertable media storage 1452 can be filled with inhalation media before being inserted into insert cartridge housing 1451, shown in section view. Cartridge outlet 202, plunger 204 (not shown) and insertable media storage 1452 can be pre-assembled into a single unit before being inserted into insert cartridge housing 1451. Because the outlet of the cartridge outlet 202 must be positioned close to the vaporizer element 109 in order for inhalation media to come into contact with the vaporizer element 109, cartridge limit stops 1458, shown in cross section, can be provided to allow for precise positioning of the cartridge outlet 202. Cartridge limit stops 1458*a* and 1458*b* can be formed integrally with the insert cartridge housing 1451. It can also be desired to permanently retain the insertable media storage 1452 within the insert cartridge housing 1451 once it has been assembled. This not only helps ensure proper positioning of the cartridge outlet 202, it also prevents the user from removing and tampering with the insertable media storage 1452 and inhalation media. Insert cartridge housing 1451 can be configured with retention features (not shown), such as one-way snaps, that permanently retain the insertable media storage 1452.

Insert cartridge housing 1451 can further provide on or more electrical pads 1454*a* and 1454*b* for the purpose of providing an electrical connection between the insert cartridge 1450 and an embodiment of control device 100 configured to mate with insert cartridge 1450. One or more insertable heater leads 1456*a* and 1456*b* provide an electrical connection between electrical pads 1454*a* and 1454*b* and the vaporizer element 109. Insertable heater leads 1456*a* and 1456*b* can generally be constructed from electrically conductive wire, flex circuitry, printed contacts or formed from sheets of conductive material such as sheet metal. It should be understood that the vaporizer element 109 contained within insert cartridge 1450 can replaced with any of cylindrical vaporizer element 900, center hole cylindrical vaporizer element 1000, through hole cylindrical vaporizer element 1100, compound cylindrical vaporizer element 1200 or crucible vaporizer element 1300 without impacting functionality. One or more memory pads 1455*a* and 1454*b* can be provided to provide additional electrical connection points between the insert cartridge 1450 and control device 100. One or more memory leads 1457*a* and 1457*b* connect memory pads 1455*a* and 1455*b* to memory IC 205. Memory leads 1457*a* and 1457*b* can generally be constructed from electrically conductive wire, flex circuitry, printed contacts or formed from sheets of conductive material such as sheet metal.

Insert cartridge 1450 can optionally be configured to include one or both of outlet heater 1460 or storage heater 1461 in order to heat inhalation media before or during the act of dispensing inhalation media onto vaporizer element 109. Outlet heater 1460 and storage heater 1461 can be constructed from a variety of materials, including, but not limited to: resistive thin film, resistive foil, printed flexible heaters, resistive wire, resistive mesh, and formed resistive metals. By heating the inhalation media before dispensing, the viscosity of the inhalation media will decrease, allowing it to more easily pass through cartridge outlet 202. This allows for relatively high viscosity inhalation media to be used with the system. If one or both of outlet heater 1460 or storage heater 1461 are employed, additional electrical connections would need to be provided to connect them to an embodiment of control device 100 configured to control outlet heater 1460 and/or storage heater 1461.

Insert cartridge housing can also contain an insert cartridge airflow inlet 1453 that allows air to enter into insert cartridge housing 1451 for the purpose of mixing with vaporized inhalation media to create an aerosol. Insert cartridge airflow inlet 1453 can also be in fluid communication with inhalation sensor 119 for the purpose of signaling to the control device 100 that the user is inhaling A seal (not shown) can be provided to ensure a good fluid connection between insert cartridge airflow inlet 1453 and the control device 100.

Figure 14E:
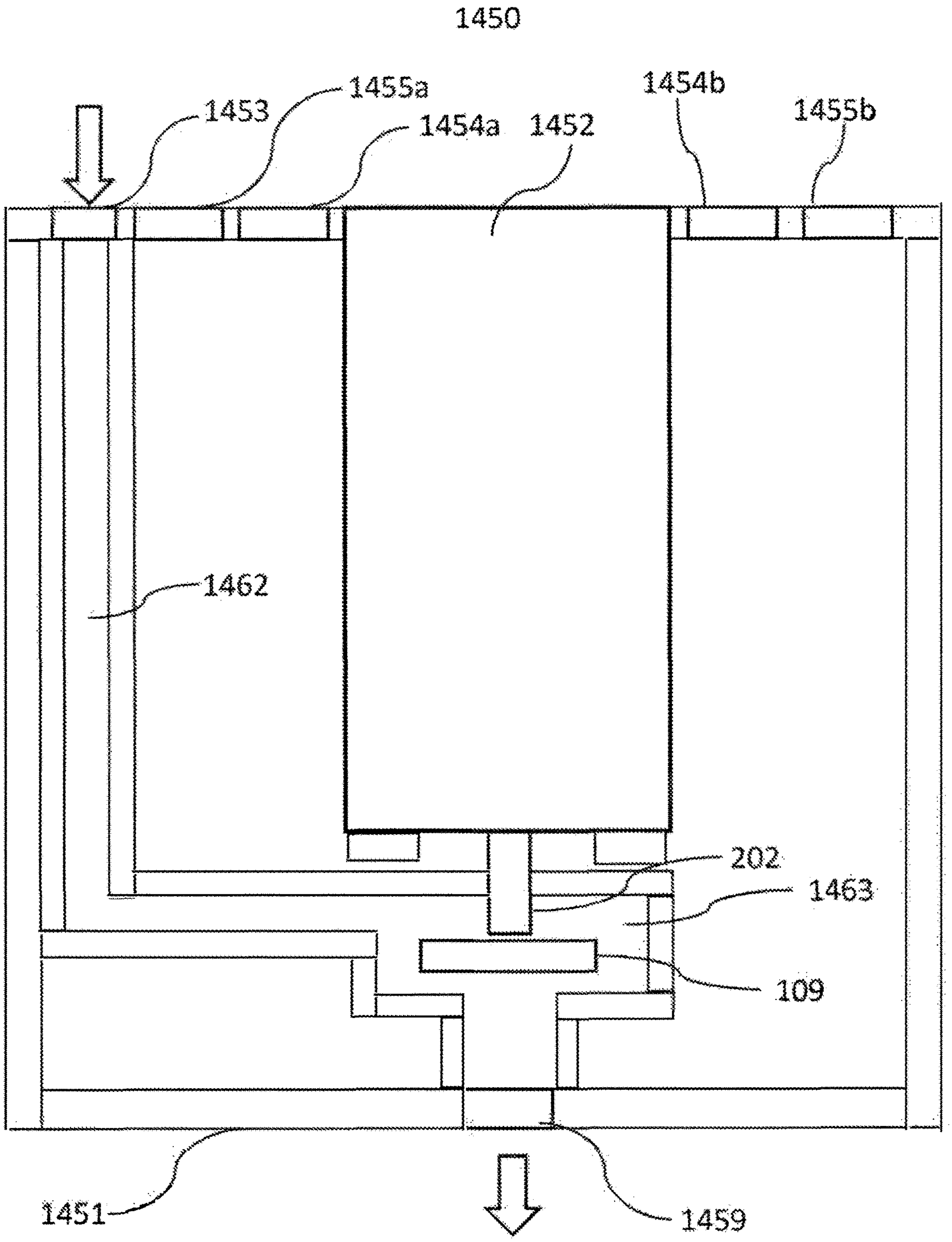

FIG. 14E shows a view of insert cartridge 1450 where certain components have been hidden and an insert airflow pathway 1462 is shown in cross section. When the user inhales, air can enter via insert cartridge airflow inlet 1453 into insert airflow pathway 1462. Insert airflow pathway can be integrally formed with insert cartridge housing 1451 or can be a separate component. Airflow then continues toward the vaporizer element 109 which can further be contained within a vaporizer cavity 1463 intended to shape and direct airflow past the vaporizer element 109. The form and size of the vaporizer cavity 1463 can be shaped to produce a particular particle size of inhalation media at a given airflow rate. After combining with vaporized media that has begun to form an aerosol in the vaporizer cavity 1463, the aerosol exits via insert cartridge vapor outlet 1459. It should be noted that while some air must flow through insert cartridge airflow inlet 1453 in order to create a signal at the inhalation sensor 119, not all air must flow through this path. A secondary air inlet (not shown) can optionally be provided within insert cartridge housing 1451 should additional air be desired to further dilute the aerosol. The secondary inlet can be located upstream or downstream of the vaporizer cavity 1463. The secondary inlet can be configured to be always open, selectably open, closed or partially open.

Figure 15A:
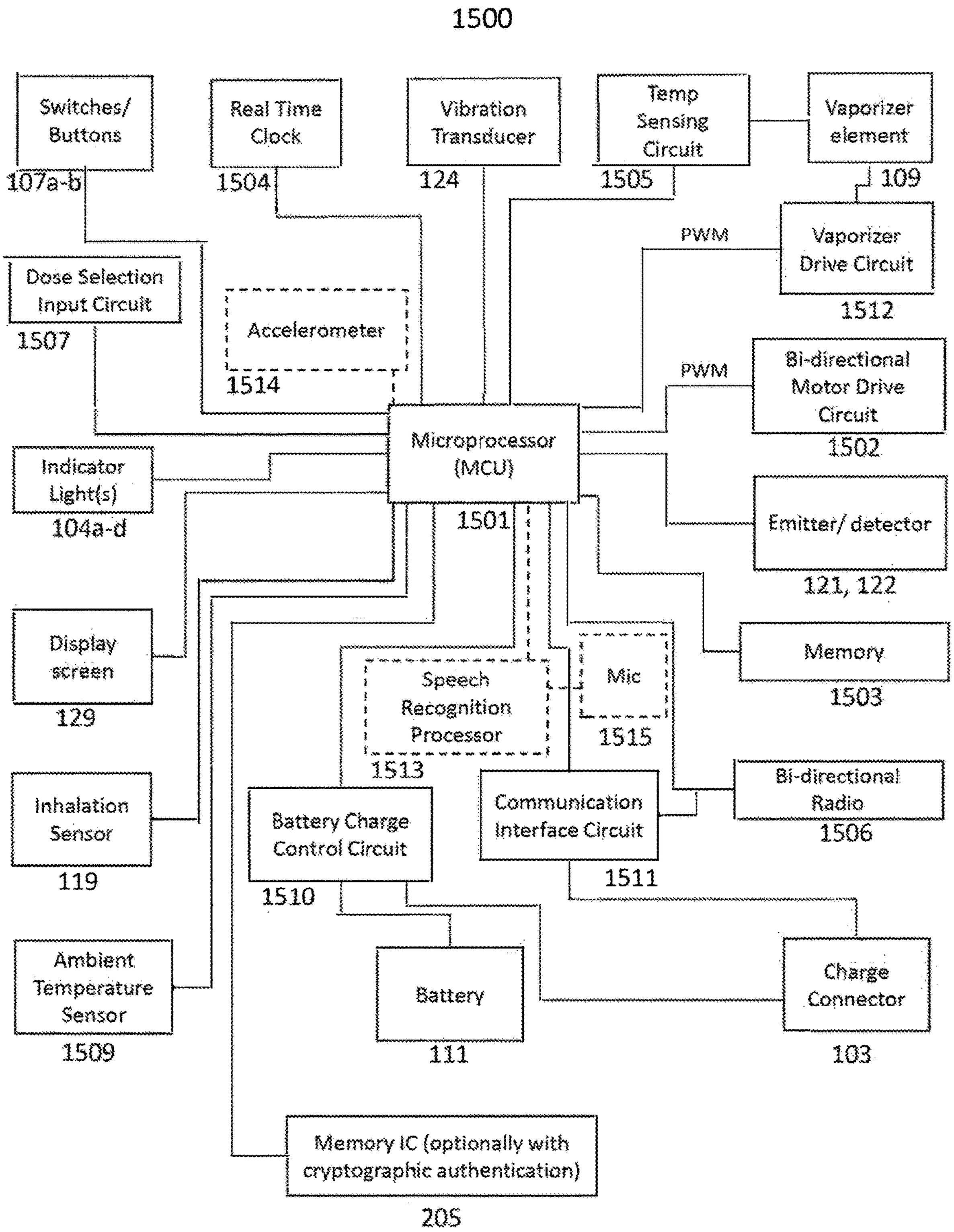
FIG. 15A shows an example of an electronic circuit that is constructed according to an aspect of the disclosure.

FIG. 15A shows a vaporizer electrical system 1500 of vaporizer article 10. The vaporizer electrical system 1500 can comprise a control circuit 120, buttons 107*a-b*, vibration transducer 124, vaporizer element 109, emitter 121, photo detector 122, charge connector 103, battery 111, inhalation sensor 119, display screen 129, indicator lights, memory IC 205, and associated electrical connections.

The control circuit can comprise a MCU 1501. MCU 1501 can be configured to read input from the dose selection input circuit 1507 which can be mechanically and/or electrically connected to dose selector dial 105. The dose selection input circuit 1507 can comprise a potentiometer and a fixed resistor configured in a voltage divider configuration. When the dose selector dial 105 turns, the voltage provided from the dose selection input circuit 1507 to the MCU 1501 changes according to the position of the dose selector dial 105. The MCU 1501 is configured to receive this analog signal and interpret its level as an indication of the amount of inhalation media that should be dispensed. Alternatively, the dose selection input circuit 1507 can be an optical encoder or Hall Effect sensor and MCU 1501 as described above.

MCU 1501 can also be configured to receive dosing information via a touch interface associated with or overlaid on display screen 129. MCU 1501 can also be configured to receive dosing information via a communication interface circuit 1511 that can interface with a bi-directional radio 1506. For example, the user can input dosing information via a mobile application which communicates with bi-directional radio 1506 via an established communication protocol such as Bluetooth, Zigbee, Wi-Fi, or digital cellular.

MCU 1501 can be configured to send and receive additional types of information including, but not limited to: control device 100 status, button state, user input, usage data, inhalation media levels, inhalation media characteristics, control device settings, display data, time, battery level, system health reports, and error conditions. MCU 1501 can be configured to store such information in memory 1503. The MCU 1501 can also be configured to send and receive the aforementioned information via a charge connector 103 which can be connected to the MCU 1501 via communication interface circuit 1511. For example, communication via a charging connector 103 is most commonly done using a USB style charging connector 103 and associated protocol.

Once the dosing information has be received and interpreted by the MCU 1501, it calculates the drive signal needed to deliver the desired dose. When the user presses the dosing button **107*a*, or alternatively requests a dose via the control pad 130 or mobile application, MCU 1501 provides a drive signal to the bi-directional motor drive circuit 1502 which is electrically connected to the dispensing motor 111. The bi-directional motor drive circuit 1502 can be comprised of transistors arranged in an H-bridge configuration and can also include diodes and/or capacitors arranged so as to minimize electrical noise and reverse current spikes. The drive signal can be analog, ON/OFF in nature, or can be pulse width modulated (PWM). It can also be comprised of multiple signals, for example a direction signal and a speed signal. Concurrent with driving the dispensing motor 111, the MCU 1501 can activate an emitter 121 and monitor the output of an optical detector 122, as described above, in order to control and record the position of the plunger driver 116. If a Hall Effect sensor is used in place of optical detector 122, the associated signal can instead be used to control and record the position of the plunger driver 116. MCU 1501 can be configured to write the plunger driver 116 position into local memory 1503 and/or the memory IC 205. MCU 1501 can also be configured to provide a drive signal that will move the plunger driver 116 in the opposite direction in order to retract the plunger driver 116 when the user presses the cartridge release button 107*b*, or alternatively requests a release via the control pad 130**, touch screen or mobile application.

After the desired dose has been dispensed, the user can trigger vaporization of the inhalation media by inhaling. The inhalation sensor 119 can be configured to detect either of a pressure change or change in air flow rate caused by the inhalation. The MCU 1501 can be configured to receive a signal from the inhalation sensor and interpret such signal as an indication of the user's desire to vaporize the inhalation media. The inhalation signal can be analog or digital. If an inhalation sensor 119 is configured to produce a digital output, the MCU 1501 can interpret this as the presence or absence of an inhalation event. However, if the inhalation sensor 119 is configured to produce an analog output, or other output that varies in accordance with the strength of the inhalation, then the MCU 1501 can be additionally configured to measure the strength of the inhalation and vary the vaporization signal according to the strength of the inhalation.

The MCU 1501 can be configured to control the vaporizer element 109 via a vaporization signal sent to the vaporizer drive circuit 1512. Vaporizer drive circuit 1512 can be minimally comprised of a transistor configured to allow electrical current to flow through vaporizer element 109 when activated by the MCU 1501. The vaporizer drive signal can be ON/OFF in nature or can be variable using PWM to regulate electrical current flowing through to the vaporizer element 109.

Figure 15B:
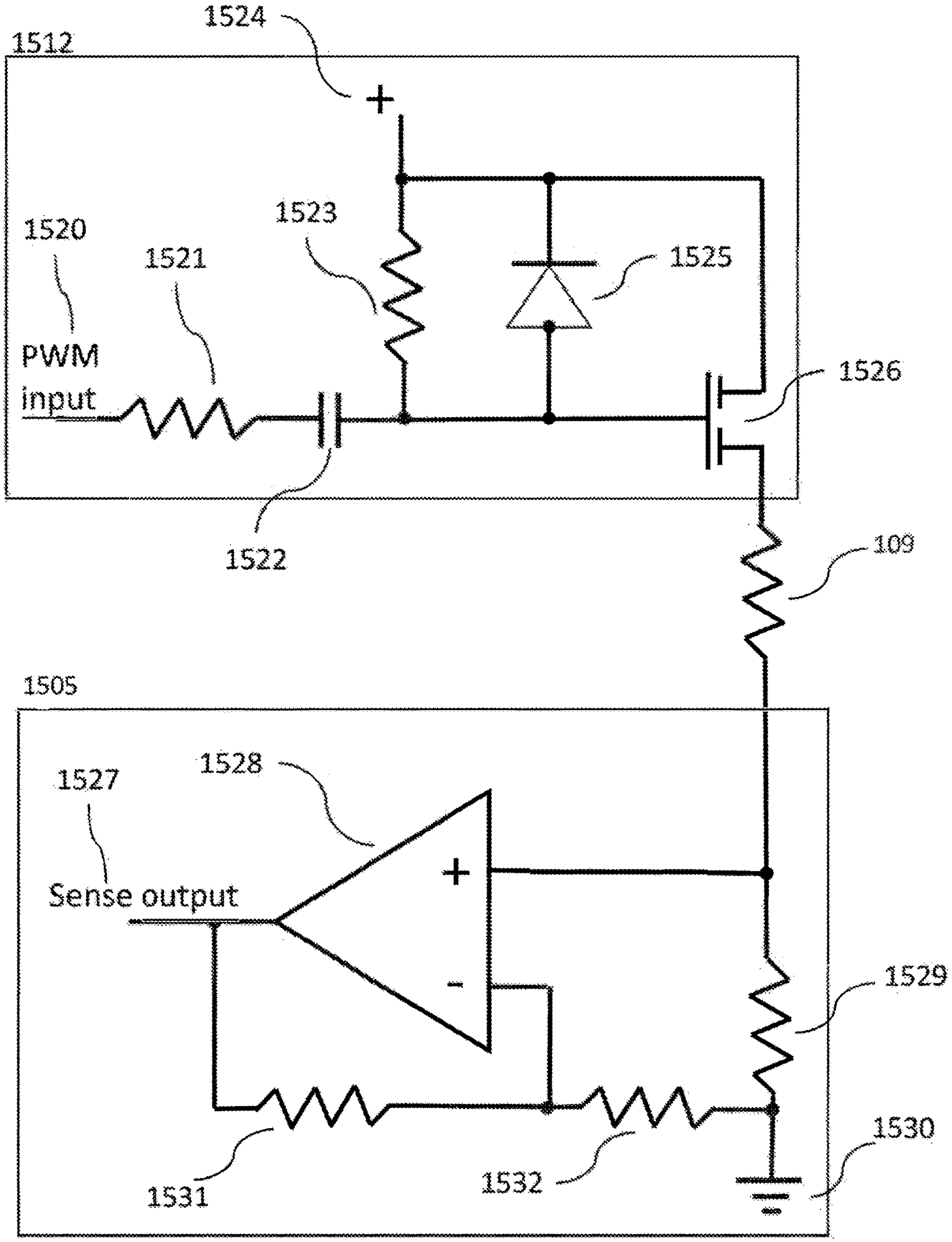
FIG. 15B shows an additional example of an electronic circuit that is constructed according to an aspect of the disclosure.

While regulating the electrical current is not necessary in order to vaporize the inhalation media, doing so is desirable in order to ensure complete vaporization without causing unwanted chemical changes that can be triggered by excessive heat. A temperature sensing circuit 1505 used in conjunction with, e.g., a PWM vaporizer drive signal can be used to accomplish this. A minimal temperature sensing circuit 1505 is shown in FIG. 15B. It includes an operational amplifier 1528, gain resistors 1531 and 1532 and voltage divider resistor 1529. The vaporizer element 109 forms a voltage divider with voltage divider resistor 1529. Voltage divider resistor 1529 is typically connected between the vaporizer element 109 and electrical ground 1530. Voltage divider resistor 1529 typically has a low resistance value in comparison with that of vaporizer element 109. This provides for a small voltage difference across voltage divider resistor 1529 without consuming too much of the energy in the system that is needed to vaporize inhalation media. As the temperature of the vaporizer element 109 changes, so does its resistance. This change in resistance causes the small voltage difference across the voltage divider resistor 1529 to change as well. This change is amplified by the operational amplifier 1528 according to a factor determined by gain resistors 1531 and 1532. The resulting signal is provided by the sense output 1527. The MCU can be configured to receive the sense output 1527 and determine the temperature of the vaporizer element 109 based on the analog level of sense output 1527. Informed by the sense output 1527, MCU 1501 can be further configured to adjust the vaporizer drive signal in order to achieve the desired temperature at vaporizer element 109.

Control circuit 120 can include a real-time clock 1504, which can be connected to MCU 1501 to determine accurate time and date information. MCU 1501 can be configured to store time and/or date information in memory 1503. For example, when a user dispenses and inhales a dose, the time and/or date of the dose can be stored in memory 1503. Furthermore, the MCU 1501 can communicate such stored information with a mobile application or computer network using the aforementioned communication interface circuit 1511. MCU 1501 can also activate the vibration transducer 124 in order to signal the activation state of the vaporizer element 109 to the user and/or the completion of vaporization of the inhalation media that was expressed onto the vaporizer element 109. MCU 1501 can be connected directly to vibration transducer 124 or it can be connected to a transistor that activates the vibration transducer 124. The vibration transducer 124 can be driven using an ON/OFF drive signal or a PWM drive signal.

By way of example, the MCU 1501 can output a low duty cycle PWM signal that causes the vibration transducer 124 to vibrate softly during inhalation and then output a high duty cycle PWM signal that causes the vibration transducer 124 to vibrate strongly to signify when a dose has been fully vaporized. The vibration transducer can also be activated to provide haptic feedback in response to user inputs when used in combination with a display screen 129 that is touch sensitive (has a touch sensitive overlay). When the user selects an on-screen element, the vibration transducer 124 can be activated for a duration of time, typically less than 500 ms, to coincide with the selection of the element and provide such haptic feedback.

Control circuit 120 can also include a battery charge control circuit 1510 which is responsible for managing the charge of battery 111 when connected to a power source via charge connector 103. The MCU 1501 can be configured to activate and deactivate the battery charge control circuit 1510. It can also be configured to receive information from battery charge control circuit 1510 such as charge status. The battery charge control circuit 1510 can include a temperature sensor such as a thermistor that is located in proximity to the battery 111 for the purpose of determining charging conditions.

Control circuit 120 can also contain an ambient temperature sensor 1509. The ambient temperature sensor 1509 can be comprised of a thermistor and fixed resistor that are arranged in a voltage divider configuration. MCU 1501 can be configured to receive analog signal information from the temperature sensor and take certain actions based on temperature. For example, the MCU 1501 can be configured to prevent control device 100 operation when the ambient temperature is above or below the rated operating conditions of its components. For example, MCU 1501 can be configured to prevent device 100 operation when the ambient temperature is outside the temperature ratings of battery 111. MCU 1501 can also be configured to adjust operating parameters based on temperature conditions. The MCU 1501 can also be configured to periodically record temperature information and store it in memory 1503 and/or memory IC 205 or communicate with a computer or computer network via communication interface circuit 1511. Temperature information can be useful to determine user behavioral habits as well as predict, notify, and/or compensate for temperature-based changes or spoilage of the inhalation media.

Control circuit 120 can also include a speech recognition processor 1513 and microphone 1515 for the purpose of accepting verbal commands from the user. If a speech recognition processor 1513 and microphone 1515 are incorporated, the MCU 1501 can be configured to accept input from the speech recognition processor 1513 for a number of purposes including, but not limited to: setting dose level, dispensing a dose, ejecting a cartridge 200, initiating data transfers, connecting to a wireless network, changing device settings, and locking or unlocking the control device 100.

MCU 1501 can be configured to turn on and off indicator lights 104*a*-104*d*. It can also be configured to drive a display screen 129. MCU 1501 can be configured to communicate with memory IC 205. MCU 1501 can read certain information from memory IC 205 for many purposes including, but not limited to: determining the composition of inhalation media, dosing, the quantity of inhalation media in cartridge 200, vaporization parameters, determining age of inhalation media, and displaying information about inhalation media. MCU 1501 can also be configured to enable control device 100 only when security information from memory IC 205 is validated. For example, MCU 1501 can read a serial number from memory IC 205 and compare that to a list of known serial numbers in order to ensure that cartridge 200 is not counterfeit. Alternatively, MCU 1501 can be configured to read information from memory IC 205 and compare it to an expected format in order to validate that the cartridge 200 is genuine. MCU 1501 can be further configured to implement advanced security algorithms (e.g. SHA-256) in conjunction with information stored within memory IC 205 in order to prevent usage of unauthorized cartridges 200. The MCU 1501 can be configured to implement such security validations either upon connection of cartridge 200 or upon one or more exchanges of data between MCU 1501 and cartridge 200.

Returning to FIG. 15B, a detailed view of vaporizer drive circuit 1512 and temperature sensing circuit 1505 is provided. The vaporizer drive circuit 1512 can be comprised of a vaporizer transistor 1526 which can typically be a Field Effect Transistor (FET) with an electrical current carrying capacity sufficient to supply current to the vaporizer element 109. The vaporizer transistor 1526 is configured to allow electrical current to flow from positive power supply 1524 toward power ground 1530 when commanded to do so by the MCU 1501. MCU 1501 provides a PWM drive signal to PWM input 1520 in order to activate the vaporizer transistor 1526. In the instant example, the circuit uses a PFET style vaporizer transistor 1526 and can also include a pull up resistor 1523 that serves to ensure the vaporizer transistor remains in the OFF state when not receiving the necessary PWM drive signal. The circuit can further include an RC resistor 1521 and RC capacitor 1522. These two components form a filter that keeps the transistor on only when the PWM input is oscillating within the desired frequency range. The inclusion of RC resistor 1521 and RC capacitor 1522 prevent the vaporizer transistor 1526 from remaining ON in the event that the MCU 1501 malfunctions and produces an incorrect PWM drive signal. Vaporizer diode 1525 is provided to ensure that the voltage present at the gate of the vaporizer transistor 1526 doesn't temporarily go outside of allowable operating range as the RC capacitor 1522 discharges and charges.

FIG. 16A shows an example of the type of data elements that can be written into the memory IC 205. The memory can be formatted in a manner such that each data element has its own size and address. For example, Device Serial number which indicates the serial number of the cartridge 200 can be 4 bytes in size and located at memory location 0001. For example, media type, which indicates what type of media has been filled into a particular cartridge 200 can be 2 bytes and located a memory location 0010. Memory IC 205 can be used to store non-mutable data elements that pertain to the cartridge 200 itself, such as the serial number, manufacturing date, and storage volume of cartridge 200.

Memory IC 205 can additionally be used to store non-mutable data elements that pertain to the inhalation media, including, but not limited to: fill date, expiration date, fill amount, optimal vaporization parameters, viscosity, density, default dose, ingredients, chemical composition, genetic information, raw material information, grower information, weather conditions during the raw material growth process, raw material origin information, test lab digital authentication, testing information, processing and production parameters, digital authentication parameters and names of persons and/or entities associated with various phases of the creation of the inhalation media. Such non-changing data elements can be programmed into memory IC 205 at the time of manufacture of cartridge 200, the time of testing of cartridge 200, or when the cartridge 200 is filled with inhalation media.

These non-changing data elements typically indicate intrinsic qualities about each cartridge and are often not to be changed by the user or by the system and can be write protected so that they can't be accidentally erased or overwritten. The memory IC 205 can also contain mutable data elements such as Number of inhalation events, Media amount remaining and Plunger Position. This type of mutable data element can be updated with new data as the product is used and inhalation media is consumed.

Memory IC 205 can also include unassigned data elements such as Parameter #1, Parameter #2 and Parameter #n. Such unassigned data elements provide for the tracking of additional information that may not be known to be needed at the time of manufacture or first use. Such data elements can also provide the user with the ability to customize the information tracked by the system. It should be understood that FIG. 16A shows only a limited number of examples of the data elements that can possibly be stored in memory IC 205.

Figure 16B:
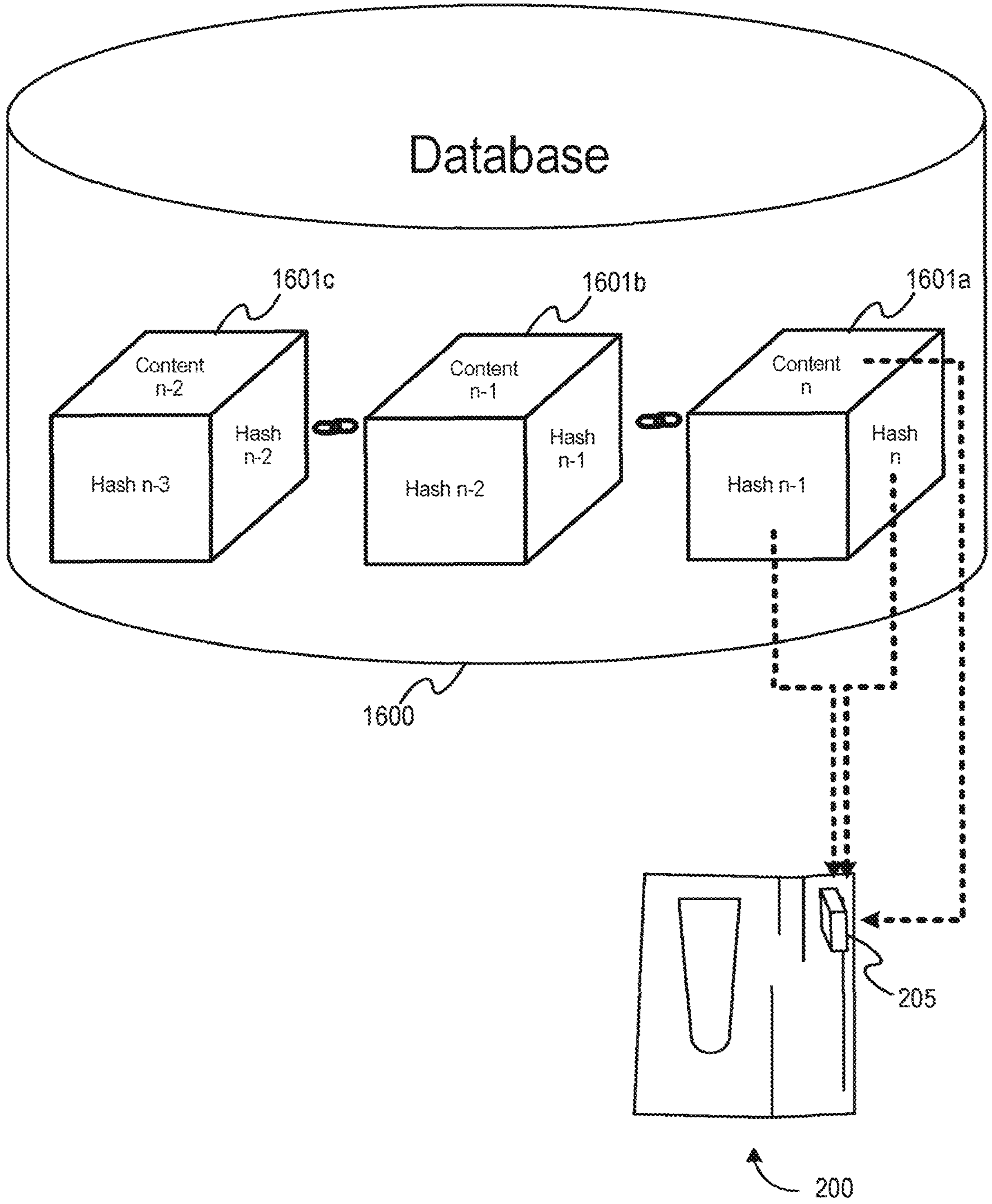
FIG. 16B shows an example of data that can be programmed into a cartridge component and database according to an aspect of the disclosure.

FIG. 16B shows how data elements from cartridge 200 can be stored in a networked computing environment. In addition to being stored in memory IC 205, any one or more of the data elements described in FIG. 16A can be duplicated in database 1600. Furthermore, certain data elements described in FIG. 16A can preferably be stored in database 1600 instead of memory IC 205. This can be advantageous for certain data elements, especially where its format can be variable. For example, testing information can come from multiple laboratories that report results in different formats. Rather than attempting to store such information in memory IC 205, it can be more practical to store in database 1600 and cross-reference to one or more individual cartridges 200 via a data element such as Device Serial number. Database 1600 can reside entirely on a single computer, have multiple full copies distributed across a plurality of computers or can be stored in segments distributed among multiple computers.

It can be desirable to store certain information about the inhalation media or cartridge 200 in a traceable manner that is difficult to counterfeit or manipulate. For example, certificate of origin, testing results, extraction process parameters, formulations, chemical identifiers, and genetic identifiers can all be information that benefits from being stored in this manner. Blockchain systems are a way to perform this task.

FIG. 16B also shows how data elements from memory IC 205 can be stored in a blockchain arrangement within the database 1600. While certain data elements from memory IC 205 can be stored within the database 1600 but outside of the blockchain, one or more data elements from memory IC 205 can serve as content that is included in the blockchain. For example, the Device Serial number data element, among other data elements, can be used as the Content n for data block 1601*a*. The Device Serial number is used as an input to the hashing algorithm that creates Hash n. This uniquely ties each cartridge 200 to the blockchain via its unique Device Serial number located in memory IC 205 and makes counterfeiting cartridges 200 more difficult. In this manner, traceability of inhalation media stored in each cartridge 200 is enhanced via the connection with information which can be stored in data blocks 1601*b* and 1601*c*. Hash values such as Hash n and Hash n−1 can also be written to memory IC 205, thus connecting the digital security elements with a physical item.

Figure 17A:
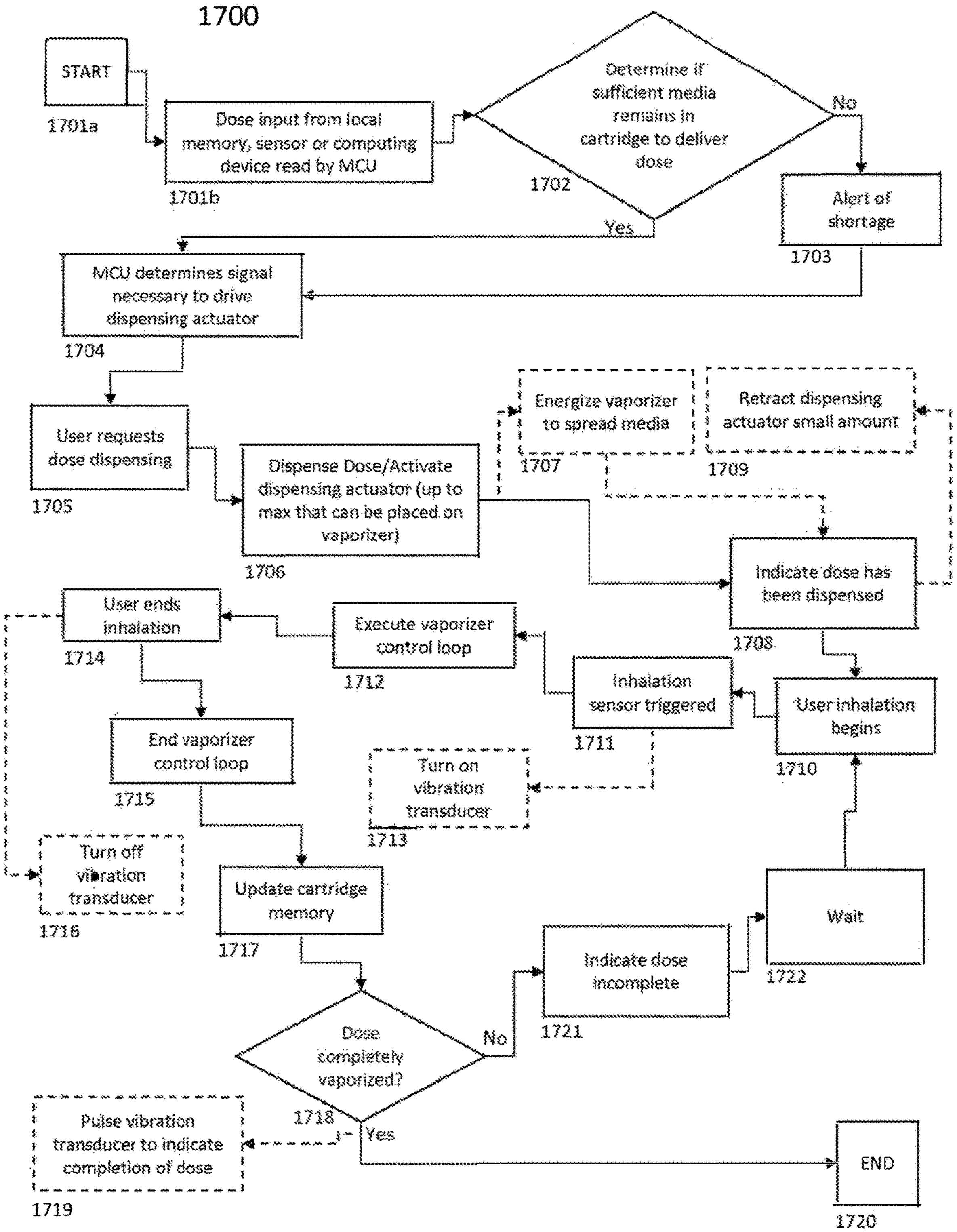
FIG. 17A shows an example of how to control the dispensing and vaporization of inhalation media according to an aspect of the disclosure.

FIG. 17A shows device control scheme 1700 that describes the how vaporizer article 10 configured in accordance with the systems and methods described herein can dispense and vaporize doses of inhalation media. Device control scheme 1700 can be executed by a program or plurality of functions programmed to be executed by MCU 1501. The device control scheme 1700 begins at block 1701*a*. In block 1701*b*, the MCU 1501 can periodically check to see whether a new dose has been selected or a new dosing command has been received. This check can be initiated by the MCU 1501 or by the system providing the updated input. If this occurs, the new dose information will be read into the memory 1503, otherwise, pre-existing dose information will remain in memory. In decision block 1702, the MCU 1501 determines whether there is sufficient inhalation media remaining in cartridge 200 to deliver the next dose. If there is insufficient inhalation media remaining, then the MCU will perform block 1703 where it alerts the user to the shortage. If there is sufficient inhalation material, then the MCU proceeds to block 1704 where it calculates the drive signal needs to dispense the desired dose.

The user request the dose, for example by pressing dosing button 107*a*, is represented in block 1705. When this occurs, the MCU 1501 executes block 1706 by delivering the drive signal needed to dispense the dose, up to a maximum value that can be placed on the vaporizer element 109 at any one time. Certain inhalation media can have a high viscosity and may not evenly cover the surface of the vaporizer element 109. In order to spread the inhalation media, the MCU can execute the optional block 1707 by energizing the vaporizer element 109 for a short period of time or with a low power level in order to gently heat the inhalation media in order to reduces its viscosity and cause it to spread. After the dose has been dispensed, block 1708 is executed by giving the user a visual, audible or tactile indication. Depending on the surface tension and viscosity of the inhalation media as well as the distance between the cartridge outlet 202 and vaporizer element 109, a small amount of inhalation media may remain suspended at the exit of the cartridge outlet 202. In order to prevent inadvertent vaporization and/or leakage of the inhalation media, optional block 1709 can be executed by retracting the dispensing motor 112 a small amount in order to draw any such inhalation media away from the vaporizer element 109. Doing so can also relieve any residual pressure in the inhalation media storage area 206 and thus reduce the tendency for inhalation media to leak out.

At block 1710, the user begins his inhalation which produces a signal output or signal output change at the inhalation sensor 119 which is shown in block 1711. Following the detection of such inhalation, block 1712 is executed. Block 1712, vaporizer control loop, is responsible for energizing and controlling the temperature of the vaporizer element 109 and will be described in further detail below. While the user is inhaling, optional block 1713 can be executed. In block 1713, the vibration transducer 124 can be turned on at a specific level or on and off in a distinct pattern in order to indicate that inhalation media is being vaporized. For example, the specific level can cause a low intensity level vibration that is perceivable, but not disruptive nor distracting from the inhalation experience. Once the user inhalation ceases, represented by block 1714, block 1715 is executed by terminating the vaporizer control loop 1712. If optional block 1713 was executed, then it can be terminated in optional block 1716.

In block 1717, the memory IC 205 can be updated to reflect the most recent consumption information. For example, the number of inhalation events can be incremented by one in order to reflect the inhalation event that just terminated. Other examples of information that can be updated can include, but are not limited to, the position of the plunger driver 116, duration of most recent inhalation event, total duration of all inhalation events for a given cartridge 200, time of most recent inhalation, volume of most recent inhalation, speed of most recent inhalation and amount of inhalation media remaining in cartridge 200. A copy of such aforementioned information can also be updated in memory 1503 and/or transmitted to a computing device 1803 and/or database 1600.

In decision block 1718, the MCU 1501 determines whether the dose has been completely vaporized. This decision can be based on a known relationship between inhalation duration and vaporization rate or other methods involving temperature, power, and/or current monitoring described below. If the dose has been completely vaporized, optional block 1719 can be executed by generating a distinctive vibration pattern using the vibration transducer 124. Examples of such a pattern include a single strong pulse and a series of discrete pulses. At this point, the device control scheme 1700 can terminate with block 1720, at which time MCU can perform other tasks and/or restart at block 1701*a*. If the outcome of decision block 1718 is negative, block 1721 can be triggered to indicate to the user that the dose was not fully vaporized. This indication can be audible, visual or haptic, leveraging the various indication components present in the control device 200. For example, a message can be displayed on display screen 129 to inform the user that the dose was not fully vaporized. After such indication, the MCU waits in block 1722 until such time as the user initiates a new inhalation in block 1710. This process can repeat until such time as the entire dose has been vaporized.

Figure 17B:
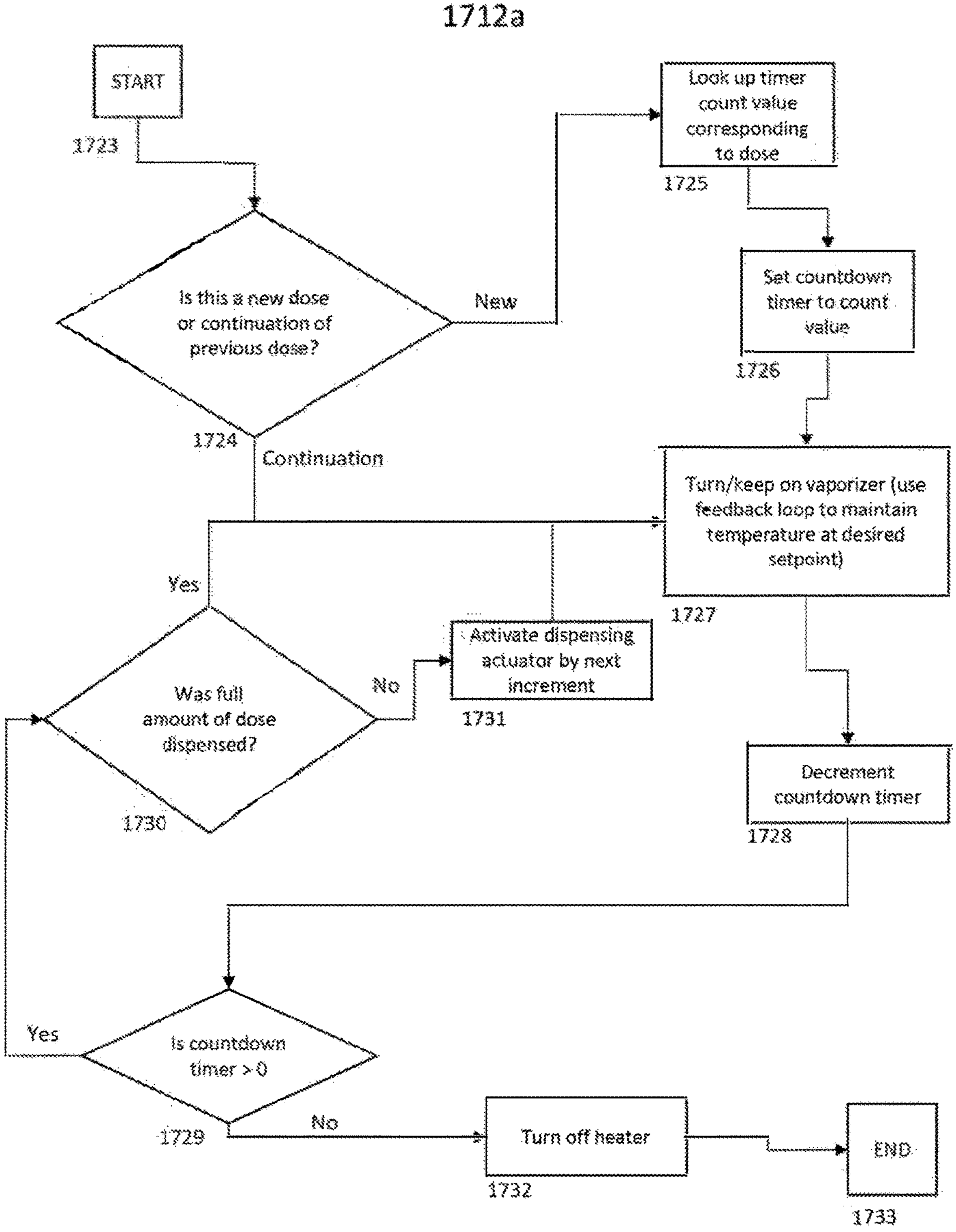
FIG. 17B shows an example detail of how to control the dispensing and vaporization of inhalation media according to an aspect of the disclosure.

FIG. 17B describes one example embodiment of block 1712. In this embodiment, time-based vaporization control loop 1712*a* involves using a relationship between vaporization duration, temperature, and vaporization rate in order to determine when the vaporization media is fully vaporized. For example, it can be determined through testing, that 1 unit of mass of a particular formulation of inhalation media takes 1 unit of time to fully vaporize at a given temperature. This relationship can be expressed in a formula $R_{temp} \times Time_{vaporize} = Mass_{vaporized}$. The value of $R_{temp}$ can be unique to each inhalation formulation and can be stored in the memory IC 205, memory 1503 computing device 1803, and/or database 1600. The time-based vaporization control loop 1712*a* starts at block 1723. In decision block 1724, the MCU 1501 checks to see whether the dose to be vaporized during the current inhalation is a new dose or a continuation of a previous dose that has been partially dispensed and/or partially vaporized. This can be accomplished by checking the value of a countdown timer and/or a value of a continuation state variable stored in any of memory IC 205, memory 1503 and database 1600.

The dose to be vaporized during the current inhalation is a new dose, block 1725 is executed. In order to calculate how long to vaporize a requested dose, the MCU 1501, can read in the necessary constant $R_{temp}$ and perform the calculation $Mass_{vaporized}/R_{temp} = Time_{vaporize}$ $Time_{vaporize}$ can be expressed in terms of a number of timer count values. In alternative embodiments, a table or list of $Time_{vaporize}$ values corresponding to possible doses at given temperatures can be stored in database 1600 and retrieved by the MCU 1501, however, storing the $R_{temp}$ values for a given inhalation media in memory IC 205 and performing the calculation on the MCU 1501 allows the control device 200 to function while not connected to a network.

In block 1726, a countdown timer is set to the number of counts determined in block 1725. In block 1727, the vaporizer element 109 is energized and a temperature feedback loop is used to maintain it at the desired temperature. In block 1728, the countdown timer is decremented and in decision block 1729, the countdown timer is evaluated to determine whether it is above zero. If the countdown timer is greater than zero, decision block 1730 is executed to determine whether the full requested dose has been dispensed. If the user requests a dose larger than can be placed on the vaporizer element 109 at a given time, an amount less than the requested dose will be initially placed on the vaporizer element 109. The amount initially placed can be recorded in memory 1503 and/or memory IC 205 and compared against the requested amount. This comparison is done in decision block 1730. If the requested dose has been fully dispensed, the program loops to block 1727. If the requested dose has not been fully dispensed, then the MCU 1501 can drive dispensing motor 112 to dispense an incremental amount of inhalation media onto vaporizer element 109 before looping to block 1727. The MCU 1501 can loop through the aforementioned processes until such time as the countdown timer value reaches zero. At such time, block 1732 is executed by deactivating the vaporizer element 109 and terminating the process in block 1733.

It should be noted that, in accordance with the device control scheme 1700, looping through the time-based vaporization control loop 1712*a* can also be interrupted by the termination of the user's inhalation. If this occurs before block 1733 is reached, the most recent value stored in the countdown timer is preserved and a continuation state variable can also be set in memory IC 205 and/or memory 1503. Upon the next initiation of the time-based vaporization control loop 1712*a*, the result of decision block 1724 will be a continuation directly to block 1727 because the value of the countdown timer is greater than zero and/or because the continuation state variable is set to indicate continuation.

Figure 17C:
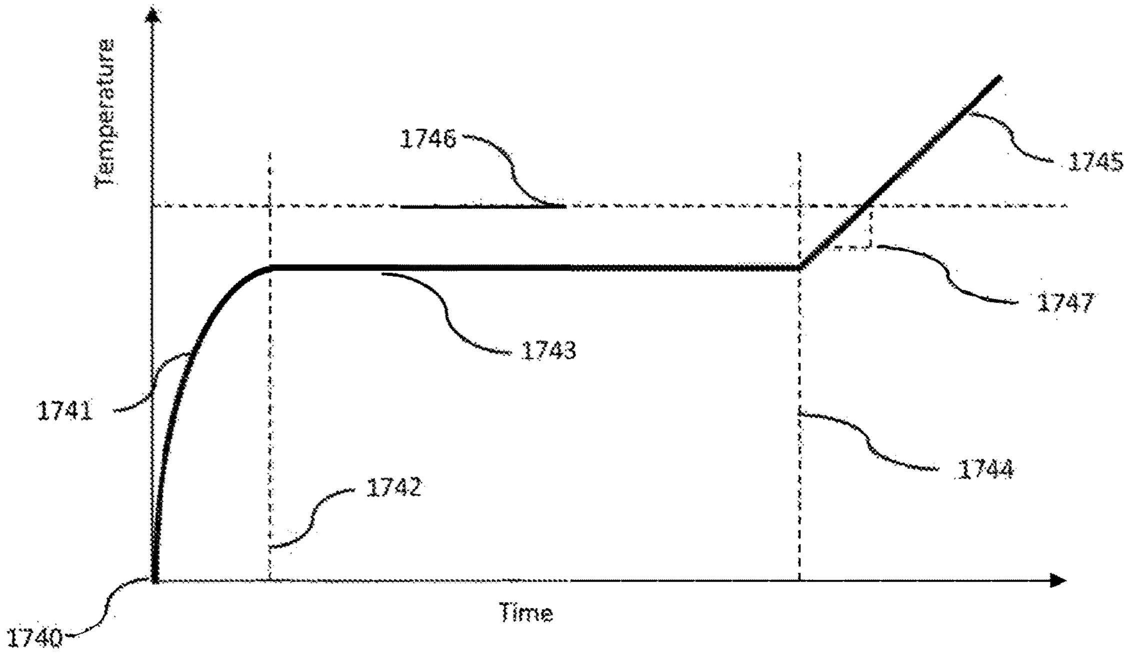
FIG. 17C shows an alternative example detail of how to control the dispensing and vaporization of inhalation media according to an aspect of the disclosure.

FIG. 17C describes an alternative embodiment of block 1712. Temperature-based vaporization control loop 1712*b* involves setting the power delivered to the vaporizer element 109 to a given level and monitoring the temperature. Temperature control curve 1740 represents the temperature of the vaporizer element 109 for a given power level. Upon initially energizing the vaporizer element 109, the temperature climbs rapidly in temperature warmup region 1741 as energy flowing from the vaporizer element 109 increases the temperature of the inhalation media. As the inhalation media reaches its vaporization temperature, energy from the vaporizer element 109 causes a phase change in the inhalation media, producing vapor for inhalation beginning approximately at the temperature vaporization threshold 1742. As vaporization occurs, the temperature stabilizes in the temperature stability region 1743. When the inhalation media is exhausted (fully or near fully vaporized off of the vaporizer element 109) at media exhaustion time 1744, energy from the vaporizer element 109 no longer flows into inhalation media and the temperature of the vaporizer element 109 begins to rise rapidly in the temperature exhaustion region 1745.

The MCU 1501 can be configured to recognize the characteristics of the aforementioned regions. When the temperature exhaustion region 1745 is reached, the MCU 1501 can be configured to detect a temperature rise above the temperature limit 1746, de-energize the vaporizer element and terminate the temperature-based vaporization control loop 1712*b*. The temperature limit 1746 can be a value that is unique to each inhalation media formulation and can be stored in memory IC 205, memory 1503, computing device 1803, and/or database 1600. Alternatively, the temperature limit 1746 can be set to a percentage above the temperature stability region 1743. The MCU 1501 can be further configured to calculate a rate of temperature rise 1747 in order to determine when the inhalation media is exhausted. This method is possible because the rate of temperature change during the temperature exhausting region 1745 can be distinguishably different than that of the temperature stability region 1743.

Similar to block 1730 and block 1731 of the time-based vaporization control loop 1712*a*, the temperature-based vaporization control loop 1712*b* can include provisions to dispense additional inhalation media during inhalation if necessary, for example to deliver a dose greater than that which can be initially dispensed onto the vaporizer element 109. This would preferably be done during the temperature stability region 1743. Also similar to the time-based vaporization control loop 1712*a*, the temperature-based vaporization control loop 1712*b* can be interrupted by the termination of the user's inhalation.

Figure 17D:
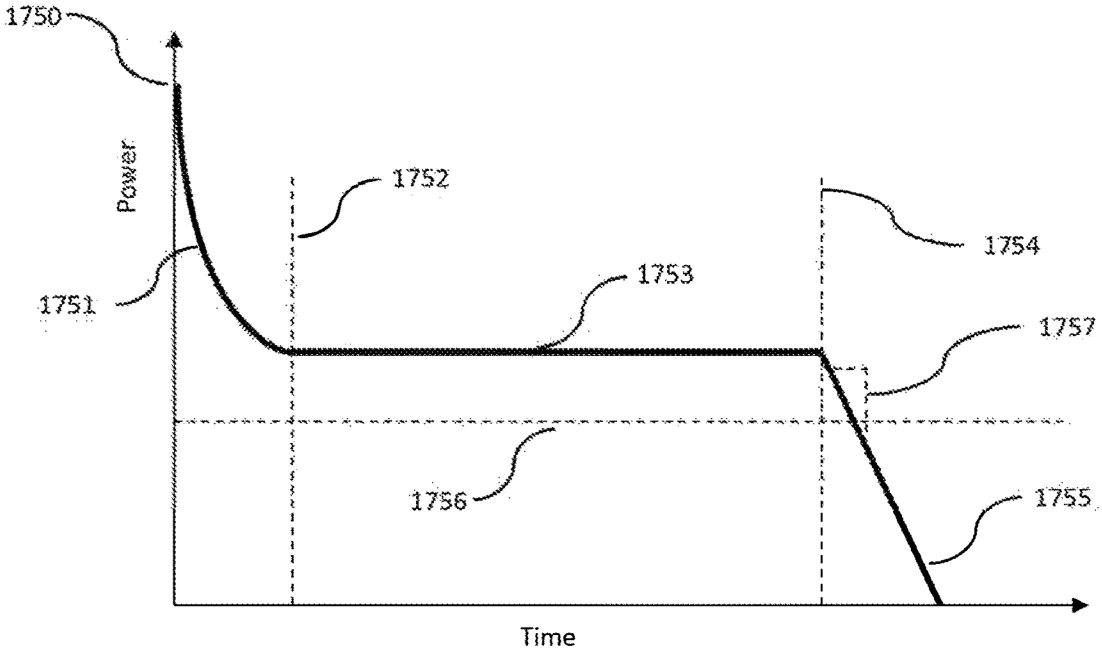
FIG. 17D shows an alternative example detail of how to control the dispensing and vaporization of inhalation media according to an aspect of the disclosure.

FIG. 17D describes another example embodiment of block 1712. Power-based vaporization control loop 1712*c* involves setting the temperature delivered to the vaporizer element 109 to a given level and monitoring the power needed to maintain that temperature. Power control curve 1750 represents the power delivered to the vaporizer element 109 in order to maintain it at a set temperature. Upon initially energizing the vaporizer element 109, the power needed to achieve the desired temperature declines rapidly in power initiation region 1751 as energy flowing from the vaporizer element 109 increases the temperature of the inhalation media. As the inhalation media reaches its vaporization temperature, energy from the vaporizer element 109 causes a phase change in the inhalation media, producing vapor for inhalation at approximately the power vaporization threshold 1752.

As vaporization occurs, the power needed to maintain the desired temperature stabilizes in the power stability region 1753. When the inhalation media is exhausted at power media exhaustion time 1754, energy from the vaporizer element 109 no longer flows into inhalation media and the power delivered to the vaporizer element 109 begins to decrease rapidly in the power exhaustion region 1755.

The MCU 1501 can be configured to recognize the characteristics of the aforementioned regions. When the power exhaustion region 1755 is reached, the MCU 1501 can be configured to detect a power decrease below the power limit 1756, de-energize the vaporizer element and terminate the power-based vaporization control loop 1712*c*. The power limit 1756 can be a value that is unique to each inhalation media formulation and can be stored in memory IC 205, memory 1503, computing device 1803, and/or database 1600. Alternatively, the power limit 1756 can be set to a percentage below the power stability region 1753. The MCU 1501 can be further configured to calculate a rate of power decrease 1757 in order to determine when the inhalation media is exhausted. This method is possible because the rate of power change during the power exhausting region 1755 can be distinguishably different than that of the power stability region 1753.

Similar to block 1730 and block 1731 of the time-based vaporization control loop 1712*a*, the power-based vaporization control loop 1712*c* can include provisions to dispense additional inhalation media during inhalation if necessary, for example to deliver a dose greater than that which can be initially dispensed onto the vaporizer element 109. This would preferably be done during the power stability region 1753. Also similar to the time-based vaporization control loop 1712*a*, the power-based vaporization control loop 1712*c* can be interrupted by the termination of the user's inhalation.

Figure 18:
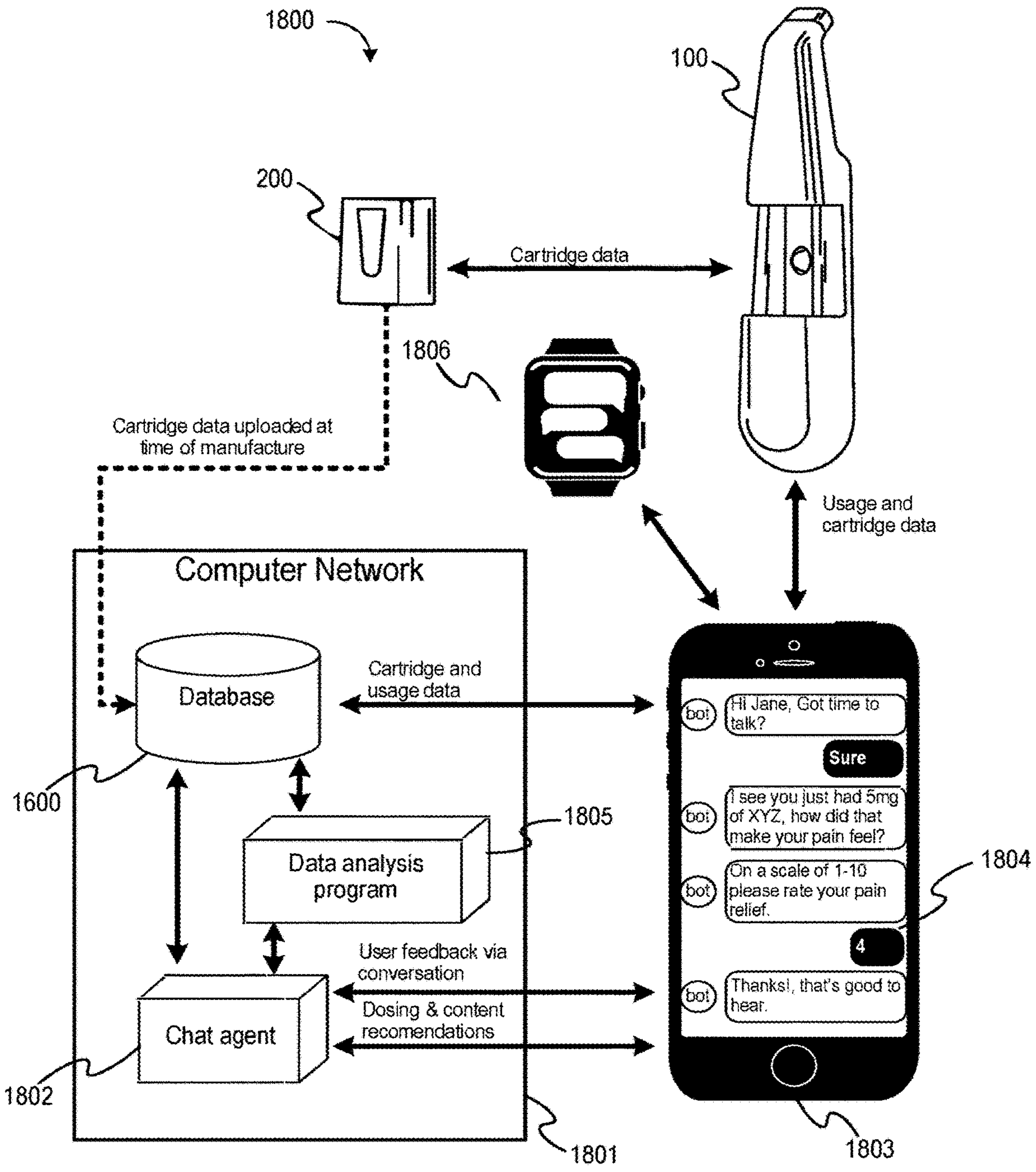
FIG. 18 shows an example of a networked system for exchanging data according to an aspect of the disclosure.

FIG. 18 describes the dosing network system 1800 which can be comprised of control device 100, cartridge 200, computing device 1803 and computer network 1801. Data elements related to the characteristics of the inhalation media, cartridge 200 and/or manufacture thereof can be exchanged between the control device 100 and cartridge 200. The data elements stored in cartridge 200 can also be uploaded to a database 1600 located within the computer network 1801 at any time during the manufacturing, filling or use of cartridge 200. Uploading such data elements during manufacturing or filling can be accomplished via a control device 100 or via a manufacturing fixture (not shown) designed to interface with memory IC 205 and computer network 1801. Uploading data elements immediately after manufacturing and/or filling creates a record of the cartridge 200 associated inhalation media that can be beneficial to the management and tracking of inventory as well as anti-counterfeit and validation measures.

Data elements related to product consumption, including, but not limited to: dose event time, dose event duration, dose quantity, dose properties and inhalation media amount remaining are typically generated or updated by the control device 100. While such consumption related data elements can also be stored in memory IC 205, memory 1503, and/or computing device 1803, they are typically uploaded to database 1600 via a first communication link between control device 100 and computing device 1803 which in turn links to computer network 1801 via a second communication link. The second communication link can typically be a digital cellular, Zigbee, or Wi-Fi connection. In other embodiments, control device 100 can incorporate circuitry necessary to communicate directly to computer network 1801.

Such consumption related data elements can be uploaded to the database 1600 upon each triggering event, typically an inhalation, or as a batch. Computing device 1803 can have a feedback application 1804 configured to display communications and accept feedback from the user regarding the effects of the doses of inhalation media. Feedback application 1804 can be additionally configured to accept background information from the user, including, but not limited to age, weight, gender, physical conditions, and the user's reason for consuming inhalation media. Feedback application 1804 can be a computer application residing on computing device 1803 or it can be a remote interface of an application executing within computer network 1801. Communications, feedback and information provided via computing device 1803 can alternatively or additionally be provided through a constituent display enabled control device 2100 or a connected accessory such as a smart watch 1806.

Computer network 1801 can contain a chat agent 1802 configured to solicit feedback from the user and store said feedback in the database 1600. Chat agent 1802 can be further configured to solicit background information from the user. Feedback can be solicited at any time, however, it can be especially useful to solicit such feedback in response to dosing events. For example, if it is expected that the pain relief effects of a particular inhalation media would be felt 10 minutes after dosing, the chat agent 1802 can be configured to send the user a communication 10 minutes after a dosing event occurs and/or is received in the database 1600. The chat agent 1802 can ask the user a series of questions and can tailor its questions according to the answers given by the user. For example, the chat agent 1802 can ask the user to rate the pain relief provided by a dose of a particular inhalation media on a numeric scale, higher values providing higher degrees of pain relief. If the user responds with a low numeric value, the chat agent 1802 can ask the user why they thought the pain relief value was low. By way of an additional example, the chat agent 1802 can also solicit feedback if there are unusual patterns in dosing behavior and/or extended periods without dosing. For example, if the user discontinues consuming inhalation media designed to provide pain relief that can indicate that the underlying condition which was causing the pain was resolved. The chat agent 1802 can ask questions regarding the underlying condition.

Computer network 1801 can further contain a data analysis program 1805, configured to analyze information stored in the database and determine the optimal dose amount, frequency, timing, type and other properties for a given user. Such dosing information can be provided to the user via the chat agent 1802. The data analysis program 1805 can be additionally configured to monitor user consumption and provide additional types of feedback. For example, the data analysis program 1805 can determine that the data element associated with the plunger driver 116 indicates that the majority of the inhalation media within cartridge 200 has been consumed and can trigger the chat agent 1802 to send a communication to the user in order to alert them to this condition and provide the user with information regarding how to purchase an additional cartridge 200, a coupon for the purchase of an additional cartridge 200 or even connect the user with a digital order fulfillment system for the purpose of purchasing additional cartridges 200. Data analysis program 1805 can be additionally configured to initiate other types of communication to the user, including, but not limited to: sales promotions, discounts, educational information, inventory levels, new product introduction, expiration dates, and recall information. While providing such dosing and other types of communications to the user via a chat agent 1802 provides an easy-to-understand interface to the user, alternative embodiments exist where such information is sent to the computing device 1803 and displayed by an application that is not a chat type of application or interface.

Figure 19:
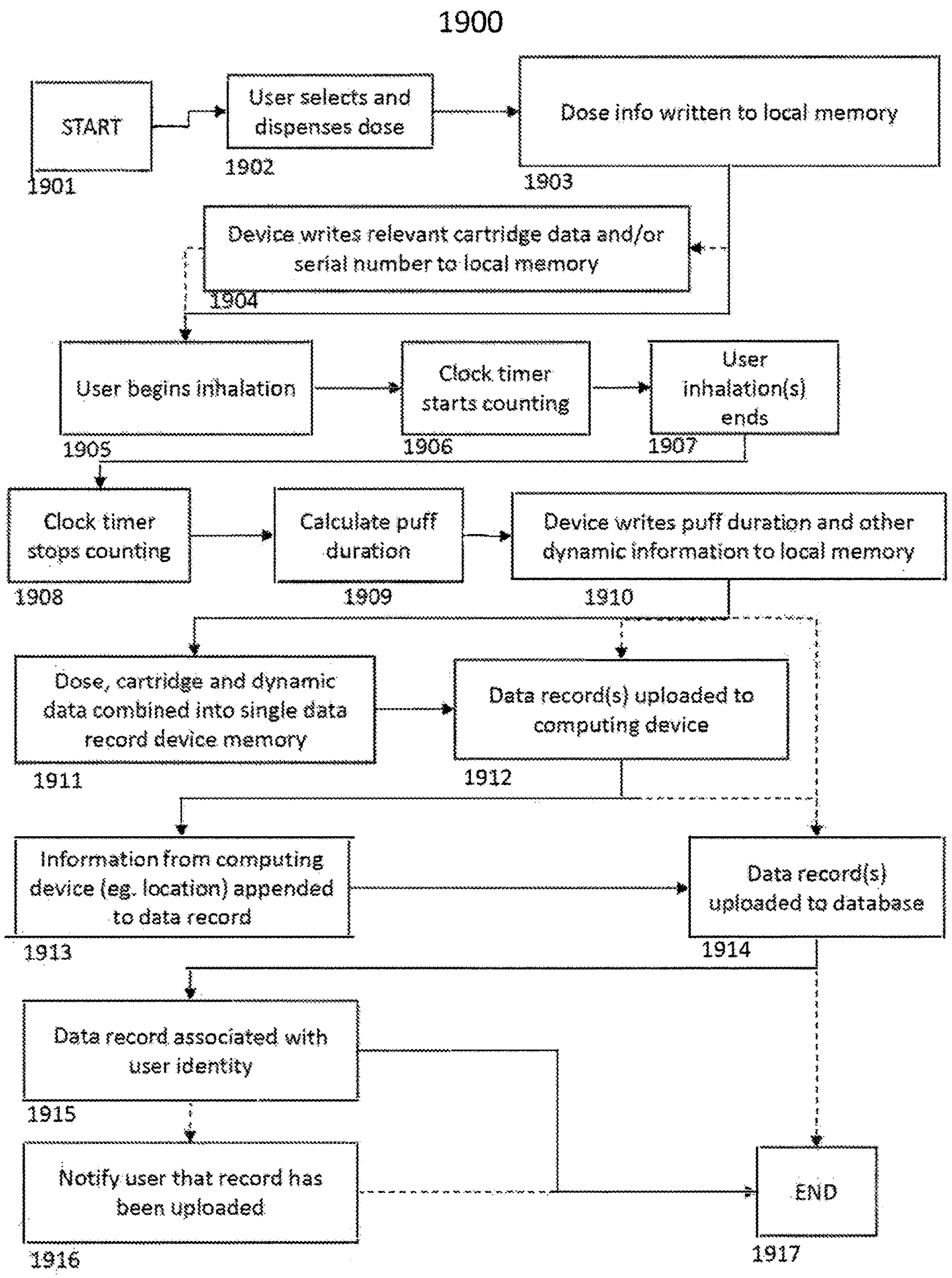
FIG. 19 shows an example of how usage data is generated according to an aspect of the disclosure.

FIG. 19 shows a dose recording process 1900 which can be used to capture dosing information and store it in the database 1600. Dose recording process 1900 starts at block 1901. When the user selects and dispenses the desired dose in block 1902, the dosing information, including dose amount, is stored in memory 1503 in block 1903. MCU 1501 can be additionally configured to read and store certain data elements from the memory IC 205 in memory 1503 in block 1904. In this way, the memory 1503 has a full record of the dose that is to be inhaled. When the user begins inhalation in block 1905, the MCU 1501 starts a clock timer in block 1906 until the user completes his inhalation in block 1907 and the clock timer stops in block 1908. The MCU 1501 can be configured to use an internal timer as the clock timer or can be configured to use an external clock such as real-time clock 1504 to provide accurate time information. Next, the duration of the inhalation can be calculated in block 1909 by subtracting the clock timer start value from the clock timer end value. In block 1910, inhalation duration and other dynamic information can be written to memory 1503. Such dynamic information can include, but is not limited to, time of day of the inhalation, strength of inhalation, ambient temperature, temperature of the vaporizer element 109 during the inhalation, and strength of inhalation. At this point, memory 1503 now contains a record of the inhalation that includes both the inherent characteristics of the inhalation media and the dynamic characteristics of the individual inhalation event. Such information can be combined into a single data structure in block 1911 then sent to computing device 1803 in block 1912. Alternatively, such information can be sent piece-by-piece directly to the computing device 1803.

Once the record is stored in the computing device 1803, additional information can be added to the record in block 1913. Such additional information can include information that may be knowable to the computing device 1803, but not the control device 100. Such additional information can include, but is not limited to, GPS coordinates, weather conditions, account information, recent medication, mood, heart rate, blood pressure, physical movement, respiratory rate, blood oxygen level, ECG, EKG and other biometric information that can be available to computing device 1803. Some of such additional information can be provided to computing device 1803 via a connected accessory such as a smart watch 1806, heart rate monitor, ECG monitor, or blood pressure monitor. The data record can now include information from the cartridge 200, control device 100 and computing device 1803. This complete data record can be uploaded to database 1600 in block 1914. In the process of storing the record in the database, it can be associated with the user in block 1915. One way an association may be made is via a user account name or account number. Once the record has been associated with the user, the computer network 1801 can be optionally configured to send a message to the user via computing device 1803 indicating that the most recent dose has been recorded, thus ending the process at block 1917. The step-wise assemblage of the data record does not need to be performed. Rather, the data elements can be uploaded to the database 1600 separately, as they become available, and then associated at the database 1600 level. In additional alternative embodiments, control device 100 can communicate directly with the computer network 1801 and may not necessarily include information provided by the computing device 1803.

Figure 20:
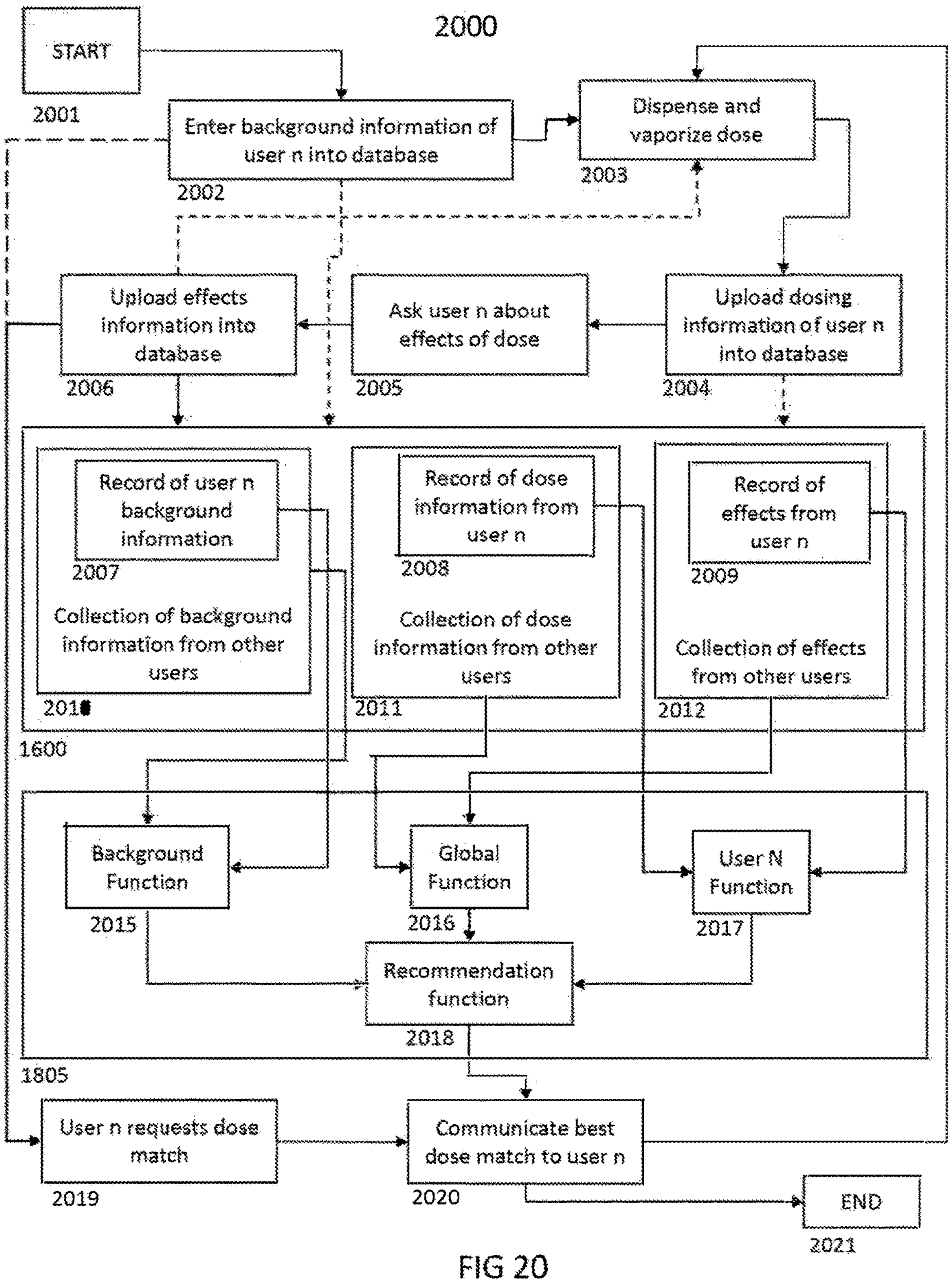
FIG. 20 shows an example of how effects and dosing recommendations are determined and communicated according to an aspect of the disclosure.

FIG. 20 shows a dose recommendation process 2000 by which the dosing network system 1800 can determine and provide dosing suggestions to the user. Dose recommendation process 2000 can contain information pertaining to a plurality of users. Each user can be differentiated by a unique account number, name, or other form of unique identifier. For the purpose of the present description, "user n" refers to a specific user defined by his unique identifier "n" where n is a unique number associated with that user. The process starts at block 2001. In block 2002, the user n enters background information into the database 1600 via a feedback application 1804, other application on computing device 1803, control device 100, in-line constituent control device 3501, or constituent display enabled control device 2100. Such background information can be comprised of user n characteristics and other information relevant to determining optimal dose parameters of inhalation media. Such background information can include, but is not limited to: age, weight, gender, physical conditions including ailments, the user's mental condition and ailments, prior consumption of other inhalation media, drug and medication usage, and the user's reason for consuming inhalation media. The user n can provide and update such information at any time, however, it is preferable to provide such information before initial use.

After providing such information, user n consumes the inhalation media in block 2003. In response to the inhalation, user n's dosing information can be uploaded to the database 1600 in block 2004. Blocks 2003 and 2004 can collectively be performed in accordance with dose recording process 1900. After inhalation, chat agent 1802 solicits feedback regarding the effects of the dose from user n in block 2005. The type of effect feedback requested, can include, but is not limited to, rating pain relief, rating effect on a physical ailment or condition, mood change, state of mind change, level of anxiety, change in appetite, and side effects. Chat agent 1802 can also solicit other relevant feedback at this time, including, but not limited to: other medications taken recently, recent notable events, and recent food and beverage consumption. Such feedback from user n is stored in database 1600 in block 2006. It should be noted that although blocks 2002 through 2006 can occur in a sequential manner, it is also possible that certain blocks can be skipped in certain instances. For example, user n can perform block 2002, then skip directly to a dose recommendation in block 2019 before performing block 2003. The dashed lines in FIG. 20 indicate where the user can skip to different steps in the process.

Data elements and feedback stored in database 1600 can be labeled and grouped in such a manner so as to facilitate data analysis. For example, database 1600 can contain a global background collection 2010, which is a collection of background information from all users of the system, including a user n background record 2007. Database 1600 can also contain a global dose collection 2011, which is a collection of the dosing information from all users of the system, including a user n dosing information record 2008. Database 1600 can further contain a global effects collection 2012, which is a collection of the effect information reported by all users of the system, including a user n effects record 2009. Data analysis program 1805 can be configured to analyze global background collection 2010, global dose collection 2011, and global effects collection 2012 in order to extrapolate patterns and/or find correlations. Such extrapolations or correlations can be used to identify the optimal dose information for user n. Modern data mining techniques offer many approaches to make such extrapolations, including, but not limited to: tracking patterns, classification, association, outlier detection, clustering, regression and prediction. Data analysis program 1805 can employ one or more of these techniques in order to identify the optimal dose for user n.

One example simplified approach is shown in FIG. 20. Background function 2015 can be a function that compares user n background record 2007 with all users in the global background collection 2010 in order to determine which users are most similar to user n. It can assign a value to each user as a function of their similarity to user n. Global function 2016 can be a function that receives data from the global dose collection 2011 and the global effects collection 2012 and determines which doses have the maximum effect on the entire user population. User n function 2017 can be a function that receives data from user n dosing information record 2008 and user n effects record 2009 and determines which doses had the maximum effect on user n.

The outputs of the background function 2015, global function 2016 and user n function 2017 can be received by the recommendation function 2018. Recommendation function can be configured to determine which doses had the maximum effect for users who are most similar to user n and compare that to the most effective doses consumed by user n. If the doses for similar users had a greater effect than those already consumed by user n, then recommendation function 2018 can suggest that user n try the dose that had a greater effect for similar users. Data analysis program 1805 can also be configured to extrapolate other patterns or find other correlations, including, but not limited to: drug interactions, side effects, tolerance build-up, adaptation, treatment of disease, improvement of physical or mental condition, and food interactions. The data analysis program 1805 can adjust recommendations in response to such patterns. For example, it may notice that users tend to develop a tolerance to a certain inhalation media and can adjust the recommendation in order to compensate accordingly.

After recommendation function 2018 has produced a recommendation, the recommendation can be communicated to the user in block 2020. This can be communicated via feedback application 1804 or some other application program executing on computing device 1803, control device 100, in-line constituent control device 3501, or constituent display enabled control device 2100. It should also be noted, that such communication can be in response to a request for dose match from user n in block 2019. Alternatively, data analysis program 1805 can be configured to trigger such a communication whenever a dose that produces a greater effect for similar users to that of user n is identified. Dose recommendation process 2000 terminates with block 2021. It should be further noted that dose recommendation process can be a perpetual process where additional data is continuously added to the database 1600 via one or more users, analysis is performed on an on-going basis, and recommendations are made on and on-going basis.

Figure 21A:
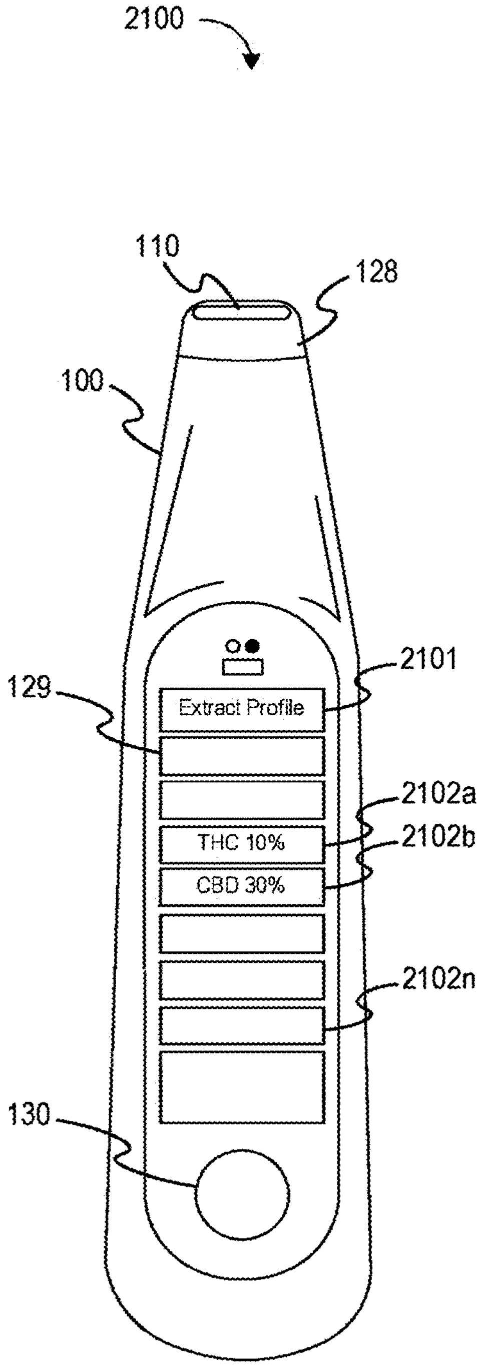
FIG. 21A shows an example of how cartridge information is displayed according to an aspect of the disclosure.

FIG. 21A shows a constituent display enabled control device 2100 which is an embodiment of control device 100 that contains a display screen 129 configured to display the composition of inhalation media contained in cartridge 200. Display screen 129 can display a header 2101 that provides a general description and/or name of the inhalation media contained in cartridge 200. Display screen 129 can be further configured to display one or more key constituents 2102_a_-2102n of the inhalation media. Key constituents can include, but are not limited to, cannabinoids, nicotine, flavonoids, terpenes, terpenoids, drugs, medicines, active ingredients, preservatives, solvents, and carrier materials. Display screen 129 can be further configured to display additional information about the inhalation media, cartridge 200, and/or constituent display enabled control device 2100. Control pad 130 can be used to navigate the displayed information in order to see additional constituents not displayed on the display screen 129. Control pad 130 can additionally be configured to select constituents for the purpose of indicating to the constituent display enabled control device 2100 which constituent the user desires to dose as well as the amount of the constituent the user wants to consume.

Figure 21B:
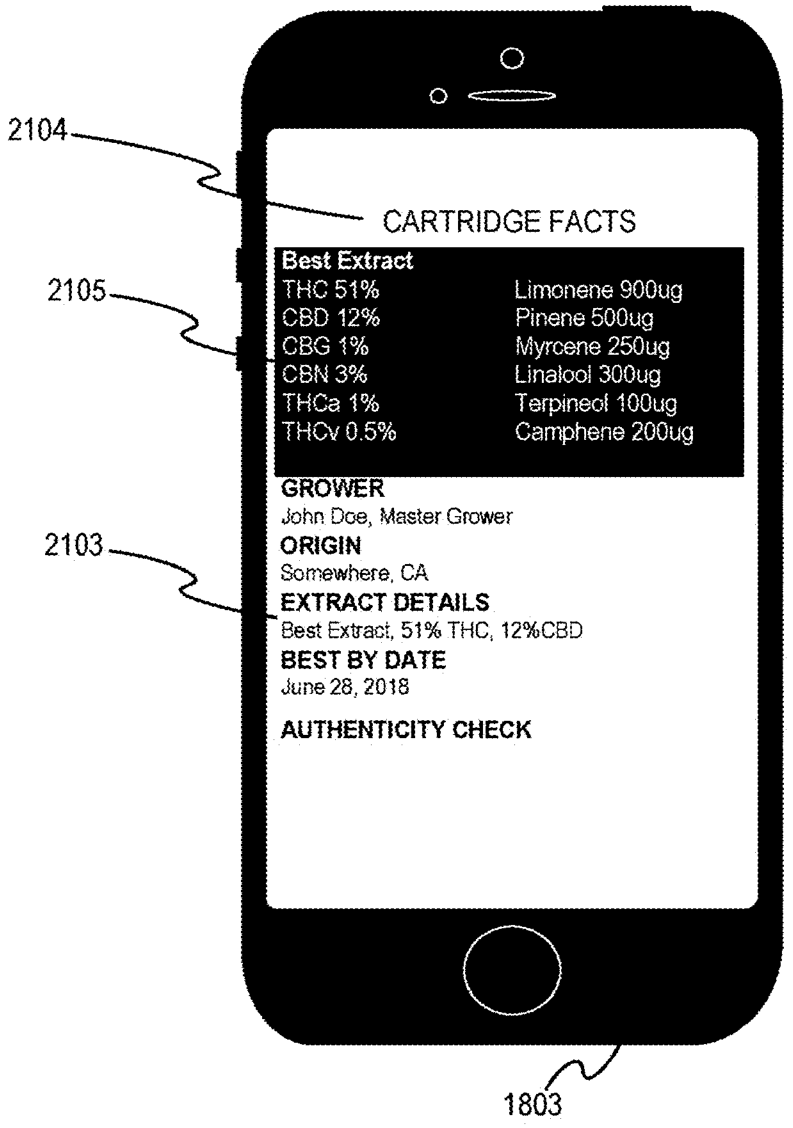
FIG. 21B shows another example of how cartridge information is displayed according to an aspect of the disclosure.

FIG. 21B shows a dose visualization application 2103 configured to communicate with control device 100, in-line constituent control device 3501, or constituent display enabled control device 2100 and display the composition of inhalation media in cartridge 200. Dose visualization application 2103 can be configured to run on computing device 1803. Dose visualization application 2103 can be additionally configured to display an application header 2104 and a constituent listing 2105. The user can use the controls provided by computing device 1803 to navigate through the constituent listing. Dose visualization application 2103 can be additionally configured to allow the user to select the constituent the user desires to dose as well as the amount of the constituent the user wants to consume in a dose. Dose visualization application can be additionally configured to display other information related to the inhalation media, including, but not limited to: the date of manufacture, expiration date, origin information, producer information, production process information, testing information, potency, and proof of authenticity.

Figure 21C:
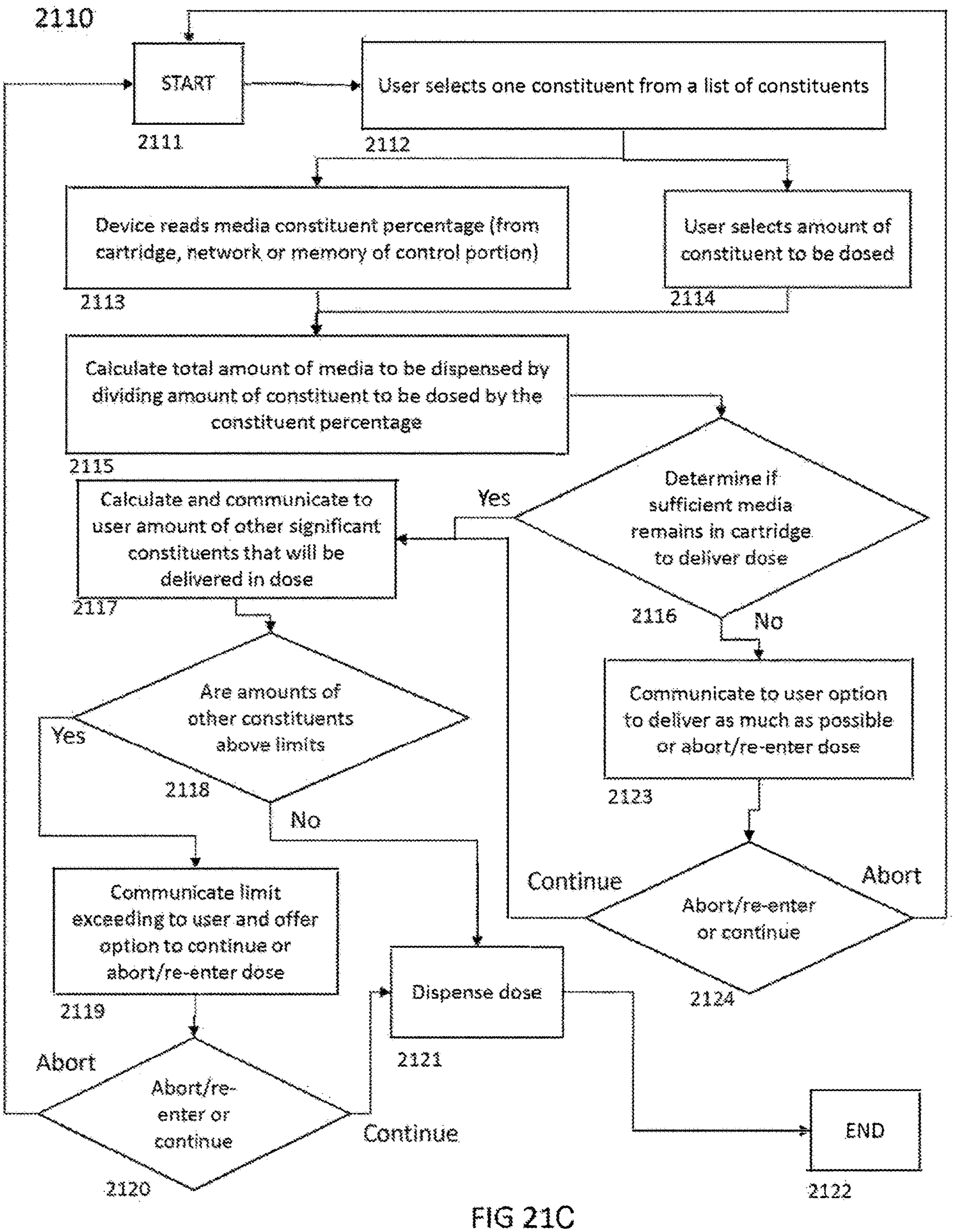
FIG. 21C shows an example of how dosing controls are generated according to an aspect of the disclosure.

FIG. 21C shows constituent dosing process 2110 which starts with block 2111. The user selects the constituent to be dosed in block 2112 and the amount of constituent to be dosed in block 2114. Such selection can be made via a constituent display enabled control device 2100, in-line constituent control device 3501, or a dose visualization application 2103 that is in communication with either a control device 100, constituent display enabled control device 2100, or in-line constituent control device 3501. In block 2113, the percentage composition of the selected constituent and other key constituents is read into memory 1503. In block 2115, the total amount of inhalation media to be dispensed in order to deliver the requested dose of the target constituent is calculated by MCU 1501.

The mathematical formula for the calculation can be represented as, (Requested Dose of Constituent–Percentage by Mass of Requested Constituent Present in Inhalation Media=Total Amount of Inhalation Media to be Delivered). By way of example, if the user requested a dose of 5 mg of CBD from a cartridge 200 that contained inhalation media with a CBD composition of 25% by mass, then 20 mg of total inhalation media can be the result of the calculation. In decision block 2116, the MCU 1501 reads the memory IC 205 and determines whether sufficient inhalation media remains to deliver the requested dose. Continuing the example from above, the cartridge 200 would need to contain at least 20 mg of inhalation media.

If there is not sufficient inhalation media remaining, then this condition is communicated to the user in block 2123 and in decision block 2124, the user is given the choice to either continue and dispense a partial dose or to abort the dose request and restart the process. If there is sufficient inhalation media to deliver the requested dose or if the user choses to receive a partial dose, the amount of other key constituents that will be delivered is calculated and communicated to the user in block 2117. Continuing the example above, if the inhalation media contained 1% pinene, and pinene had been selected as a constituent of interest, control device 100 can communicate to the user that 0.20 mg of pinene would be delivered in the dose. Constituents of interest can be determined by the user or can be automatically retrieved from a list stored in database 1600 or computing device 1803. By way of example, constituents with known toxicity above certain amounts can be included in the list of constituents of interest.

In decision block 2118, MCU 1501 can be configured to compare the amount of one or more constituents in the requested dose to a limit. A list of dose constituent limits can be stored in memory 1503, memory IC 205, computing device 1803 or database 1600 where such limit information can be accessed by MCU 1501 via aforementioned communication links. Such limits can be set by the user, a third party, or determined by data analysis program 1805. If such limits are exceeded, the condition is communicated to the user in block 2119 and the user may choose to abort the requested dose and start over or continue with the dose in decision block 2120.

Continuing with the aforementioned example, if the dose limit for pinene had been set to be 0.10 mg, then the user can be notified of this condition in block 2119. If the user either selects to continue the dose in decision block 2120 or no limit is exceeded in block 2118, then the control device 100, in-line constituent control device 3501, or constituent display enabled control device 2100 dispenses the dose in block 2121 followed by completion of the process in block 2122. Completing the aforementioned example, 20 mg of inhalation media would be dispensed for inhalation by the user. It should be noted that by knowing the density of the inhalation media and percentage constituent composition by mass, which can be stored in memory IC 205, memory 1503, computing device 1803, and/or database 1600, the MCU can calculate the volume of inhalation media to dispense in order to deliver the requested dose.

The calculation of constituent amounts, checks for sufficient inhalation media, and comparison with constituent dosing limits need not occur in a constituent display enabled control device 2100, in-line constituent control device 3501, or a control device 100. These actions can be performed by an application residing on the computing device 1803 or computer network 1801. In such embodiments, the resultant amount of dose to dispense can be communicated to the constituent display enabled control device 2100, in-line constituent control device 3501, or control device 100. It should be further noted in embodiments where constituent display enabled control device 2100, in-line constituent control device 3501, or control device 100 are be configured to receive and dispense inhalation media from a plurality of simultaneously connected cartridges 200, the amount of inhalation media to be dispensed from each cartridge 200 can be determined separately in order to provide the user with the closest match to their requested dose constituent profile. For example, it may be determined that 7 mg should be dispensed from a first cartridge 200 and 3 mg from a second cartridge 200 in order to produce a 10 mg dose with the desired constituent composition.

Figure 22A:
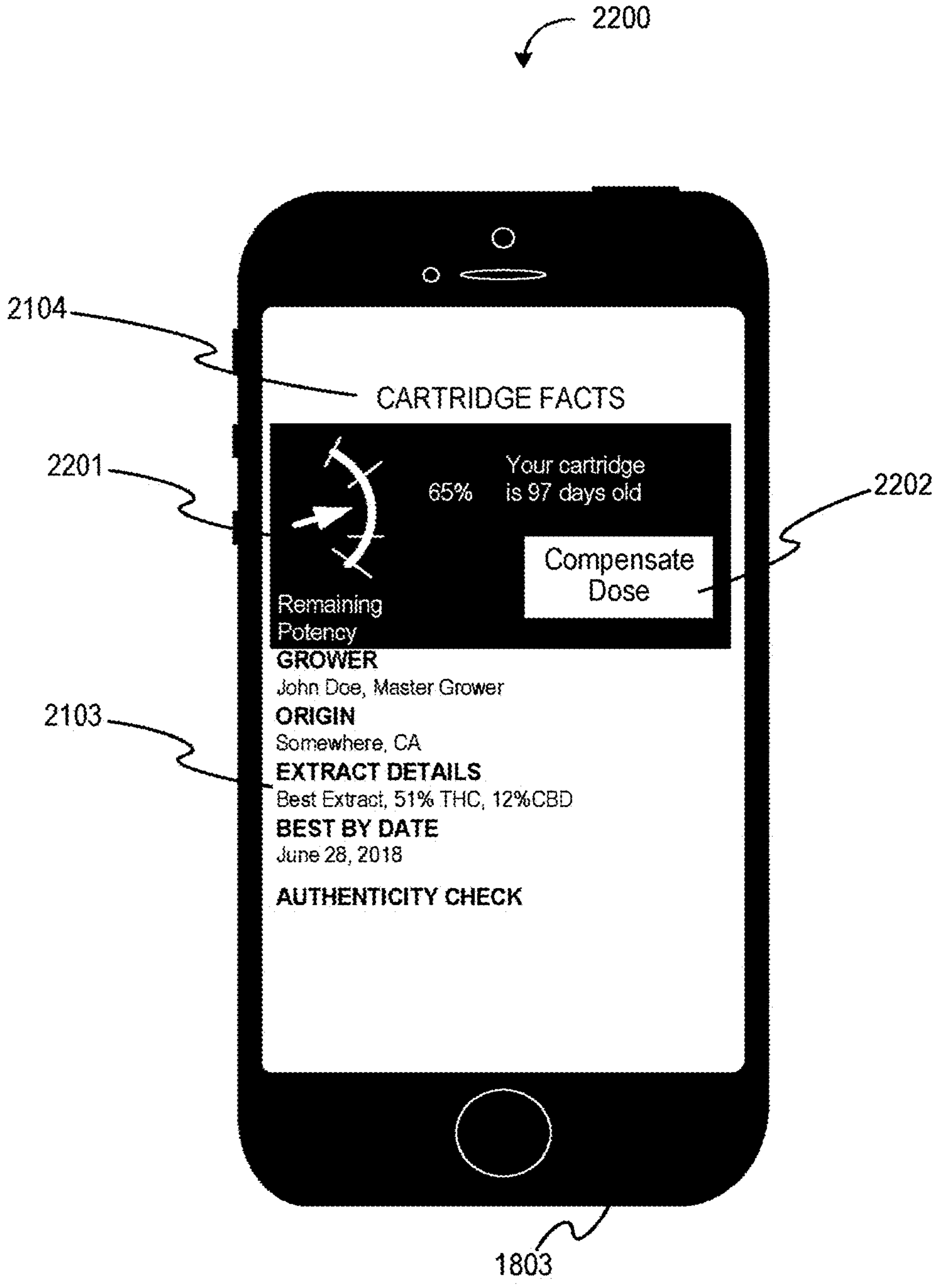
FIG. 22A shows another example of information that can be used to inform dosing controls according to an aspect of the disclosure.

Inhalation media can change in composition over time due to a number of factors, including, but not limited to: exposure to elevated temperature, radiation, moisture, UV light, oxygen, and chemical reaction with other constituents. FIG. 22A shows an aspect of the dose visualization application 2103 configured to display such changes in the potency or composition of inhalation media in cartridge 200 and compensate doses to account for such changes. The dose visualization application 2103 can contain a constituent change indicator 2201 which provides the user with a visual representation of the degree to which a particular constituent or group of constituents has changed since it was manufactured, tested, and/or filled into cartridge 200. The dose visualization application 2103 can further include a compensation selector 2202 which will cause the control device 100, constituent display enabled control device 2100, or in-line constituent control device 3501 to dispense a compensated dose. For example, if a user wanted to consume a 1 mg dose of nicotine from an inhalation media that was originally 5% nicotine by mass, but it was determined that the percentage of nicotine in the inhalation media had decreased by 50%, then a total dose of 40 mg would be dispensed so that the user would receive the desired 1 mg of nicotine.

Figure 22B:
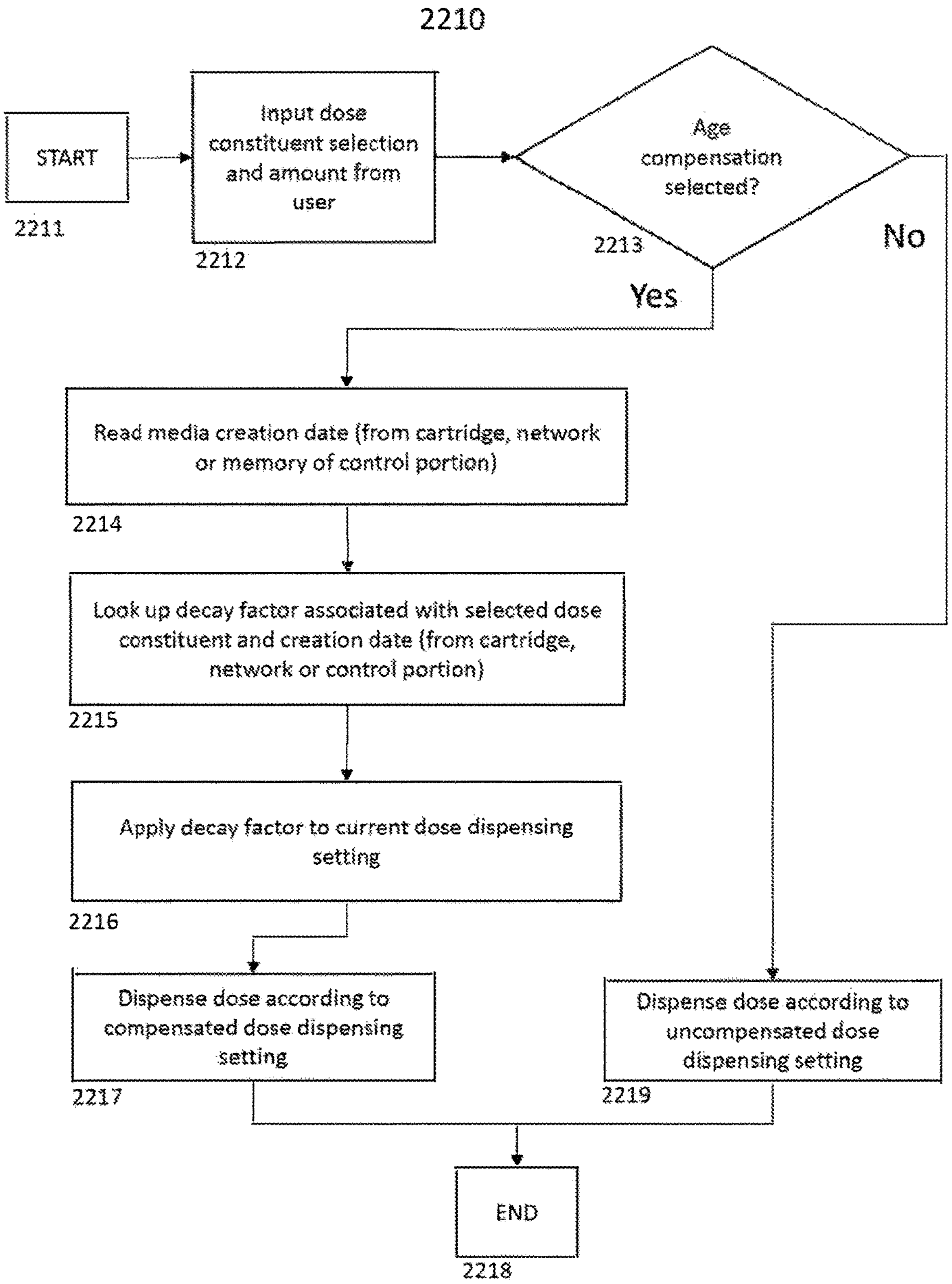
FIG. 22B shows another example of how dosing controls are generated according to an aspect of the disclosure.

FIG. 22B shows a dose compensation process 2210 used to adjust the dose in order to compensate for changes in composition. The process begins with block 2211. In block 2212, the user inputs the desired constituent for dosing and the amount of that constituent he desires, i.e., the dose target. As noted above, a control circuit comprising a processor, e.g., control circuit 120 that can comprise an MCU 1501, will then determine the inhalation media dose needed to deliver the dose target. In the process of FIG. 22B, however, the user selects whether he wants to use dose compensation in decision block 2213. If the user does not so select, then the uncompensated inhalation media dose is delivered in block 2219 followed by completion of the process in block 2218.

If on the other hand, the user requests dose compensation, then the control circuit can consult one or more compensation values, e.g., stored in memory, for one or more compensation categories, in order to determine the properly compensate inhalation media dose to ensure that the dose target is met. For example, if the compensation category is age, then creation date, testing date, or age of the inhalation media can be read from the memory IC 205, memory 1503, computing device 1803, or database 1600 in block 2114. In block 2215, an age-related compensation factor, the compensation value in this case, associated with the selected constituent at its current age is retrieved from the memory IC 205, memory 1503, computing device 1803, or database 1600, any of which can contain a list of compensation factors for one or more constituents at a plurality of ages. Then the retrieved compensation factor is applied to the dose calculation.

For example, if a user wanted to consume a 5 mg dose of THC from an inhalation media that was originally 50% THC by mass, and the retrieved compensation factor based on the determined age was 1.5, then a total dose of 15 mg would be dispensed so that the user would receive the desired 5 mg of THC. In block 2217, the compensated inhalation media dose is dispensed then the process ends at block 2218.

Dose compensation process 2210 can be executed on control device 100, constituent display enabled control device 2100, in-line constituent control device 3501, computing device 1803, computer network 1801 or distributed among any one or more of these elements. Dose compensation process 2210 can also be combined with other processes such as constituent dosing process 2110.

Alternatively, or conjunctively, the dose compensation process 2210 can use equations rather than stored lists of compensation factors in order to adjust the dose. For example, if the change of one or more constituents follows a first order equation, the compensation factor of a given constituent can be calculated as: Compensation factor$=1 \div e^{-kt}$; where e=base of the natural logarithm, k=rate constant, and t=time. Each constituent can have its own unique rate constant k, the compensation value in this case, which can be stored in one or more of memory IC 205, memory 1503 computing device 1803, or database 1600 and retrieved for the purpose of performing the calculation.

It can be desirable not only to know by how much a first constituent increases or decreases, but also by how much other constituents change due to the change in a first constituent. For example, it is known that THC degrades into CBN over time, depending on temperature and exposure to other conditions. Thus, the rate of conversion from a first constituent into a second constituent can be characterized and captured in an equation or compensation factor such that the dose of the second constituent can be compensated according to the same process described above. As noted, the rate of conversion can be influenced by external conditions, e.g., compensation categories such as temperature.

In another alternative embodiment, the dose compensation process 2210 can take additional input from any of an ambient temperature sensor 1509, temperature sensor and data logger built into cartridge 200, oxygen sensor, moisture sensor, UV light sensor, radiation sensor or other environmental sensor. Using such environmental information, a more accurate compensation factor or rate constant, i.e., compensation value can be selected for use in the dose compensation calculation. In other words, compensation values for a plurality of compensation categories, e.g., temperature, oxygen level, moisture, UV light exposure, radiation exposure, etc., can be determined and stored for use in determining a inhalation media dose compensation.

It should be further understood that certain constituents may increase over time, as CBN does due to THC degradation. In certain cases, where the user requests a dose of a first constituent, the amount of one or more other constituents calculated to be in the dose after application of the dose compensation process 2210 can exceed threshold values. A list of dose constituent threshold values can, therefore, also be stored in memory 1503, memory IC 205, computing device 1803 or database 1600. By way of example, a threshold can be related to constituent toxicity at a level identified through pharmacological studies. Dose compensation process 2210 can be configured to automatically calculate the amounts of other constituents present in the inhalation media dose, notify the user if such amounts exceed any thresholds, and provide the user with a course of actions to take such as aborting the dose or adjusting the inhalation media dose.

Figure 23:
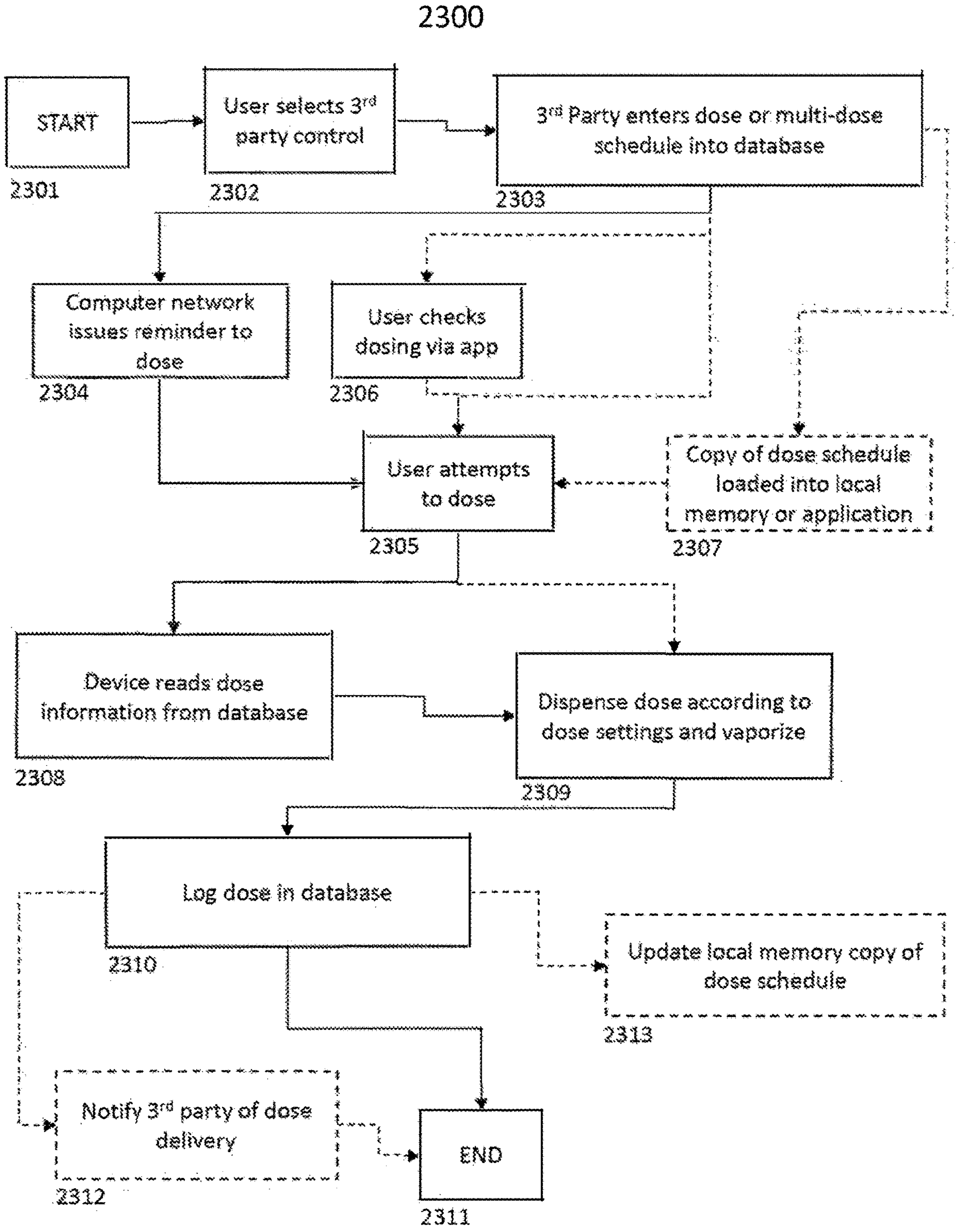
FIG. 23 shows another example of how dosing controls are generated according to an aspect of the disclosure.

FIG. 23 shows a remote dosing process 2300 in which dosing can be controlled by a third-party. Examples of third-parties include, but are not limited to: doctors, health care providers, nutritionists, advisors, and virtual agents, including data analysis program 1805. The potential benefits of remote control dosing include enabling third-parties to monitor the effects of dosing and adjust dosing accordingly, improving adherence to the correct dosing schedule, and ensuring the correct amount of inhalation media is consumed, thus reducing the likelihood of under-dosing and over-dosing. Data collected through monitoring remote control dosing by professionals can be used as training data to train machine learning systems to perform the dose recommendation function. The remote dosing process 2300 starts at block 2301. In block 2302, the user selects third-party control. Such a selection can be made via a dose visualization application 2103 configured to communicate with control device 100, in-line constituent control device 3501, or constituent display enabled control device 2100 or can be made directly via the built-in interfaces of control device 100, in-line constituent control device 3501, or constituent display enabled control device 2100. Alternative embodiments of control device 100, in-line constituent control device 350, and constituent display enabled control device 2100 can be pre-configured to only function with via remote dosing. In block 2303, the third party enters the dosing information into database 1600. In block 2304, an application running on computer network 1801 can issue reminders to the user when it is time to take a dose. Such reminders can typically be displayed on computing device 1803, although they can also be displayed on in-line constituent control device 3501 and constituent display enabled control device 2100. In block 2306, the user can optionally check for reminders and dosing information via an application, such as dose visualization application 2103, running on computing device 1803. When the user attempts to dose in block 2305, control device 100, constituent display enabled control device 2100, or in-line constituent control device 3501 can download the most current dosing information from database 1600 in block 2308. Optionally, a copy of such dosing information can be periodically downloaded in advance to any of control device 100, constituent display enabled control device 2100, in-line constituent control device 3501, or computing device 1803 to enable dosing when a connection to computer network 1801 is unavailable. In block 2309, the dose is dispensed and vaporized according to the processes previously described in this document. Once the dose has been vaporized, information about the consumption of that dose can be logged in database 1600 in block 2310. If the control device 100, constituent display enabled control device 2100, or in-line constituent control device 3501 also maintains a local copy of the dosing regimen, then the information about the consumption of that dose can also be logged in the memory of either control device 100, constituent display control device 2100, or in-line constituent control device 3501 in block 2313. Optionally, after the dose has been logged in block 2310, an application running on computer network 1801 can generate a notification to the third-party in block 2312. Such a notification can indicate that the dose has been consumed and/or certain characteristics about the dose such as the time when the dose was consumed. The process ends in block 2311.

It should be noted that remote dosing process 2300 can be used not just by third-parties, but also by the user himself. For example, the user may be concerned that he may be temporarily cognitively impaired by a certain inhalation media in his dosing regimen and may not be able to make good decisions once he begins to consume doses. In this situation, the user may wish to establish a dosing schedule of his own in database 1600 while not cognitively impaired. Since the system has the ability to limit the delivery of doses according to the schedule set in database 1600, the user would not be able to exceed the dosing limits while cognitively impaired. Third-parties and/or the user can also include lockout times in the dosing schedule in order to prevent doses from being delivered during certain times of day, days of the week, or within a certain amount of time since the most recent dose.

Figures 24A, 24B:
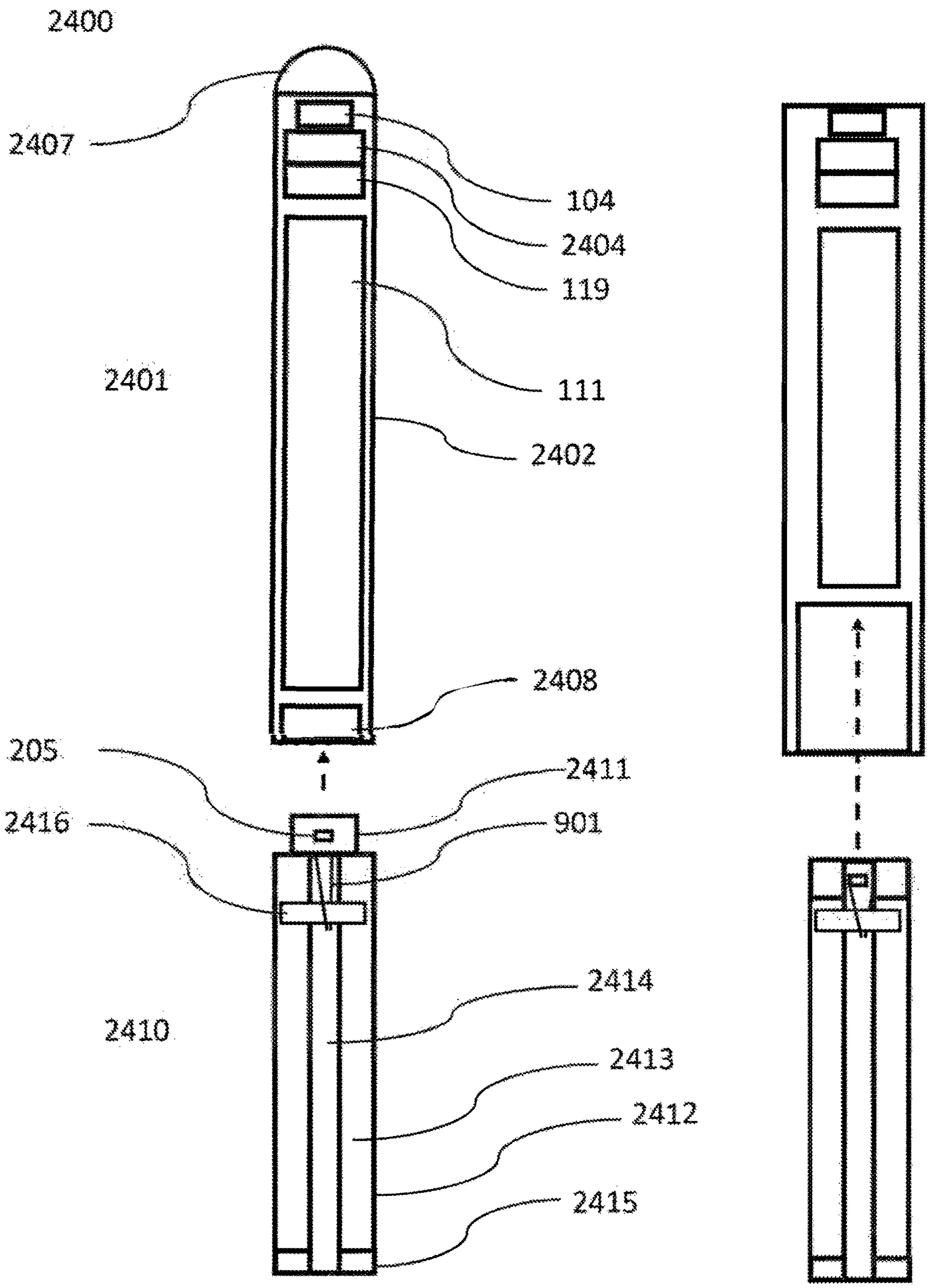
FIGS. 24A and 24B show additional examples of a vaporizer article that is constructed according to an aspect of the disclosure.

FIGS. 24A and 24B describe a passive vaporizer article 2400 comprised of a passive control device 2401 and passive inhalation media cartridge 2410. The passive vaporizer article 2400 can be commonly referred to as an ecig and is the basic design used by well-known products, including, but not limited to: blu ecigs plus+, blu ecigs my blu, RJ Reynolds Vuse, and JUUL. The passive inhalation media cartridge 2410 is further comprised of a passive cartridge housing 2412 and an internal air tube 2414 located within the passive cartridge housing 2412. The space between the passive cartridge housing 2412 and internal air tube 2414 forms a passive inhalation media storage area 2413 for the storage of inhalation media. The passive cartridge housing 2412 can be a circular tube, like blu ecigs plus+, or can have a non-circular cross section, like JUUL. The internal air tube 2414 can be circular tube or can have a non-circular cross section. The passive inhalation media storage area 2413 can be bounded at one end by the passive mouthpiece 2415 or an internal wall feature (not shown). The passive media storage area 2413 can be bounded at the opposite end by the passive cartridge connector 2411, exposed electrical contacts or other component (not shown). A passive wick 2416 is located within the passive cartridge housing 2412 and is in fluid communication with the inhalation media. Passive wick 2416 can pass through one or more openings formed in the internal air tube 2414, passive cartridge connector 2411, vaporization chamber, or other internal component in order to transport inhalation media from the passive inhalation media storage area 2413 to the cylindrical heater 901 where it can be vaporized and entrained in the air stream for deliver to the user via the internal air tube 2414 and passive mouthpiece 2415. The passive wick 2416 can be constructed from a non-electrically conductive porous material that transports the inhalation media via capillary action. Such materials can include, but are not limited to: porous ceramic, non-conductive treated metal mesh, cotton, stranded or woven silica or other similar material. In alternative embodiments, the passive wick can be situated within internal components other than the internal air tube 2414, for example, an internal vaporization chamber that is fluidly connected with the internal air tube 2414.

The passive inhalation media cartridge 2410 can further contain a memory IC 205 that provides functionality previously described in this document. The memory IC 205 can be in electrical communication with the passive control device 2401 via electrical contacts provided on or within the passive cartridge connector 2411. The passive cartridge connector 2411 can also provide electrical connections between the passive control device 2401 and the cylindrical heater 901. The passive cartridge connector 2401 can be shaped so as to mechanically and electrically connect with the passive control device connector 2408. Mechanical alignment and interlocking features, such as snap detents and mating gaps, can be provided on one or both the passive cartridge connector 2401 and passive control device connector 2408 in order to ensure robust mechanical and electrical connections. Some versions of passive vaporizer article 2400 eliminate the need for a passive cartridge connector 2411 by having the passive inhalation media cartridge 2410 extend within the passive control device 2401 for mechanical alignment and interlocking, typically using snap detents on the passive control device 2401 and mating gaps on one or more exterior surfaces of the passive inhalation media cartridge 2410, shown in FIG. 24*b*. Such systems can commonly be referred to as “pod” systems.

The passive control device 2401 can be comprised of a passive control device housing 2402, battery 111, inhalation sensor 119, passive control circuit 2404, one or more indicator lights 104 and a light cover 2407. The passive control circuit 2404 can be substantially similar to control circuit 120, but may lack one or more elements, especially a bi-directional motor drive circuit 1502. Because the passive vaporizer article 2400 delivers inhalation media to the cylindrical heater 901 via capillary action rather than the positive placement of a pre-determined volume, certain features and the dosing precision offered by vaporizer article 10, constituent display enabled control device 2100, and or in-line constituent control device 3501 are not possible. However, the passive vaporizer article 2400 can approximate certain important features. Specifically, with regard to dosing, the passive control circuit 2404 can be configured to estimate the amount of dose inhaled by measuring the duration of an inhalation and assuming a certain amount of dose is delivered per unit time for a given set of vaporization parameters. The passive control circuit 2404 can be further configured to disable the cylindrical heater 901 when the desired dose level is reached via this method of dose delivery estimation. The passive control circuit 2404 can be further configured to inform the user that the desired dose has been inhaled.

The inhalation sensor can be configured to detect either of a pressure change or change in air flow rate caused by the inhalation of the user. The inhalation sensor can alternatively be replaced with a button or switch that can be activated manually by the user. The passive control device 2401 can be capable of performing some of the functions performed by the control device 100, constituent display enabled control device 2100, and in-line constituent control device 3501, including, but not limited to: connecting to a computer network 1801, recording doses, sending and receiving dosing information, exchanging data with a computing device 1803, dose compensation, remote dosing, controlling the temperature of the cylindrical heater 901, and reading and writing data elements to memory IC 205. For example, the passive control device 2401 can be configured to read a serial number from memory IC 205 and check database 1600 for the presence of that serial number before enabling the use of passive inhalation cartridge 2410. One embodiment of the passive control device 2401 can also contain a display screen (not shown) configured to display the composition of inhalation media contained in passive inhalation media cartridge 2410. The display screen can be further configured to display additional information about the inhalation media, passive inhalation media cartridge 2410, and/or passive control device 2401.

Figure 25:
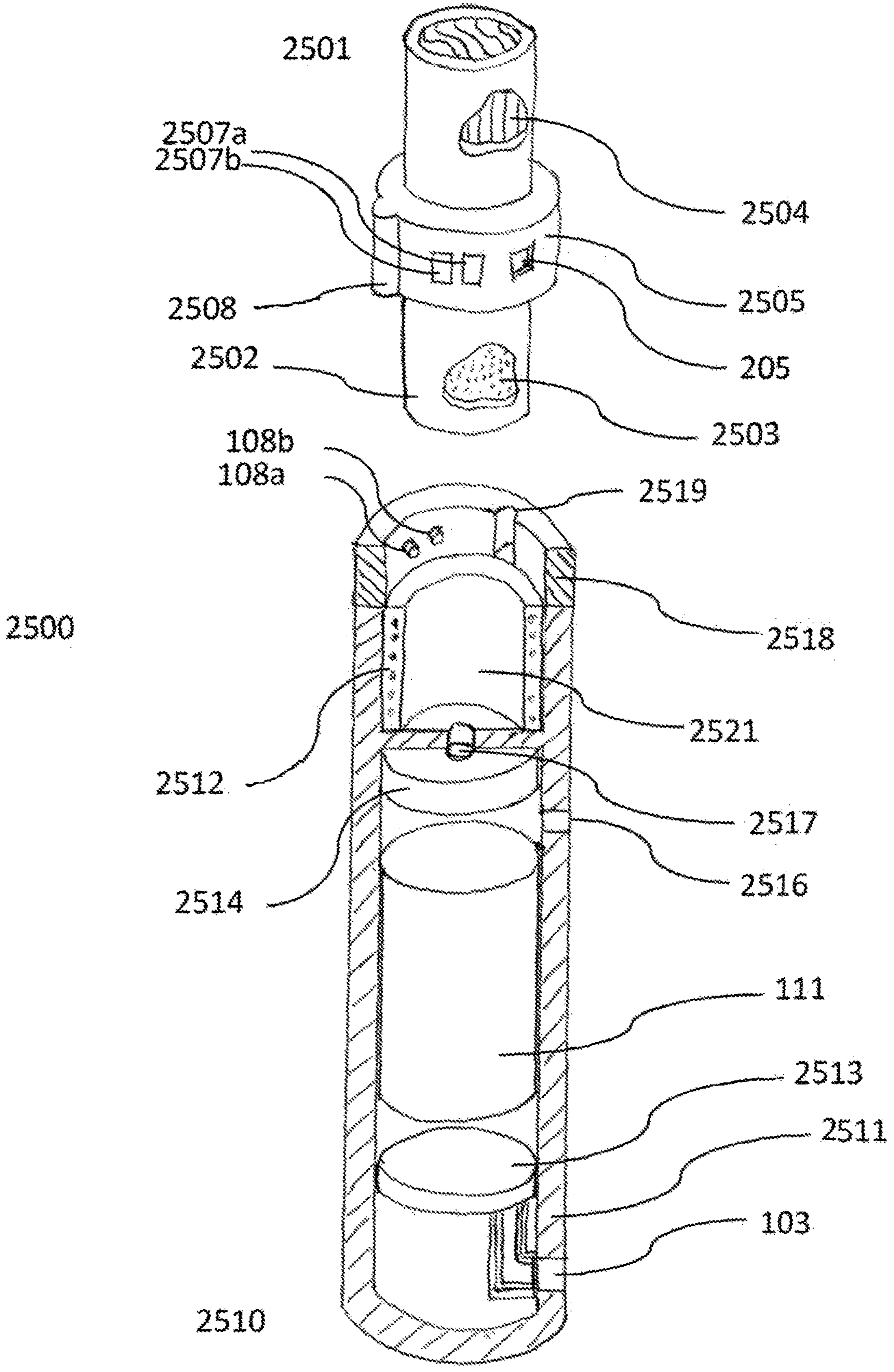
FIG. 25 shows an example of a solid media vaporizer article that is constructed according an aspect of the disclosure.

A certain class of vaporizers operate by heating a solid media, such as dried tobacco leaf or *cannabis* plant matter. In such vaporizers, the solid media is heated to a temperature well below the temperature of combustion in order to produce an aerosol without combustion and its associated byproducts. The solid media can be heated to or near the pyrolytic temperature of the material. The solid media can be pre-processed in order to promote aerosol formation. For example, the solid media can be flattened, dried, made into granules, mixed with binder material, and/or mixed with aerosol forming substances such as propylene glycol or glycerin. FIG. 25 describes solid media vaporizer article 2500 capable of providing many of the functions and benefits offered by vaporizer article 10. The solid media vaporizer article 2500 is comprised of a solid media control device 2510 and solid media stick 2501. The solid media stick 2501 can be similar to a traditional combustible cigarette in form and composition; it can contain a solid media 2503 such as ground tobacco leaf and a filter 2504 wrapped inside a wrapper 2502. The filter 2504 can be situated between the solid media 2503 and the users mouth in order to prevent particulate matter from being inhaled. The wrapper 2502 can be made from cigarette paper in order to give it the feel of a combustible cigarette. The wrapper 2502 can alternatively be made of plastic, metal, wood, or other material suitable for containing the solid media 2503. The wrapper 2502 can be situated within an IC holder 2505. The wrapper 2502 can be adhered, woven into, or attached to the IC holder 2505 in such a manner that trying to separate the two would result in the destruction of the wrapper 2502 and render the solid media stick 2501 unusable. This would discourage tampering with the IC holder 2505 and attempting to use it with other solid media sticks 2501 or other devices.

The IC holder 2505 provides physical and electrical attachments for memory IC 205 which can contain substantially similar information as described earlier in this document. When used in conjunction with the solid media stick 2501, the memory IC 205 can additionally contain parameters specific to the solid media stick 2501 embodiment. The memory IC 205 can be electrically connected to one or more solid media electrical connectors 2507 which can be flexible metal contacts, spring loaded pins, or conductive pad contacts. The IC holder 2505 can also have a solid media alignment feature 2508 which facilitates mating with the solid media control device 2510. The distal end of the solid media stick 2501 can be inserted into the heating cavity 2521 of the solid media control device 2510 such that the solid media alignment feature 2508 aligns with the solid media guiding feature 2519 located within solid media receiving ring 2518. When inserted, solid media electrical connectors 2507 establish electrical connection with one or more electrical connectors 108. When the solid media stick 2501 is properly inserted into the solid media control device 2510, solid media 2503 can be substantially disposed within the heating cavity 2521 which is formed by the ring heater 2512. When the user inhales on the proximal end of the solid media stick 2501, air enters the solid media control device 2510 through a solid media control device air inlet 2516 located in the wall of solid media control device housing 2511. The size of the solid media control device air inlet 2516 can be used to determine the draw resistance of the device. Air then flows through an air sensor opening 2517 located in air flow sensor 2514 which generates a signal which can be read by the solid media control device circuit 2513 which in turn sends power to the ring heater 2512. The air sensor opening 2517 can also be used to determine the draw resistance of the device. When the ring heater 2512 is energized, the solid media 2503 is heated to the point where an aerosol is be formed. The aerosol can be mixed and/or entrained in the air flow which passes through the filter 2504 then into the user's mouth. A secondary air inlet (not shown) can optionally be included at or downstream from the heating cavity 2521 in order to provide additional air to mix with the aerosol and produce a cooler aerosol for inhalation by the user. In other embodiments, ring heater 2512 activation can be provided by other means such as an air pressure sensor 2613 or button rather than an air flow sensor 2514.

The solid media control device 2510 can further contain a battery 111 configured to provide power to the solid media control device circuit 2513 and ring heater 2512. A charge connector 103 can be used to provide energy to recharge the battery 111. Solid media control device circuit 2513 can contain components that electrically govern the charging of battery 111.

Because the solid media vaporizer article 2500 heats a bulk amount of solid media 2503 rather than the positively placing of a pre-determined volume of inhalation media onto a heater for vaporization, certain features and perhaps the dosing precision offered by vaporizer article 10, constituent display enabled control device 2100, and in-line constituent control device 3501 are not possible. However, the solid media vaporizer article 2500 can approximate or offer alternatives to certain important features. One way to provide for dose control is to have each solid media stick 2501 provide one dosing unit. Solid media sticks 2501 can be sold in pre-determined dosing levels, for example, in the case of *cannabis* containing solid media dosing sticks 2501, the sticks can be offered in THC levels of 2.5 mg, 5 mg, 7.5 mg and 10 mg. In the case of tobacco containing solid media dosing sticks, for example, the sticks can be offered with nicotine levels of 0.5 mg, 1.0 mg, 1.5 mg and 2.0 mg. In both examples, the user can use one or more sticks in combination in order to consume the desired dose.

Alternatively, the solid media stick 2501 can contain sufficient solid media 2503 to provide multiple doses. When used in conjunction with such a solid media stick 2501, the solid media control device circuit 2513 can be configured to estimate the amount of dose inhaled by measuring the duration of an inhalation and assuming a certain amount of dose is delivered per unit time for a given set of heating parameters. The solid media control device circuit 2513 can be further configured to disable the ring heater 2512 when the desired dose level is reached via this method of dose delivery estimation. The solid media control device circuit 2513 can be further configured to inform the user that the desired dose has been inhaled. The solid media control device circuit 2513 can be alternatively configured to integrate a flow rate signal provided by air flow sensor 2514 over the duration of an inhalation in order to determine the amount of dose delivered to the user. As with vaporizer article 10, the solid media control device 2510 can be configured to allow the user to select the dose according to the desired constituent and can determine the inhalation duration needed in order to deliver the desired amount of the requested constituent. The solid media control device circuit 2513 can be configured to read constituent information from memory IC 205 as one of the inputs into this determination. The solid media control device circuit 2513 can alternatively be configured to read a serial number or similar identifier from memory IC 205 then download constituent dosing information from computing device 1803 or database 1600.

An alternative method of providing dosing control is to use a solid media stick 2501 containing sufficient solid media 2503 to provide multiple doses, but rather than measure the duration of inhalation and disable the ring heater 2512 when the dose level is reached, turn on the ring heater 2512 only for a discreet duration for each inhalation. For example, the solid media control device circuit 2513 can be configured to enable the ring heater 2512 long enough to deliver 1 mg of CBD during each inhalation. If the user desires 3 mg of CBD, then he would take 3 inhalations.

The solid media control device 2510 can be capable of performing many of the functions performed by the control device 100, constituent display enabled control device 2100, or in-line constituent control device 3501, including, but not limited to: communicating with a computer network 1801 and database 1600, recording and controlling doses, sending and receiving dosing information, dose compensation, remote dosing, exchanging data with a computing device 1803, controlling the temperature of the ring heater 2512, and writing and reading data elements to and from memory IC 205. For example, solid media control device circuit 2513 can read a serial number from memory IC 205 and compare that to a list of known serial numbers in order to ensure that solid media stick 2501 is not counterfeit. Alternatively, solid media control device circuit 2513 can be configured to read information from memory IC 205 and compare it to an expected format in order to validate that the solid media stick 2501 is genuine. Solid media control device circuit 2513 can be further configured to implement advanced security algorithms (e.g. SHA-256) in conjunction with information stored within memory IC 205 in order to prevent usage of unauthorized solid media sticks 2501. One embodiment of the solid media control device 2510 can also have a display screen (not shown) configured to display the composition of solid media 2503 contained in solid media stick 2501. The display screen can be further configured to display additional information about the solid media 2503, solid media stick 2501, and/or solid media control device 2510.

Some users may prefer using solid media sticks 2501 instead of cartridges 200 because solid media 2503 tends to retain more of the chemicals responsible for flavor, smell, physical and mental effects than the fluid isolates and distillates typically used in cartridges 200. However, many of those chemicals can be found deep within the materials used to form the solid media 2503 and thus may not readily enter the aerosol stream. For clarity, this may be due to physical distance between the ring heater 2512 and certain portions of the solid media 2503 resulting in less heating of certain portions of the solid media 2503. This may also be due to the fact that certain chemicals may be "locked" within the materials used to form the solid media 2503 rather than sitting on the surface of those materials where they can be more readily volatilized by the ring heater 2512. One way to increase the presence of these chemicals in the aerosol is to pre-treat the materials with a solvent then allow the materials to dry out before forming the solid media stick 2501. The treatment with solvent allows the chemicals to be "unlocked" from within the materials while the drying process tends to pull the chemicals toward the surfaces of the material as the solvent evaporates. This leaves the surfaces of the materials rich with the chemicals where they can be more easily volatilized. A number of different solvents can be appropriate for use in pre-treatment. Ethanol can be an especially good solvent for use with *cannabis* and tobacco plant materials. In addition to or in lieu of pre-treatment with solvents in order to pull certain chemicals to the surfaces of the plant materials, plant materials can be sprayed with or soaked in certain chemicals so that those chemicals reside on the surfaces of the plant materials for easy volatilization. For example, a terpene isolate such as limonene can be sprayed onto *cannabis* plant material in order to provide an aroma and taste of citrus fruit. For additional example, menthol can be sprayed onto tobacco plant material in order to provide a mint taste.

Figure 26:
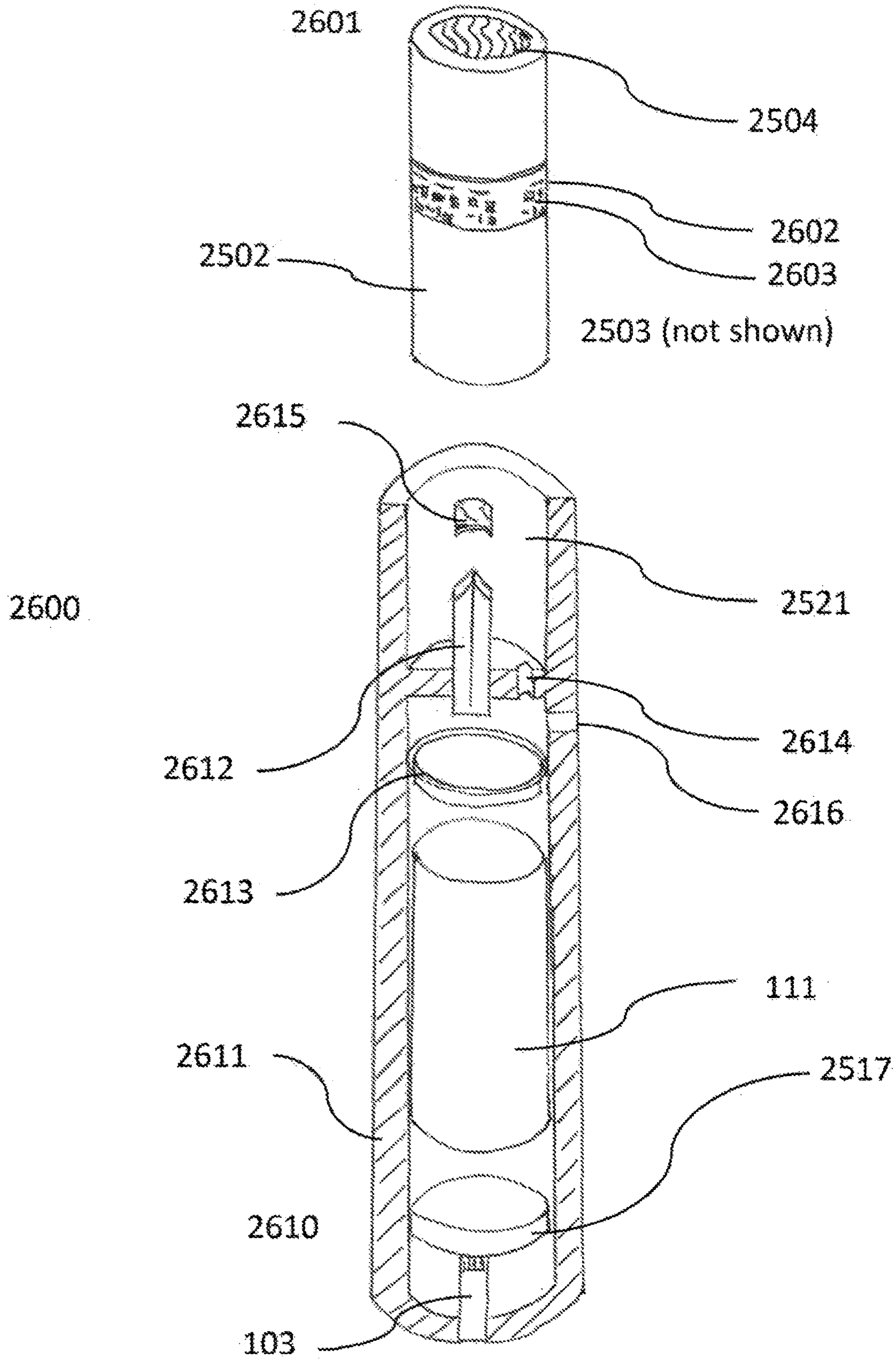
FIG. 26 shows another example of a solid media vaporizer article that is constructed according an aspect of the disclosure.

FIG. 26 describes optical solid media vaporizer article 2600. The optical solid media vaporizer article 2600 is substantially similar to the solid media vaporizer article 2500, the primary difference being that information pertaining to the solid media 2503 is printed or otherwise encoded on the surface of the solid media stick where it can be read by the optical solid media vaporizer article 2600 through optical means. In this embodiment, the components responsible for vaporization, charging, data exchange, and indication can be similar or even identical. Optical solid media vaporizer article 2600 can be comprised of an optical solid media stick 2601 and an optical solid media control device 2610. The optical solid media stick 2601 can be comprised of solid media 2503 and a filter 2504 wrapped in a wrapper 2502. Rather than using a memory IC 205 contained by IC holder 2505 to store information regarding solid media 2503, optical solid media stick 2601 contains a coded wrapper section 2602 that can be printed with optical information 2603. Optical information 2603 can represent any of the same type of information that can be stored within memory IC 205 as described earlier in this document. Optical information 2603 can be displayed in a machine-readable format such as a bar code or QR code. The coded wrapper section 2602 can be a section of wrapper 2502 or can be a separate piece of material or band affixed or adhered to the wrapper 2502. The coded wrapper section 2602 can be integrally formed with, adhered to, woven into, or attached to the wrapper 2502 in such a manner that trying to separate the two would result in the destruction of the wrapper 2502 and render the optical solid media stick 2601 unusable. In an alternative embodiment, the coded wrapper section 2602 can be replaced with a wireless memory such as an RFID tag.

The optical solid media stick 2601 can be inserted into heating cavity 2521 and its distal end can be penetrated by heater blade 2612. It should be noted that although this description of optical solid media vaporizer article 2600 uses a heater blade 2612 instead of a ring heater 2512, a ring heater 2512 can be used instead of a heater blade 2612. Likewise, the solid media vaporizer article 2500 can use a heater blade 2612 instead of a ring heater 2512. When the optical solid media stick 2601 is inserted into the optical solid media control device 2610, the coded wrapper section 2602 can align with an optical reader 2615. Optical solid media stick 2601 can have an alignment feature (not shown) that mates with an alignment feature within optical solid media control device 2610 and facilitates the alignment of optical information 2603 with optical reader 2615. Alternatively, optical information 2603 can be repeated in multiple locations around the coded wrapper section 2602 such that optical information 2603 can be within the field of view of the optical reader 2615 regardless of orientation. In the alternative embodiment where the coded wrapper section is replaced with a wireless memory such as an RFID tag, the optical reader 2615 can be replaced by an RFID reader.

When the user inhales on the proximal end of the optical solid media stick 2601, air enters the optical solid media control device 2610 through an optical solid media control device air inlet 2616 located in the wall of optical solid media control device housing 2611. The air flow creates a pressure differential within the optical solid media control device housing 2611 on one side of the air pressure sensor 2613 which generates a signal which can be read by the optical solid media control device circuit 2617 which in turn sends power to the blade heater 2612. When the blade heater 2612 is energized, the solid media 2503 is heated to the point where an aerosol can be formed. The aerosol can be mixed and/or entrained in the air flow which flows through the internal air opening 2614, the solid media 2503, the filter 2504 then into the user's mouth. In alternative embodiments, blade heater 2612 activation can be provided by other means such as an air flow sensor 2514 or button rather than an air pressure sensor 2613.

The optical solid media control device 2610 can further contain a battery 111 configured to provide power to the optical solid media control device circuit 2617 and blade heater 2612. A charge connector 103 can be used to provide energy to recharge the battery 111. Optical solid media control device circuit 2617 can contain components that electrically govern the charging of battery 111.

The optical solid media vaporizer article 2600 can function in a substantially similar manner to the solid media vaporizer article 2500. The primary differences are that the optical solid media control device 2610 can not write data to the coded wrapper section 2602 and the amount of data that can be encoded into optical information 2603 is likely less than can be stored in memory IC 205. These differences result in limitations which include that usage information cannot be written to the optical solid media stick 2601 and certain types of advanced data security techniques may not be possible. The severity of the limitation of the inability to write usage data can be mitigated by storing such data in one or more of the memory located in the optical solid media control device circuit 2617, computing device 1803, and database 1600. For example, every time the user takes an inhalation, the optical solid media control device circuit 2617 can record certain usage data such as puff duration, save that data to its local memory, and associate that data with a serial number or unique identifier encoded into optical information 2603. As the user takes subsequent inhalations, optical solid media control device circuit 2617 can add to a running total of inhalation durations associated with a particular serial number or unique identifier and disable heating of the associated optical solid media stick 2601 when a threshold associated with exhaustion of an optical solid media stick 2601 is met. This process can also be performed at the computing device 1803 or computer network 1801 levels. The severity of the data quantity limitations of optical information 2603 can likewise be mitigated through the use of information stored in database 1600. For example, the optical information 2603 can simply contain a serial number or unique identifier of a particular optical solid media stick 2601. Database 1600 can contain a record, associated by serial number or unique identifier, of all information about the history, contents and manufacture of every optical solid media stick 2601 produced. Such record can be optionally downloaded to the optical solid media control device 2610 and/or computing device 1803 when an optical solid media stick 2601 is inserted into the optical solid media control device 2610. By accessing the database 1600 and storing local copies of information in either of the optical solid media control device 2610 or computing device 1803, the data necessary to perform functions including recording and controlling doses, sending and receiving dosing information, dose compensation, remote dosing, and controlling the temperature of the blade heater 2612 is made available.

Figure 27A:
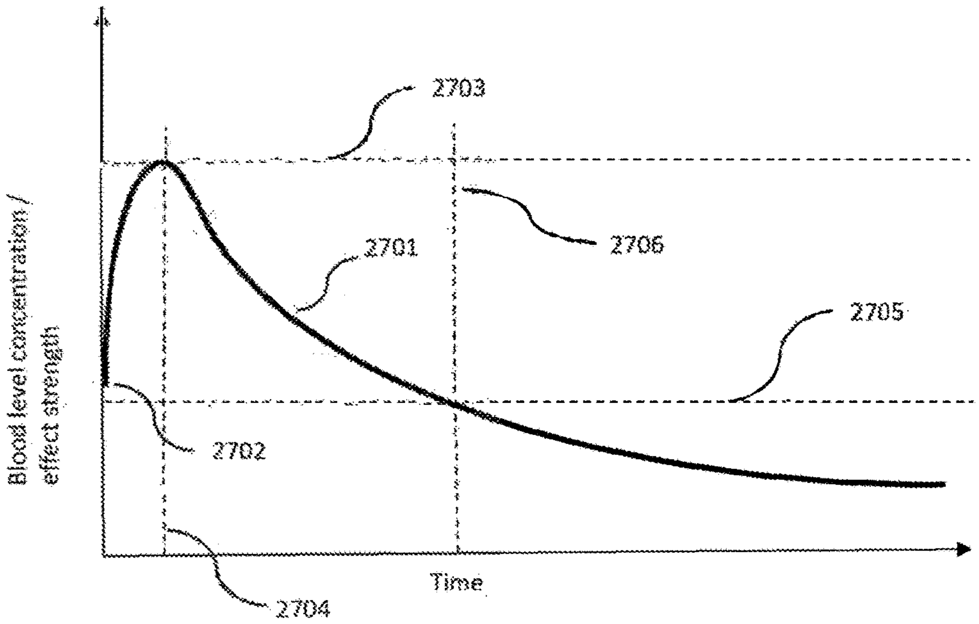
FIG. 27A shows an example response curve to a drug

FIG. 27A describes an example response curve 2701 to a single dose of a chemical or drug. The response curve 2701 can represent the concentration level of a chemical in the blood, the pharmacokinetics (PK) of the chemical. The response curve 2701 can alternatively be used to represent the effect a chemical has on the user, its pharmacodynamics (PD). For certain chemicals or drugs, the curves representing the strength of the effect and the blood level concentration can be substantially similar or even be identical, while for other drugs, the curves can differ in shape, timing and magnitude. The relationship between PK and PD can be quite complex for certain chemicals, being influenced by a multitude of factors, however, pharmacologists are able to and have built PK/PD models, mathematical expressions that allows the description of the time course of effect intensity in response to administration of a dose, for a variety of chemicals and drugs. For the purpose of this disclosure, we will generally refer to the response curve 2701 as a measure of strength of effect, while noting that using it as a representation of blood level concentration is not excluded from this invention. The response curve begins at 2702 upon the administration or consumption of the drug. Then as the drug is absorbed, the response increases until the maximum effect level 2703 is achieved at maximum effect time 2704. After the maximum effect level 2703 has been achieved, the effect generally begins to decrease until such time as the effect decreases to a minimum effect threshold level 2705 at which the effect can be deemed no longer detectable, impactful, inhibiting, therapeutic, effective, or of interest. This occurs at minimum effect threshold time 2706. The minimum effect threshold level 2705 may or may not be zero.

Figure 27B:
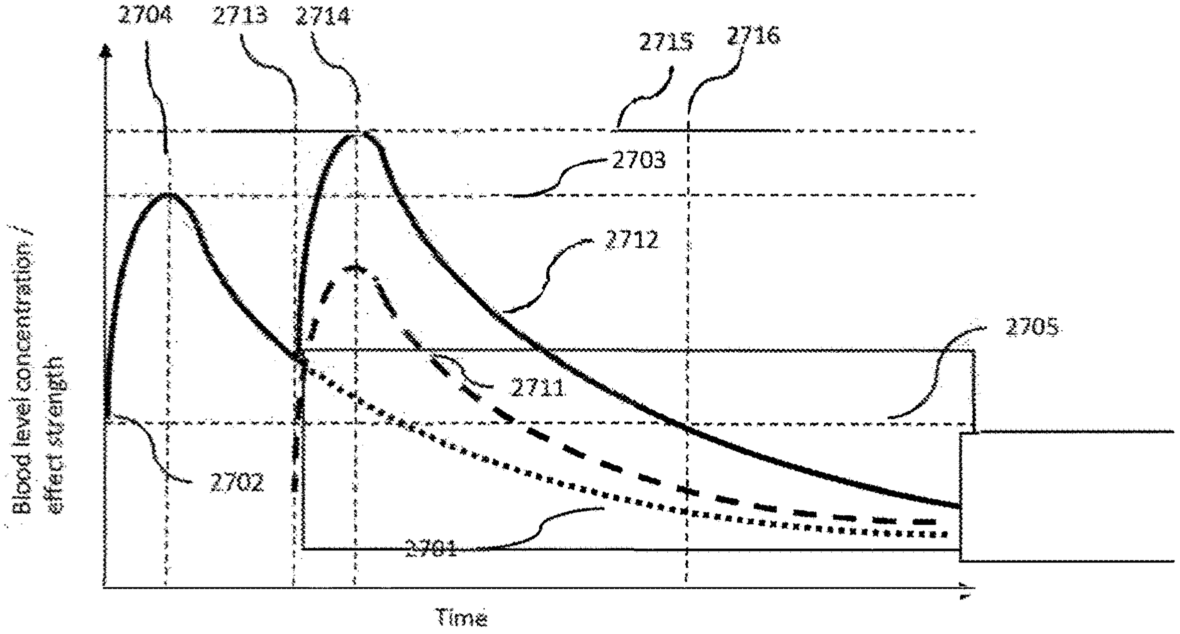
FIG. 27B shows an example response curve to multiple doses of a drug

FIG. 27B shows an example multi-dose response curve 2712. The response to the first dose follows response curve 2701 as described in FIG. 27A, however, at $2^{nd}$ dose time 2713, a second dose of the chemical is administered or consumed. The second dose response curve is represented by the dotted line 2711. The multi-dose response curve 2712 then begins to increase in response to the second dose. The multi-dose maximum effect level 2715 is achieved at multi-dose maximum time 2714. The minimum effect threshold level 2705 occurs at a multi-dose minimum effect threshold time 2716. There can be upper limits to the effect level of certain drugs as they saturate their target receptors. Therefore, an upper limit can be applied to the multi-dose response curve 2712 for certain drugs. Understanding the aforementioned response curves can help users of the vaporizer article 10 in any of its embodiments including constituent display enabled control device 2100, passive vaporizer article 2400, solid media vaporizer article 2500, optical solid media vaporizer article 2600, in-line constituent vaporizer article 3500, media delivery article 3600 and nasal delivery article 4700. Models of response curves for drugs and chemicals, including, but not limited to, THC, CBD, and nicotine can be created within computer network 1801 and used to guide dosing, including being used in conjunction with dose recommendation process 2000.

Figure 28:
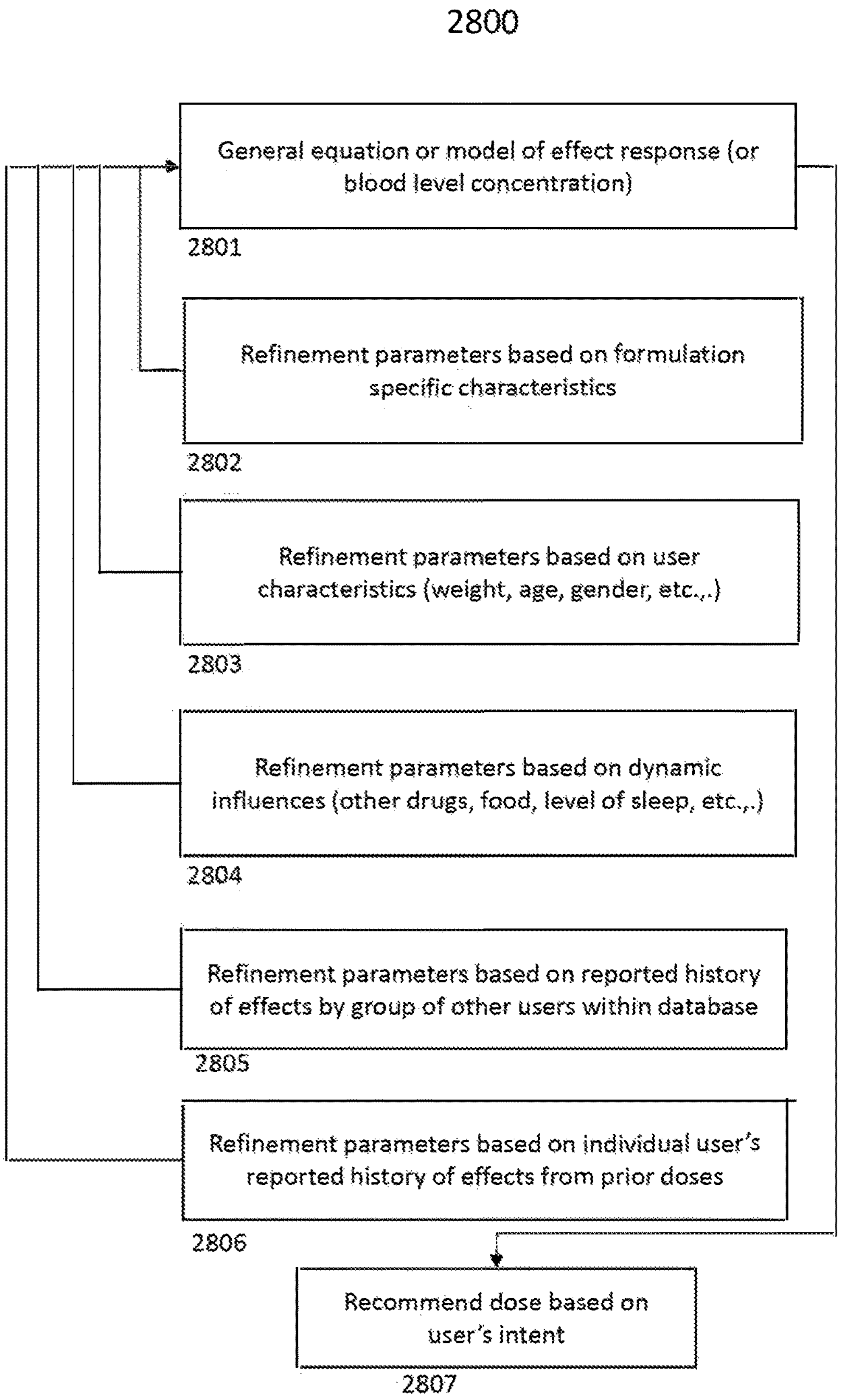
FIG. 28 shows a model or equation of a response curve to a drug can be refined according to an aspect of the disclosure.

While such models can be helpful in guiding dosing, incorporating other inputs into the models can further improve their accuracy and applicability on an individual basis. FIG. 28 shows that a model can be created and refined within a computer network 1801. In block 2801, the general equation or model of effect response can be constructed within the computer network 1801 and stored in database 1600. This model can be based on prior PK and/or PD studies performed on a given chemical or drug. It is known, however, that the response of a given drug or chemical can vary from standard models based on the presence of other chemicals that can server to promote, retard or otherwise change the response to the chemical for which the model was originally constructed. *Cannabis*, for example, contains THC and response curves exist for THC in scientific literature. This allows for the construction of a mathematical model. However, *cannabis* can also contain many other chemicals, including some that can alter the response to THC. For example, CBD, another cannabinoid found in *cannabis*, is known to alter the effect of THC. Through scientific study and/or data collected by the computer network 1801 and stored in database 1600, the data analysis program 1805 can determine parameters that improve the accuracy of the response curve based on knowing the chemical composition of the formulation being consumed by the user. In block 2802, such formulation specific refinement parameters can be applied to the general equation 2801 in order to better predict the effect on the user. Such refinement parameters can be derived through clinical testing or can be determined by the data analysis program 1805 by analyzing user reported responses to various doses of various formulations. By way of example, the data analysis program 1805 can determine through analysis of multiple data records stored in the database 1600 that CBD in formulation decreases the maximum effect level 2703 of THC by a given amount according to the proportion of CBD present. Furthermore, the data analysis program 1805 can also know that a given user is using a cartridge 200 and that cartridge 200 contains a certain proportion of CBD because its formulation composition information can be stored in memory IC 205 and/or database 1600. Given this information, the data analysis program 1805 can provide a recommended dosage to the user with improved accuracy over the general model 2801. For example, the user can request the data analysis program 1805 to suggest a dose to achieve a certain maximum effect level 2703. By determining and applying the formulation specific refinement parameters 2802 to the general model 2801, the data analysis program 1805 can provide a dose recommendation 2807 that will more likely produce the desired maximum effect level 2703.

Individual user characteristics, including, but not limited to: weight, age, gender, and existing conditions can also influence the accuracy of the general model 2801. Using a similar approach as described in the formulation specific refinement parameters 2802 discussion, user characteristic refinement parameters 2803 can also be determined via clinical methods and/or the data analysis program 1805 and then used to improve the accuracy of the general model 2801. Dynamic influences, including, but not limited to: recent consumption of alcohol, recent consumption of certain foods, recent consumption of other drugs or chemicals, recent exercise, and recent level of sleep can also influence the accuracy of the general model 2801. Using a similar approach as described in the formulation specific refinement parameters 2802 discussion, dynamic influence refinement parameters 2804 can also be determined via clinical methods and/or the data analysis program 1805 and then used to improve the accuracy of the general model 2801.

For various other reasons, including a lack of data, the general model 2801 for a particular drug or chemical may not be as accurate as desired. The data analysis program 1805 is well suited to improve the general model 2801 in such cases. The data analysis program 1805 can determine, through analysis of multiple data records of multiple users stored in the database 1600, group refinement parameters 2805 that can also be used to improve the accuracy of the general model 2801. For yet other reasons, an individual's response to a given chemical or drug may deviate from the general model 2801. These reasons include, but are not limited to: individual variations in body chemistry, individual variations in metabolism, and an individual's tolerance to the drug or chemical. The data analysis program 1805 is well suited to improve the general model 2801 in such cases. The data analysis program 1805 can determine, through analysis of multiple data records from an individual user stored in the database 1600, individual refinement parameters 2806 that can also be used to improve the accuracy of the general model 2801. By way of example, the data analysis program 1805 can analyze the past responses to questions communicated to an individual frequent nicotine user via the chat agent 1802 regarding the individual user's response to doses of nicotine. The analysis may show that the individual user has a response to nicotine below what is predicted by the general model 2800. Individual refinement parameters 2806 can then be determined for this individual user that allow the model to better predict how the individual user will respond to a given dose of nicotine. It is understood that refinements 2802 through 2806 can be applied independently, in any combination with each other, or not at all based on the configuration of the system, user configuration settings, and available data. While storing the general model 2801 and refinement parameters in the database 1600 offers advantages, it is also possible to store models and/or refinement parameters within any of the control device 100, constituent display enabled control device 2100, in-line constituent control device 3501, memory IC 205 and/or computing device 1803.

It is understood that there may be cases when a model for a given drug or chemical either does not exist or is insufficiently accurate so as to be usable. In such cases, the data analysis program 1805 can be configured to extrapolate an effect response prediction by analyzing the records of doses and responses stored in database 1600. This can be accomplished via one or more data mining techniques, including, but not limited to: tracking patterns, classification, association, outlier detection, clustering, regression and prediction.

Figures 29A, 29B, 29C:
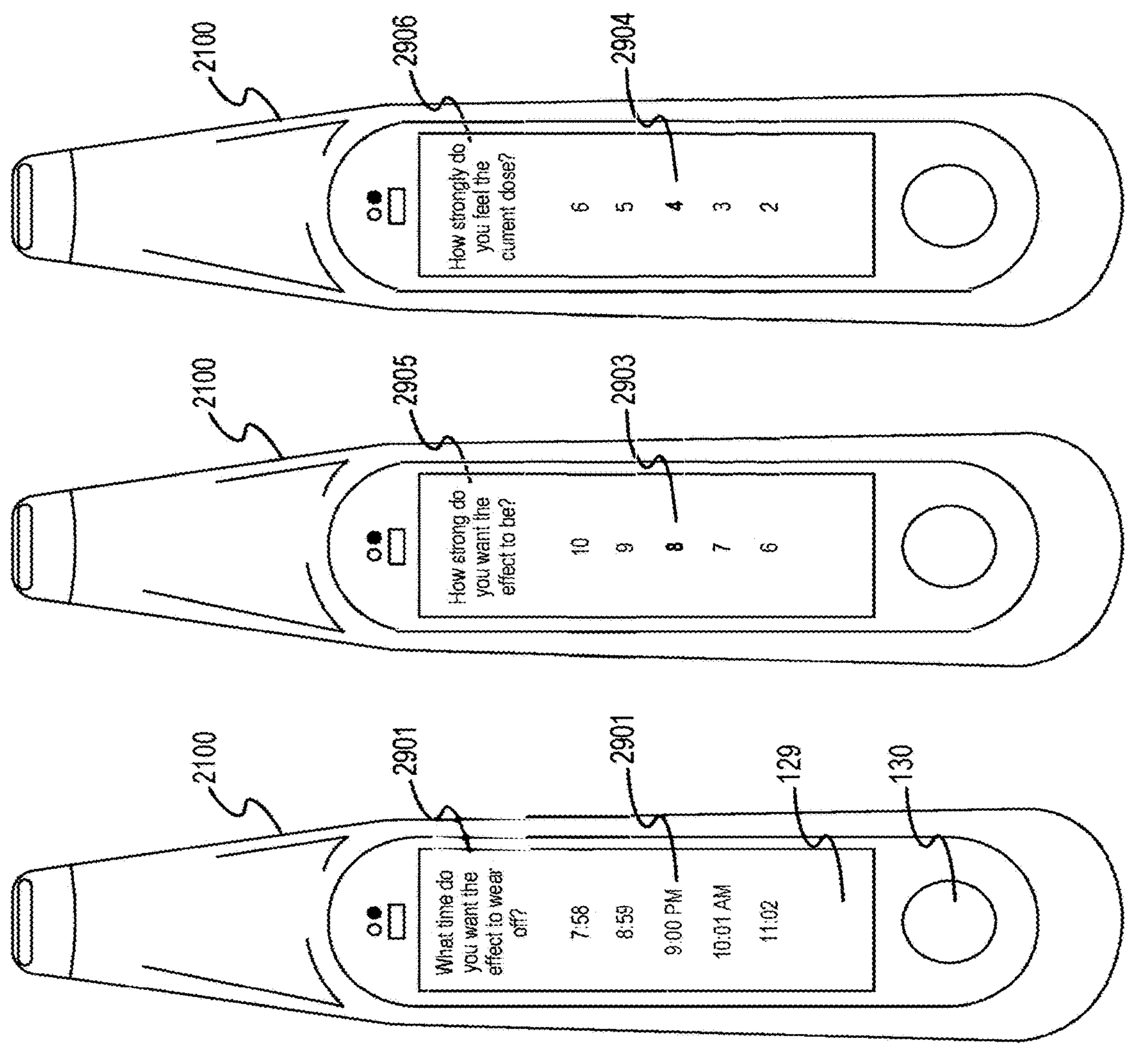
FIGS. 29A, 29B and 29C show examples of how time-based and strength-based dosing interfaces of a vaporizer article are constructed according to an aspect of the disclosure.

FIG. 29A shows one example of how constituent display enabled control device 2100 can be used in conjunction with the models described in FIGS. 27A, 27B and FIG. 28. In this example, the user inputs the time at which they want the effect to wear off in menu 2902. This can be interpreted by the data analysis program 1805 as the time which the user desires to achieve the minimum effect threshold level 2705 after the peak effect has occurred. Using this input in conjunction with the previously described models, the data analysis program 1805 can determine the amount and timing of the dose or doses the user can take in order to achieve the desired time which the effect wears off. Furthermore, the data analysis program can be configured to communicate such dose and timing information to the user. Additionally, the constituent display enabled control device 2100 can be configured to only deliver the corresponding dose to the user, thus ensuring that the user does not consume too high of a dose and that the effect wears off by the desired time.

FIG. 29B shows another example of how constituent display enabled control device 2100 can be used in conjunction with the models described in FIGS. 27A, 27B and 28. In this example, the user inputs the desired strength of the effect in menu 2903. This can be interpreted by the data analysis program 1805 as the maximum effect level 2703 or multi-dose maximum effect level 2715. Using this input in conjunction with the previously described models, the data analysis program can determine the amount and timing of the dose or doses the user can take in order to achieve the desired strength of effect. Furthermore, the data analysis program 1805 can be configured to communicate such dose and timing information to the user. Additionally, the constituent display enabled control device 2100 can be configured to only deliver the corresponding dose to the user, thus ensuring that the user achieves the desired strength of effect. In another example, the functions described in FIG. 29A and FIG. 29B can be combined in order to allow the user to select both the maximum effect strength and the time by which they want the effect to wear off FIG. 29C shows an example of how feedback can be provided to the database 1600 for use with the models described in FIGS. 27A, 27B and 28. The data analysis program 1805 can cause the constituent display enabled control device 2100 to prompt the user to rate the strength of the effect, shown in feedback prompt 2906. The user can provide such feedback in the rating menu 2904. This can be done at regular intervals or can be done at times determined by the data analysis program 1805 to be optimal. The prompt for feedback can be triggered by the data analysis program 1805. For example, if the user consumed inhalation media for the purpose of sleep, the data analysis program 1805 can prompt for feedback 8 hours after the dose was consumed. For additional example, if the user consumed inhalation media for the purpose of pain relief, the data analysis program 1805 can prompt for feedback 30 minutes after the dose was consumed. Alternatively, the constituent display enabled control device 2100 can be configured to periodically solicit such feedback without being triggered by the data analysis program 1805. Providing such feedback can enable the data analysis program 1805 to improve its ability to accurately recommend doses. It should be noted that the rating menu 2904 can be used for rating more than just strength of effect. The feedback prompt 2906 can seek feedback on any aspect of the dose that can be rated, including, but not limited to: satisfaction, sleepiness, happiness, anxiety, pain, seizure frequency, seizure strength, alertness, motor function, coordination, mental acuity, creativity, and perceived efficacy. In addition, the data analysis program 1805 can be configured to cause the constituent display enabled control device 2100 to display challenge questions in order to test the user. For example, if the user if has received a dose of THC, challenge questions can be used as a way to evaluate the sobriety of the user independently from the self-ratings. Such questions can be of the nature that would be difficult for a non-sober person to answer correctly. Such questions can be structured in the form of a quiz or memory challenge. The answers to such questions or the correctness of the answers can be provided to the database 1600 in order for the data analysis program 1805 to use in refining its prediction models.

Figures 30A, 30B, 30C:
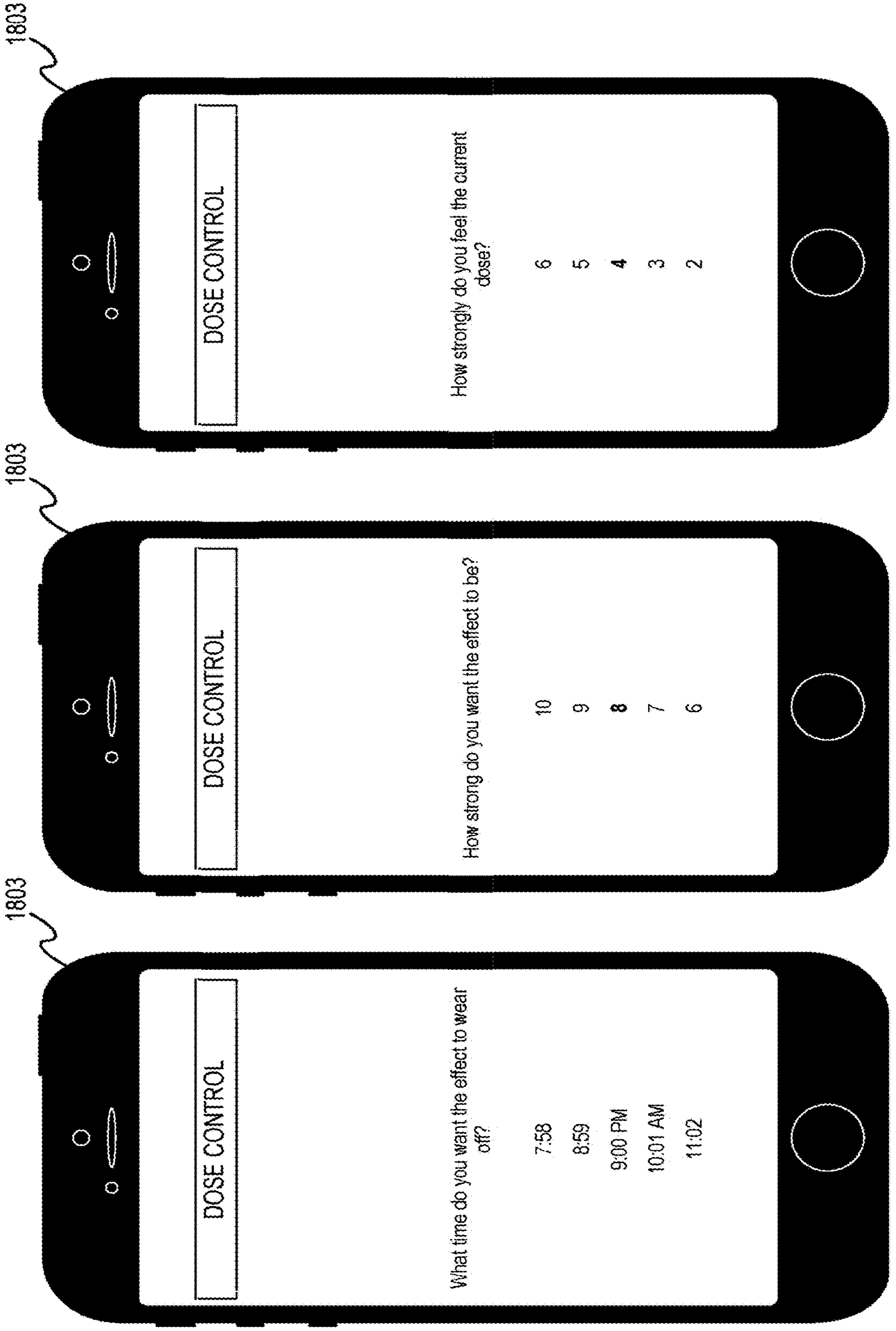
FIGS. 30A, 30B and 30C show additional examples of how time-based and strength-based dosing interfaces are constructed according to an aspect of the disclosure.

FIGS. 30A-30C mirror FIGS. 29A-29C. They demonstrate that the same functionality associated with FIGS. 29A-29C can alternatively or additionally be provided via the computing device 1803. Alternatively to the data analysis program 1805 triggering prompts and analyzing data, such activities can also be performed at the constituent display enabled control device 2100, in-line constituent control device 3501, and/or computing device 1803 level. In yet another embodiment, such activities can also be distributed between multiple elements of the system.

Figure 31:
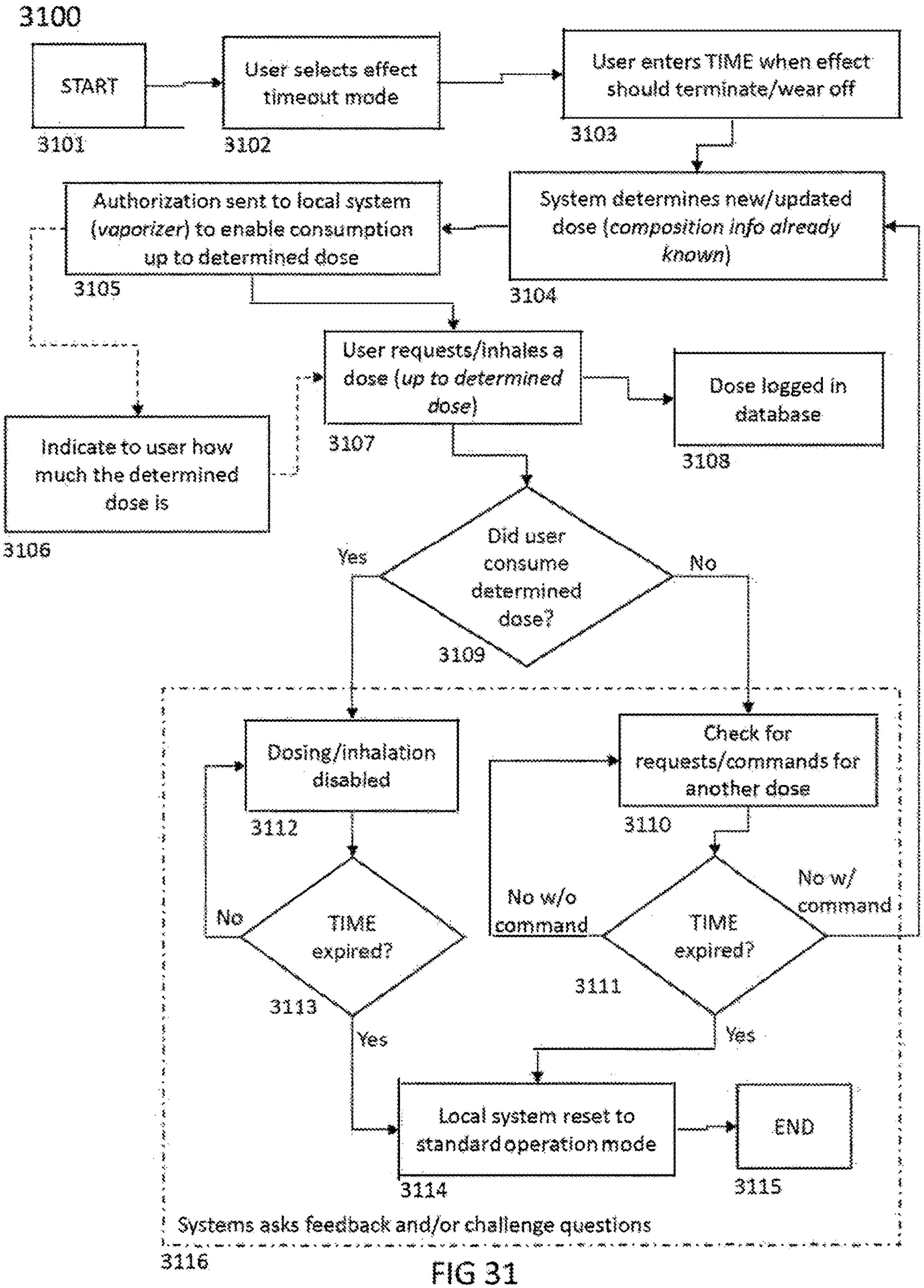
FIG. 31 shows another example of how dosing controls are generated according to an aspect of the disclosure.

FIG. 31 describes a timeout dosing process 3100 that can be used to deliver doses to the user that wear off when the user desires. The timeout dosing process 3100 starts in block 3101. In block 3102, the user puts the constituent display control device 2100 into effect timeout mode. In this mode, the constituent display control device 2100 can only deliver doses that will wear off by the time that the user sets in block 3103. In block 3104, the data analysis program 1805 uses the models described in FIGS. 27A, 27B, and 28 to determine the dose to be delivered to the user in order to for the minimum effect threshold level 2705 to be reached by the desired time. Since the data analysis program 1805 knows the composition of the cartridge 200 either through information associated in the database 1600 or by reading the memory IC 205, the correct amount of inhalation media can be dispensed in order to deliver the dose. In block 3105, an authorization is sent from the computer network 1801 to the constituent display control device 2100 to enable consumption up to the determined amount. This authorization and the associated amount can optionally be communicated to the user in block 3106. The communication can be displayed on either of the computing device 1803 or the constituent display control device 2100. In block 3107, the user initiates a dose by dispensing and inhaling on the constituent display control device 2100. The actual dose inhaled is then logged in the database 1600 in block 3108. In block 3109, the constituent display control device 2100 determines whether the user inhaled the maximum dose determined in block 3104. If the user has inhaled the maximum dose, then subsequent dosing/inhalation is disabled in block 3112 until such time as the time set by the user in block 3103 is determined to have expired in block 3113. After time expires, the constituent display control device 2100 resets to standard operating mode 3114 and the process ends in block 3115 at such time the user can once again take subsequent doses.

If in block 3109 it is determined that the user has inhaled the maximum dose determined in block 3104, then a loop is executed involving block 3110 where the constituent display control device 2100 waits for a dispensing or inhalation request/event and periodically checks to see whether the time set in block 3103 has expired in block 3111. If the time has not expired and no dispensing request or inhalation event is detected, the loop continues back through block 3110. If, however, time expires, then the process continues to block 3114 which functions as described previously. If, at block 3111, time has not expired, but a dispensing request or inhalation event is detected, then the process loops back to block 3104 where the dose can be recalculated. This is necessary because if a significant time has passed since the previous dose/inhalation, the next dose may need to be adjusted in order to ensure the that the effect will wear off by the time that the user initially set in block 3103. As discussed previously, the user can be prompted for feedback and/or ask challenge questions during the process and occur during the blocks enclosed by block 3116. It should be noted, that data analysis program 1805 can also trigger the constituent display control device 2100 or in-line constituent control device 3501 to prompt the user for feedback and/or ask challenge questions after the process terminates at block 3115 in order to check to confirm that the effect has worn off and/or collect further feedback that can improve its predictive capabilities. The timeout dosing process 3100 can be used in conjunction with the functionality associated with FIG. 29A and FIG. 30A.

The timeout dosing process can be controlled entirely by the computer network 1801, entirely by the computing device 1803, entirely by the constituent display control device 2100, in-line constituent control device 3501, or by a combination thereof. It should be further noted that while the timeout dosing process 3100 is described in the context of the constituent display control device 2100, the timeout dosing process 3100 can also be applied to other embodiments including the control device 100, manual control device 300, push button control device 500, passive control device 2401, solid media control device 2510 and optical solid media control device, 2610 in-line constituent vaporizer article 3500, media delivery article 3600 and nasal delivery article 4700.

Figure 32C:
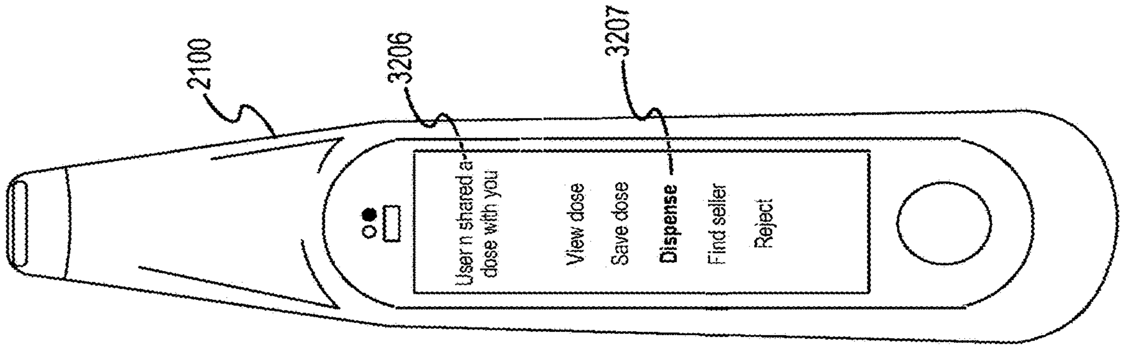
FIGS. 32A, 32B and 32C show examples of dose feedback and sharing interfaces of a vaporizer article that are constructed according to an aspect of the disclosure.
Figure 32B:
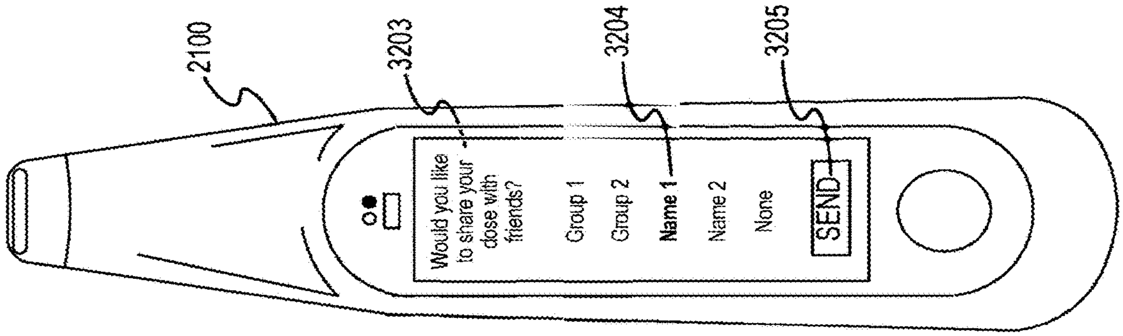
Figure 32A:
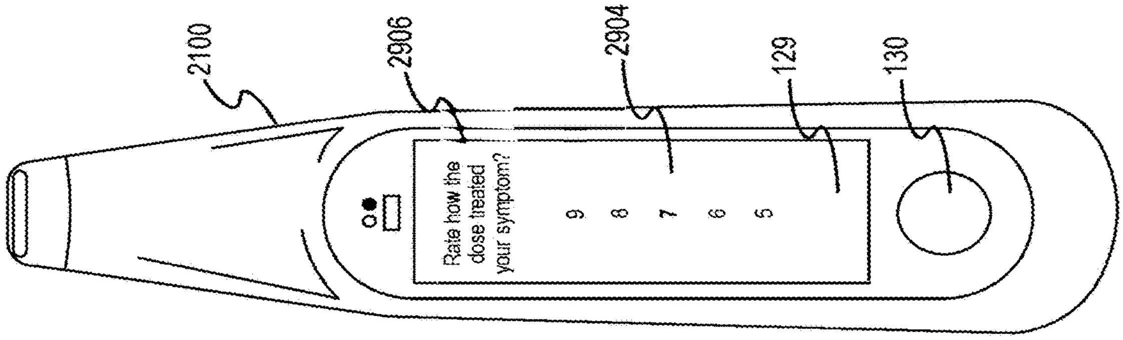

FIG. 32A shows one example of how constituent display enabled control device 2100 can be used in a social context. In this example, the user is prompted in feedback prompt 2906 to rate how well the dose treated their symptom in the rating menu 2904. Depending on how the user rates the dose, the user can be prompted by the constituent display control device 2100 to share the dosing information and/or rating with other users. FIG. 32B shows a social prompt 3203 that allows the user to determine whether and with whom they would like to share the dose in social menu 3204. The constituent display enabled control device 2100 can be configured to allow the user to share the dose information with other individuals or groups of individuals that can be pre-set by the user. After selecting the desired recipient, the user can send the dose by selecting the send button 3205. When this occurs, information regarding the dose, including, but not limited to: amount, composition, chemical profile, potency, brand name, product name, product type and testing results can be sent to the constituent display enabled control device 2100 of the recipient via the computer network 1801. When the recipient receives the shared dose, the recipient can receive a notification via their computing device 1803 and/or constituent display enabled control device 2100. FIG. 32C shows that the recipient can be prompted in social receipt prompt 3206 to select an action associated with the received dose in social receipt menu 3207. The user can take a number of actions with the received dosing information. If the recipient has a cartridge 200 that contains a substantially similar inhalation media composition, the recipient can command their constituent display enabled control device 2100 to dispense the shared dose so that they can experience it. For example, if the shared dose information was for 1 mg of a 50% THC/50% CBD inhalation media and the recipient has a cartridge with a 52% THC/48% CBD inhalation media, the recipient's device can dispense 1 mg of inhalation media. If the recipient's cartridge 200 does not contain a substantially similar composition, the recipient can be provided the option to select one of the dose constituents and dispense according to the amount of that constituent present in the shared dose.

The user can also take other actions in the social receipt menu 3207. For example, they can also view the dose to learn about its associated information. They may also elect to save the dose for later use. Such saved dosing information can be stored on any of constituent display enabled control device 2100, computing device 1803, computer network 1801 or cartridge 200. The recipient can be presented with an option to find a seller of a cartridge 200 from the shared dose. This can be especially useful if the recipient does not possess a cartridge 200 with a substantially similar composition to that of the shared dose. Such an option can be a link that can provide information about the seller and can be displayed on any of constituent display enabled control device 2100 or computing device 1803. The recipient can also choose to comment on the dose. Such a comment can take the form of a rating or comment entered via constituent display enabled control device 2100 or can be entered via computing device 1803. The recipient can alternatively reject the shared dose. If the recipient rejects the shared dose, a notification can be provided to the sender that the dose has been rejected. Alternatively, the recipient can be provided with the option to reject the dose without informing the sender.

In one embodiment, third parties, including, but not limited to: sellers of cartridges, individuals without a constituent display enabled control device 2100, manufacturers of inhalation media, doctors, health care organizations, therapists, and counselors can send such dosing information to a recipient's constituent display enabled control device 2100 and/or computing device 1803. Such third parties can use a computer interface to specify the dose and send it to the recipient via computer network 1801. The sending of such dosing information can be triggered manually or automatically via a computer program. The sending of such dosing information can also be triggered to coincide with the user's location. For example, if the user configured their computing device 1803 to provide location information such as GPS coordinates to the computer network 1801, the data analysis program 1805 can be configured to send such dosing information when the user is determined to be in proximity to a store that sells cartridges 200.

Figure 33A:
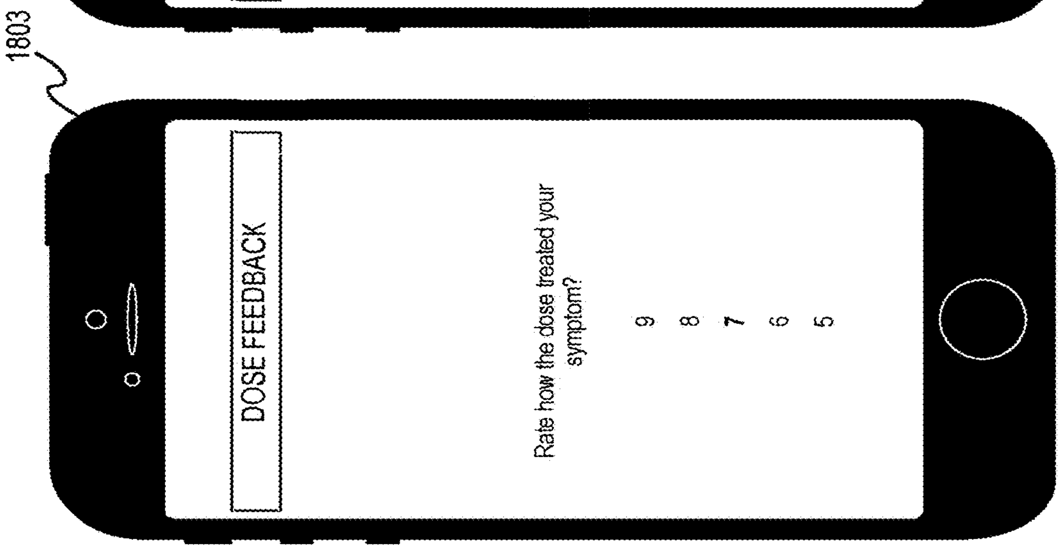
FIGS. 33A, 33B and 33C show additional examples of dose feedback and sharing interfaces that are constructed according to an aspect of the disclosure.
Figure 33B:
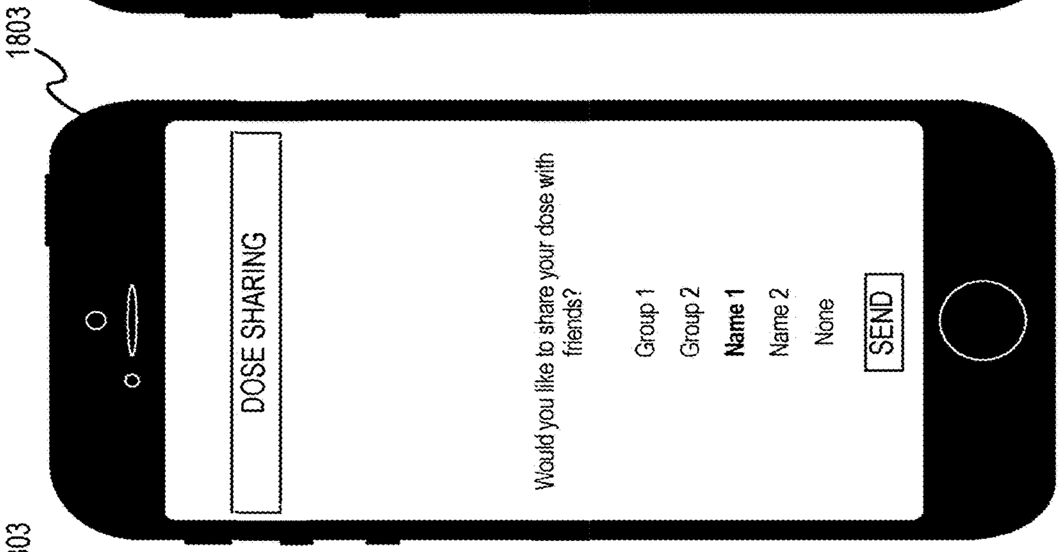
Figure 33C:
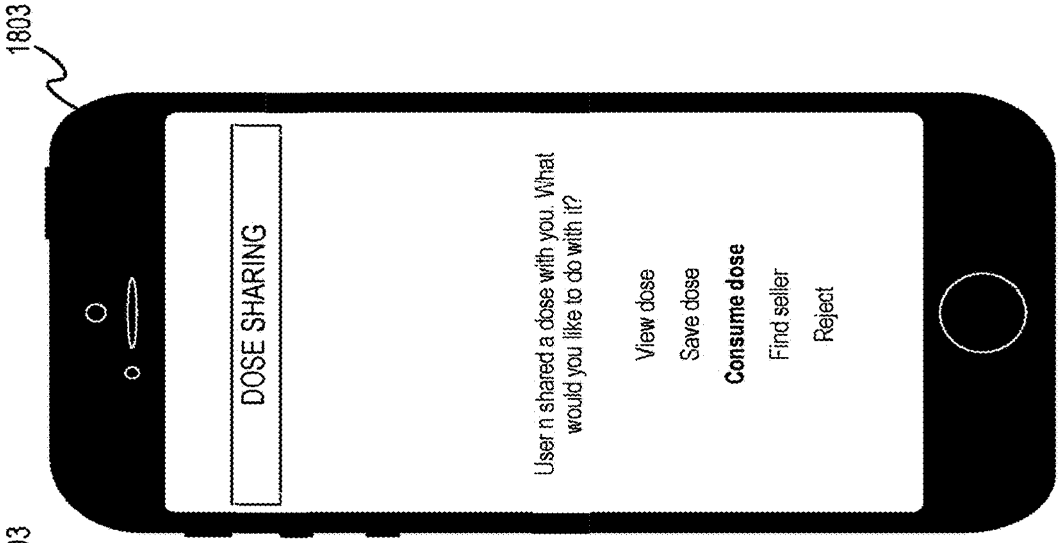

It should be noted that while the dose sharing functionality is described in the context of the constituent display control device 2100, the dose sharing functionality can also be applied to other embodiments including the control device 100, manual control device 300, push button control device 500, passive control device 2401, solid media control device 2510 and optical solid media control device 2610, in-line constituent control device 3501, sublingual control device 3601 and nasal delivery article 4700. FIGS. 33A-33C mirror FIGS. 32A-32C. They demonstrate that the same functionality associated with FIGS. 32A-32C can alternatively or additionally be provided via the computing device 1803.

Figures 34A, 34B, 34C:
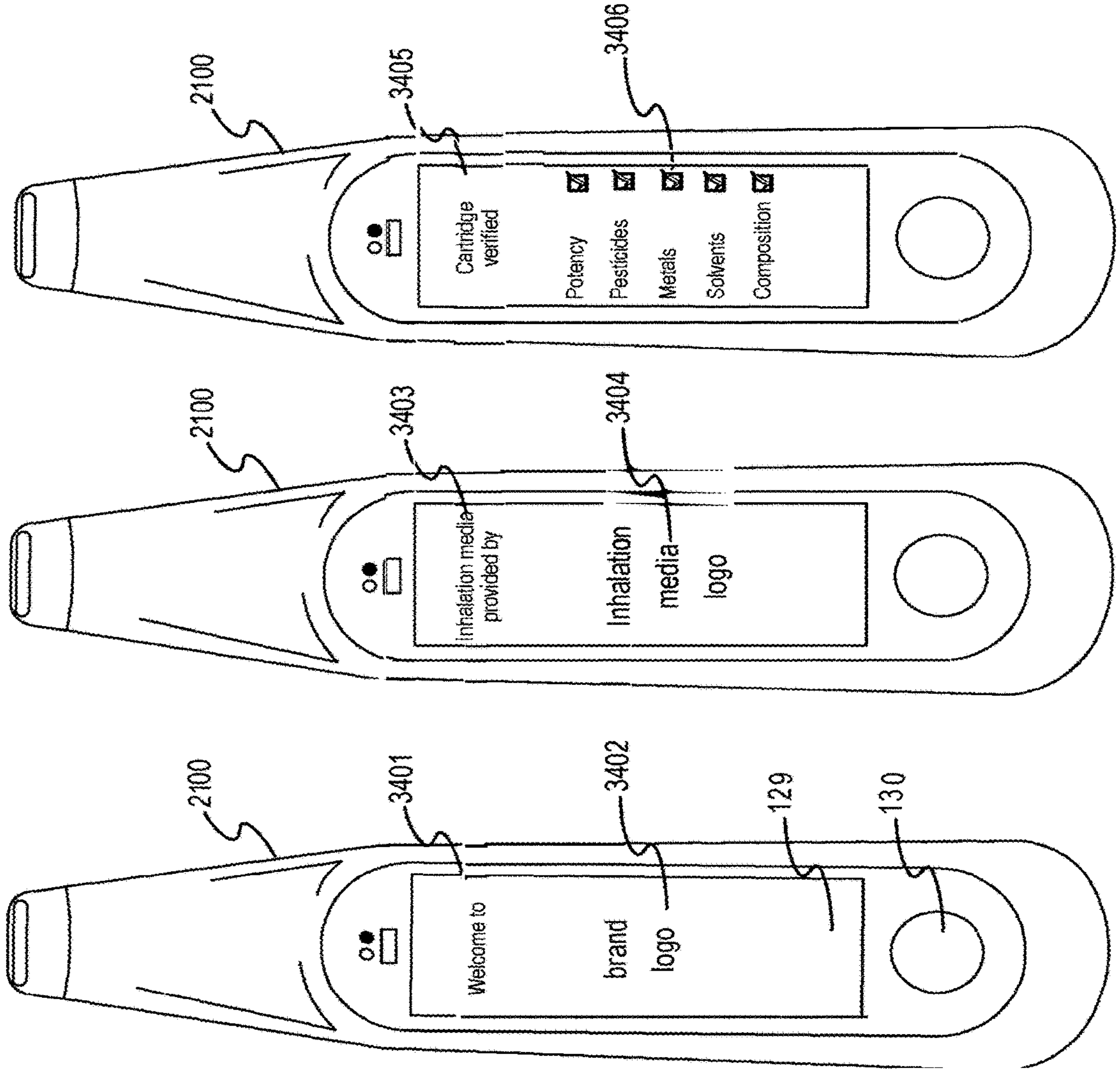
FIGS. 34A, 34B and 34C show additional examples of interfaces that are constructed according to an aspect of the disclosure.

FIG. 34A shows another example of how constituent display enabled control device 2100 can be used to provide additional information to the user. In this example, a welcome message is displayed in the welcome prompt 3401 and the brand of the product is displayed in the brand display 3402. This information can be displayed when the constituent display enabled control device 2100 is turned on and/or a cartridge 200 is connected. FIG. 34B shows another example of how constituent display enabled control device 2100 can be used to provide additional information to the user. In this example, information about the cartridge is displayed in the cartridge prompt 3403 and the brand of the inhalation media within the cartridge is displayed in the cartridge info display 3404. This information can be displayed when the constituent display enabled control device 2100 is turned on, when cartridge 200 is connected, and/or when the user selects such information to be displayed. Additional information about the cartridge 200 and inhalation media within the cartridge 200, chemical composition for example, can also be displayed in addition to or in lieu of the brand of the inhalation media. FIG. 34C shows another example of how constituent display enabled control device 2100 can be used to provide additional information to the user. In this example, a test result message is displayed in the verification prompt 3405 and the results of product testing is displayed in the testing info display 3406. This information can be displayed when the constituent display enabled control device 2100 is turned on when cartridge 200 is connected, and/or when the user selects such information to be displayed.

Figure 35A:
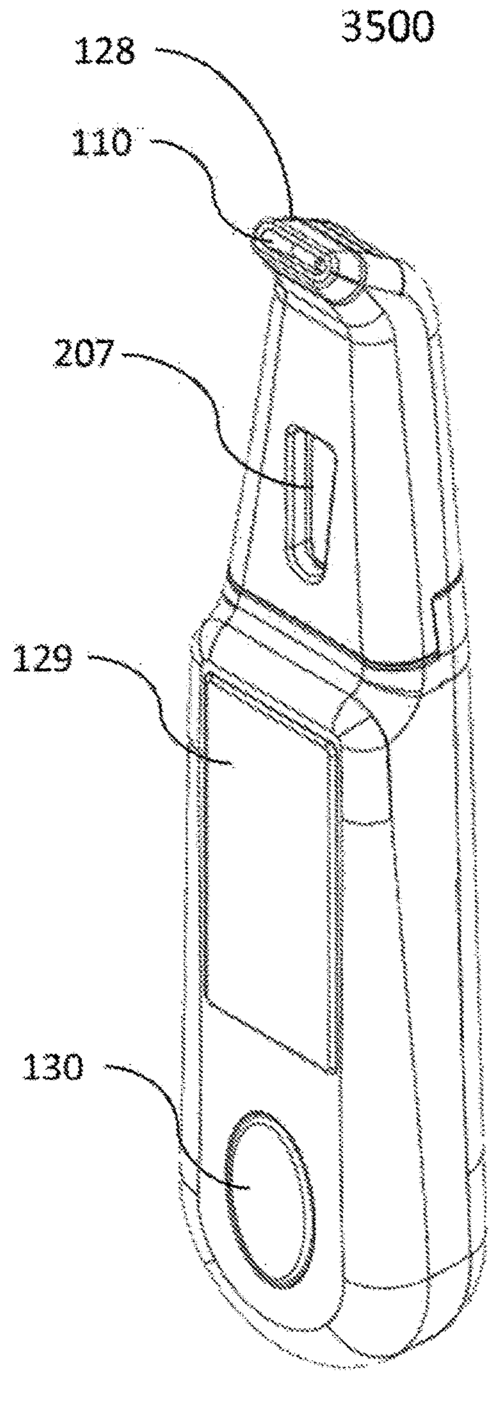
FIGS. 35A and 35B show another example of a vaporizer article that is constructed according to an aspect of the disclosure.
Figure 35B:
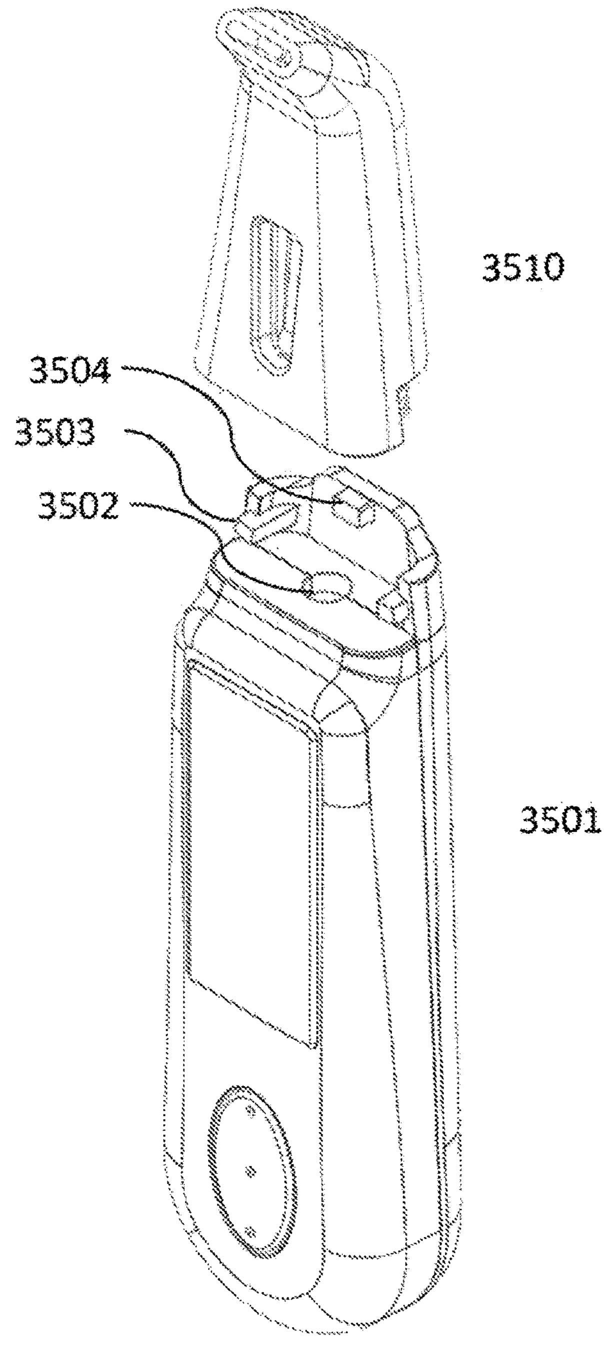

FIGS. 35A and 35B show an in-line constituent vaporizer article 3500 according to an aspect of the disclosure. The in-line constituent vaporizer article 3500 is comprised of in-line constituent control device 3501 and in-line constituent cartridge 3510. The in-line constituent control device 3510 is substantially similar to control device 100 and constituent display enabled control device 2100, with a primary difference being that the vaporizer element 109 is not contained within in-line constituent control device 3510. The vaporizer element 109 can be contained within in-line constituent cartridge 3510, which is substantially similar to the cartridge embodiments integrated cartridge 1400 and insert cartridge 1450. The in-line constituent cartridge 3510 is connectably removable from in-line constituent control device 3501. The in-line constituent control device 3501 can have a plunger portal 3502 through which the plunger driver 116 can extend. One or more guide features 3503 can be provided to assist with the mating of in-line constituent cartridge 3510 with in-line constituent control device 3501. A retention latch 3504 can also be provided to assist with retention of the in-line constituent cartridge 3510. Retention latch 3504 can be comprised of a magnet which acts upon a piece of ferrous material or magnet located within in-line constituent cartridge 3510. Retention latch 3504 can alternatively be a mechanical feature such as a snap fit or interference fit where the feature is shaped so as to provide a slight mechanical interference.

Figure 36A:
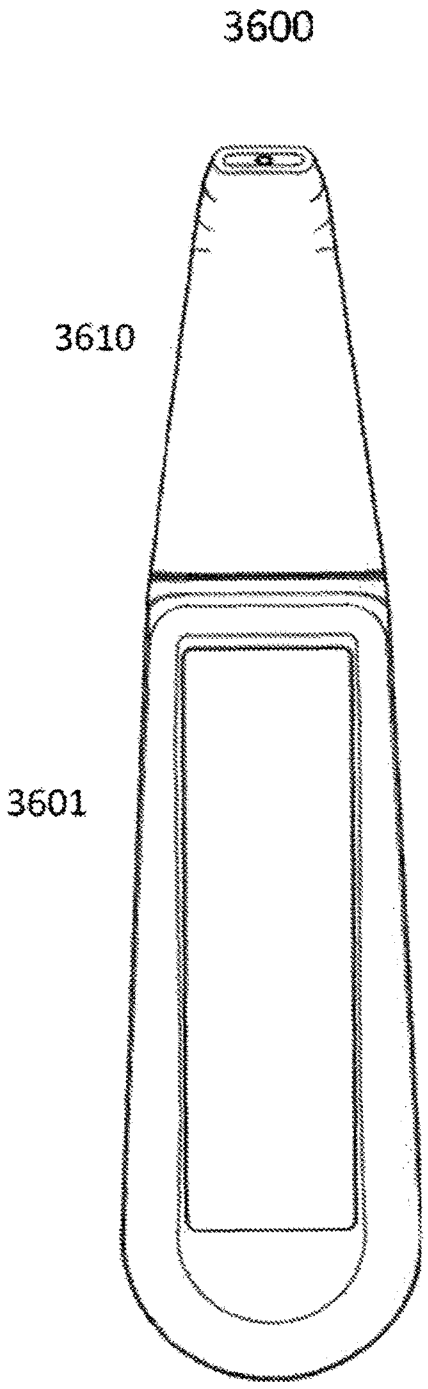
FIGS. 36A, 36B, and 36C show an example of an alternative delivery pathway device that is constructed according to an aspect of the disclosure.
Figure 36B:
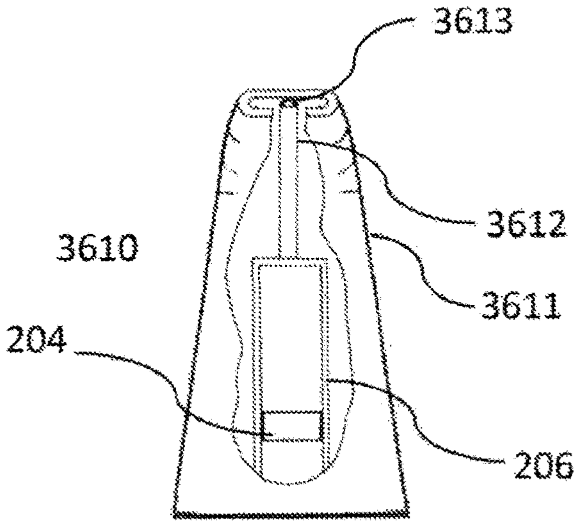
Figure 36C:
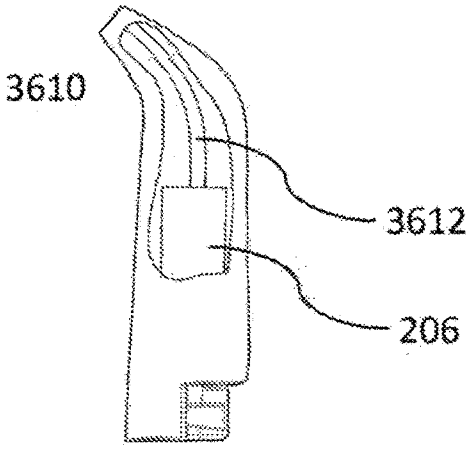

FIGS. 36A, 36B and 36C shows a media delivery article 3600 according to an aspect of the disclosure. Media delivery article is substantially similar to in-line constituent vaporizer article 3500 except that the vaporizer element 109 is eliminated from in-line constituent cartridge 3510 to create an in-line sublingual cartridge 3610. In this embodiment, the media inside the in-line sublingual cartridge 3610 can be ingested orally and either swallowed by the user or placed under the tongue to be absorbed through sublingual tissue rather than inhaled. The media stored in media storage area 206 (shown in section view in FIG. 36B and solid view in FIG. 36C) can be expressed directly into the user's mouth via sublingual tube 3612. The media, which can be in liquid or powder form, exits the sublingual tube 3612 via tube opening 3613. In one embodiment, sublingual control device 3601 can be identical to in-line constituent control device 3501. Through the ability to read memory IC 205, the in-line constituent control device 3501 can differentiate between an in-line constituent cartridge 3510 and an in-line sublingual cartridge 3610 and control each accordingly. This means that all the functionality offered by in-line constituent control device 3501 including, but not limited to: dose control, dispensing, data recording and sharing, dose compensation, and connectivity can also be delivered in a sublingual use application; only the functions specifically related to generating an aerosol would not be applicable.

Figure 37A:
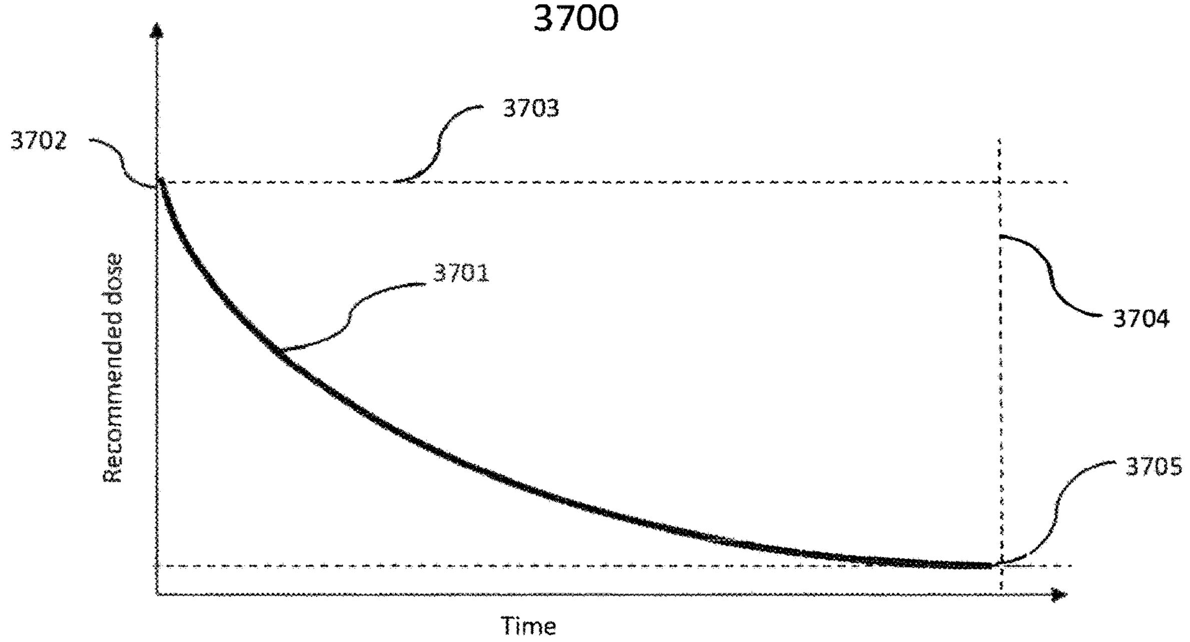
FIGS. 37A, 37B, and 37C show an example of how cessation dosing controls are generated according to an aspect of the disclosure.

FIG. 37A describes a cessation curve 3701 that represents the amount of a chemical or drug that a user can take in order to gradually reduce the amount of said chemical or drug consumed without triggering unwanted side-effects or symptoms. For example, a user who desires to consume less nicotine may want to slowly decrease consumption over time. The cessation curve can be prescribed by a third party, such as a doctor, and stored in database 1600, so that the data analysis program 1805 can then suggest doses to the user. Alternatively, the data analysis program 1805 can construct and suggest a cessation curve 3701 for an individual based on dosing data collected from other users with similar cessation goals. The cessation curve 3701 can also be a mathematical expression resulting from observations from test subjects who participate in cessation studies. The cessation curve 3701 begins at the initial cessation dose time 3702 at the initial cessation dose level 3703. The user can define one or more of the cessation completion time 3704 and the cessation dose final level 3705. Then based on such inputs, the data analysis program 1805 can determine one or more of the shape of the cessation curve 3701, cessation completion time 3704 and the cessation dose final level 3705.

Figure 37C:
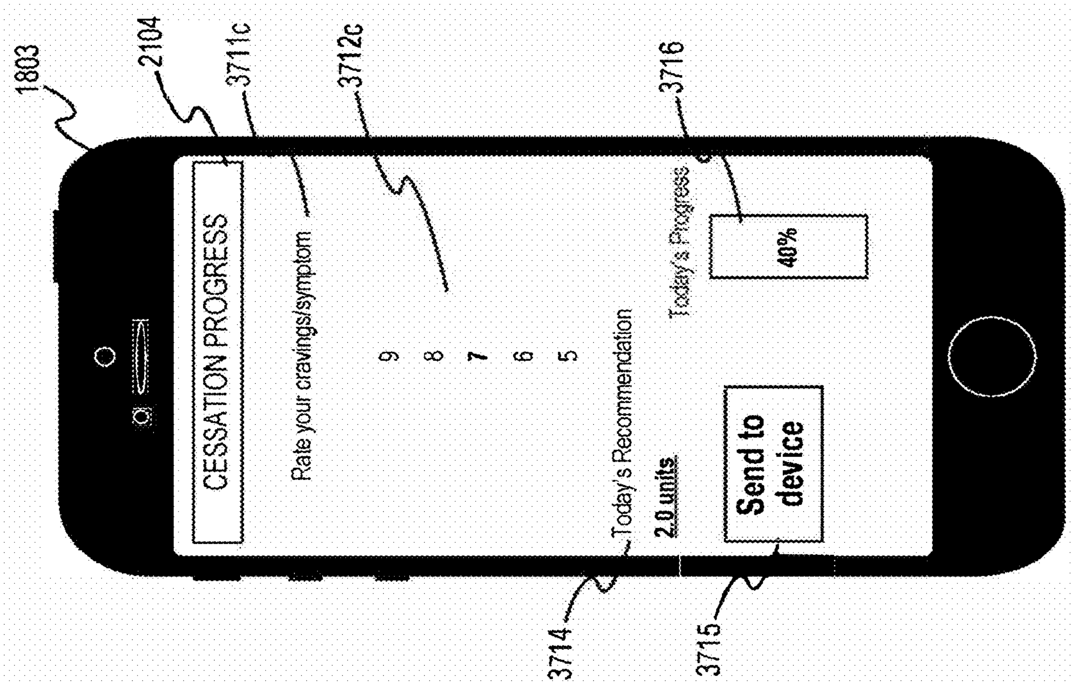
Figure 37B:
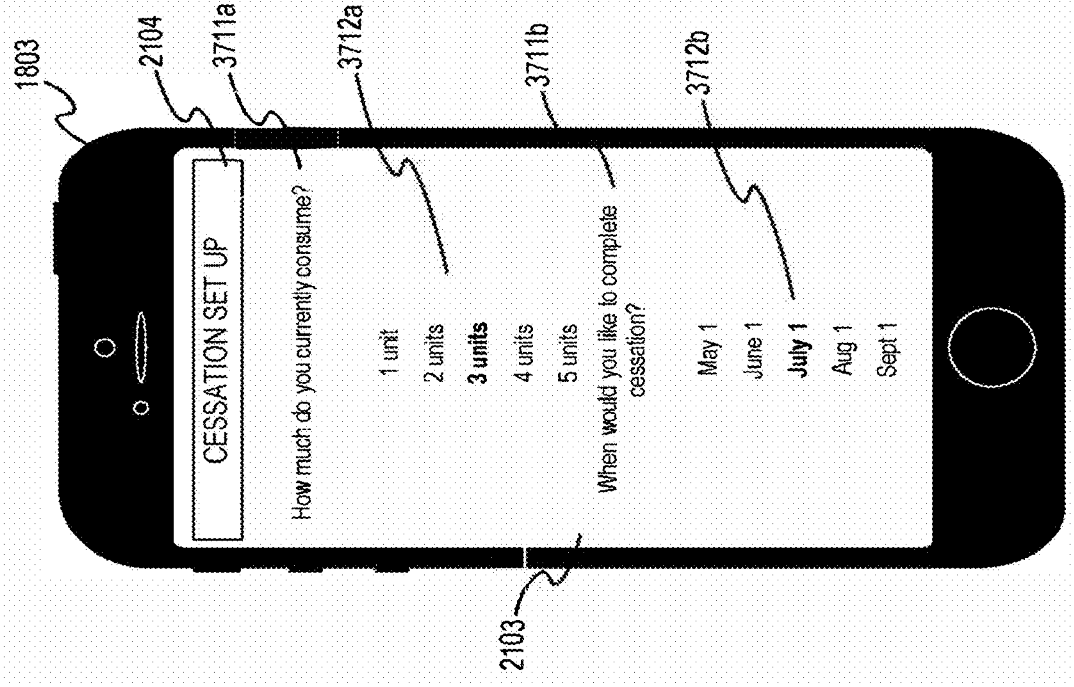
Figure 38A:
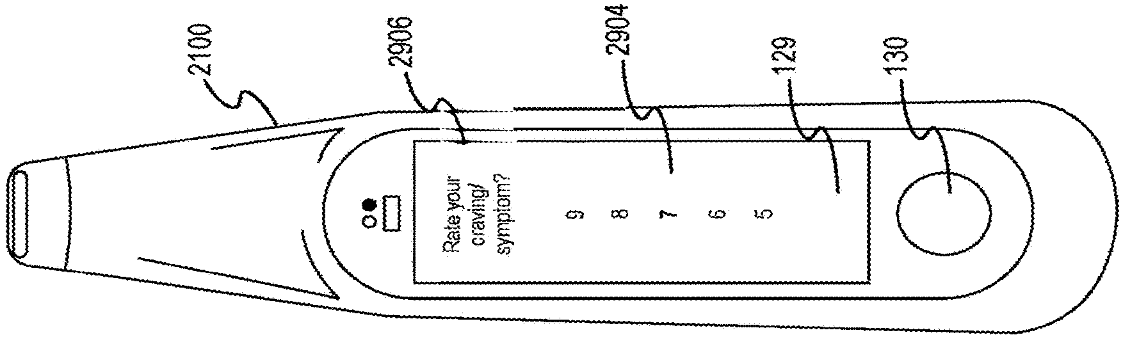
FIGS. 38A, 38B, and 38C show additional examples of how cessation dosing controls are generated according to an aspect of the disclosure.
Figure 38B:
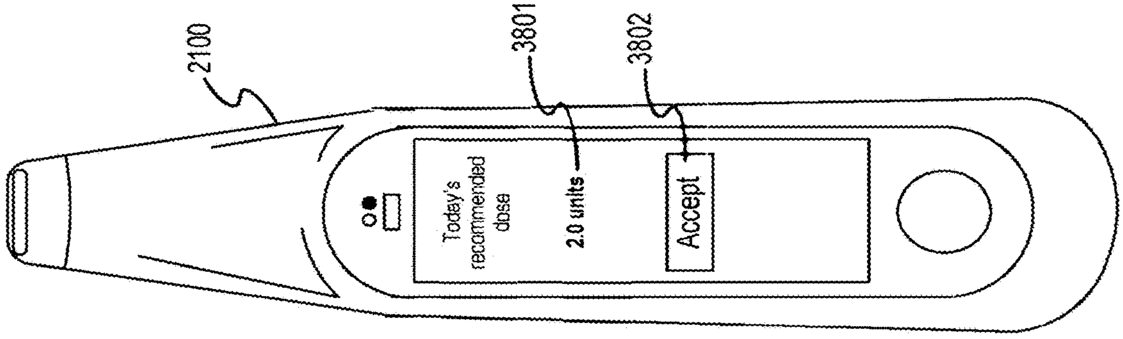
Figure 38C:
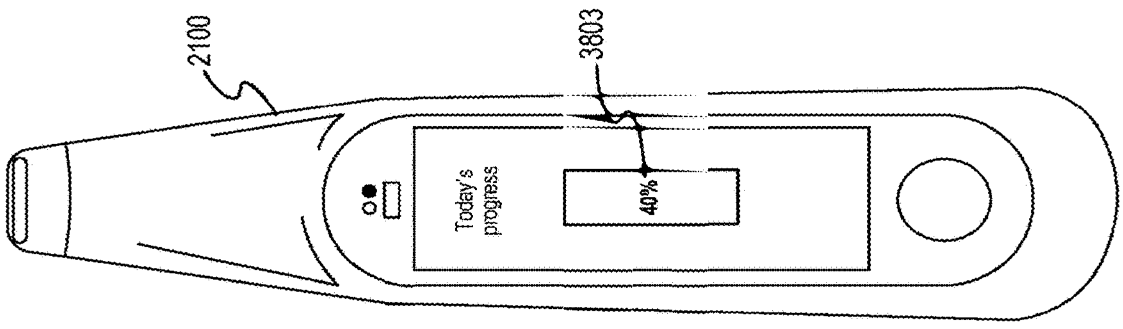

FIGS. 37B and 37C show aspects of the dose visualization application 2103 configured to inform and control cessation activities. An application header 2104 can be configured to indicate the cessation mode. The dose visualization application 2103 can display one or more cessation prompts 3711 and can also provide areas for the user to answer such prompts in one or more cessation setting menu 3712. Information entered by the user into the cessation setting menu 3712 can be used by the data analysis program 1805 to help calculate the cessation curve 3701 for an individual. Furthermore, as shown by cessation setting menu 3712*c*, the user may provide feedback that can be used by the data analysis program 1805 to confirm that side-effects are within an acceptable range or adjust the cessation curve if such side-effects fall outside of an acceptable range. The data analysis program 1805 can further provide a recommended amount 3714 of media for consumption. For example, for a user who initially consumed 4.0 mg of nicotine per day and is trying to stop using nicotine, the data analysis program 1805 can use the cessation curve 3701 to suggest a dose of 2.0 mg for a given day that is some number of days after the initiation of the cessation process. The user can be presented with the option to accept the 2.0 mg suggestion and command the vaporizer article 10, in any of its embodiments, to provide only up to 2.0 mg for that day by pressing the acceptance button 3715. The user can also monitor their progress toward staying within that 2 mg dose via the cessation gauge 3716. For example, if the user was suggested 2.0 mg of nicotine for a given day and the user had already had 0.8 mg, then the cessation gauge can display a 40% reading. The system can be configured to disallow further dosing for the day once the user has reached 100% of the recommended amount 3714. FIGS. 38A, 38B and 38C demonstrate how certain functionality provided by the dose visualization application 2103 and shown in FIGS. 37B and 37C can also be provided, in part, by the constituent display enabled control device 2100, in-line constituent vaporizer article 3500, and media delivery article 3600. This provides the user with the option to enter such information and track their progress in the manner most convenient to them.

Figure 39B:
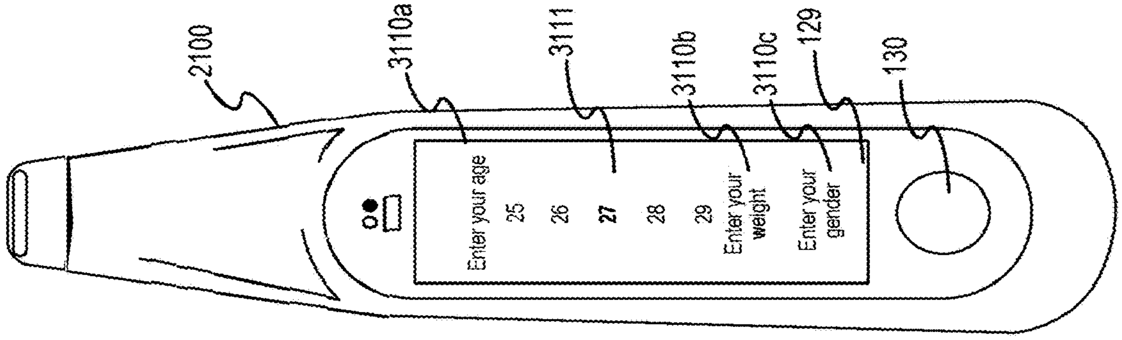
FIGS. 39A and 39B show examples of how dosing and cessation controls are generated according to an aspect of the disclosure.
Figure 39A:
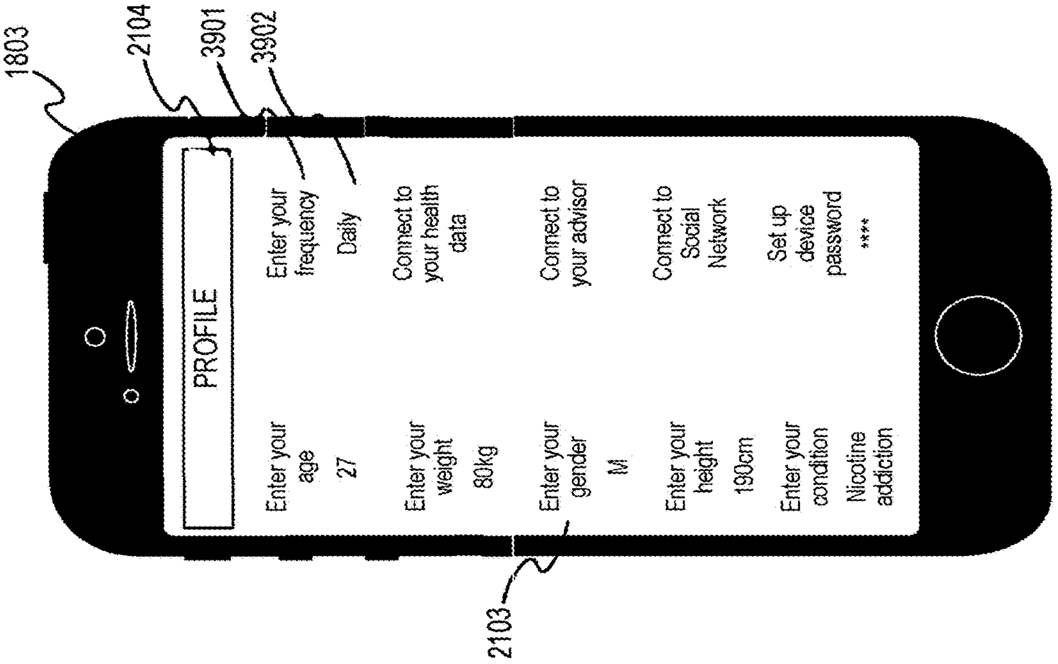

FIG. 39A shows an embodiment of dose visualization application 2103 configured to accept and display background information from the user, including, but not limited to age, weight, gender, height, physical conditions, mental conditions, ailments, usage history, external health data, external advisors, social network, and the user's reason for consuming inhalation media. FIG. 39B shows an embodiment of the constituent display enabled control device 2100, and by extension, in-line constituent vaporizer article 3500 and media delivery article 3600, configured to accept and display part or all of the same information shown in FIG. 39A.

Figure 40A:
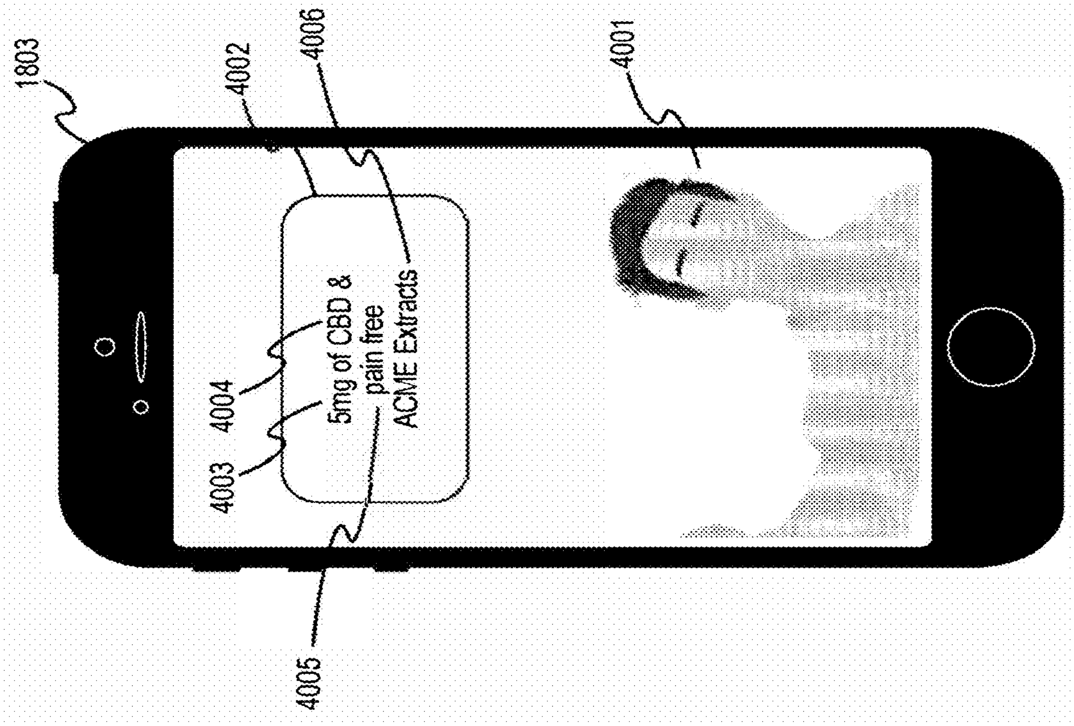
FIGS. 40A and 40B show examples of how dosing information can be displayed and shared according to an aspect of the disclosure.
Figure 40B:

Sharing information via imagery and photography is common practice in social networks and users may want to share their experiences with inhaled or orally ingested media via social networks. For example, a user may wish to share that a particular dose of a particular formulation helped relieve their back pain. FIGS. 40A and 40B show an embodiment of the dose visualization application 2103 configured to display certain information related to dosing on an image or digital photograph 4001. A badge 4002 can be a graphical element placed onto the digital photograph 4001. The badge 4002 can contain fields such as badge dose amount 4003, badge dose substance 4004, badge effect 4005 and badge provider 4006. Badge dose amount 4003 can be the amount of dose consumed by the user. Badge dose substance 4004 can be the media consumed by the user, for example, nicotine, CBD, THC, cannabinoids, or a combination thereof. Badge effect 4005 can be the effect the user previously told the system it was trying to achieve or can be entered manually by the user to describe their current state. Badge provider 4006 can contain a company or personal name, for example the name of the company that provided the inhalation media, the name of the company that produced the cartridge 200 or the name of the company that produced the vaporizer article 10, the constituent display enabled control device 2100, in-line constituent vaporizer article 3500, media delivery article 3600, or nasal delivery article 4700.

Figure 41:
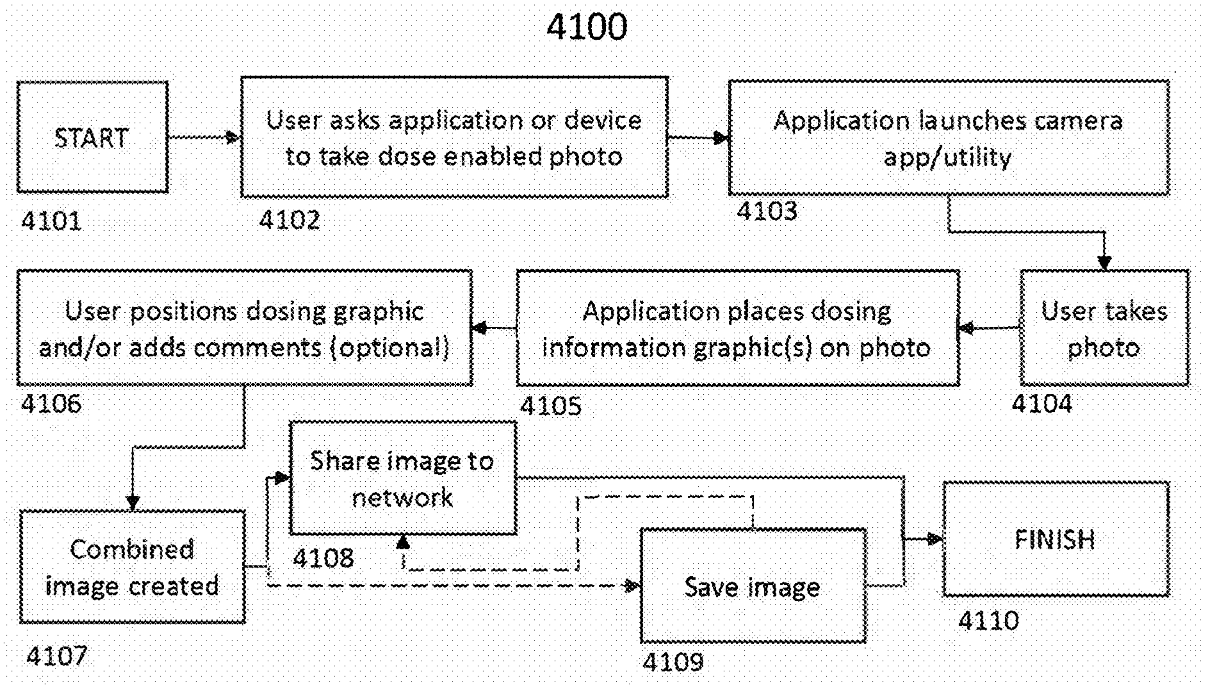
FIG. 41 shows an examples of how dosing information can be generated and shared according to an aspect of the disclosure.

FIG. 41 describes dose enabled photograph process 4100. The dose enabled photograph process 4100 begins with block 4101. In block 4102, the user asks the dose visualization application 2103 or any of the constituent display enabled control device 2100, in-line constituent vaporizer article 3500, or media delivery article 3600 to take a dose enabled photograph. In block 4103, the feedback application 1804 launches a utility or application where the user can take a digital photograph 4001. In block 4104, the user can take the digital photograph 4001. In block 4105, the dose visualization application 2103 places a badge 4002 at an initial location on the digital photograph 4001. In block 4106, the user can be provided with the option to select a final location, style, color, content and format of the badge 4002. In block 4107, a combined or merged image is created. In block 4108, the user can be presented with the ability to share the dose enabled photograph with a social network, for example, a network defined to the dose visualization application 2103 in FIG. 39A. In block 4109, the user can alternatively or additionally have the ability to save the dose enabled photograph to their computing device 1803 for later use, including sharing a dose enabled photograph with a social network without going through the dose visualization application 2103. The dose visualization application 2103 can further be configured to apply badge 4002 to photographs that already exist on the user's computing device 1803 or are downloaded to the user's computing device 1803 from a network.

FIGS. 42A through 42D show several embodiments of network architectures configured to enable functionality on computing device 1803 and in-line constituent vaporizer article 3500. (Note: Although the in-line constituent vaporizer article 3500 is specified in FIGS. 42A through 42D, it should be understood that any vaporizer article 10 in any of its embodiments including constituent display enabled control device 2100, passive vaporizer article 2400, solid media vaporizer article 2500, and optical solid media vaporizer article 2600, in-line constituent vaporizer article 3500, media delivery article 3600 and nasal delivery article 4700 can be used.) Much in the same way that the functionality and user experience of a mobile phone is defined by the applications running on said mobile phone, the system described by the present invention can provide a variety of functionality and experiences that are determined by the applications running on the computing device 1803 and computer network 1801 and the inhalation media or orally ingested media. The knowledge needed to design different applications can be quite specific for each individual application and difficult for any one party to possess. Therefore, a network architecture is provided in order to allow different parties with application specific knowledge to design applications that provide specific functionality. And it can be desirable to have certain applications separate from other applications in order to allow for individual development and data management. For example, it can be desirable to use the in-line constituent vaporizer article 3500 as part of a nicotine cessation regimen in conjunction with in-line constituent cartridges 3510 that are filled with a nicotine solution. An application can be created to help determine when to provide doses, what the dosing size should be, and what types of behavioral queues should be given to the user. Deep knowledge of nicotine addiction and human behavior can be necessary to design such an application. A party with such knowledge can design an application to run on computing device 1803 and/or computer network 1801. Such party can also manage data associated with its user base separately from users of other applications for any number of reasons, including, but not limited to data privacy. In another example, it can be desirable to use the in-line constituent vaporizer article 3500 as part of a sleep assistant program in conjunction with in-line constituent cartridges 3510 that are filled with a melatonin solution for people with insomnia. An application can be created to help determine when to provide doses, what the dosing size should be, and what types of user feedback should be collected. Deep knowledge of sleep science and the pharmacodynamics of melatonin may be necessary to design such an application. A party with such knowledge can design an application to run on computing device 1803 and/or computer network 1801. In another example, it can be desirable to use the in-line constituent vaporizer article 3500 as part of an anxiety reduction program in conjunction with in-line constituent cartridges 3510 that are filled with a CBD formulation. An application can be created to help determine when to provide doses, what the dosing size should be, and what types of user feedback should be collected. Deep knowledge of psychology and the pharmacodynamics of CBD may be necessary to design such an application. A party with such knowledge can design an application to run on computing device 1803 and/or computer network 1801. The differences between these three applications highlight the need for an architecture that allows for a variety of applications to be developed, run and managed independently.

Figure 42A:
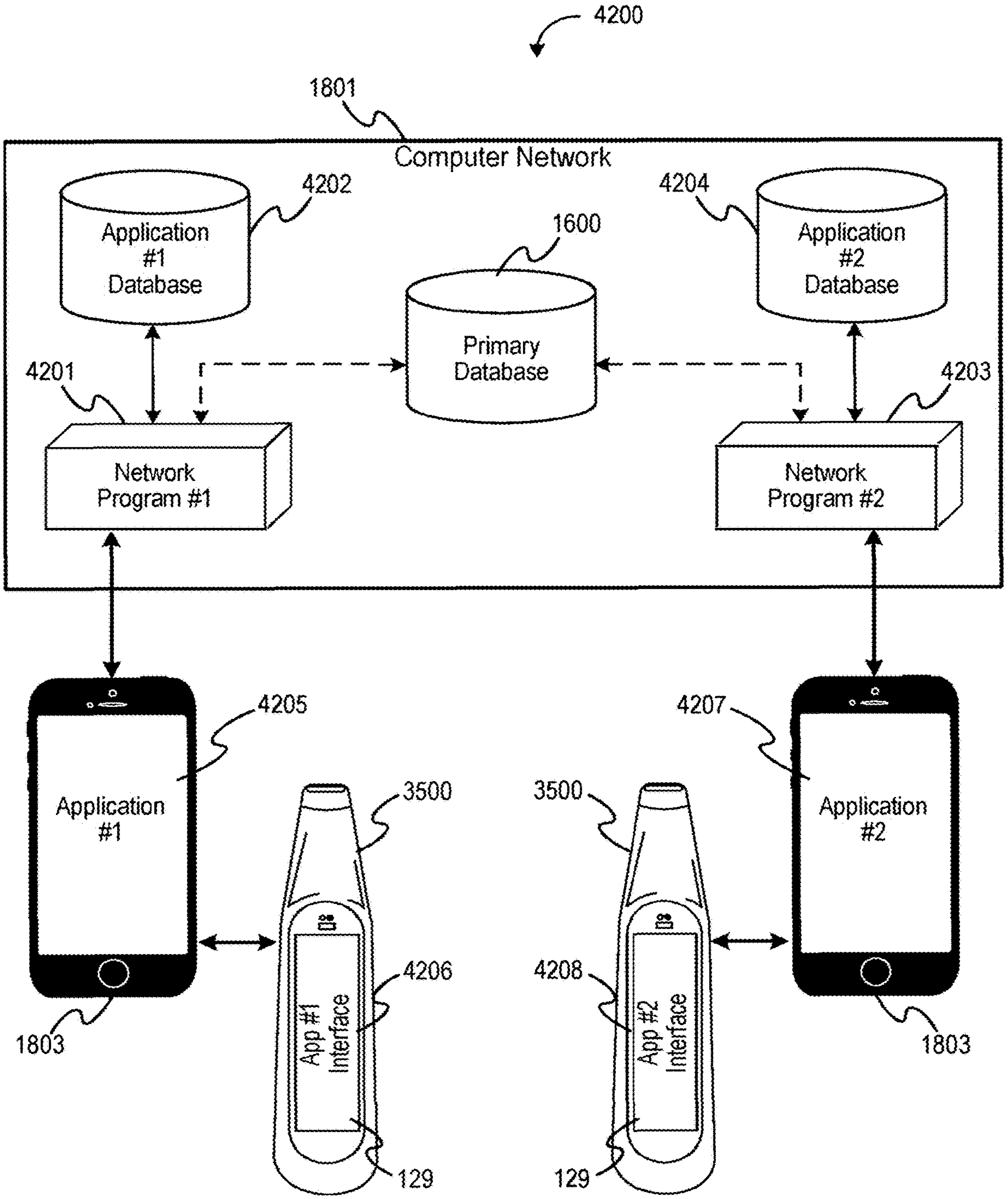
FIGS. 42A, 42B, 42C and 42D show example network system architectures for selecting and executing applications according to an aspect of the disclosure.

FIG. 42A shows a non-gateway architecture 4200 where each application has a corresponding program running within computer network 1801. The user can download mobile application 4205 onto their computing device 1803 in order to enable certain functionality. Mobile application 4205 is configured to communicate with network program 4201. Mobile application 4205 can also be configured cause an application specific interface 4206 to be displayed on display screen 129. Such application specific interface 4206 can be pre-loaded into the in-line constituent vaporizer article 3500 or it can be downloaded from mobile application 4205 or network program 4201. Mobile application 4205 can also customize the operational parameters of in-line constituent vaporizer article 3500. Data from the in-line constituent vaporizer article 3500 and mobile application 4205 are sent to network program 4201, which in turn, decides how to process the data and where to store said data. Certain data specific to mobile application 4205 can be stored in application database 4202. Other data or modified copies of the data can also be stored in database 1600. For example, user names and usage data can be stored in application database 4202 while anonymized copies of usage data can be stored in database 1600. Data and commands from the network program 4201 can be sent to the mobile application 4205 and onward to the in-line constituent vaporizer article 3500.

Figure 42B:
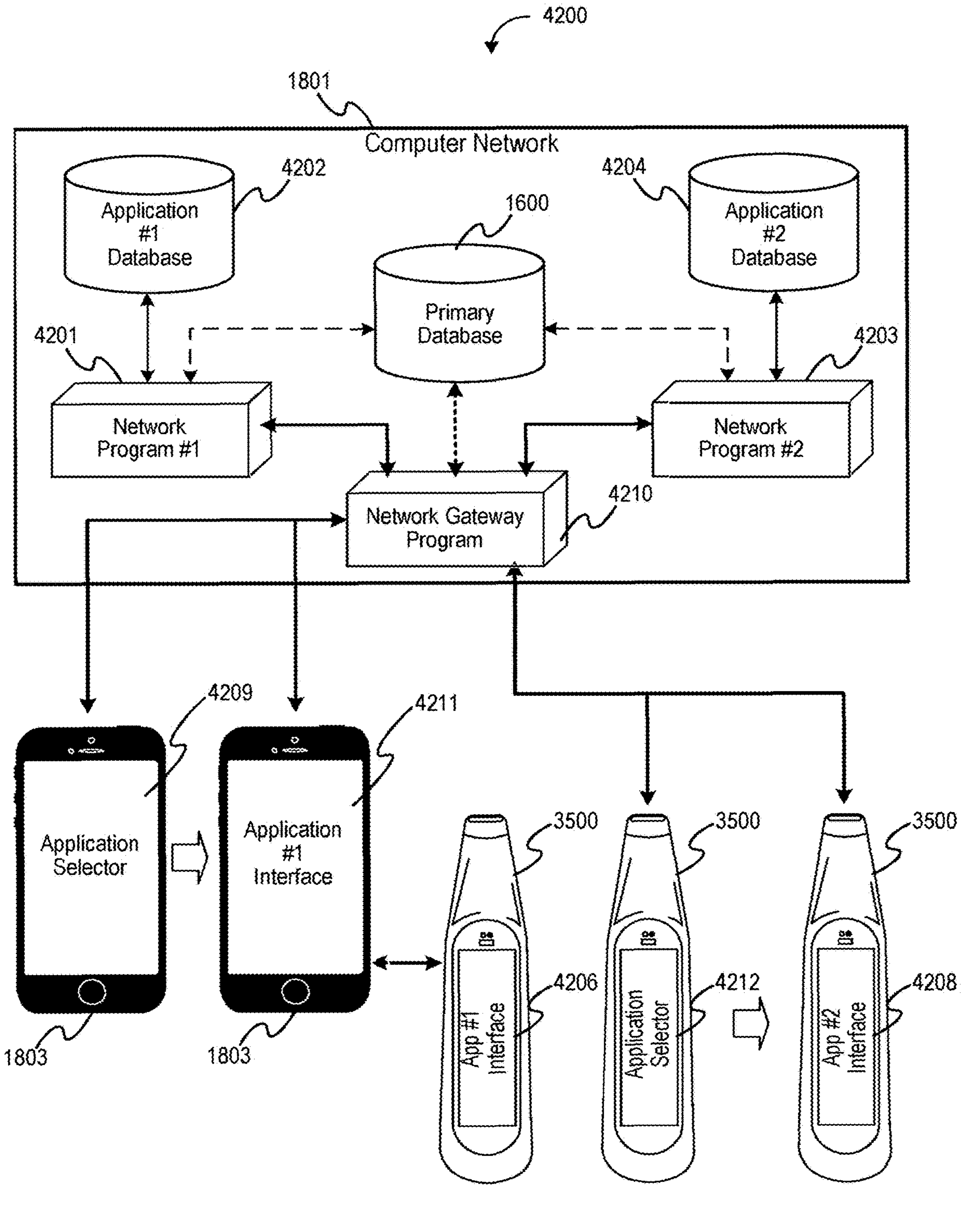

FIG. 42B shows a gateway architecture 4200 where applications communicate through a central network gateway program 4210. The user may use the application selector 4209, which can be part of a native application that is pre-installed or downloaded by the user in conjunction with the purchase of the in-line constituent vaporizer article 3500, to select which application they wish to run. When the user selects an application, for example the application associated with network program 4201, the network gateway program 4210 communicates with network program 4201 and causes the associated mobile application interface 4211 to be displayed. It can also cause application specific interface 4206 to be displayed on display screen 129 if a specific interface is required by network program 4201. The application specific interface 4206 can be pre-loaded into the in-line constituent vaporizer article 3500 or it can be downloaded from network program 4201. Data from the in-line constituent vaporizer article 3500 and mobile device 1803 are routed through the network gateway program 4210, which determines where to send said data. Data and commands from the network program 4201 can be routed through the network gateway program 4210 to the mobile device 1803 and onward to the in-line constituent vaporizer article 3500. Network program 4201 can also make requests to network gateway program 4210 that cause certain actions to occur on in-line constituent vaporizer article 3500. For example, network program 4201 can send a request to the network gateway program 4210 to send a dose recommendation to the in-line constituent vaporizer article 3500. The network gateway program 4210 can receive said request and send a command to the computing device 1803 in a format that the native application understands. The network program 4201 can read data from and store data in application database 4202. Network program 4201 can also cause data or modified copies of data to be stored in database 1600. It can also read data from database 1600. Additionally, network gateway program 4210 can be configured to route certain data directly to and from the database 1600. The preceding description of gateway architecture 4200 describes an embodiment where a particular mobile application interface 4211 is displayed using the native application, however, it should be noted that embodiments exist where the application selector 4209 causes a separate application to be installed on computing device 1803.

Figure 42C:
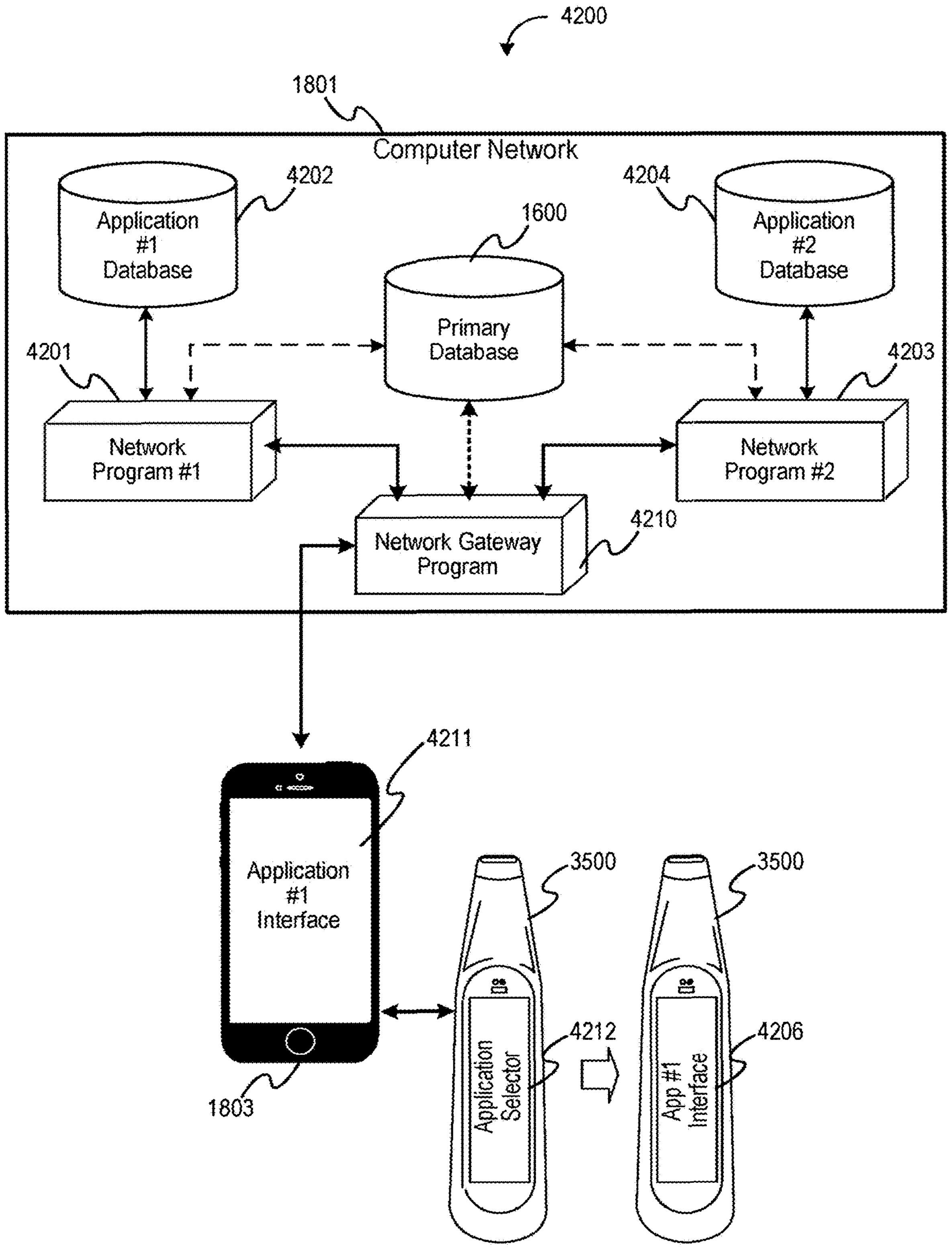

FIG. 42B also describes how the gateway architecture 4200 functions when no computing device 1803 is present. In the embodiment where the in-line constituent vaporizer article 3500 is configured with the circuitry necessary to connect directly to computer network 1801, applications can still be selected and executed on the computer network 1801. In such an embodiment, the in-line constituent vaporizer article 3500 can be equipped with Zigbee, Wi-Fi, or digital cellular circuitry configured to connect with computer network 1801. In such an embodiment, the user can use the device application selector 4212, which can be pre-loaded onto the in-line constituent vaporizer article 3500, to select an application such as network program 4203. Network gateway program 4210 can establish the connection to the correct program. If Network program 4203 requires a unique interface, network program 4203 can then cause the device application interface 4208 to be displayed on the in-line constituent vaporizer article 3500. The device application interface 4208 can be pre-loaded onto the in-line constituent vaporizer article 3500 or it can be downloaded from network program 4203. Once the device application interface 4208 is displayed, if required for the operation of network program 4203, the user can access the functionality of network program 4203, and the data exchange and command communication between the in-line constituent vaporizer article 3500 and network program 4203 can be facilitated by the network gateway program 4210 as previously described. FIG. 42C shows an embodiment similar to that described in FIG. 42B. The sole difference is that the application is selected by the device application selector 4212 rather than the application selector 4209.

Figure 42D:
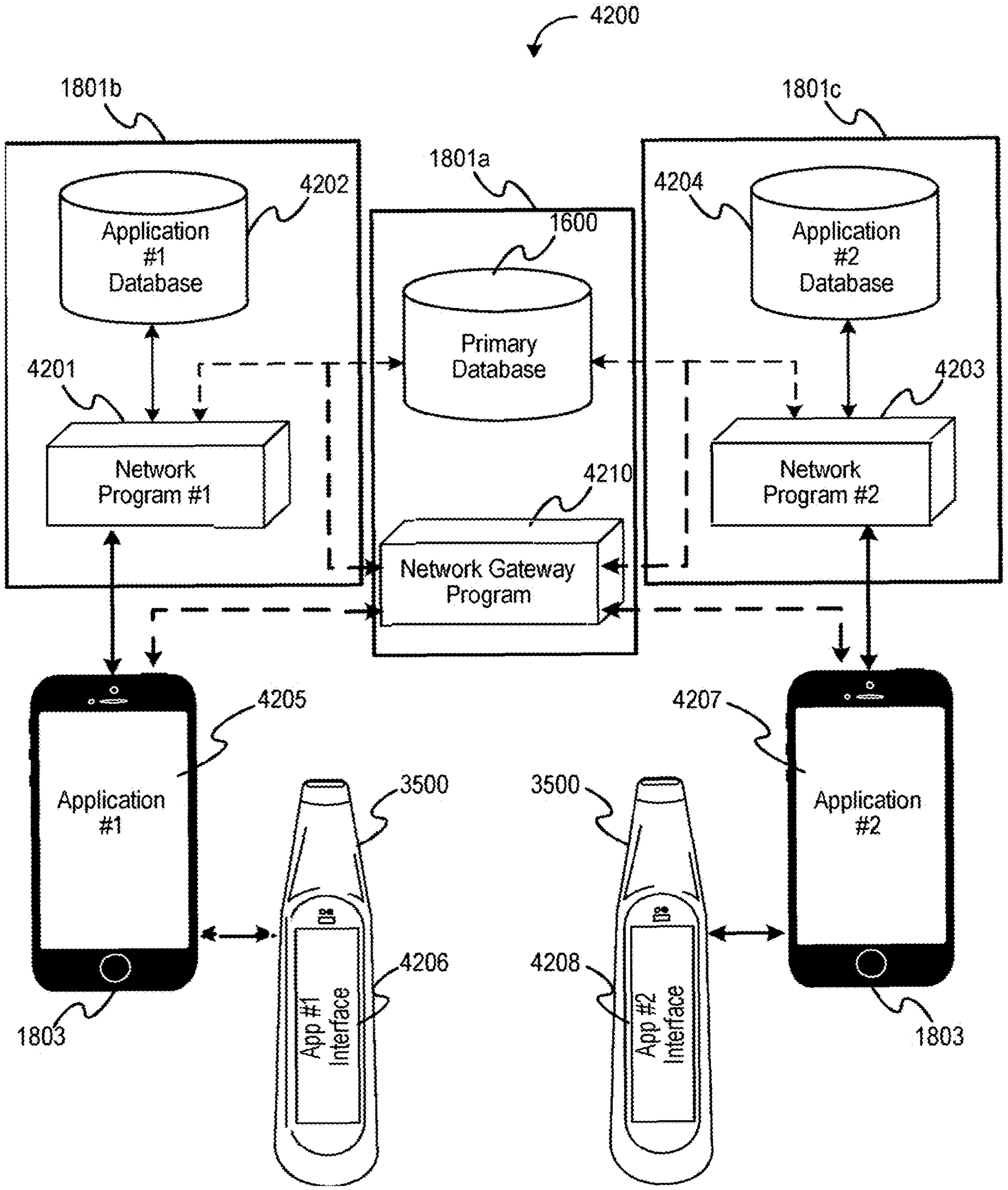

FIG. 42D shows a distributed architecture 4240 where different applications run on different computer networks 1801*a* through 1801*c*. One benefit of this architecture is that each party has more direct control of the data and data privacy within their respective computer network. In this architecture, the option of using a network gateway program 4210 to facilitate connecting to the correct network program and sending commands to the in-line constituent vaporizer article 3500 still exists, however, the preferred communication path for non-anonymized user related data is directly to the appropriate network program. Although not shown, embodiments of application selectors, device application selectors, and direct communication between the in-line constituent vaporizer article 3500 and network program can be implemented within the distributed architecture 4240. (Note: Although the in-line constituent vaporizer article 3500 is specified in FIGS. 42A through 42D, it should be understood that any vaporizer article 10 in any of its embodiments including constituent display enabled control device 2100, passive vaporizer article 2400, solid media vaporizer article 2500, and optical solid media vaporizer article 2600, in-line constituent vaporizer article 3500, media delivery article 3600, nasal delivery article 4700 and their respective components can include this functionality.)

Figure 43A:
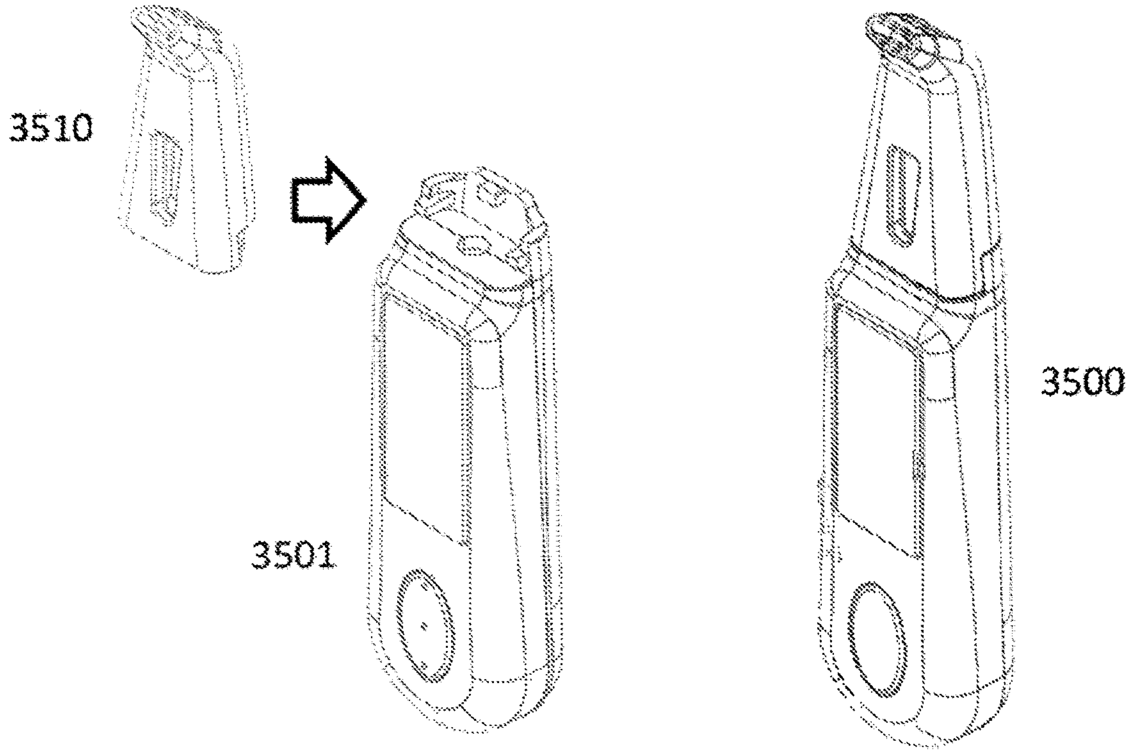
FIGS. 43A and 43B show an example of how applications can be triggered according to an aspect of the disclosure.
Figure 43B:
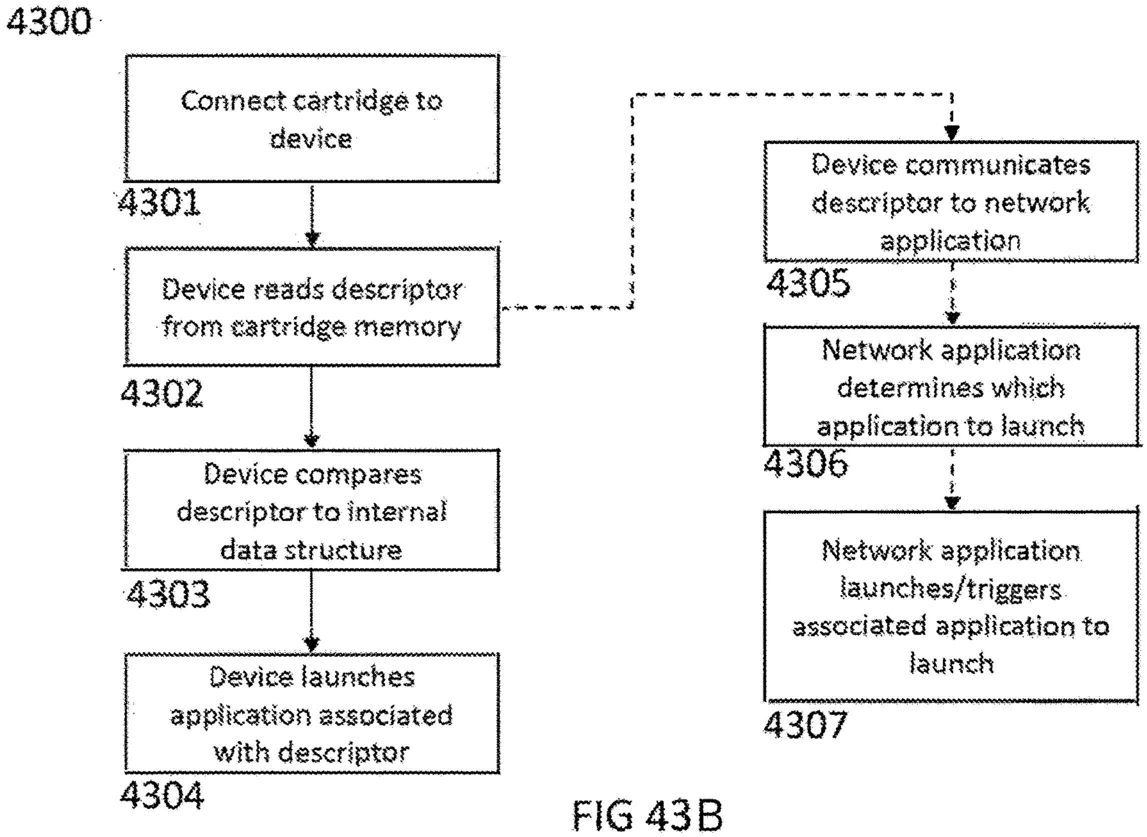

Rather than having the user select an application, in certain circumstances, it may be more convenient or desirable for the application to be selected based on the characteristics of the cartridge and/or inhalation media or orally ingestible media. FIGS. 43A and 43B describe how the act of connecting in-line constituent cartridge 3510 to in-line constituent control device 3501 can cause a particular application to be executed. (Note: Although the in-line constituent vaporizer article 3500 is specified in FIGS. 43A and 43B, it should be understood that any vaporizer article 10 in any of its embodiments including constituent display enabled control device 2100, passive vaporizer article 2400, solid media vaporizer article 2500, and optical solid media vaporizer article 2600, in-line constituent vaporizer article 3500, media delivery article 3600, nasal delivery article 4700 and their respective components can include this functionality.) FIG. 43B describes an application selection process 4300. The application selection process 4300 begins with block 4301 when the user connects the cartridge 3510 to the in-line constituent control device 3501. In block 4302, the in-line constituent control device 3501 reads memory IC 205. The in-line constituent control device 3501 then compares the data element associated with applications with a list of data elements stored in memory 1503 in block 4303. If a match is found, then the in-line constituent control device 3501 will cause the correct corresponding application to be launched in block 4304. The selection and launch of the corresponding application can be triggered by the in-line constituent control device 3501 sending a notification message to either of the computing device 1803 or computing network 1801. An alternative method of launching the corresponding application can be used if a complete list of application data elements is not stored in memory 1503. In this case, the in-line constituent control device 3501 sends a notification to the computer network 1801 in block 4305. This notification can contain the application data element that was read from memory IC 205. The application data element can be a unique element or the system can use another data element such as serial number for cross referencing purposes in the database 1600. In block 4306, the network application can select the appropriate application based on comparing the application data element read from memory IC 205 with a list of application data elements stored in database 1600. When a match is found, the network application can cause the corresponding application to be triggered in block 4307.

Figure 44A:
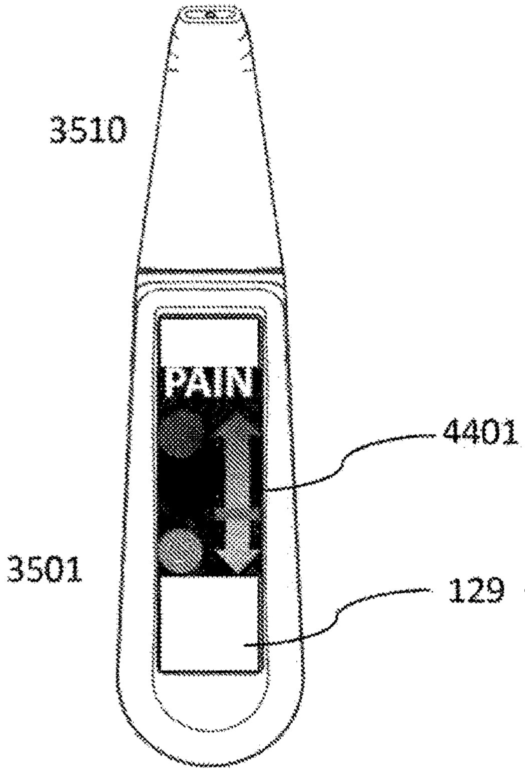
FIGS. 44A and 44B show examples of how dosing controls are generated according to an aspect of the disclosure.
Figure 44B:
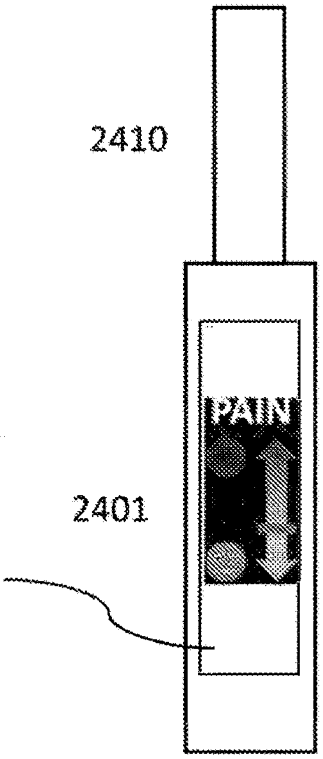
Figure 44C:
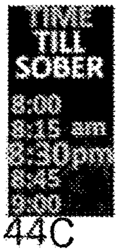
FIGS. 44C through 44CC show additional examples of controls and displays are generated according to an aspect of the disclosure.
Figure 44D:
Figure 44E:
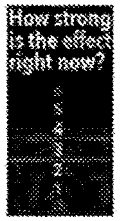
Figure 44F:
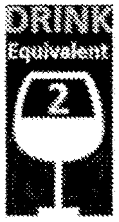

FIG. 44A describes an application interface 4401, shown in the context of the in-line constituent control device 3501, that represents an example application according to an aspect of the invention. The user can select their level of pain using a visual analog scale and then, utilizing all available data regarding the user, other users in the network, and the pharmacodynamics of the inhalation media, the application can recommend the appropriate dose corresponding to the level of pain. It should be noted that the visual analog scale shown in FIG. 44A is a representation of the Wong-Baker Faces Pain Rating Scale. Alternative visual analog scales can be implemented for applications configured to provide dosing recommendations for other conditions, including, but not limited to anxiety, depression, mental focus, tremors, intestinal distress, urge to smoke and appetite management. FIG. 44B demonstrates that such applications can run on alternative embodiments such as passive control device 2401 should it be configured to have a display screen. FIG. 44C shows an application that enables the consumer to dose according to the time they want the effect to wear off. The user selects a time then the application determines the appropriate dose that will wear off at the selected time. FIG. 44D describes an application that displays the constituent components of the inhalation media. FIG. 44E shows an application that solicits feedback from the user regarding the strength of the effect or other characteristic of the dose at a particular moment. The application, which can employ artificial intelligence techniques, uses available information to determine the optimal time to solicit such feedback. It can also determine the most appropriate question to ask. For example, other than numerical scale questions, the application can ask questions from Amsterdam Resting State Questionnaire, the Brunel Mood Scale questionnaire, the Fagerstrom Test For Nicotine Dependence (FTND), the Minnesota Nicotine Withdrawal Scale (MNWS) Shif man Craving Scale (SCS), the Wisconsin Smoking Withdrawal Scale (WSWS), the Cigarette Withdrawal Scale (CWS), the Mood and Physical Symptoms Scale (MPSS), the Questionnaire on Smoking Urges (QSU) or the Single rating of craving Smoker Complaint Scale (Schneider). Such a feedback interface can also be used to "onboard" new users; collecting background information by asking as series of questions, including, but not limited to: age, weight, gender, physical conditions including ailments, the user's mental condition and ailments, prior consumption of other inhalation media, drug and medication usage, and the user's reason for consuming inhalation media. The feedback can be stored in a database such as database 1600. FIG. 44F describes an application that suggests a dose of the currently installed inhalation media that can provide an equivalent effect to another substance. For example, the user may want an equivalent effect to a particular amount of alcohol. In this example, the application can use available data to recommend a dose of inhalation media that can provide an approximately equivalent effect. This application can also be used to provide equivalent effects between inhalation media of different compositions.

Figure 44G:
Figure 44H:
Figure 44I:
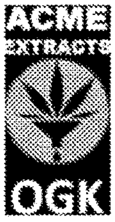
Figure 44J:
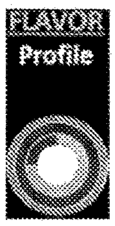
Figure 44K:
Figure 44L:
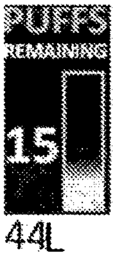

FIG. 44G shows an application that uses dosing information, available data and optionally pharmacodynamic models to predict when the effect from a dose will be perceived by the user. FIG. 44H shows an application that helps the user determine and/or recommends the timing, dose and formulation of inhalation media to be taken to assist with insomnia. The application can also determine when to ask feedback from the user regarding the user's quality of sleep. FIG. 44I shows an application for displaying brand information regarding the inhalation media. When the in-line constituent cartridge 3510 is connected to in-line constituent control device 3501, the application can read the serial number of the in-line constituent cartridge 3510 and compare that to a list of serial numbers associated with a given inhalation media type, name or brand. One or more images associated with that inhalation media can then be displayed on display screen 129. Such images can communicate information including, but not limited to: brand logo, product image, inhalation media flavor, and purchase location of inhalation media. FIG. 44J shows an image of a flavor display application. In certain embodiments, the flavor of the currently attached inhalation media may not be known or have a predetermined image that communicates the flavor characteristics. The flavor display application can analyze the constituents of the inhalation media, which can be stored on any of memory IC 205, computing device 1803, or database 1600, and create a flavor graphic image that corresponds to the levels of certain constituents in the inhalation media. FIG. 44K shows an application for displaying information related to the currently installed inhalation media. The functionality is the same at that described in FIG. 44I. FIG. 44L shows an application for displaying the amount of inhalation media remaining in a given cartridge. The initial position of the plunger 204 can represent the full state of the cartridge. The maximum travel position of the plunger 204, which can represent the fully empty state of the cartridge, can be known to the system either by having been downloaded or programmed into the in-line constituent control device 3501 or by being stored as a data element in memory IC 205. By knowing these two pieces of information and the current position of the plunger 204, the application can determine the amount of inhalation media remaining and display such information to the user. When the amount of inhalation media drops below a threshold, the application can provide a notification to the user that in-line constituent cartridge 3510 is running low. It can also be configured to estimate for the user when the in-line constituent cartridge 3510 will be empty according to the current rate of consumption. A corresponding notification can also be sent to other parties, including, but not limited to: retailers, inhalation media manufacturers, distributors, social network and health care providers. A notification can also be configured to be sent to a purchasing system for the purpose of ordering additional in-line constituent cartridges 3510.

Figure 44M:
Figure 44N:
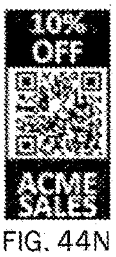
Figure 44O:
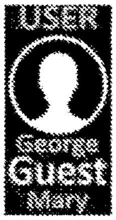
Figure 44P:
Figure 44Q:
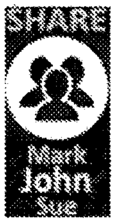

FIG. 44M shows an application that facilitates the purchase of inhalation media. One example use of this application is to facilitate the purchase of the inhalation media, for example, in conjunction with having received a notification that the amount of inhalation media in the cartridge is below a threshold amount, as shown in FIG. 44M. The application can also facilitate the purchase on inhalation media that is selected from a list shown on the display screen 129 or suggested via a message or notification. The application can connect to an order fulfillment and payment processing service for the purpose of purchasing products. The application that facilitates purchases can also work in conjunction with an application that provides coupons to incentivize purchase, shown in FIG. 44N. The application can make a determination of when to send a coupon and the value of the coupon by analyzing available information such as prior purchase behavior and consumption data. It can also send coupons triggered by the action of third parties. For example, a different user within the user's network can share a recommendation for a particular inhalation media, which can cause the application to send a coupon. Additionally, a third party, such as a seller of inhalation media, can cause a coupon to be sent to the user. FIG. 44O shows an application that allows the user to switch between profiles, allowing the same in-line constituent control device 3501 to be used by multiple users while still associating the data with the correct user and applying the appropriate user specific settings. This application can also enable a guest mode where the data collected is not associated with any particular user, nor are any particular user specific settings applied. FIG. 44P shows an application that allows users to rate a given inhalation media. The application can present the user with the opportunity to rate the inhalation media after consumption. The ratings for a given inhalation media can be stored in database 1600 or separate database. The cumulative rating and number or ratings can be displayed for other users to view. The user providing the rating can earn incentives in exchange for providing such ratings. As shown in FIG. 44Q, the user can also share their rating with other users or groups in their network of connections. The application can also be configured to share dosing information. For example, the application can share the amount and chemical composition of the dose consumed by the user. The application can also share other information, including, but not limited to: brand name, product name, time of consumption, location of consumption, product imagery, and effect characteristics. The application can give the user control over which individuals or groups receive the shared information.

Figure 44R:
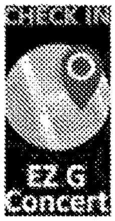
Figure 44S:
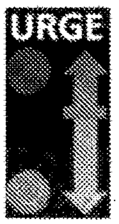
Figure 44T:
Figure 44U:
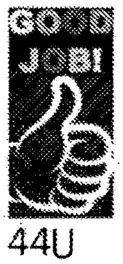

FIG. 44R shows another type of information sharing, geo location. In this embodiment, the application can enable the user to log and/or share the location of where they consumed doses on inhalation media. The application can be configured to log the location of each dose when activated. The location can be determined from location information provided by the computing device 1803 or the in-line constituent control device 3501 if equipped with GPS or similar location technology. The location can be stored in database 1600 and the application can also be configured to allow the user to annotate the location. Dosing information and/or information pertaining to the inhalation media can also be recorded in the database 1600 an associated with a location. FIG. 44S shows another embodiment of the visual analog scale shown in FIG. 44A. Based on the user's indicated urge to smoke, available data regarding the user, data from other users in the network, and the pharmacodynamics of the inhalation media, the application can recommend the appropriate dose of nicotine or tobacco replacement inhalation media to satiate the urge to smoke. FIG. 44T shows an embodiment of an application configured to inform and assist the user in achieving cessation goals. In this embodiment, the user is provided with a daily budget for nicotine consumption and is also provided information regarding their current consumption. The application can be further configured to automatically determine the appropriate daily budget based on a number of factors, including, but not limited to: prior use patterns of the user, use patterns of other users within the network, step-down dosing models, cessation models, calendar events, the start date of the cessation program, the target end date of the cessation program. The application can be configured to temporarily disallow further consumption of the inhalation media in the event that the daily budget is exceeded. Furthermore, the application can be configured to display and/or determine the budget on different time scales, including, but not limited to: hourly, daily, weekly and monthly. Behavioral modification techniques can be employed to increase the effectiveness of a cessation program. FIG. 44U shows an embodiment of the application configured to provide messages to the user designed to improve cessation program outcomes via behavioral queues. A well-timed message of encouragement may help the user remain compliant with the cessation program. Likewise, well-timed messages describing the negative consequences of departure from a cessation program may solicit the desired behavioral outcome. The application can be configured to monitor prior use patterns of the user, use patterns of other users within the network, step-down dosing models, cessation models, calendar events, the start date of the cessation program, the target end date of the cessation program in order to determine the optimal time to deliver such a message. It can also be configured to determine the content of the message based on the aforementioned inputs. For example, if a user has a pattern of consuming extra inhalation media on Friday evenings, the application can send the user a message encouraging less consumption the following Friday afternoon in order to preempt the next instance of possible overconsumption. It can also be configured to receive messages from other users on the network describing their progress toward their cessation goals. It can also be configured to deliver such a message when the in-line constituent control device 3501 detects that has been picked up or turned on after some period on inactivity. This can be determined by the user touching one of the input controls of the in-line constituent control device 3501 or by a signal from optional accelerometer 1514.

Figure 44V:
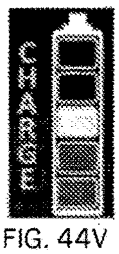
Figure 44W:
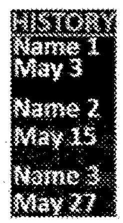
Figure 44X:
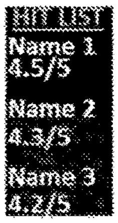
Figure 44Y:
Figure 44Z:
Figure 44A:
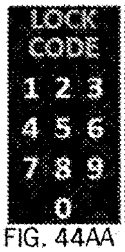
Figure 44B:
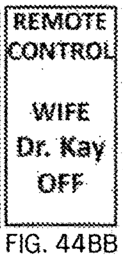
Figure 44C:
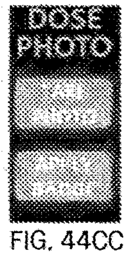

FIG. 44V describes an application configured to display the operational status of the in-line constituent control device 3501. Many operational status elements can be displayed, including, but not limited to: battery charge status, progress of battery charge, time until charge completion, time until charge depleted, wireless communication connection status, operating mode, operational errors, and status of connection of in-line constituent cartridge 3510. FIG. 44W shows an application configured to display the history of inhalation media used in conjunction with the in-line constituent control device 3501. The descriptions of the inhalation media being known by the processes described earlier, can be stored in one or more of the in-line constituent control device 3501, computing device 1803, and database 1600. The consumption history of the associated inhalation media can be displayed to the user in a variety of orders, including, but not limited to: chronological, frequency, cost, total consumption, popularity, and rating. FIG. 44X shows an application configured to recall the inhalation media most frequently consumed or most favored by the user. It can be configured to allow the user to construct, organize and recall a list of inhalation media. It can further be configured to allow the consumer to create a plurality of lists, for example, the user can create one list of inhalation media for pain relief and a second list of inhalation media for insomnia. FIG. 44Y describes an application configured to broadcast dosing event streams to other users or groups within the network, without the user having to actively trigger the sending of each dosing event to specific individuals or groups. When the user consumes a dose of inhalation media, information about that dose, including, but not limited to: user name, amount, brand name, product name, product type, time of consumption, location of consumption, product imagery, and effect characteristics can be sent to recipients of the dosing stream. The application can be configured to allow the user to create groups and select the recipients of the dosing stream. The application can be configured to store the doses in database 1600. The application can further be configured to automatically delete or anonymize the dose stream events stored on the database 1600 after a configurable or pre-determined period of time. FIG. 44Z shows an application configured to receive and display such dosing stream events. The application can cause such notifications to be displayed on any of display screen display screen 129, computing device 1803 and smart watch 1806. The application can also be configured to display a summary of recent dose activities of groups on the network. The application can also be configured to allow users to select individual dose events in order to display more information about such doses. It can also be configured to allows users to delete notifications. It can also be configured to automatically delete such notifications after a configurable or pre-determined period of time.

FIG. 44AA shows an application configured to restrict the use of the in-line constituent control device 3501 via the use of a passcode. The application can be configured to allow the user to establish a custom passcode. The passcode can consist of one or more letters, numbers, symbols or patterns. The passcode can be stored in one or more of in-line constituent control device 3501, computing device 1803, and database 1600. The passcode can also be cartridge specific and can additionally be stored in memory 205. FIG. 44BB shows an application configured to implement remote dosing process 2300. FIG. 44CC shows an application configured to implement all or a portion of dose enabled photograph process 4100. The application can be configured to trigger blocks 4102 and 4105. It should be noted that the applications described in FIGS. 44A through 44CC can be configured to reside natively, in whole or in part, on the in-line constituent control device 3501 and/or computing device 1803, can be downloaded, in whole or in part, to the in-line constituent control device 3501 and/or computing device 1803, or can reside in whole or in part on the computer network 1801. Furthermore, the applications can be combined in a plurality of combinations to provide unique functional combinations. It should be further understood that although the in-line constituent control device 3501 was used in the context of the description of the applications, the application functionality can be implemented in conjunction with other embodiments of control device 100 such as constituent display enabled control device 2100, solid media control device 2510, optical solid media control device 2610, sublingual control device 3601, or a dedicated nasal delivery article 4700 (not shown).

Figure 45A:
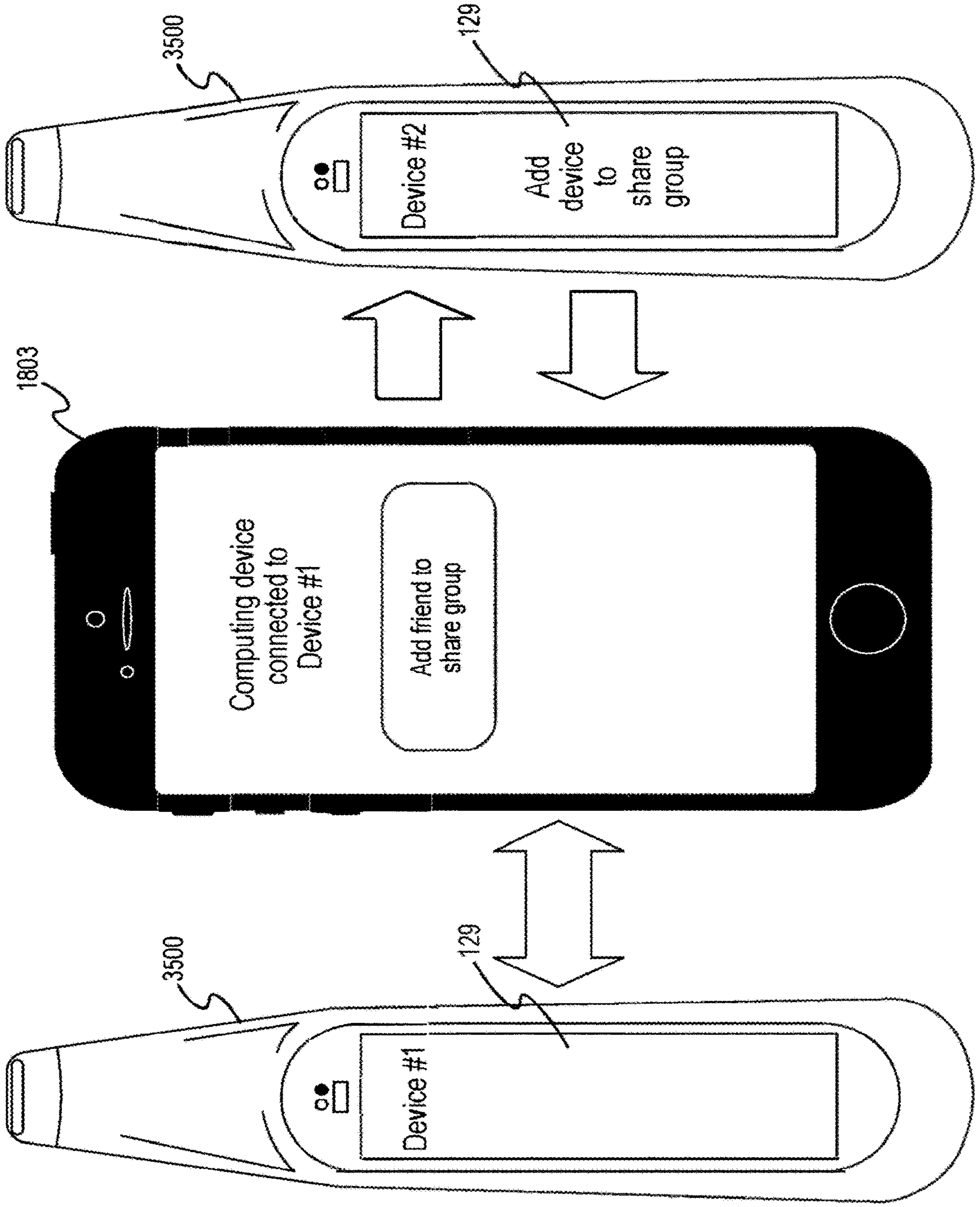
FIGS. 45A and 45B show how sharing interfaces are constructed and sharing connections are made according to an aspect of the disclosure.
Figure 45B:
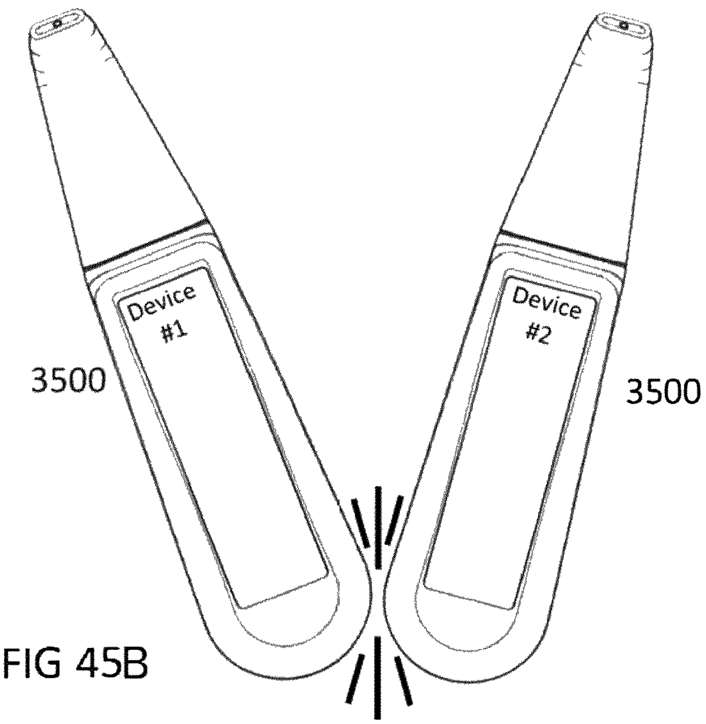

FIG. 45A describes an embodiment of the system configured to associate users on the computer network 1801, for example, for the purpose of sharing dosing information as previously described herein. The first in-line constituent control device 3501, belonging to the first user, can have an already established connection with computing device 1803, also belonging to the first user. The computing device 1803 can be configured with an interface/application for associating with other users. The user can trigger the interface to cause the computing device to look for signals from a second in-line constituent control device 3501. A second user can configure the second in-line constituent control device 3501 to send a signal broadcasting an identifier unique to the second in-line constituent control device 3501. The computing device 1803 can receive the signal and record the identifier. The interface/application can transmit the identifier to the computer network 1801 where it can be matched with the account of the second user and can be configured to be associated with the first user. FIG. 45B shows an alternative embodiment for establishing connections between users on the computer network 1801. When a first the second in-line constituent control device 3501 and second the second in-line constituent control device 3501 are tapped together, the respective accelerometers 1514 can produce signals that are interpreted by the respective MCUs 1501 as triggers to broadcast their respective identifiers and record identifiers being broadcast. These identifiers can then be used to make associations as described above. Alternatively, the network 1801 can be configured to automatically associate users whose devices experience tap events at the same time within a certain geographic radius as identified by the computing devices 1803 of the first and second users.

Figure 46A:
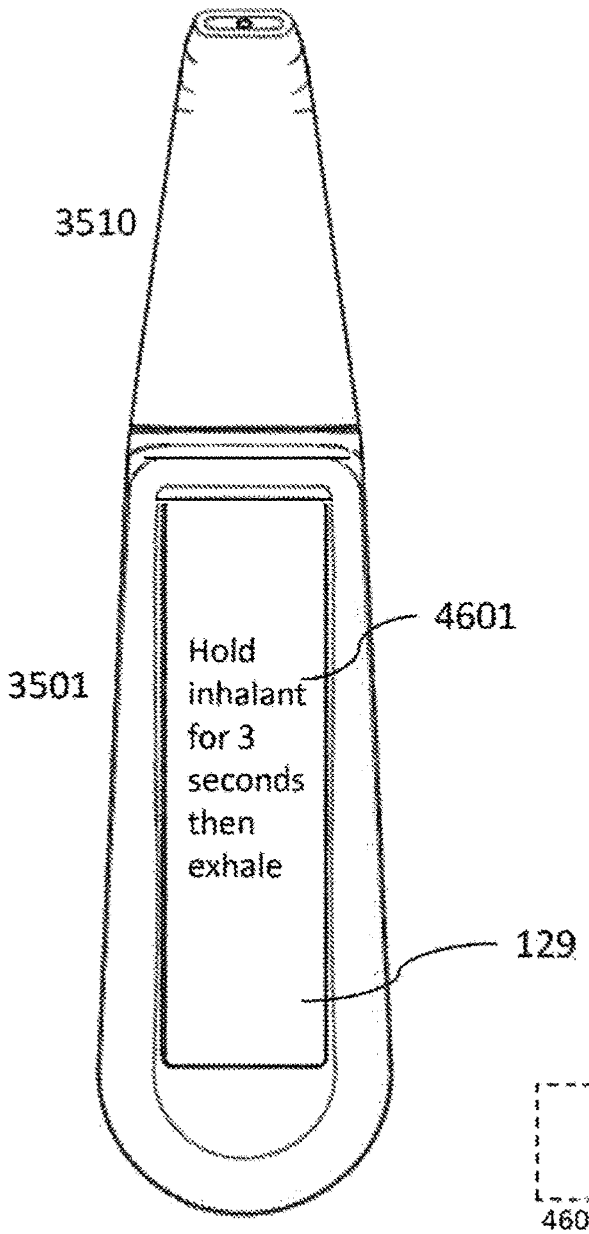
FIGS. 46A and 46B show how operational instructions can be conveyed according to an aspect of the disclosure.

FIG. 46A shows an embodiment for providing operational instructions 4601 to the user.

Figure 46B:
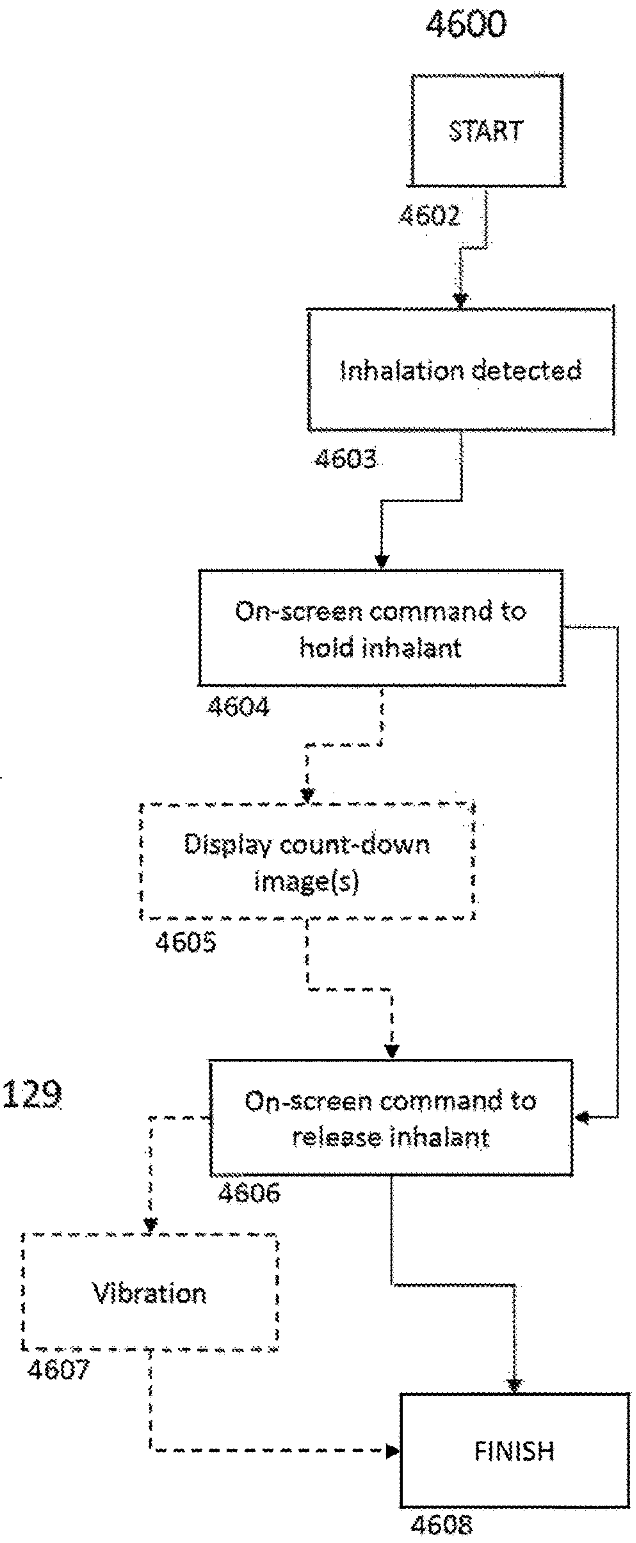

Operational instructions 4601 can be displayed on display screen 129. The operational instructions 4601 can be comprised of text characters, one or more static images, video animations, or a combination thereof. FIG. 46B shows an inhalation normalization process 4600 that can be configured to control the delivery of a particular operational instruction 4601. The particular operational instruction in this example relates to the normalization of inhalation media holding time. In order for a dose to achieve a desired effect, it may need to be held in the lungs for a set period of time. Additionally, normalizing the inhalation media hold time across a population decreases the variability in outcomes and effects. The process starts at block 4602. When an inhalation is detected in block 4603, an instruction is displayed in block 4604. In this example, the instruction is displayed for 3 seconds, then an instruction to exhale is provided in block 4606. Optionally, if the instruction is comprised of a series of images or animation such as a count-down timer, a series of images or animation can be displayed in block 4605 before proceeding to block 4606. In order to provide the user with additional notification to exhale, block 4607 can optionally be implemented to turn on vibration transducer 124 for a period of time to signal to the user that it is time to exhale. Alternatively, the system can be configured to activate the vibration transducer 124 during the count down, then deactivate it when the count down is complete. The process terminates in block 4608. It should be noted that other operational instructions can be displayed on display screen 129, including, but not limited to: a count-down timer to indicate how to wait for the plunger driver 116 to be fully retracted before removing in-line constituent cartridge 3510, how to connect in-line constituent cartridge 3510 to in-line constituent control device 3501, when to take doses during a meditation session, and how to share doses with other users in the network. Another embodiment of operational instructions can be considered a "demo mode" where a series of images, text, video, and/or instructions are displayed on display screen 129 without regard to the input of the user. The display of images, text, and/or instructions can be configured to repeat until the user turns off demo mode. In-line constituent control device 3501 can be configured to perform no other functions while in demo mode. Demo mode may be a desirable feature for a retail environment where the in-line constituent control device 3501 can provide information to prospective buyers without relying on retail personnel to provide such information. For example, in-line constituent control device 3501 can be configured to be in demo mode and placed into a display case in a store. It should be further understood that although the in-line constituent control device 3501 was used in the context of the description of the operational instructions and demo mode, such functionality can be implemented in conjunction with other embodiments of control device 100 such as constituent display enabled control device 2100, solid media control device 2510, optical solid media control device 2610, sublingual control device 3601, or a dedicated nasal delivery article 4700 (not shown).

Figure 47A:
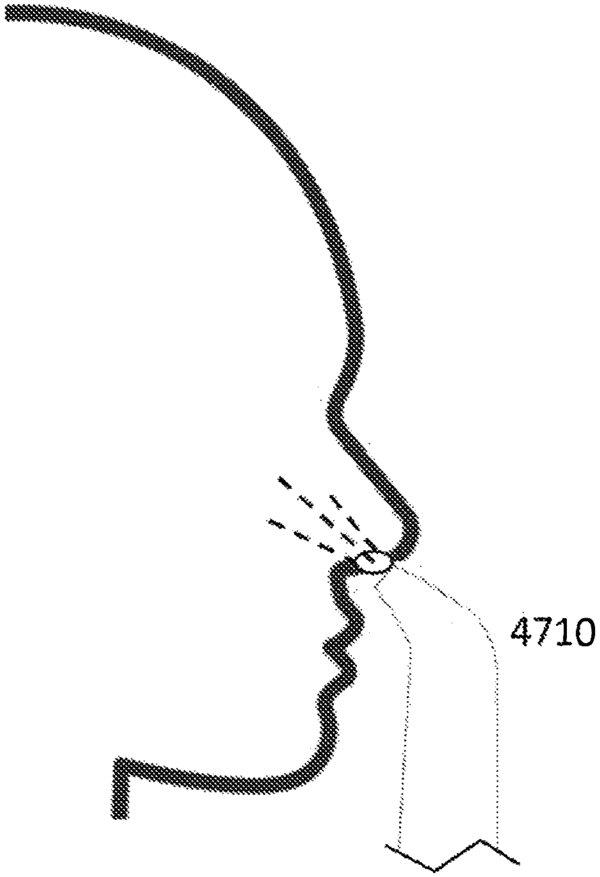
FIGS. 47A and 47B show an example of an alternative delivery pathway device that is constructed according to an aspect of the disclosure.
Figure 47B:
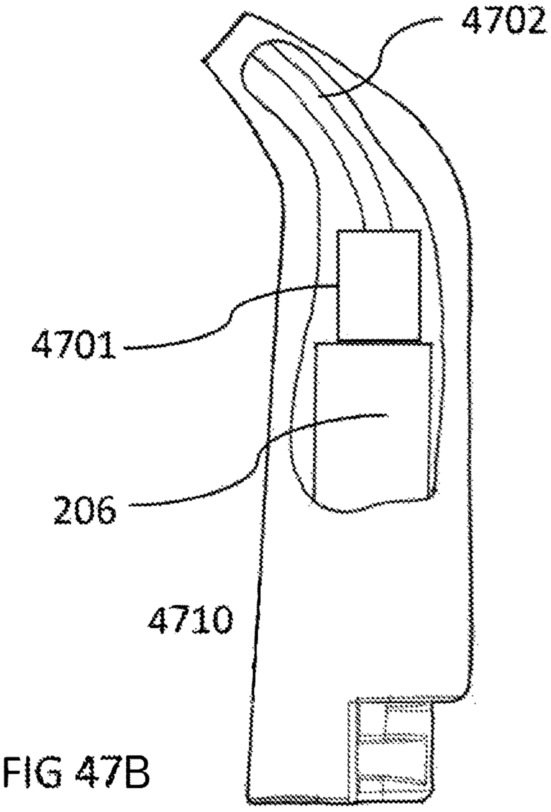

FIGS. 47A and 47B show a nasal cartridge 4710 according to an aspect of the disclosure. Nasal cartridge 4710, which is designed to function with embodiments of control device 100 such as in-line constituent control device 3501, sublingual control device 3601, or a dedicated nasal delivery article 4700 (not shown), is substantially similar to in-line constituent cartridge 3510 except that the vaporizer element 109 is replaced with a mister 4701. The mister 4701 can be comprised of an actuator/motor, a small chamber and nozzle configured to pressurize the media so that it is forcibly ejected from the mister 4701. In this embodiment, the media inside the nasal cartridge 4710 can be expressed into the nasal passages of the user. The media stored in media storage area 206 can be dispensed/feed into the mister 4701 then expressed directly into the user's nasal pathway via the nasal tube 4702 after exiting the mister 4701. Through the ability to read memory IC 205, the in-line constituent control device 3501 can differentiate between an in-line constituent cartridge 3510, an in-line sublingual cartridge 3610 and a nasal cartridge 4710. Using this differentiation, it can then control each accordingly. This means that all the functionality offered by in-line constituent control device 3501 including, but not limited to: dose control, dispensing, data recording and sharing, dose compensation, and connectivity can also be delivered in a nasal application; only the functions specifically related to generating an aerosol would not be applicable.

Figure 48A:
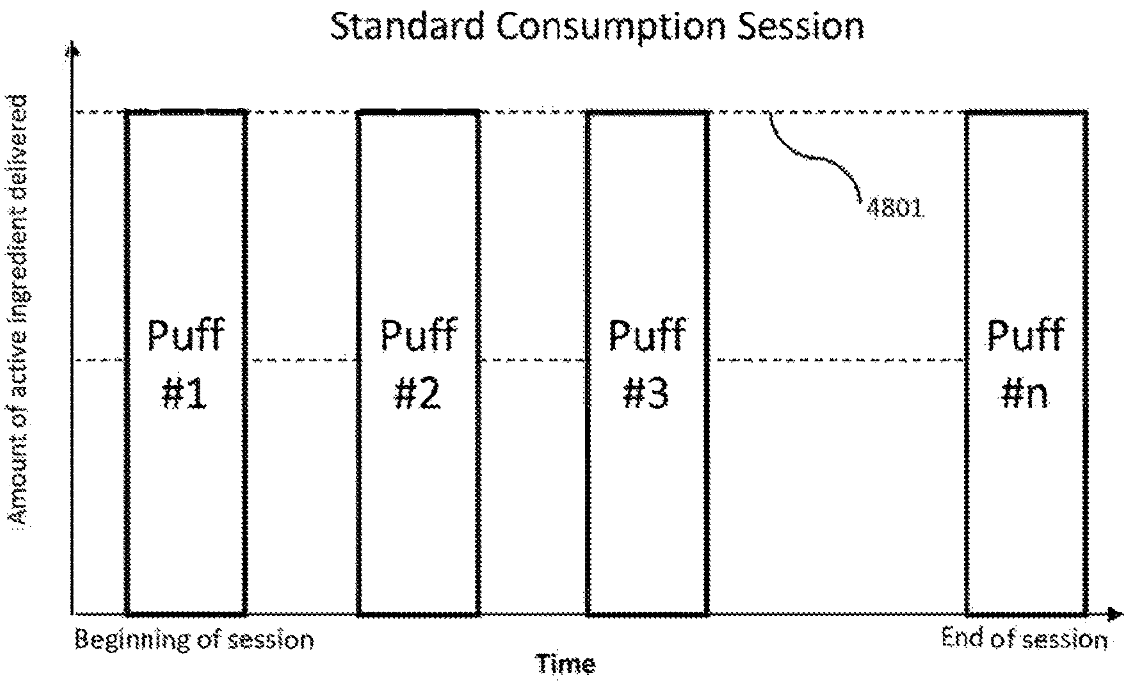
FIGS. 48A through 48D show examples of how cessation dosing controls can be generated according to an aspect of the disclosure.

The consumption of cigarettes is usually broken into sessions that are largely governed by the time a cigarette takes to be consumed. Furthermore, the number and timing of session is usually similar from day-to-day and typically associated in time with routine behaviors such as a morning meal, work break, lunch break, post-dinner, etc. On average, a standard 80 mm long cigarette with a filter can provide about 10 inhalations. The average user takes approximately 7 inhalations before extinguishing the cigarette. And most users smoke 1 cigarette per session. Within an individual user, the number of inhalations per cigarette and the duration of each inhalation does not typically vary significantly. FIG. 48A represents a standard consumption session of a typical smoker where the user takes a number of inhalations up to their usual maximum number of inhalations, "Puff #n", with pauses between each inhalation. The duration of each inhalation is relatively the same as the other inhalations and therefore, the total amount of active ingredients delivered, represented by standard dosage line 4801, is relatively similar across all inhalations. (Note that as a cigarette is consumed, there is a shift in chemical composition due to distillation effects over time and successive inhalations, but this is considered small and therefore not addressed in this discussion.) The same is true for traditional electronic cigarettes where the duration of each inhalation does not vary significantly, however, because electronic cigarettes last much longer than combustible cigarettes, the session is less well defined and less constant.

Figure 48B:
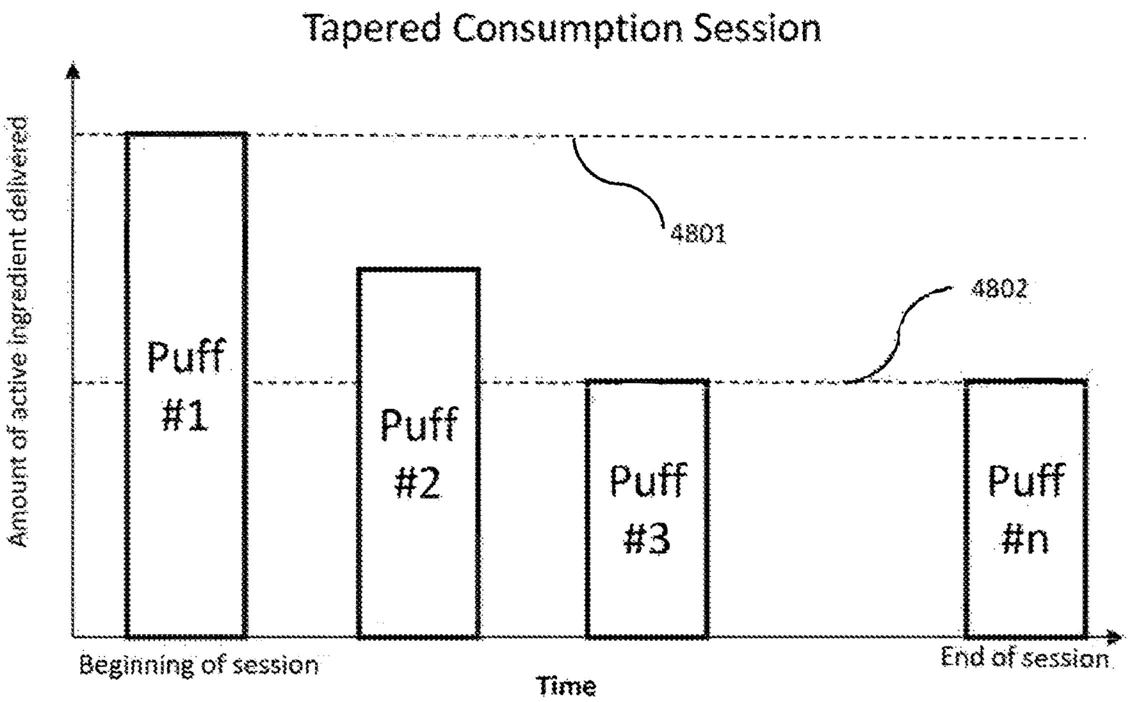

In order to provide improved cessation functionality, an embodiment of the invention, informed by the standard consumption pattern shown in FIG. 48A, is contemplated and represented by a tapered consumption session shown in FIG. 48B. Although electronic vaporizers do not typically limit the number of inhalations, the tapered consumption session imposes a limit on the number of inhalations per session. This number can be similar to the number of inhalations provided by a combustible cigarette, can be set at a number determined by user testing, or can be determined dynamically by an application that monitors the user's consumption patterns, consumption patterns of other users of the network, and/or the feedback of users of the network in order to suggest the optimal number of puffs per session for the individual user. A defined lockout/inactivity period between sessions can likewise be determined by the above methods. Additionally, the amount of active ingredient delivered per inhalation can be programmatically reduced over the course of the session. The first inhalation or first few inhalations of a combustible cigarette smoking session generate the largest effect and largest degree of craving satiation. Subsequent inhalations within a session deliver decreasing amounts of effect and satiation. Some users even continue to smoke combustible cigarettes beyond the point of reaching full satiation out of habit or a feeling that they should not waste part of the cigarette. A tapered consumption session can be configured to deliver the maximum amount of active ingredients during the first inhalation of a session. Such amount can reach the standard dosage line 4801. Subsequent inhalations can be configured to successively reduce the amount of active ingredient delivered until a minimum acceptable dosage 4802 is reached. The minimum acceptable dosage 4802 can be configured to deliver the minimum amount of active ingredients necessary to provide the user with the effect, taste and/or satisfaction necessary. By way of example, the amount of active ingredients delivered per inhalation can be decreased linearly between the initial inhalation and the inhalation where the minimum acceptable dosage is reached. The amount can alternatively be decreased in a non-linear manner, for example decaying by a 211*d* or multi-order equation. The rate of change can be fixed formula determined by user testing or can be determined dynamically by an application that monitors the user's consumption patterns, consumption patterns of other users of the network, and/or the feedback of users of the network in order to suggest the optimal rate of decay for the individual user. The tapered consumption session can be implemented in conjunction with any embodiments of control device 100 including constituent display enabled control device 2100, solid media control device 2510, optical solid media control device 2610, in-line constituent control device 3501, sublingual control device 3601, and dedicated nasal delivery article 4700.

Figure 48C:
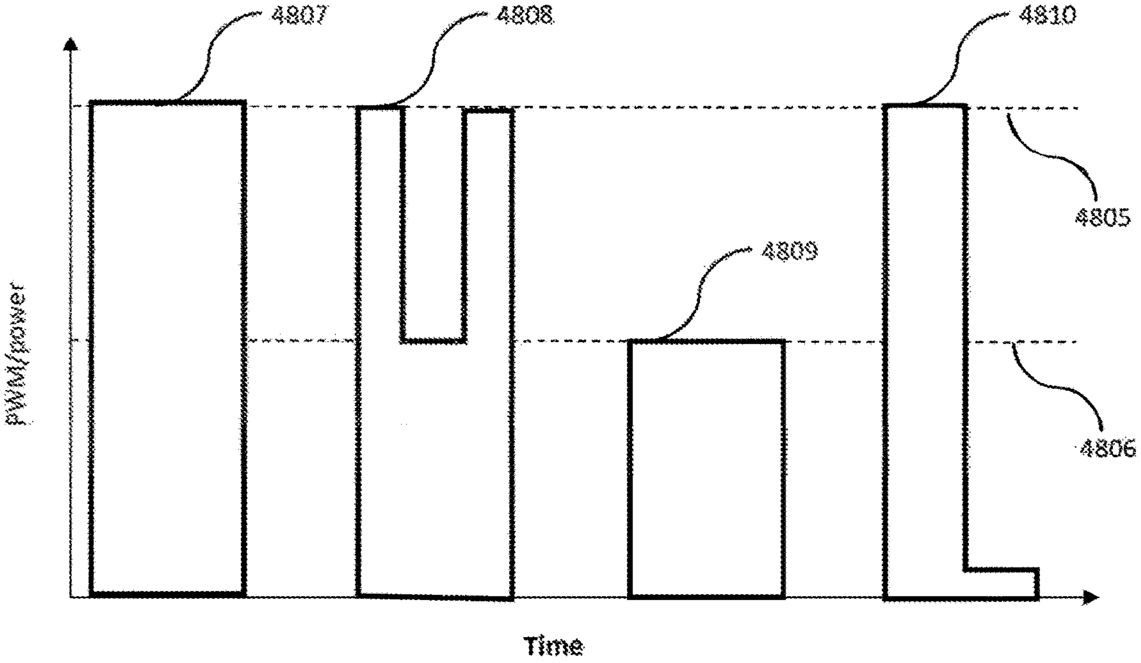

FIG. 48C indicates how the drive signal to the vaporizer element 109 can be controlled in order to reduce the amount of active ingredient delivered during an inhalation. Modulation signal 4807 delivers a constant amount of energy to the vaporizer element 109 during the course of the inhalation. Modulation signal 4807 is also provided at the maximum PWM level 4805. Modulation signal 4807 can typically be used for the first inhalation of a session. As the amount of active ingredients to be delivered decreases, modulation signals 4808 through 4810 can be used to decrease the energy transferred to the vaporizer element 109. Modulation signal 4808 starts at the maximum PWM level 4805 in order to produce an initial user perception of the inhalation that is comparable to that of the first inhalation, but is then reduced during a portion of the inhalation in order to decrease the amount of energy and thus the amount of inhalation media that is vaporized. Depending on the duration of the inhalation, the modulation signal 4808 can then be increased in order to preserve the user perception. Modulation signal 4809 represents an alternative approach to reducing the amount of active ingredients delivered. This signal is held constant, at a lower level than modulation signal 4807 during the duration of an inhalation. The modulation signal 4809 can be decreased as low as the minimum constant PWM level 4809 which is the minimum signal needed to produce a satisfactory inhalation. Modulation signal 4810 represents another approach to reducing the amount of active ingredients delivered. Modulation signal 4810 initiates at the maximum PWM level 4805 for a period of time, but can be reduced for the remainder of the inhalation. Modulation signal 4810 can be reduced to a level lower than the minimum constant PWM level 4809. It should be understood that the underlying goal is to modulate the power delivered to the vaporizer element 109 in order to control how much inhalation media is vaporized. Modulation of the PWM drive signal approximately accomplishes this goal so long as the resistance of the vaporizer element 109 is constant. In an embodiment where the resistance of the vaporizer element 109 changes significantly with temperature, the modulation must be performed with respect to power rather than PWM, hence the dual label on the vertical axis of FIG. 48C. Embodiments of control device 100 can be configured to modulate the power delivered to the vaporizer element 109 according to FIG. 48C. Gradually reducing the amount of inhalation media dispensed onto vaporizer element 109 via dispensing motor 112 during each subsequent inhalation event within a session affords an alternative way to reduce the amount of inhalation media vaporized within a session. The amount of inhalation media dispensed during an inhalation can follow the same schemes described in FIG. 48C.

Figure 48D:
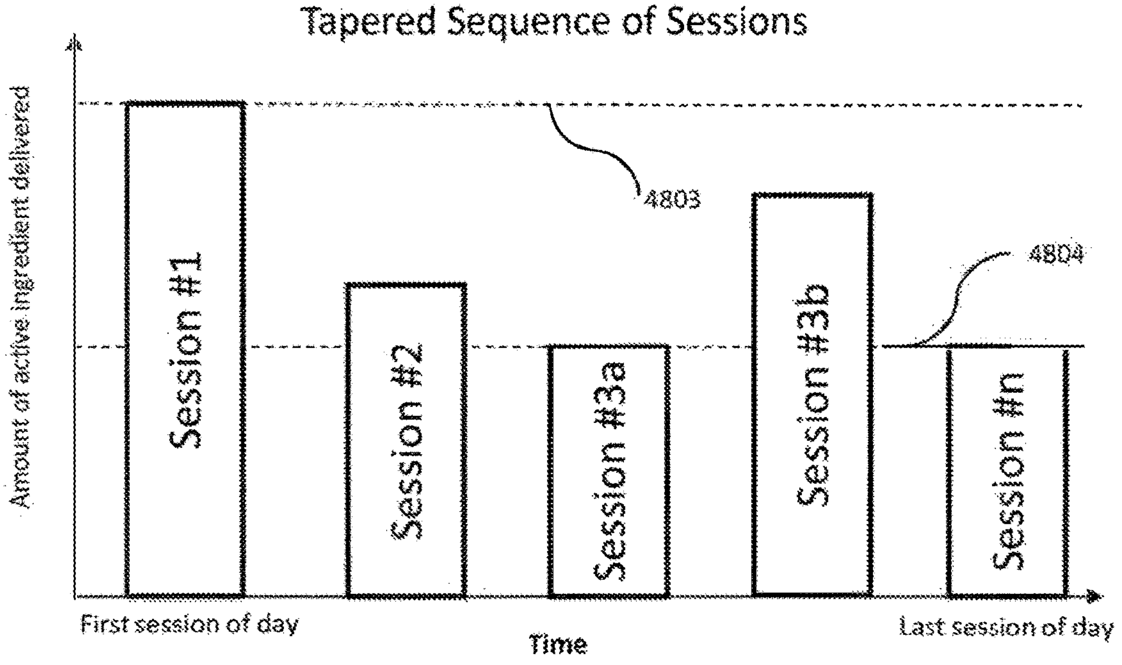

Not only is controlling the amount of active ingredients delivered within a session important, so is controlling the amount of active ingredients delivered across multiple sessions. For example, controlling the amount of active ingredients delivered within a day can be important in order to achieve cessation goals. FIG. 48D demonstrates that the amount of active ingredients delivered within each session can be varied and controlled in order to achieve the daily goal. For a combustible cigarette smoker, the early morning is typically a time when nicotine cravings are high due to the lack of smoking while sleeping. Considerable nicotine can need to be delivered in order for the user to be satiated. This amount of nicotine can be represented by the maximum session level 4803. As the day progresses, lesser amounts of nicotine can be needed within a session in order to reach satiation. For example, sessions #2, #3a and #4 can require less nicotine. A minimum session level 4804 can also be implemented in order to ensure that any one session meets a minimum threshold to provide satisfaction. The amount of active ingredients to be delivered in each session can be based on a fixed formula determined by user testing or can be determined dynamically by an application that monitors the user's consumption patterns, consumption patterns of other users of the network, and/or the feedback of users of the network in order to suggest the optimal amount for each session. It should also be understood that cessation behavior can be non-linear; users may make progress on a cessation program then regress or plateau for a period of time or an occasion. The application can take this into account when determining the amount of active ingredients to be delivered. Regression or plateau is a phenomenon that can be exhibited on many time scales, including daily, weekly or monthly. It can also be triggered by external conditions or events. For example, it can be common for an individual to have an increased urge to smoke when they have an alcoholic drink with dinner on weekends. By way of example, the application can note this pattern and adjust session #3b upward in order to provide the extra nicotine needed to achieve satiation at such moments while adjusting session #2 down in order to keep the user on track with their overall cessation program. If the application did not allow for such an adjustment, the urge to smoke may be too strong and the user may be tempted to smoke a combustible cigarette. Adjustments and compensation for regression and plateau can be implemented on various time scales, including, but not limited to: daily, weekly, bi-weekly and monthly. Furthermore, it should be understood that while nicotine is the example active ingredient used to explain FIGS. 48A through 48D, the invention can be more broadly applied to cessation from other active ingredients, including, but not limited to opioids and THC.

While the disclosure has been described in terms of exemplary embodiments, those skilled in the art will recognize that the disclosure can be practiced with modifications in the spirit and scope of the appended claims. These examples given above are merely illustrative and are not meant to be an exhaustive list of all possible designs, embodiments, applications, or modifications of the disclosure.

What is claimed is:

1. A system for dispensing ingestible media, comprising:

a device comprising:

a driver component having an end configured to act on a movable surface of a cartridge, a motor configured to controllably position the driver component, at least one hardware processor, and one or more software modules that are configured to, when executed by the at least one hardware processor, receive media dose information and control the motor based on the media dose information in order to dispense a dose of the media;

a cartridge having:

a media storage area for storing the media, at least one movable surface that changes a volume of the media stored in the media storage area under control of the driver component, and an outlet through which the media is dispensed in order to change the volume of the media stored in the media storage area under control of the driver component, wherein the ingestible media is dispensed from the outlet without inhalation of the media.

2. The system of claim 1, wherein the device is configured to receive the cartridge.

3. The system of claim 1, wherein the device comprises a guide feature for aligning the cartridge.

4. The system of claim 1, wherein the cartridge further comprises programmable memory storing a value associated with the amount of media contained in the media storage area.

5. The system of claim 4, wherein the programmable memory is configured to store a value associated with one or more of:

a device serial number;
a media type;
a manufacturing date;
a fill date;
an expiration date;
a fill amount;
a storage volume;
characteristics of the media;
dosing information;
control information;
usage information;
a number of inhalation events;
a media amount remaining;
a plunger position;
a running total of dispensed media or drive counts;
an amount of media previously expressed;
optimal vaporization parameters;
viscosity;
density;
a default dose;
ingredients;
chemical composition;
genetic information;
raw material information;
grower information;
weather conditions during raw material growth;
raw material origin information;
test lab digital authentication information;
testing information;
processing parameters;
production parameters;
digital authentication parameters;
identities of persons or entities associated with manufacture or production; and
user-defined or unassigned parameters.

6. The system of claim 1, wherein the motor has a shaft that rotates.

7. The system of claim 6, wherein the device further comprises a drive screw that connects the motor to the driver component.

8. The system of claim 1, wherein the motor is a linear motor.

9. The system of claim 1, wherein the media is a liquid.

10. The system of claim 1, wherein the media is a powder.

11. The system of claim 1, wherein the media contains a medication.

12. The system of claim 1, wherein the media contains a drug and/or a supplement.

13. The system of claim 1, wherein the device further comprises a user interface for displaying information associated with the media.

14. The system of claim 13, wherein the information associated with the media is an amount of media dispensed.

15. The system of claim 13, wherein the user interface accepts touch inputs for controlling the device.

16. The system of claim 1, wherein the device is in communication with a mobile device.

17. The system of claim 1, wherein the device is in communication with a server.

18. The system of claim 1, wherein the device further comprises a component that amplifies the force of the motor and connects the motor to the driver component.

19. The system of claim 18, wherein the component that amplifies the force of the motor is comprised of one or more gears.

20. The system of claim 18, wherein the device further comprises a drive screw that connects the component that amplifies the force of the motor to the driver component.

21. The system of claim 1, where the device further comprises a sensor for determining a position of the driver component.

22. The system of claim 21, wherein the sensor reads the position of a movable portion of the motor.

23. The system of claim 21, wherein the sensor is an optical encoder.

24. The system of claim 21, wherein the sensor is a hall effect sensor.

25. The system of claim 21, wherein the sensor is configured to read a position of the driver component.

26. The system of claim 1, wherein the driver component is configured to retract after dispensing a dose of media.

27. The system of claim 1, wherein the movable surface that changes the volume of the media storage area is part of a plunger.

28. The system of claim 1, wherein the movable surface that changes the volume of the media storage area is integrally formed with the media storage area.

29. The system of claim 1, further including a flexible material that defines the media storage area.

30. The system of claim 1, wherein an amount of media to be dispensed is communicated from a computer network to the device.

31. The system of claim 1, wherein information associated with the amount of media dispensed is stored within a computer network.

32. The system of claim 4, wherein the media dose information is based, at least in part, on information read from the programmable memory.

33. The system of claim 1, wherein the media dose information is based, at least in part, on user characteristics related to a user.

34. The system of claim 1, wherein the media dose information is based, at least in part, on a selection by a user.

35. The system of claim 1, wherein the media dose information is based, at least in part, on information received from or provided by a third party.

36. The system of claim 1, wherein the media dose information is based, at least in part, by determination of a data analysis program.

37. The system of claim 1, wherein the media comprises at least one of melatonin, CBD, CBN, nicotine or THC.

38. The system of claim 1, wherein the cartridge further comprises programmable memory storing a value associated with an updated amount of media contained in the media storage area.

39. The system of claim 1, wherein the device comprises an opening through which the driver component can extend when acted upon by the motor.

* * * * *